US006858599B2

(12) United States Patent
Nishida et al.

(10) Patent No.: US 6,858,599 B2
(45) Date of Patent: Feb. 22, 2005

(54) TRICYCLIC COMPOUND HAVING SPIRO UNION

(75) Inventors: Hidemitsu Nishida, Tokyo (JP);
Fumihiko Saitoh, Tokyo (JP); Kousuke Harada, Shizuoka (JP); Ikuya Shiromizu, Tokyo (JP); Takafumi Mukaihira, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 136 days.

(21) Appl. No.: 10/026,606

(22) Filed: Dec. 27, 2001

(65) Prior Publication Data

US 2003/0045520 A1 Mar. 6, 2003

Related U.S. Application Data

(63) Continuation-in-part of application No. PCT/JP00/04374, filed on Jun. 30, 2000.

(30) Foreign Application Priority Data

Jun. 30, 1999 (JP) .............................. 11-222883
Dec. 28, 2000 (JP) ....................... 2000-399998

(51) Int. Cl.[7] ..................... A61K 31/33; A61K 31/495; C07D 241/00; C07D 491/00; C07D 243/00
(52) U.S. Cl. ..................... 514/183; 514/248; 514/245; 514/250; 514/252.16; 514/252.13; 514/211.01; 544/336; 544/387; 544/358; 544/380; 544/384; 540/543; 540/547; 540/553; 540/557; 540/569; 540/570
(58) Field of Search ................................. 514/183, 248, 514/245, 250, 252.15, 252.13, 211.01; 544/336, 387, 358, 380, 384; 540/543, 547, 553, 557, 569, 570

(56) References Cited

U.S. PATENT DOCUMENTS 5,292,747 A 3/1994 Davis et al.
5,691,356 A * 11/1997 Das et al. .................. 514/326

FOREIGN PATENT DOCUMENTS

EP 0 300 541 1/1989
WO 9616940 * 6/1996

OTHER PUBLICATIONS

Copy of claims of U. S. Sr #v10451728, fied Jun. 25, 2003.*

(List continued on next page.)

Primary Examiner—Richard L. Raymond
Assistant Examiner—Sudhaker B. Patel
(74) Attorney, Agent, or Firm—Birch, Stewart, Kolasch & Birch, LLP

(57) ABSTRACT

This invention relates to tricyclic compounds having spiro union represented by the following formula (I) or its salt which is useful as a drug, and in particular, as an inhibitor for activated blood coagulation factor X, which can be administered orally and which exhibits strong anticoagulation action.

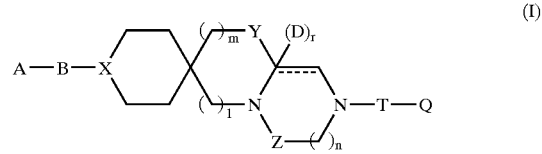

The invention also relates to a pharmacophore which was derived from the compound and is useful in molecular designing of the FXa inhibitor.

12 Claims, 48 Drawing Sheets

OTHER PUBLICATIONS

Brandstetter et al., J. Biological Chemistry, vol. 271, No. 47 (1996) pp. 29988–29992.

Kamata et al., Proc. Natl. Acad. Sci USA, vol. 95 (1998) pp. 6630–6635.

Mochalkin et al., Acta Cryst, D55 (1999) pp. 785–793.

Maduskuie et al., Book of Abstracts, 214th ACS National Meeting, Las Vegas (1997) MEDI–048.

Wiley ate al., Book of Abstracts, 218th ACS National Meeting, New Orleans (1999) MEDI–026.

Ostrem et al., Biochemistry, vol. 37 (1998) pp. 1053–1059.

Hauptmann et al., Thrombosis Research 93 (1999) pp. 203–241.

* cited by examiner

FIG. 1
Ex. 1
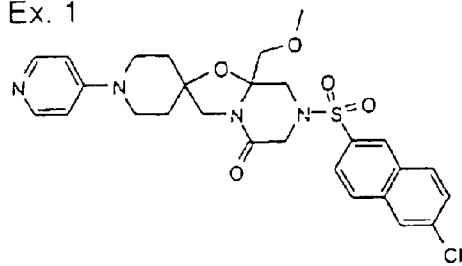
Ex. 2
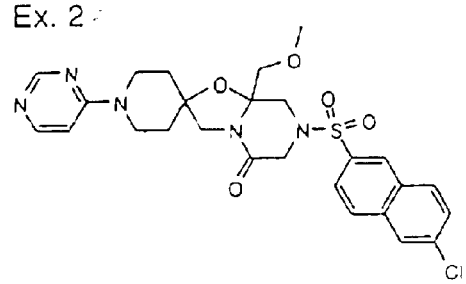
Ex. 3
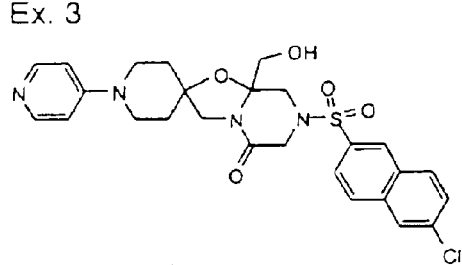
Ex. 4
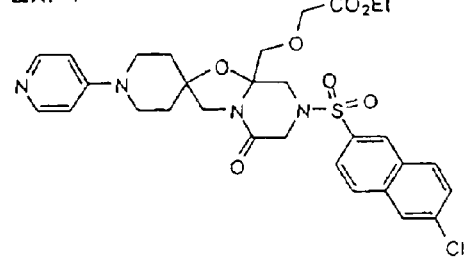
Ex. 5
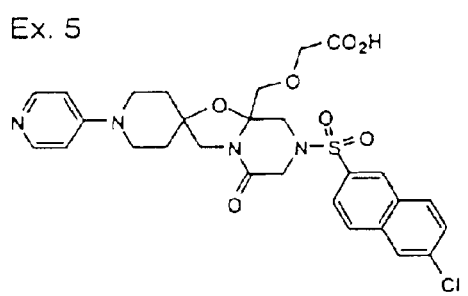
Ex. 6
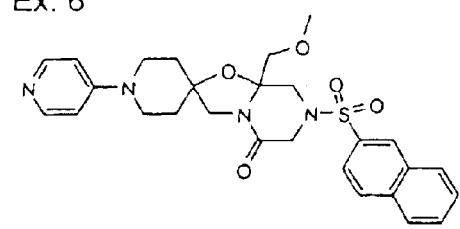
Ex. 7
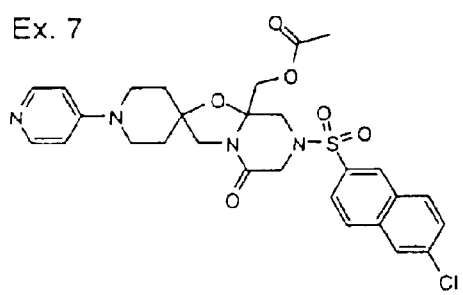
Ex. 8
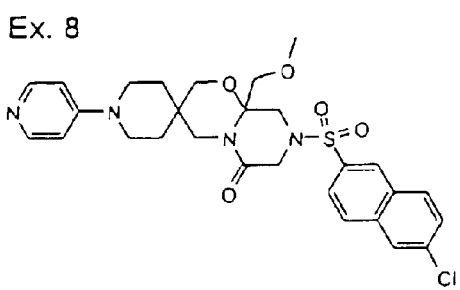
Ex. 9
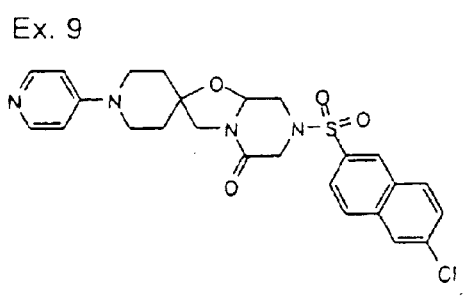
Ex. 10
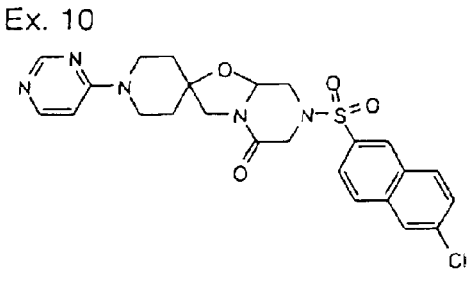

FIG. 2
Ex. 11
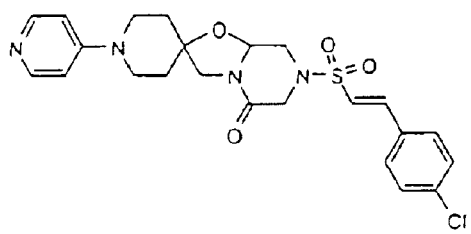
Ex. 12
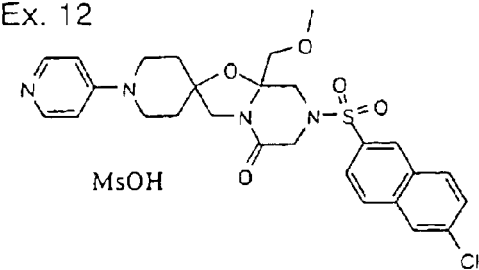
MsOH
Ex. 13
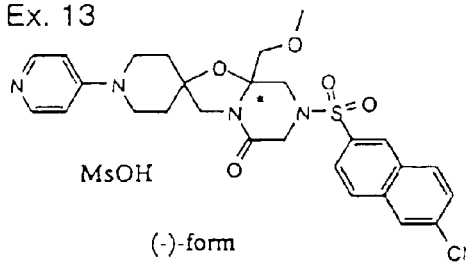
MsOH
(−)-form
Ex. 14
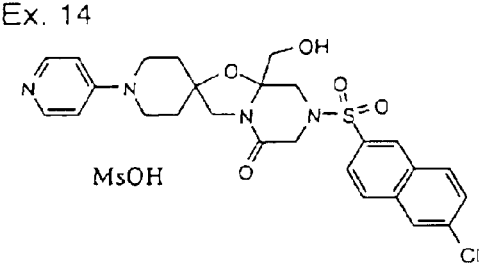
MsOH
Ex. 15
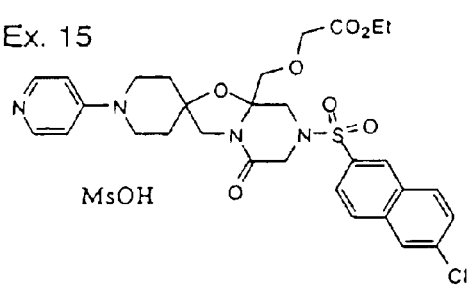
MsOH
Ex. 16
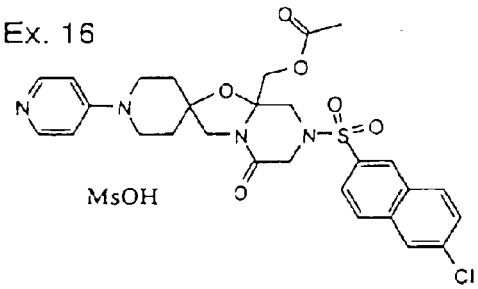
MsOH
Ex. 17
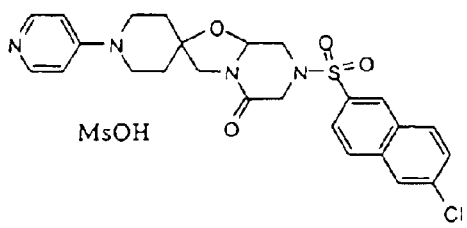
MsOH
Ex. 18
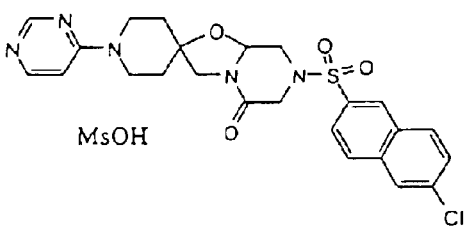
MsOH
Ex. 19
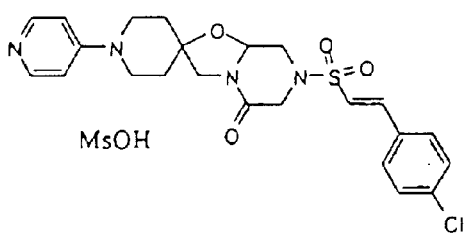
MsOH
Ex. 20
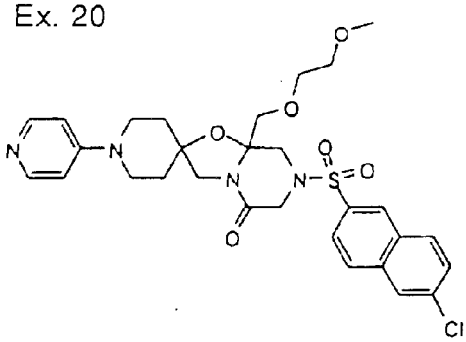

FIG. 3
Ex. 21
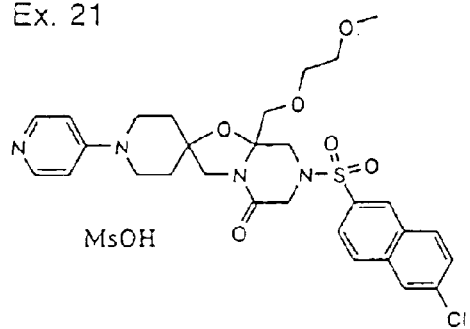
Ex. 22
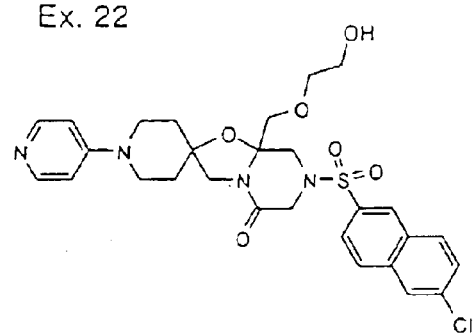
Ex. 23
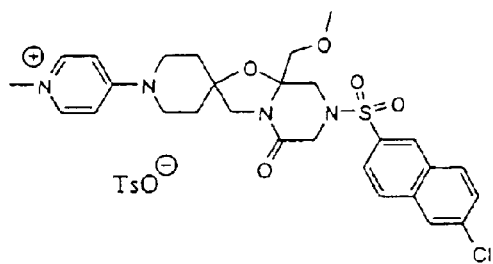
Ex. 24
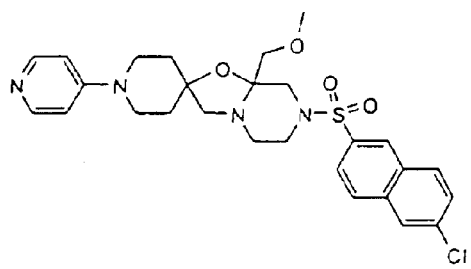
Ex. 25
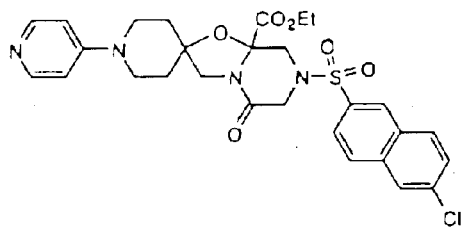
Ex. 26
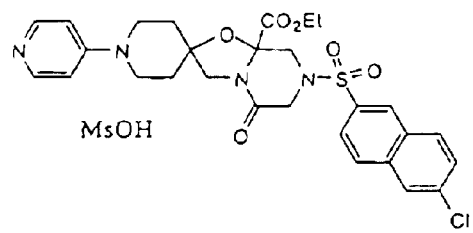
Ex. 27
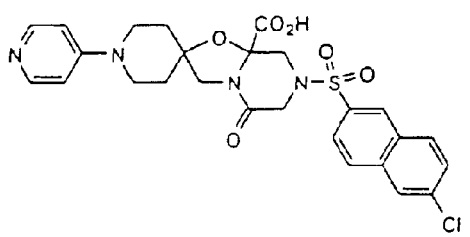
Ex. 28
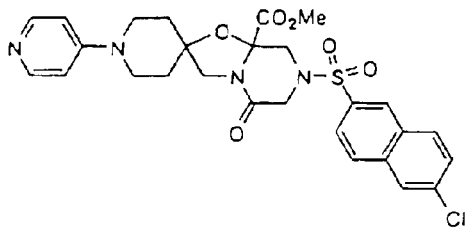
Ex. 29
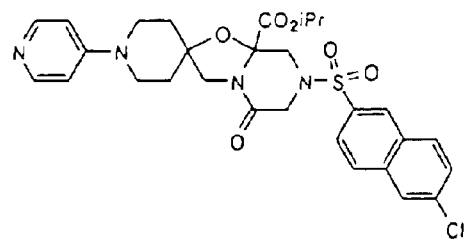
Ex. 30
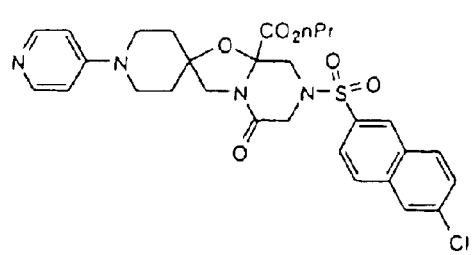

FIG. 4
Ex. 31
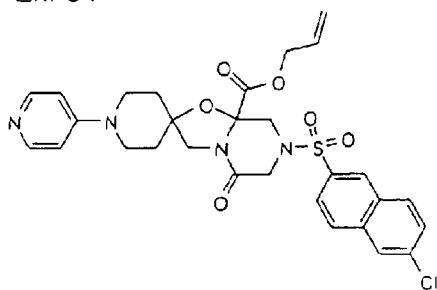
Ex. 32
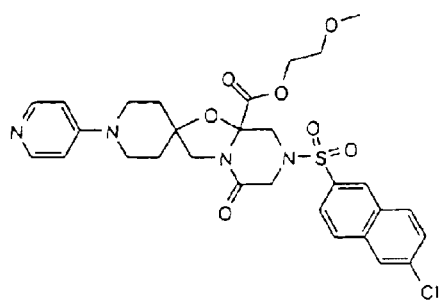
Ex. 33
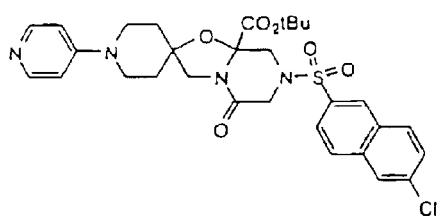
Ex. 34
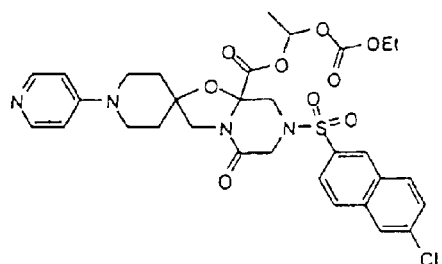
Ex. 35
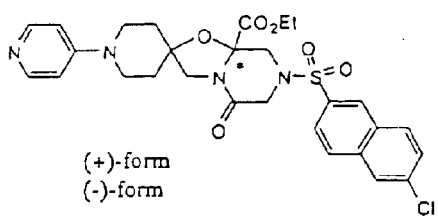
(+)-form
(−)-form
Ex. 36
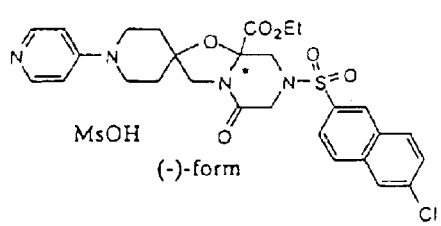
MsOH
(−)-form
Ex. 37
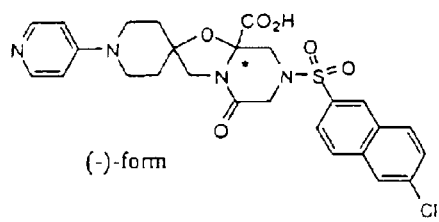
(−)-form
Ex. 38
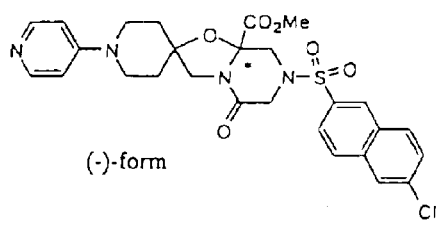
(−)-form
Ex. 39
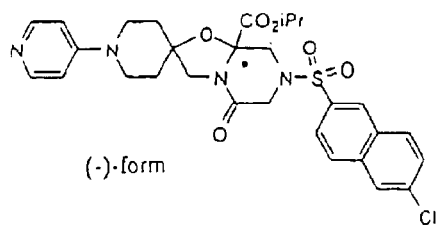
(−)-form
Ex. 40
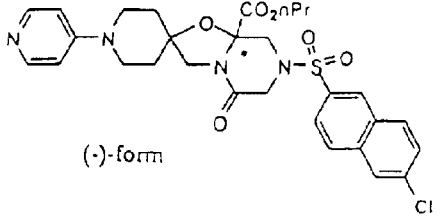
(−)-form FIG. 5
Ex. 41
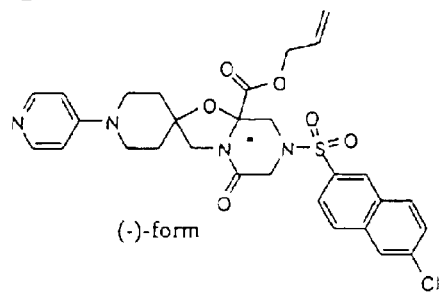
(-)-form
Ex. 42
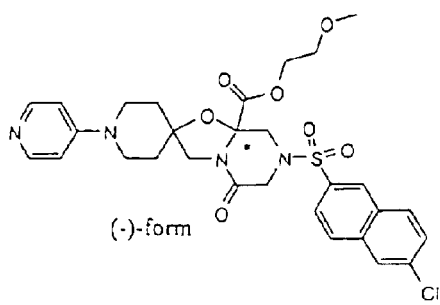
(-)-form
Ex. 43
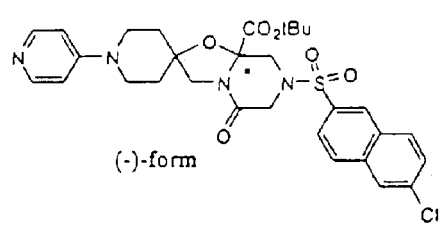
(-)-form
Ex. 44
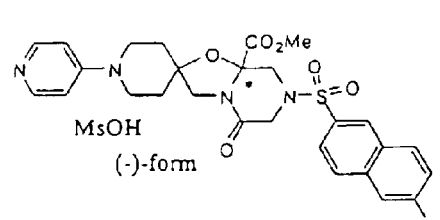
MsOH
(-)-form
Ex. 45
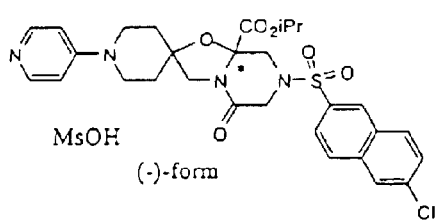
MsOH
(-)-form
Ex. 46
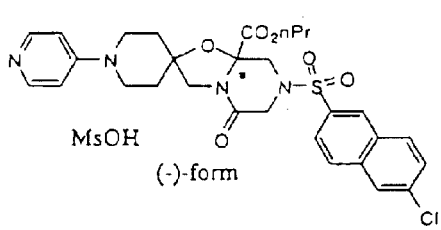
MsOH
(-)-form
Ex. 47
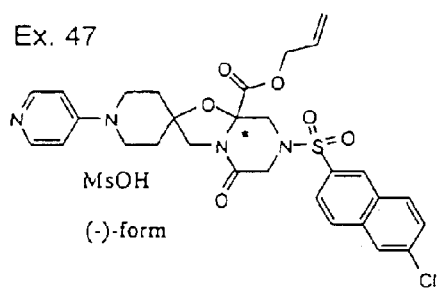
MsOH
(-)-form
Ex. 48
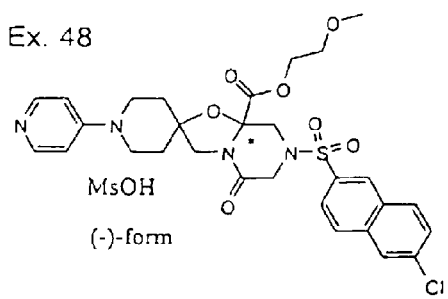
MsOH
(-)-form
Ex. 49
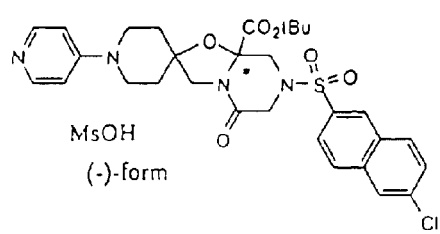
MsOH
(-)-form
Ex. 50
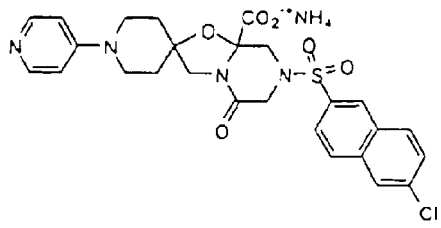

FIG. 6
Ex. 51
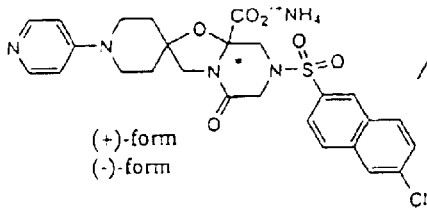
(+)-form
(−)-form
Ex. 52
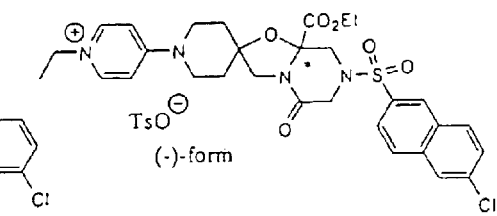
(−)-form
Ex. 53
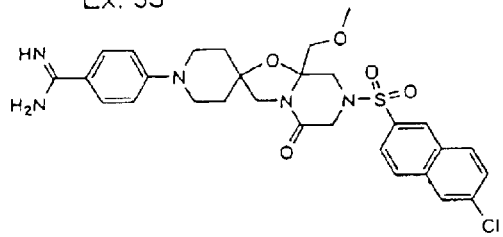
Ex. 54
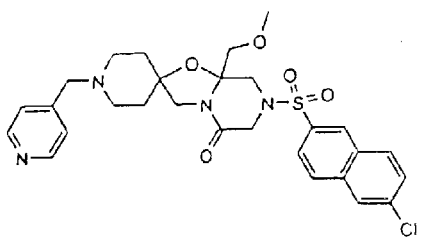
Ex. 55
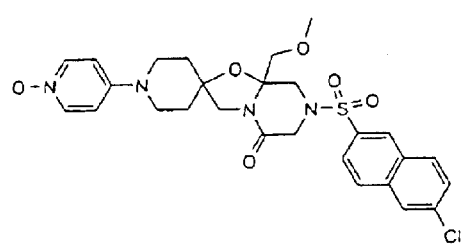
Ex. 56
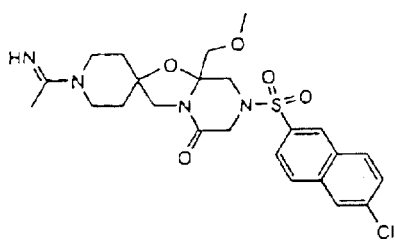
Ex. 57
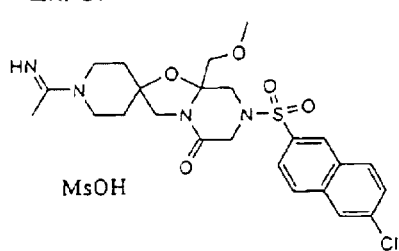
MsOH
Ex. 58
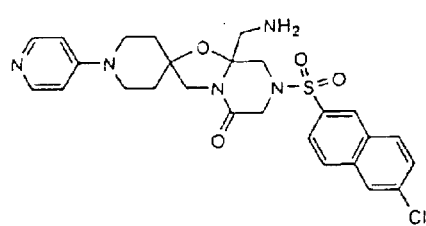
Ex. 59
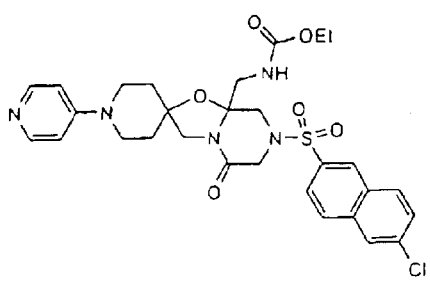
Ex. 60
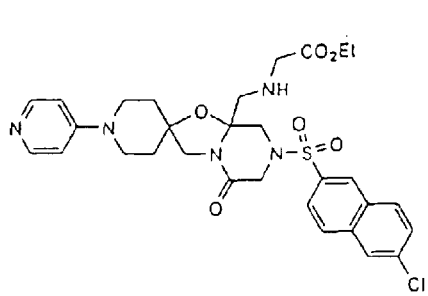

FIG. 7
Ex. 61
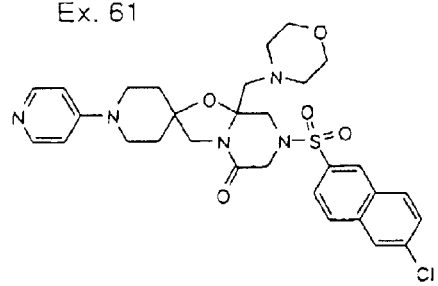
Ex. 62
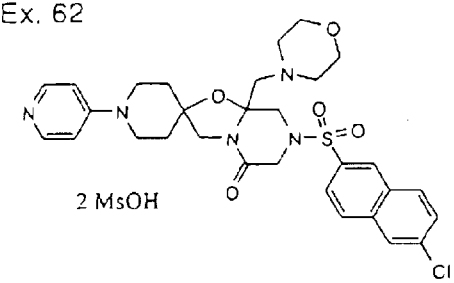
2 MsOH
Ex. 63
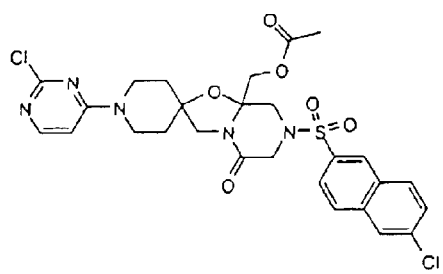
Ex. 64
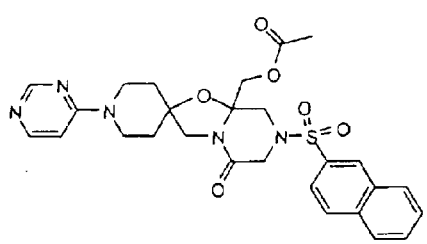
Ex. 65
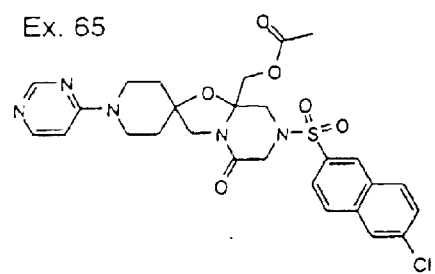
Ex. 66
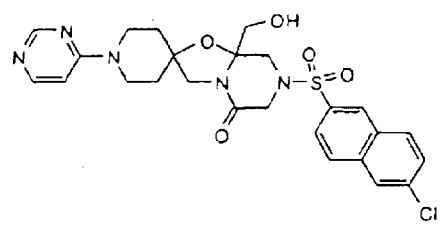
Ex. 67
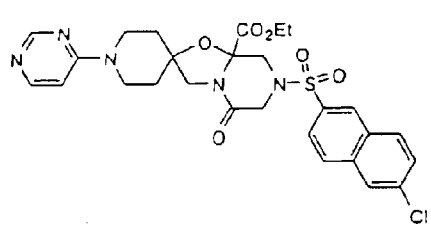
Ex. 68
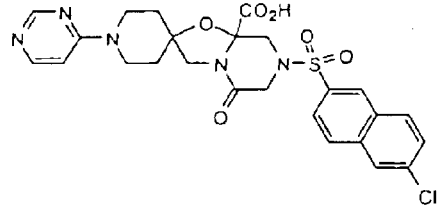
Ex. 69
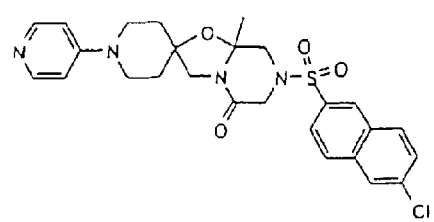
Ex. 70
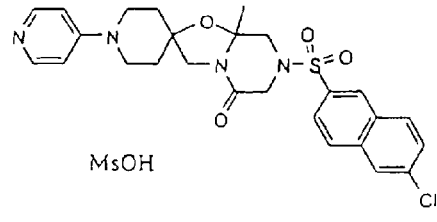
MsOH FIG. 8
Ex. 71
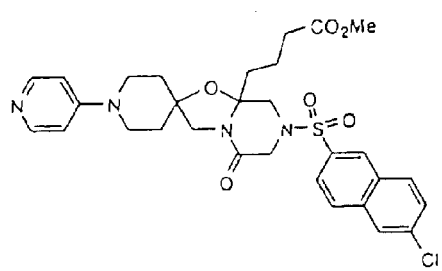
Ex. 72
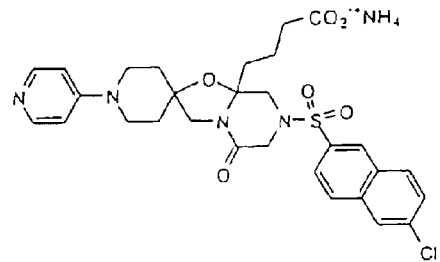
Ex. 73
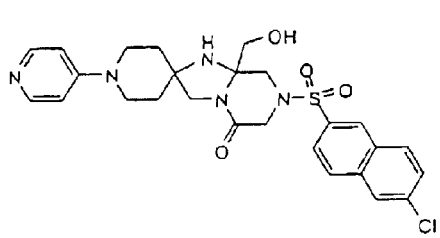
Ex. 74
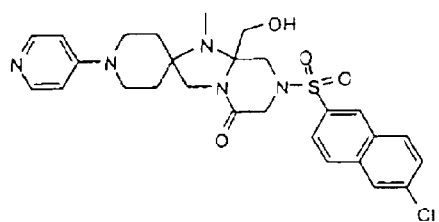
Ex. 75
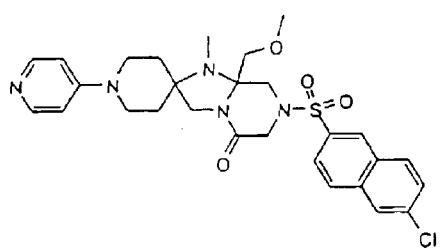
Ex. 76
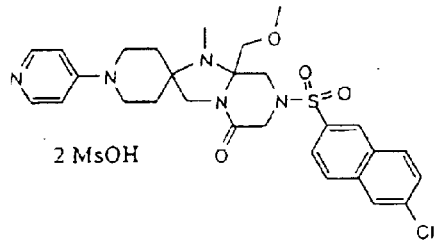
2 MsOH
Ex. 77
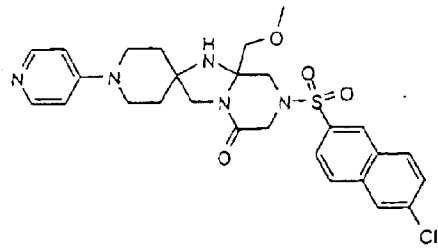
Ex. 78
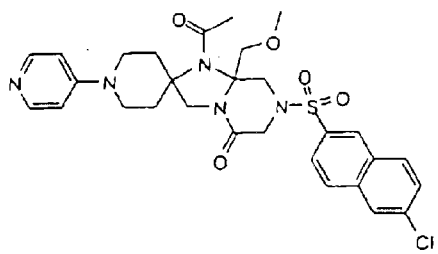
Ex. 79
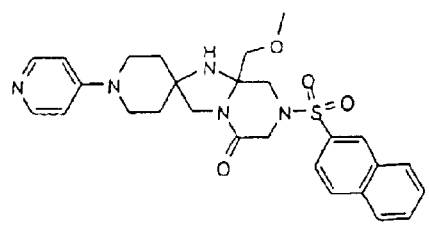
Ex. 80
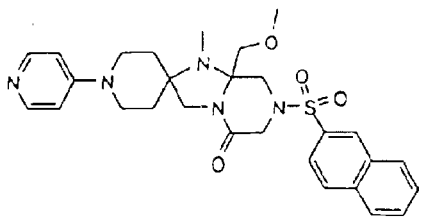

FIG. 9
Ex. 81
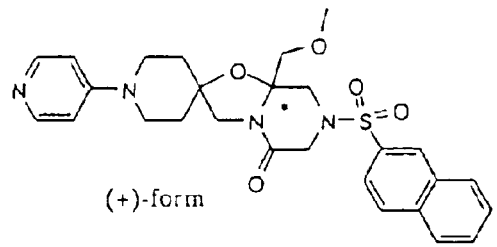
(+)-form
Ex. 82
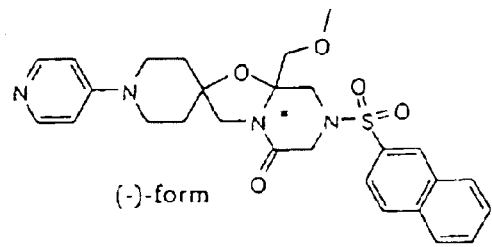
(−)-form
FIG. 10
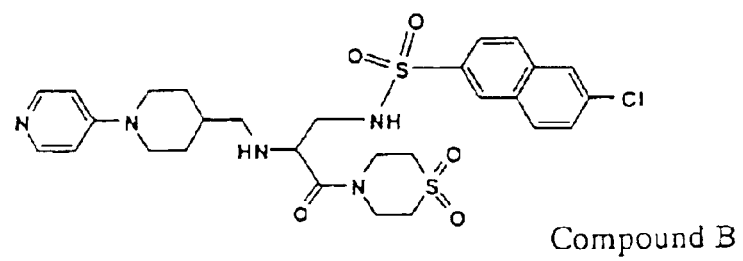
Compound B
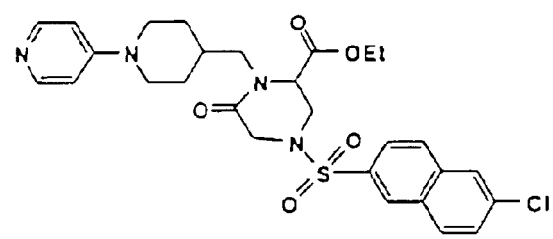
Compound C <Production Method 1>

<Production Method 4>

X=N

<Production Method 4>
Alternate Production Method of (IIIk)

FIG. 21

| Ex. No. | NMR (270MHz) (ppm) (* : 300MHz) |
|---|---|
| 1 | $CDCl_3$*: 8.38-8.33 (1H, m), 8.27-8.20 (2H, m), 7.99-7.92 (3H, m), 7.79 (1H, dd, J=2, 9Hz), 7.65-7.59 (1H, m), 6.66-6.58 (2H, m), 4.42-4.32 (2H, m), 4.25-4.17 (1H, m), 3.71-3.58 (2H, m), 3.53-3.17 (5H, m), 3.43 (3H, s), 3.35 (1H, d, J=17Hz), 2.30 (1H, d, J=12Hz), 2.03-1.80 (2H, m), 1.57-1.45 (2H, m) |
| 2 | $CDCl_3$: 8.56 (1H, s), 8.38-8.33 (1H, m), 8.18 (1H, d, J=6Hz), 7.99-7.92 (3H, m), 7.82-7.76 (1H, m), 7.65-7.58 (1H, m), 6.50-6.45 (1H, m), 4.42-4.30 (2H, m), 4.20 (1H, d, J=12Hz), 3.94-3.37 (4H, m), 3.68 (1H, d, J=10Hz), 3.63 (1H, d, J=10Hz), 3.43 (3H, s), 3.36 (1H, d, J=17Hz), 3.22 (1H, d, J=12Hz), 2.31 (1H, d, J=12Hz), 2.02-1.72 (2H, m), 1.53-1.43 (2H, m) |
| 3 | $CDCl_3$: 8.38-8.34 (1H, m), 8.28-8.19 (2H, m), 7.98-7.92 (3H, m), 7.82-7.76 (1H, m), 7.62 (1H, dd, J=2, 9Hz), 6.66-6.58 (2H, m), 4.48-4.22 (3H, m), 3.98-3.88 (1H, m), 3.80-3.69 (1H, m), 3.54-3.15 (5H, m), 3.40 (1H, d, J=17Hz), 2.33 (1H, d, J=12Hz), 2.22-1.82 (2H, m), 1.58-1.48 (2H, m) |
| 4 | $CDCl_3$*: 8.37-8.32 (1H, m), 8.28-8.21 (2H, m), 7.99-7.91 (3H, m), 7.78 (1H, dd, J=2, 9Hz), 7.62 (1H, dd, J=2, 9Hz), 6.65-6.58 (2H, m), 4.42-4.10 (7H, m), 3.92 (1H, d, J=10Hz), 3.80 (1H, d, J=10Hz), 3.57-3.16 (6H, m), 2.32 (1H, d, J=12Hz), 2.17-2.06 (1H, m), 1.96-1.83 (1H, m), 1.56-1.47 (2H, m), 1.35-1.20 (3H, m) |
| 5 | $CD_3OD$: 8.53-8.47 (1H, m), 8.18-8.03 (5H, m), 7.92-7.83 (1H, m), 7.68-7.62 (1H, m), 7.18-7.09 (2H, m), 4.34 (1H, d, J=12Hz), 4.35-4.20 (1H, m), 4.20-3.26 (11H, m), 2.65 (1H, d, J=12Hz), 2.22-2.10 (1H, m), 2.02-1.88 (1H, m), 1.73-1.55 (2H, m) |
| 6 | $CDCl_3$*: 8.40-8.37 (1H, m), 8.28-8.20 (2H, m), 8.07-7.93 (3H, m), 7.80-7.64 (3H, m), 6.66-6.58 (2H, m), 4.42-4.30 (2H, m), 4.20 (1H, d, J=12Hz), 3.72-3.61 (2H, m), 3.52-3.18 (4H, m), 3.44 (3H, s), 3.35 (1H, d, J=17Hz), 3.21 (1H, d, J=12Hz), 2.28 (1H, d, J=12Hz), 2.04-1.79 (2H, m), 1.57-1.45 (2H, m) |
| 7 | $CDCl_3$*: 8.40-8.36 (1H, m), 8.29-8.20 (2H, m), 8.00-7.94 (3H, m), 7.80 (1H, dd, J=2, 9Hz), 7.63 (1H, dd, J=2, 9Hz), 6.66-6.59 (2H, m), 4.54-4.15 (5H, m), 3.60-3.14 (6H, m), 2.36 (1H, d, J=12Hz), 2.13 (3H, s), 1.99-1.73 (2H, m), 1.62-1.46 (2H, m) |

FIG.22

| Ex. No. | NMR (270MHz) (ppm) (* : 300MHz) |
|---|---|
| 8 | CDCl₃*:8.37-8.34 (1H, m), 8.26-8.19 (2H, m), 7.99-7.91 (3H, m), 7.79 (1H, dd, J=2, 9Hz), 7.65-7.59 (1H, m), 6.62-6.55 (2H, m), 4.72 (1H, dd, J=2, 14Hz), 4.35-4.25 (2H, m), 4.07 (1H, d, J=11Hz), 3.74 (1H, d, J=12Hz), 3.63 (1H, d, J=11Hz), 3.49 (3H, s), 3.34 (1H, d, J=17Hz), 3.63-3.28 (3H, m), 3.26-3.11 (2H, m), 2.68 (1H, d, J=14Hz), 2.42 (1H, d, J=12Hz), 1.68-1.40 (4H, m) |
| 9 | CDCl₃:8.45-8.13 (3H, m), 8.00-7.90 (3H, m), 7.79 (1H, dd, J=2, 8Hz), 7.62 (1H, dd, J=2, 9Hz), 6.82-6.58 (2H, m), 5.26-5.18 (1H, m), 4.45-4.26 (2H, m), 3.77 (1H, d, J=12Hz), 3.70-3.51 (2H, m), 3.47-3.23 (2H, m), 3.32 (1H, d, J=17Hz), 3.19 (1H, d, J=12Hz), 2.52-2.39 (1H, m), 2.06-1.88 (1H, m), 1.85-1.59 (3H, m) |
| 10 | CDCl₃*:8.59 (1H, s), 8.40-8.35 (1H, m), 8.20 (1H, d, J=6Hz), 8.04-7.87 (3H, m), 7.80 (1H, dd, J=2, 9Hz), 7.61 (1H, dd, J=2, 9Hz), 6.52 (1H, d, J=6Hz), 5.27-5.18 (1H, m), 4.45-4.28 (2H, m), 4.12-3.94 (2H, m), 3.81-3.71 (1H, m), 3.55-3.32 (2H, m), 3.32 (1H, d, J=17Hz), 3.23-3.15 (1H, m), 2.46 (1H, dd, J=9, 12Hz), 2.01-1.88 (1H, m), 1.79-1.60 (3H, m) |
| 11 | CDCl₃*:8.31-8.25 (2H, m), 7.50 (1H, d, J=15Hz), 7.49-7.38 (4H, m), 6.72-6.60 (3H, m), 5.23-5.17 (1H, m), 4.33-4.22 (2H, m), 3.87-3.80 (1H, m), 3.65-3.51 (2H, m), 3.59 (1H, d, J=17Hz), 3.44-3.27 (2H, m), 3.25-3.19 (1H, m), 2.78-2.69 (1H, m), 2.02-1.92 (1H, m), 1.88-1.69 (3H, m) |
| 12 | CDCl₃:14.2 (1H, brs), 8.40-8.33 (1H, m), 8.28-8.15 (2H, m), 8.02-7.92 (3H, m), 7.83-7.75 (1H, m), 7.67-7.58 (1H, m), 6.94-6.82 (2H, m), 4.45-4.26 (2H, m), 4.26-4.13 (1H, m), 3.96-3.23 (8H, m), 3.43 (3H, s), 2.86 (3H, s), 2.34 (1H, d, J=12Hz), 2.18-2.04 (1H, m), 1.96-1.79 (1H, m), 1.68-1.54 (2H, m) |
| 13 | CDCl₃:14.21 (1H, brs), 8.40-8.33 (1H, m), 8.28-8.15 (2H, m), 8.02-7.92 (3H, m), 7.83-7.75 (1H, m), 7.67-7.58 (1H, m), 6.94-6.82 (2H, m), 4.45-4.26 (2H, m), 4.26-4.13 (1H, m), 3.96-3.23 (8H, m), 3.43 (3H, s), 2.86 (3H, s), 2.34 (1H, d, J=12Hz), 2.18-2.04 (1H, m), 1.96-1.79 (1H, m), 1.68-1.54 (2H, m) |
| 14 | CD₃OD:8.53-8.48 (1H, m), 8.16-8.03 (5H, m), 7.91-7.85 (1H, m), 7.66 (1H, dd, J=2, 9Hz), 7.18-7.08 (2H, m), 4.32-4.12 (3H, m), 4.08-3.96 (1H, m), 3.94-3.60 (4H, m), 3.58-3.42 (1H, m), 3.50 (1H, d, J=17Hz), 3.38-3.27 (1H, m), 2.69 (3H, s), 2.62 (1H, d, J=12Hz), 2.13-1.85 (2H, m), 1.72-1.53 (2H, m) |

FIG. 23

| Ex. No. | NMR (270MHz) (ppm) (* : 300MHz) |
|---|---|
| 15 | DMSO-d$_6$:13.32-13.10 (1H, br), 8.61 (1H, s), 8.34-8.12 (5H, m), 7.95-7.86 (1H, m), 7.79-7.70 (1H, m), 7.24-7.14 (2H, m), 4.22-4.03 (6H, m), 3.94-2.90 (9H, m), 2.71 (1H, d, J=11Hz), 2.30 (3H, s), 1.97-1.81 (2H, m), 1.64-1.49 (2H, m), 1.26-1.16 (3H, m) |
| 17 | CDCl$_3$:8.40-8.35 (1H, m), 8.30-8.21 (2H, m), 8.00-7.92 (3H, m), 7.82-7.76 (1H, m), 7.65-7.59 (1H, m), 6.93-6.85 (2H, m), 5.28-5.20 (1H, m), 4.44-4.32 (1H, m), 4.33 (1H, d, J=17Hz), 4.00-3.80 (3H, m), 3.65-3.40 (2H, m), 3.34 (1H, d, J=17Hz), 3.21 (1H, d, J=12Hz), 2.85 (3H, s), 2.58-2.47 (1H, m), 2.20-1.70 (4H, m) |
| 20 | CDCl$_3$*:8.37-8.33 (1H, m), 8.28-8.20 (2H, m), 7.98-7.92 (3H, m), 7.81-7.75 (1H, m), 7.65-7.59 (1H, m), 6.65-6.59 (2H, m), 4.40-4.28 (2H, m), 4.17 (1H, d, J=11Hz), 3.83-3.73 (2H, m), 3.72-3.66 (2H, m), 3.59-3.53 (2H, m), 3.38 (3H, s), 3.51-3.22 (6H, m), 2.31 (1H, d, J=12Hz), 2.09-1.98 (1H, m), 1.93-1.80 (1H, m), 1.54-1.46 (2H, m) |
| 21 | DMSO-d$_6$*:13.34-13.12 (1H, br), 8.62 (1H, s), 8.34-8.25 (2H, m), 8.24-8.13 (3H, m), 7.96-7.87 (1H, m), 7.79-7.72 (1H, m), 7.24-7.16 (2H, m), 4.18-4.02 (3H, m), 3.94-3.80 (1H, m), 3.80-3.68 (1H, m), 3.26 (3H, s), 3.68-3.15 (10H, m), 2.70 (1H, d, J=11Hz), 2.30 (3H, s), 1.94-1.81 (2H, m), 1.64-1.51 (2H, m) |
| 22 | CDCl$_3$*:8.37-8.34 (1H, m), 8.27-8.21 (2H, m), 7.99-7.92 (3H, m), 7.81-7.76 (1H, m), 7.65-7.60 (1H, m), 6.64-6.58 (2H, m), 4.55-4.48 (1H, m), 4.39 (1H, d, J=17Hz), 4.25 (1H, d, J=12Hz), 3.88 (1H, d, J=10Hz), 3.85-3.72 (3H, m), 3.72-3.60 (2H, m), 3.50-3.42 (2H, m), 3.34 (1H, d, J=17Hz), 3.42-3.23 (2H, m), 3.18 (1H, d, J=12Hz), 2.27 (1H, d, J=12Hz), 2.02-1.80 (2H, m), 1.56-1.46 (2H, m) |
| 23 | CDCl$_3$*:8.37-8.33 (1H, m), 8.22-8.14 (2H, m), 7.99-7.92 (3H, m), 7.80-7.71 (3H, m), 7.60 (1H, dd, J=2, 9Hz), 7.15-7.07 (4H, m), 4.38-4.26 (2H, m), 4.13 (1H, d, J=12Hz), 3.96 (3H, s), 3.95-3.80 (2H, m), 3.65 (2H, s), 3.41 (3H, s), 3.63-3.35 (2H, m), 3.35 (1H, d, J=17Hz), 3.23 (1H, d, J=12), 2.35 (1H, d, J=12Hz), 2.31 (3H, s), 2.09-1.99 (1H, m), 1.90-1.76 (1H, m), 1.60-1.50 (2H, m) |
| 24 | CDCl$_3$*:8.36-8.31 (1H, m), 8.26-8.18 (2H, m), 7.98-7.90 (3H, m), 7.81-7.75 (1H, m), 7.63-7.56 (1H, m), 6.66-6.59 (2H, m), 3.81-3.72 (1H, m), 3.63 (1H, d, J=11Hz), 3.40 (3H, s), 3.50-3.22 (7H, m), 3.10-3.01 (1H, m), 2.97-2.84 (2H, m), 2.77-2.66 (1H, m), 2.25 (1H, d, J=12Hz), 2.01-1.90 (1H, m), 1.76-1.59 (3H, m) |

FIG. 24

| Ex. No. | NMR (270MHz) (ppm) (* : 300MHz) |
|---|---|
| 25 | CDCl$_3$:8.35 (1H, s), 8.30-8.20 (2H, m), 8.00-7.86 (3H, m), 7.82-7.71 (1H, m), 7.66-7.56 (1H, m), 6.66-6.57 (2H, m), 4.76 (1H, d, J=12Hz), 4.38-4.21 (3H, m), 4.11 (1H, d, J=12Hz), 3.54-3.23 (6H, m), 2.49 (1H, d, J=12Hz), 1.89-1.73 (2H, m), 1.73-1.52 (2H, m), 1.41-1.29 (3H, m) |
| 26 | CDCl$_3$:14.43 (1H, brs), 8.36 (1H, s), 8.28-8.16 (2H, m), 8.02-7.86 (3H, m), 7.82-7.73 (1H, m), 7.66-7.57 (1H, m), 6.97-6.88 (2H, m), 4.82-4.70 (1H, m), 4.40-4.21 (3H, m), 4.14 (1H, d, J=12Hz), 3.95-3.80 (2H, m), 3.66-3.29 (4H, m), 2.82 (3H, s), 2.58-2.48 (1H, m), 1.98-1.77 (2H, m), 1.77-1.63 (2H, m), 1.44-1.30 (3H, m) |
| 27 | DMSO-d$_6$*:8.60 (1H, s), 8.30 (1H, d, J=9Hz), 8.27-8.21 (1H, m), 8.21-8.08 (3H, m), 7.94-7.84 (1H, m), 7.77-7.69 (1H, m), 6.99 (2H, d, J=7Hz), 4.48 (1H, d, J=11Hz), 3.98-3.82 (2H, m), 3.76-3.54 (2H, m), 3.54-3.17 (2H, m), 3.39 (1H, d, J=16Hz), 3.23 (1H, d, J=12Hz), 2.71 (1H, d, J=11Hz), 1.79-1.64 (2H, m), 1.64-1.47 (2H, m) |
| 28 | CDCl$_3$*:8.42-8.32 (1H, m), 8.31-8.18 (2H, m), 8.02-7.88 (3H, m), 7.83-7.73 (1H, m), 7.67-7.57 (1H, m), 6.70-6.58 (2H, m), 4.80-4.68 (1H, m), 4.33 (1H, d, J=17Hz), 4.13 (1H, d, J=12Hz), 3.82 (3H, s), 3.56-3.25 (6H, m), 2.57-2.47 (1H, m), 2.04-1.54 (4H, m) |
| 29 | CDCl$_3$*:8.39-8.31 (1H, m), 8.31-8.18 (2H, m), 8.00-7.88 (3H, m), 7.86-7.75 (1H, m), 7.65-7.58 (1H, m), 6.64 (2H, d, J=7Hz), 5.22-5.07 (1H, m), 4.80-4.72 (1H, m), 4.36-4.25 (1H, m), 4.07 (1H, d, J=11Hz), 3.57-3.25 (6H, m), 2.46 (1H, d, J=11Hz), 1.88-1.72 (2H, m), 1.72-1.50 (2H, m), 1.39 (3H, d, J=6Hz), 1.34 (3H, d, J=6Hz) |
| 30 | CDCl$_3$*:8.39-8.32 (1H, m), 8.31-8.18 (2H, m), 8.00-7.88 (3H, m), 7.82-7.74 (1H, m), 7.66-7.57 (1H, m), 6.70-6.55 (2H, m), 4.83-4.70 (1H, m), 4.32 (1H, d, J=17Hz), 4.25-4.05 (3H, m), 3.58-3.23 (6H, m), 2.55-2.44 (1H, m), 2.00-1.50 (6H, m), 1.05-0.93 (3H, m) |
| 31 | CDCl$_3$*:8.36 (1H, s), 8.32-8.17 (2H, m), 8.04-7.85 (3H, m), 7.83-7.72 (1H, m), 7.68-7.56 (1H, m), 6.70-6.55 (2H, m), 6.05-5.85 (1H, m), 5.48-5.26 (2H, m), 4.85-4.60 (3H, m), 4.33 (1H, d, J=17Hz), 4.12 (1H, d, J=12Hz), 3.57-3.20 (6H, m), 2.51 (1H, d, J=12Hz), 1.90-1.72 (2H, m), 1.72-1.50 (2H, m) |

FIG. 25

| Ex. No. | NMR (270MHz) (ppm) (* : 300MHz) |
|---|---|
| 32 | CDCl₃*:8.36 (1H, s), 8.31-8.18 (2H, m), 8.03-7.87 (3H, m), 7.83-7.73 (1H, m), 7.67-7.56 (1H, m), 6.72-6.56 (2H, m), 4.78(1H, d, J=12Hz), 4.45-4.25 (3H, m), 4.10 (1H, d, J=12Hz), 3.75-3.58 (2H, m), 3.40 (3H, m), 3.57-3.23 (6H, m), 2.51 (1H, d, J=12Hz), 1.93-1.53 (4H, m) |
| 33 | CDCl₃*:8.38-8.32 (1H, m), 8.32-8.20 (2H, m), 8.01-7.91(3H, m), 7.82-7.75 (1H, m), 7.66-7.58 (1H, m), 6.68-6.60(2H, m), 4.79-4.70 (1H, m), 4.32 (1H, d, J=17Hz), 4.04 (1H, d, J=12Hz), 3.56-3.22 (5H, m), 3.28 (1H, d, J=17Hz), 2.42 (1H, d, J=2, 11Hz), 1.92-1.76 (2H, m), 1.70-1.48(2H, m), 1.58 (9H, s) |
| 34 | CDCl₃*:8.38-8.31 (1H, m), 8.31-8.16 (2H, m), 8.00-7.90 (3H, m), 7.82-7.73 (1H, m), 7.65-7.58 (1H, m), 6.92-6.82 (1H, m), 6.70-6.60 (2H, m), 4.80-4.71 (1H, m), 4.39-4.18 (3H, m), 4.14-4.00 (1H, m), 3.64-3.20 (6H, m), 2.54-2.43 (1H, m), 2.40-1.55 (7H, m), 1.40-1.29 (3H, m) |
| 35(+) | CDCl₃*:8.38-8.34 (1H, m), 8.30-8.22 (2H, m), 7.99-7.92 (3H, m), 7.78 (1H, dd, J=2, 9Hz), 7.62 (1H, dd, J=2, 9Hz), 6.66-6.60 (2H, m), 4.81-4.73 (1H, m), 4.38-4.24 (3H, m), 4.11 (1H, d, J=12Hz), 3.54-3.24 (6H, m), 2.49 (1H, d, J=12Hz), 1.84-1.77 (2H, m), 1.67-1.58 (2H, m), 1.36 (3H, t, J=7Hz) |
| 35(-) | CDCl₃*:8.38-8.34 (1H, m), 8.29-8.23 (2H, m), 7.99-7.92 (3H, m), 7.78 (1H, dd, J=2, 9Hz), 7.62 (1H, dd, J=2, 9Hz), 6.66-6.60 (2H, m), 4.81-4.73 (1H, m), 4.38-4.24 (3H, m), 4.11 (1H, d, J=12Hz), 3.54-3.25 (6H, m), 2.49 (1H, d, J=12Hz), 1.84-1.76 (2H, m), 1.68-1.58 (2H, m), 1.36 (3H, t, J=7Hz) |
| 36 | DMSO-d₆*:13.24 (1H, s), 8.64 (1H, s), 8.35-8.20 (5H, m), 7.95-7.85 (1H, m), 7.76 (1H, dd, J=2, 9Hz), 7.35-7.20 (2H, m), 4.50-4.35 (1H, m), 4.25-4.15 (2H, m), 4.14-4.00 (2H, m), 3.90-3.75 (2H, m), 3.65-3.20 (4H, m), 3.00-2.85 (1H, m), 2.29 (3H, s), 1.90-1.60 (4H, m), 1.25 (3H, t, J=7Hz) |
| 37 | DMSO-d₆*:8.61 (1H, s), 8.30 (1H, d, J=9Hz), 8.27-8.22 (1H, m), 8.22-8.08 (3H, m), 7.93-7.86 (1H, m), 7.77-7.69 (1H, m), 6.98 (2H, d, J=7Hz), 4.54-4.41 (1H, m), 4.00-3.80 (2H, m), 3.80-3.16 (4H, m), 3.39 (1H, d, J=16Hz), 3.23 (1H, d, J=12Hz), 2.75-2.65 (1H, m), 1.80-1.65 (2H, m), 1.65-1.45 (2H, m) |

FIG. 26

| Ex. No. | NMR (270MHz) (ppm) (* : 300MHz) |
|---|---|
| 38 | CDCl₃*:8.39-8.33 (1H, m), 8.30-8.22 (2H, m), 8.00-7.91 (3H, m), 7.81-7.74 (1H, m), 7.62 (1H, dd, J=2, 9Hz), 6.67-6.59 (2H, m), 4.80-4.70 (1H, m), 4.33 (1H, d, J=17Hz), 4.13 (1H, d, J=11Hz), 3.82 (3H, s), 3.54-3.24 (6H, m), 2.56-2.47 (1H, m), 1.90-1.55 (4H, m) |
| 39 | CDCl₃*:8.36-8.33 (1H, m), 8.30-8.21 (2H, m), 8.00-7.90 (3H, m), 7.82-7.70 (1H, m), 7.65-7.58 (1H, m), 6.68-6.58 (2H, m), 5.22-5.08 (1H, m), 4.82-4.71 (1H, m), 4.32(1H, d, J=17Hz), 4.07 (1H, d, J=12Hz), 3.58-3.23 (5H, m), 3.39 (1H, d, J=12Hz), 2.46 (1H, d, J=11Hz), 1.88-1.72 (2H, m), 1.72-1.53 (2H, m), 1.39 (3H, d, J=6Hz), 1.34 (3H, d, J=6Hz) |
| 40 | CDCl₃*:8.39-8.32 (1H, m), 8.30-8.20 (2H, m), 8.02-7.88 (3H, m), 7.83-7.73 (1H, m), 7.66-7.57 (1H, m), 6.69-6.57 (2H, m), 4.82-4.73 (1H, m), 4.32 (1H, d, J=17Hz), 4.24-4.05 (3H, m), 3.58-3.23 (6H, m), 2.55-2.44 (1H, m), 1.87-1.54 (6H, m), 1.06-0.94 (3H, m) |
| 41 | CDCl₃*:8.33-8.39 (1H, m), 8.30-8.20 (2H, m), 7.99-7.91 (3H, m), 7.82-7.73 (1H, m), 7.62 (1H, dd, J=2, 9Hz), 6.67-6.58 (2H, m), 6.04-5.88 (1H, m), 5.46-5.30 (2H, m), 4.83-4.63 (3H, m), 4.33 (1H, d, J=17Hz), 4.12 (1H, d, J=12Hz), 3.55-3.22 (6H, m), 2.51 (1H, d, J=12Hz), 1.85-1.75 (2H, m), 1.70-1.57 (2H, m) |
| 42 | CDCl₃*:8.38-8.33 (1H, m), 8.30-8.20 (2H, m), 8.00-7.90 (3H, m), 7.83-7.74 (1H, m), 7.62 (1H, dd, J=2, 9Hz), 6.67-6.58 (2H, m), 4.83-4.73 (1H, m), 4.42-4.27 (3H, m), 4.09 (1H, d, J=12Hz), 3.75-3.58 (2H, m), 3.40 (3H, s), 3.55-3.22 (6H, m), 2.55-2.46 (1H, m), 1.92-1.53 (4H, m) |
| 43 | CDCl₃*:8.40-8.32 (1H, m), 8.32-8.19 (2H, m), 8.02-7.89(3H, m), 7.84-7.75 (1H, m), 7.68-7.57 (1H, m), 6.70-6.59 (2H, m), 4.81-4.69 (1H, m), 4.31 (1H, d, J=17Hz), 4.04 (1H, d, J=12Hz), 3.57-3.20 (5H, m), 3.28 (1H, d, J=17Hz), 2.48-2.37 (1H, m), 1.92-1.72 (2H, m), 1.72-1.45 (2H, m), 1.58 (9H, m) |
| 44 | CDCl₃*:14.36 (1H, brs), 8.38-8.34 (1H, m), 8.25-8.17 (2H, m), 8.00-7.93 (3H, m), 7.77 (1H, dd, J=2, 9Hz), 7.62 (1H, dd, J=2, 9Hz), 7.00-6.91 (2H, m), 4.74 (1H, d, J=12Hz), 4.32 (1H, d, J=17Hz), 4.15 (1H, d, J=12Hz), 3.95-3.80 (2H, m), 3.83 (3H, s), 3.63-3.35 (4H, m), 2.83 (3H, s), 2.57 (1H, d, J=12Hz), 1.95-1.78 (2H, m), 1.76-1.66 (2H, m) |

FIG. 27

| Ex. No. | NMR (270MHz) (ppm) (* : 300MHz) |
|---|---|
| 49 | CDCl$_3$*:14.22 (1H, brs), 8.38-8.32 (1H, m), 8.27-8.17 (2H, m), 8.00-7.90 (3H, m), 7.82-7.74 (1H, m), 7.62 (1H, dd, J=2, 9Hz), 6.99-6.89 (2H, m), 4.78-4.69 (1H, m), 4.36-4.25 (1H, m), 4.06 (1H, d, J=12Hz) 3.96-3.80 (2H, m), 3.66-3.38 (3H, m), 3.34-3.23 (1H, m), 2.83 (3H, s), 2.51-2.42 (1H, m), 1.99-1.78 (2H, m), 1.75-1.65 (2H, m), 1.58 (9H, s) |
| 50 | CD$_3$OD*:8.47 (1H, s), 8.12 (1H, d, J=9Hz), 8.12-7.99 (4H, m), 7.92-7.83 (1H, m), 7.63 (1H, dd, J=2, 9Hz), 6.82-6.74 (2H, m), 4.65-4.55 (1H, m), 4.14 (1H, d, J=16Hz), 3.89 (1H, d, J=12Hz), 3.68-3.25 (6H, m), 2.72-2.64 (1H, m), 2.02-1.87 (1H, m), 1.82-1.68 (1H, m), 1.68-1.52 (2H, m) |
| 51(+) | CD$_3$OD*:8.49 (1H, s), 8.23-8.01 (5H, m), 7.88-7.86 (1H, m), 7.70-7.61 (1H, m), 6.89-6.71 (2H, m), 4.65-4.54 (1H, m), 4.20-4.08 (1H, m), 3.89 (1H, d, J=12Hz), 3.69-3.18 (6H, m), 2.78-2.64 (1H, m), 2.00-1.52 (4H, m) |
| 51(-) | CD$_3$OD*:8.48 (1H, s), 8.12 (1H, d, J=9Hz), 8.16-8.00 (4H, m), 7.94-7.83 (1H, m), 7.67-7.60 (1H, m), 6.86-6.75 (2H, m), 4.63-4.53 (1H, m), 4.12 (1H, d, J=17Hz), 3.89 (1H, d, J=11Hz), 3.69-3.21 (6H, m), 2.74-2.65 (1H, m), 1.97-1.86 (1H, m), 1.81-1.52 (3H, m) |
| 52 | CDCl$_3$*:8.33 (1H, s), 8.24-8.13 (2H, m), 7.99-7.89 (3H, m), 7.80-7.69 (3H, m), 7.59 (1H, dd, J=2, 9Hz), 7.22-7.13 (2H, m), 7.12-7.06 (2H, m), 4.79-4.68 (1H, m), 4.36-4.21 (3H, m), 4.19-4.02 (3H, m), 3.98-3.84 (2H, m), 3.56-3.28 (4H, m), 2.59-2.50 (1H, m), 2.30 (3H, s), 1.87-1.72 (2H, m), 1.70-1.55 (2H, m), 1.46-1.30 (6H, m) |
| 53 | CD$_3$OD:8.52-8.48 (1H, m), 8.16-8.04 (3H, m), 7.88 (1H, dd, J=2, 9Hz), 7.69-7.60 (3H, m), 7.04-6.95 (2H, m), 4.35-4.10 (3H, m), 3.39 (3H, s), 3.68-3.22 (8H, m), 2.58 (1H, d, J=12Hz), 1.98-1.86 (2H, m), 1.62-1.51 (2H, m) |
| 54 | CDCl$_3$*:8.54-8.49 (2H, m), 8.36-8.33 (1H, m), 7.97-7.91 (3H, m), 7.80-7.75 (1H, m), 7.61 (1H, dd, J=2, 9Hz), 7.24-7.19 (2H, m), 4.40-4.30 (2H, m), 4.19 (1H, d, J=12Hz), 3.46 (2H, s), 3.41 (3H, s), 3.68-3.52 (2H, m), 3.32 (1H, d, J=17Hz), 3.12 (1H, d, J=12Hz), 2.66-2.54 (1H, m), 2.52-2.20 (3H, m), 2.25 (1H, d, J=12Hz), 2.00-1.77 (2H, m), 1.54-1.36 (2H, m) |

FIG. 28

| Ex. No. | NMR (270MHz) (ppm) (*: 300MHz) |
|---|---|
| 55 | CDCl₃*:8.38-8.34 (1H, m), 8.20-7.92 (5H, m), 7.78 (1H, dd, J=2, 9Hz), 7.62 (1H, dd, J=2, 9Hz), 6.65-6.58 (2H, m), 4.42-4.30 (2H, m), 4.21 (1H, d, J=12Hz), 3.67 (1H, d, J=10Hz), 3.63 (1H, d, J=10Hz), 3.43 (3H, s), 3.50-3.18 (6H, m), 2.30 (1H, d, J=12Hz), 2.06-1.80 (2H, m), 1.59-1.50 (2H, m) |
| 56 | CDCl₃*:8.37-8.33 (1H, m), 7.98-7.91 (3H, m), 7.81-7.75 (1H, m), 7.61 (1H, dd, J=2, 9Hz), 4.40-4.30 (2H, m), 4.19 (1H, d, J=12Hz), 3.69-3.56 (2H, m), 3.42 (3H, s), 3.54-3.26 (4H, m), 3.34 (1H, d, J=17Hz), 3.18 (1H, d, J=12Hz), 2.28 (1H, d, J=12Hz), 2.06 (3H, s), 1.94-1.72 (2H, m), 1.46-1.38 (2H, m) |
| 57 | DMSO-d₆(100°C) *:9.04-8.70 (1H, m), 8.56-8.51 (1H, m), 8.50-8.30 (1H, m), 8.23 (1H, d, J=9Hz), 8.19-8.10 (2H, m), 7.86 (1H, dd, J=2, 9Hz), 7.71-7.65 (1H, m), 4.16-4.03 (3H, m), 3.79-2.44 (9H, m), 3.28 (3H, s), 2.32 (3H, s), 2.28-2.21 (3H, m), 1.99-1.84 (2H, m), 1.68-1.58 (2H, m) |
| 58 | CDCl₃:8.39-8.33 (1H, m), 8.28-8.20 (2H, m), 7.99-7.90 (3H, m), 7.84-7.76 (1H, m), 7.65-7.58 (1H, m), 6.66-6.58 (2H, m), 4.53 (1H, d, J=12Hz), 4.38 (1H, d, J=17Hz), 4.26 (1H, d, J=12Hz), 3.55-3.10 (7H, m), 2.89 (1H, d, J=14Hz), 2.24 (1H, d, J=12Hz), 1.94-1.84 (2H, m), 1.57-1.48 (2H, m) |
| 59 | DMSO-d₆*:8.56-8.52 (1H, m), 8.22 (1H, d, J=9Hz), 8.18-8.08 (4H, m), 7.91-7.85 (1H, m), 7.70-7.64 (1H, m), 6.74-6.64 (3H, m), 4.14-3.96 (5H, m), 3.62 (1H, d, J=16Hz), 3.50-3.12 (6H, m), 3.08 (1H, d, J=12Hz), 2.81 (1H, d, J=12Hz), 1.90-1.74 (2H, m), 1.50-1.43 (2H, m), 1.19-1.13 (3H, m) |
| 60 | CDCl₃*:8.40-8.33 (1H, m), 8.28-8.20 (2H, m), 8.02-7.88 (3H, m), 7.84-7.77 (1H, m), 7.61 (1H, dd, J=2, 9Hz), 6.66-6.58 (2H, m), 4.67 (1H, d, J=11Hz), 4.37 (1H, d, J=17Hz), 4.28-4.15 (3H, m), 3.61-3.21 (7H, m), 3.17 (1H, d, J=12Hz), 2.97 (2H, s), 2.27-1.84 (3H, m), 1.56-1.46 (2H, m), 1.30 (3H, t, J=7Hz) |
| 61 | CDCl₃*:8.37 (1H, s), 8.28-8.12 (2H, m), 8.02-7.93 (3H, m), 7.85-7.77 (1H, m), 7.66-7.60 (1H, m), 6.66-6.58 (2H, m), 4.72 (1H, d, J=11Hz), 4.36 (1H, d, J=17Hz), 4.27 (1H, d, J=12Hz), 3.77-3.67 (4H, m), 3.56-3.17 (6H, m), 2.94-2.46 (6H, m), 2.15 (1H, d, J=11Hz), 2.00-1.70 (2H, m), 1.54-1.43 (2H, m) |

FIG. 29

| Ex. No. | NMR (270MHz) (ppm) (* : 300MHz) |
|---|---|
| 62 | DMSO-$d_6$*:13.3 (1H, brs), 8.62 (1H, s), 8.33 (1H, d, J=9Hz), 8.31-8.16 (4H, m), 7.95-7.87 (1H, m), 7.80-7.72 (1H, m), 7.19 (2H, d, J=7Hz), 4.51-4.40 (1H, m), 4.34-4.05 (2H, m), 4.05-2.20 (17H, m), 2.34 (6H, s), 2.04-1.82 (2H, m), 1.66-1.46 (2H, m) |
| 63 | CDCl$_3$*:8.40-8.35 (1H, m), 8.05-8.00 (1H, m), 8.00-7.93 (3H, m), 7.84-7.77 (1H, m), 7.63 (1H, dd, J=9, 2Hz), 6.49-6.35 (1H, m), 4.55-4.48 (1H, m), 4.42 (1H, d, J=12Hz), 4.42-4.33 (1H, m), 4.26 (1H, d, J=12Hz), 4.23-4.15 (1H, m), 4.05-3.80 (2H, m), 3.49-3.28 (3H, m), 3.19 (1H, d, J=12Hz), 2.37 (1H, d, J=12Hz), 2.13 (3H, s), 2.00-1.89 (1H, m), 1.85-1.73 (1H, m), 1.53-1.43 (2H, m) |
| 64 | CDCl$_3$:8.56 (1H, s), 8.40 (1H, s), 8.20-8.15 (1H, m), 8.08-7.93 (3H, m), 7.81-7.63 (3H, m), 6.50-6.44 (1H, m), 4.55-4.15 (3H, m), 4.38 (1H, d, J=17Hz), 4.26 (1H, d, J=12Hz), 3.96-3.80 (2H, m), 3.54-3.30 (2H, m), 3.38 (1H, d, J=17Hz), 3.18 (1H, d, J=12Hz), 2.36 (1H, d, J=12Hz), 2.12 (3H, s), 1.98-1.68 (2H, m), 1.52-1.43 (2H, m) |
| 65 | CDCl$_3$*:8.56 (1H, s), 8.40-8.36 (1H, m), 8.21-8.15 (1H, m), 8.02-7.94 (3H, m), 7.83-7.77 (1H, m), 7.63 (1H, dd, J=2, 8Hz), 6.50-6.46 (1H, m), 4.51 (1H, d, J=12Hz), 4.47-4.23 (3H, m), 4.19 (1H, d, J=12Hz), 3.96-3.83 (2H, m), 3.53-3.34 (3H, m), 3.18 (1H, d, J=12Hz), 2.38 (1H, d, J=12Hz), 2.13 (3H, s), 1.98-1.88 (1H, m), 1.85-1.59 (1H, m), 1.52-1.45 (2H, m) |
| 66 | CDCl$_3$*:8.57 (1H, s), 8.39-8.35 (1H, m), 8.28-8.12 (1H, m), 7.99-7.93 (3H, m), 7.82-7.76 (1H, m), 7.62 (1H, dd, J=2, 9Hz), 6.53-6.46 (1H, m), 4.49-4.24 (3H, m), 3.94 (1H, d, J=12Hz), 3.99-3.76 (2H, m), 3.73 (1H, d, J=12Hz), 3.69-3.55 (1H, m), 3.51-3.36 (2H, m), 3.20 (1H, d, J=12Hz), 2.34 (1H, d, J=12Hz), 1.98-1.60 (2H, m), 1.54-1.46 (2H, m) |
| 67 | CDCl$_3$*:8.57 (1H, s), 8.38-8.34 (1H, m), 8.22-8.17 (1H, m), 7.98-7.93 (3H, m), 7.82-7.75 (1H, m), 7.65-7.60 (1H, dd, J=2, 8Hz), 6.52-6.46 (1H, m), 4.82-4.74 (1H, m), 4.37-4.24 (3H, m), 4.11 (1H, d, J=12Hz), 3.97-3.85 (2H, m), 3.60-3.32 (4H, m), 2.50 (1H, d, J=12Hz), 1.85-1.54 (4H, m), 1.36 (3H, t, J=7Hz) |

FIG. 30

| Ex. No. | NMR (270MHz) (ppm) (*: 300MHz) |
|---|---|
| 68 | CD₃OD+CDCl₃*:8.47-8.40 (2H, m), 8.10-7.99 (4H, m), 7.86 (1H, dd, J=2, 9Hz), 7.67-7.60 (1H, m), 6.70-6.64 (1H, m), 4.67 (1H, d, J=11Hz), 4.20 (1H, d, J=16Hz), 4.08-3.94 (2H, m), 3.90 (1H, d, J=12Hz), 3.68-3.31 (4H, m), 2.63 (1H, d, J=11Hz), 2.02-1.92 (1H, m), 1.78-1.66 (1H, m), 1.65-1.54 (2H, m) |
| 69 | CDCl₃*:8.37-8.34 (1H, m), 8.28-8.22 (2H, m), 7.99-7.92 (3H, m), 7.82-7.75 (1H, m), 7.65-7.59 (1H, m), 6.65-6.59 (2H, m), 4.35 (1H, d, J=17Hz), 4.27-4.12 (2H, m), 3.31 (1H, d, J=17Hz), 3.56-3.17 (4H, m), 3.13 (1H, d, J=12Hz), 2.37 (1H, d, J=11Hz), 1.93-1.83 (2H, m), 1.64 (3H, s), 1.53-1.45 (2H, m) |
| 70 | CDCl₃*:14.49 (1H, brs), 8.36 (1H, s), 8.32-8.12 (2H, m), 8.05-7.89 (3H, m), 7.79 (1H, d, J=8Hz), 7.63 (1H, d, J=9Hz), 7.05-6.75 (2H, m), 4.35 (1H, d, J=17Hz), 4.30-4.10 (2H, m), 4.01-3.70 (2H, m), 3.70-3.52 (1H, m), 3.52-3.33 (1H, m), 3.33 (1H, d, J=17Hz), 3.25-3.12 (1H, m), 2.85 (3H, s), 2.48-2.35 (1H, m), 2.02-1.80 (2H, m), 1.72-1.49 (2H, m), 1.66 (3H, s) |
| 71 | CDCl₃*:8.39-8.33 (1H, m), 8.29-8.21 (2H, m), 8.00-7.90 (3H, m), 7.83-7.76 (1H, m), 7.65-7.58 (1H, m), 6.66-6.59 (2H, m), 4.40-4.26 (2H, m), 4.20 (1H, d, J=12Hz), 3.71 (3H, s), 3.59-3.48 (1H, m), 3.48-3.33 (2H, m), 3.34 (1H, d, J=17Hz), 3.33-3.18 (1H, m), 3.13 (1H, d, J=12Hz), 2.50-2.31 (2H, m), 2.27 (1H, d, J=12Hz), 2.14-1.70 (6H, m), 1.56-1.45 (2H, m) |
| 72 | DMSO-d₆*:8.58 (1H, s), 8.32-7.96 (5H, m), 7.96-7.78 (1H, m), 7.74-7.60 (1H, m), 6.84-6.62 (2H, m), 4.19-3.95 (3H, m), 3.72-2.94 (6H, m), 2.63-1.00 (12H, m) |
| 73 | CDCl₃*:8.36-8.33 (1H, m), 8.26-8.21 (2H, m), 7.98-7.92 (3H, m), 7.80-7.75 (1H, m), 7.62 (1H, dd, J=2, 9Hz), 6.64-6.59 (2H, m), 4.36 (1H, d, J=17Hz), 4.27-4.17 (2H, m), 4.06-4.00 (1H, m), 3.65-3.58 (1H, m), 3.53-3.16 (5H, m), 3.02 (1H, d, J=12Hz), 2.46 (1H, brs), 2.29 (1H, d, J=12Hz), 1.93-1.75 (2H, m), 1.49-1.41 (2H, m) |
| 74 | CDCl₃*:8.35 (1H, s), 8.28-8.18 (2H, m), 8.01-7.88 (3H, m), 7.82-7.72 (1H, m), 7.62 (1H, dd, J=2, 9Hz), 6.68-6.58 (2H, m), 4.35 (1H, d, J=12Hz), 4.34 (1H, d, J=17Hz), 4.25-4.18 (1H, m), 4.00-3.68 (4H, m), 3.43 (1H, d, J=17Hz), 3.20-3.12 (1H, m), 3.03-2.70 (2H, m), 2.42 (1H, d, J=12Hz), 2.42 (3H, s), 2.10-1.95 (1H, m), 1.84-1.66 (2H, m), 1.15-1.02 (1H, m) |

FIG. 31

| Ex. No. | NMR (270MHz) (ppm) (* : 300MHz) |
|---|---|
| 75 | CDCl$_3$*:8.38-8.33 (1H, m), 8.28-8.22 (2H, m), 8.00-7.90 (3H, m), 7.82-7.74 (1H, m), 7.65-7.58 (1H, m), 6.65-6.55 (2H, m), 4.38-4.15 (3H, m), 3.97-3.87 (1H, m), 3.83-3.72 (1H, m), 3.75 (1H, d, J=10Hz), 3.67 (1H, d, J=10Hz), 3.38 (3H, s), 3.34 (1H, d, J=17Hz), 3.22 (1H, d, J=11Hz), 2.87-2.66 (2H, m), 2.37 (3H, s), 2.26 (1H, d, J=11Hz), 1.98-1.81 (2H, m), 1.77-1.58 (1H, m), 1.15-1.05 (1H, m) |
| 76 | CD$_3$OD*:8.56-8.52 (1H, m), 8.18-8.06 (5H, m), 7.91 (1H, dd, J=2, 9Hz), 7.66 (1H, dd, J=2, 9Hz), 7.18-7.12 (2H, m), 4.51 (1H, d, J=12Hz), 4.43-4.28 (3H, m), 4.26-4.15 (1H, m), 3.89-3.75 (2H, m), 3.50 (1H, d, J=16Hz), 3.39 (3H, s), 3.56-3.11 (3H, m), 2.77-2.66 (1H, m), 2.68 (6H, s), 2.61 (3H, s), 2.15-2.02 (2H, m), 1.93-1.77 (1H, m), 1.50-1.40 (1H, m) |
| 77 | CDCl$_3$*:8.38-8.32 (1H, m), 8.28-8.20 (2H, m), 8.00-7.90 (3H, m), 7.82-7.75 (1H, m), 7.61 (1H, dd, J=2, 9Hz), 6.63-6.56 (2H, m), 4.35 (1H, d, J=17Hz), 4.23-4.12 (2H, m), 3.73 (1H, d, J=10Hz), 3.48 (1H, d, J=10Hz), 3.53-3.13 (5H, m), 3.44 (3H, s), 2.97 (1H, d, J=12Hz), 2.52-2.44 (1H, brs), 2.24 (1H, d, J=12Hz), 1.91-1.69 (2H, m), 1.47-1.30 (2H, m) |
| 78 | CDCl$_3$*:8.37-8.32 (1H, m), 8.31-8.24 (2H, m), 8.00-7.90 (3H, m), 7.81-7.74 (1H, m), 7.61 (1H, d, J=2, 9Hz), 6.67-6.60 (2H, m), 5.15 (1H, d, J=13Hz), 4.67 (1H, d, J=11Hz), 4.45 (1H, d, J=17Hz), 4.34 (1H, d, J=10Hz), 4.00-3.77 (2H, m), 3.89 (1H, d, J=10Hz), 3.51-3.28 (2H, m), 3.36 (3H, s), 3.05-2.90 (1H, m), 2.85-2.71 (1H, m), 2.55-2.38 (1H, m), 2.32 (1H, d, J=13Hz), 2.20-1.95 (2H, m), 2.10 (3H, s), 1.41-1.22 (1H, m) |
| 79 | CDCl$_3$*8.40-8.35 (1H, m), 8.28-8.20 (2H, m), 8.07-7.93 (3H, m), 7.81-7.63 (3H, m), 6.65-6.57 (2H, m), 4.36 (1H, d, J=17Hz), 4.24-4.14 (2H, m), 3.74 (1H, d, J=9Hz), 3.53-3.13 (6H, m), 3.45 (3H, s), 2.97 (1H, d, J=12Hz), 2.51-2.44 (1H, brs), 2.24 (1H, d, J=12Hz), 1.92-1.68 (2H, m), 1.47-1.28 (2H, m) |
| 80 | CDCl$_3$*:8.40-8.34 (1H, m), 8.28-8.21 (2H, m), 8.07-7.92 (3H, m), 7.79-7.62 (3H, m), 6.66-6.57 (2H, m), 4.34 (1H, d, J=17Hz), 4.28-4.14 (2H, m), 3.97-3.87 (1H, m), 3.83-3.65 (3H, m), 3.38 (3H, s), 3.35 (1H, d, J=17Hz), 3.21 (1H, d, J=11Hz), 2.88-2.67 (2H, m), 2.37 (3H, s), 2.24 (1H, d, J=12Hz), 1.98-1.80 (2H, m), 1.77-1.62 (1H, m), 1.15-1.05 (1H, m) |

FIG. 32

| Ex. No. | NMR (270MHz) (ppm) (* : 300MHz) |
|---|---|
| 81 | CDCl$_3$*:8.40-8.36 (1H, m), 8.28-8.20 (2H, m), 8.07-7.92 (3H, m), 7.81-7.60 (3H, m), 6.64-6.58 (2H, m), 4.43-4.32 (2H, m), 4.20 (1H, d, J=12Hz), 3.72-3.60 (2H, m), 3.50-3.17 (5H, m), 3.44 (3H, s), 3.35 (1H, d, J=17Hz), 2.28 (1H, d, J=12Hz), 2.03-1.78 (2H, m), 1.54-1.46 (2H, m) |
| 82 | CDCl$_3$*:8.40-8.36 (1H, m), 8.28-8.20 (2H, m), 8.06-7.92 (3H, m), 7.79-7.64 (3H, m), 6.64-6.57 (2H, m), 4.43-4.30 (2H, m), 4.20 (1H, d, J=12Hz), 3.68 (1H, d, J=10Hz), 3.63 (1H, d, J=10Hz), 3.49-3.17 (5H, m), 3.44 (3H, s), 3.35 (1H, d, J=17Hz), 2.28 (1H, d, J=12Hz), 2.03-1.79 (2H, m), 1.53-1.45 (2H, m) |

FIG. 33

| Ex. No. | NMR(ppm) (*:300MHz, 270MHz) |
|---|---|
| 201 | CDCl$_3$*:8.30-8.23 (2H, m), 7.37-7.18 (3H, m), 7.07-6.88 (2H, m), 6.70-6.63 (2H, m), 5.21-5.15 (1H, m), 4.94-4.82 (2H, m), 4.31-4.20 (2H, m), 3.84 (1H, d, J=12Hz), 3.66 (1H, d, J=17Hz), 3.67-3.52 (2H, m), 3.43-3.25 (2H, m), 3.22 (1H, d, J=12Hz), 2.89-2.80 (1H, m), 2.01-1.91 (1H, m), 1.89-1.70 (3H, m) |
| 202 | CDCl$_3$*:8.32-8.24 (2H, m), 7.30 (1H, s), 7.17-7.11 (1H, m), 7.04-6.91 (2H, m), 6.70-6.63 (2H, m), 5.22-5.15 (1H, m), 4.95-4.82 (2H, m), 4.32-4.18 (2H, m), 3.85 (1H, d, J=12Hz), 3.65 (1H, d, J=17Hz), 3.65-3.53 (2H, m), 3.43-3.18 (3H, m), 2.90-2.80 (1H, m), 2.02-1.91 (1H, m), 1.89-1.70 (3H, m) |
| 209 | CDCl$_3$*:8.29-8.24 (2H, m), 7.96-7.86 (3H, m), 7.58-7.48 (2H, m), 6.69-6.64 (2H, m), 5.23 (1H, d, J=4, 9Hz), 4.42-4.30 (2H, m), 3.78 (1H, d, J=12Hz), 3.65-3.48 (2H, m), 3.47 (1H, d, J=17Hz), 3.45-3.16 (3H, m), 2.56 (1H, dd, J=9, 12Hz), 2.01-1.92 (1H, m), 1.85-1.62 (3H, m) |
| 210 | CDCl$_3$*:8.30-8.24 (2H, m), 7.87-7.81 (1H, m), 7.83 (1H, s), 7.62-7.56 (1H, m), 7.36-7.28 (1H, m), 6.68-6.63 (2H, m), 5.26-5.19 (1H, m), 4.41-4.29 (2H, m), 3.78 (1H, d, J=12Hz), 3.63-3.49 (2H, m), 3.48 (1H, d, J=17Hz), 3.43-3.24 (2H, m), 3.20 (1H, d, J=12Hz), 2.62-2.52 (1H, m), 2.00-1.90 (1H, m), 1.84-1.62 (3H, m) |
| 211 | CDCl$_3$*:8.30-8.24 (2H, m), 7.93-7.90 (1H, m), 7.85-7.79 (2H, m), 7.54-7.48 (1H, m), 6.69-6.63 (2H, m). 5.22 (1H, dd, J=4, 9Hz), 4.41-4.28 (2H, m), 3.82-3.75 (1H, m), 3.64-3.48 (2H, m), 3.47 (1H, d, J=17Hz), 3.43-3.24 (2H, m), 3.24-3.18 (1H, m), 2.57 (1H, dd, J=9, 12Hz), 2.00-1.91 (1H, m), 1.84-1.63 (3H, m) |
| 213 | CDCl$_3$*:8.30-8.24 (2H, m), 7.90-7.88 (1H, m), 7.86 (1H, d, J=9Hz), 7.85-7.83 (1H, m), 7.48 (1H, dd, J=2, 9Hz), 6.69-6.64 (2H, m), 5.26-5.19 (1H, m), 4.41-4.29 (2H, m), 3.78 (1H, d, J=12Hz), 3.64-3.50 (2H, m), 3, .47 (1H, d, J=17Hz), 3.43-3.24 (2H, m), 3.21 (1H, d, J=12Hz), 2.62-2.52 (1H, m), 2.01-1.91 (1H, m), 1.85-1.64 (3H, m) |
| 219 | CDCl$_3$*:8.30-8.24 (2H, m), 7.94 (1H, d, J=6Hz), 7.80 (1H, s), 7.67 (1H, d, J=9Hz), 6.70-6.63 (2H, m), 5.26-5.19 (1H, m), 4.42-4.28 (2H, m), 3.83-3.75 (1H, m), 3.64-3.48 (2H, m), 3.47 (1H, d, J=17Hz), 3.43-3.24 (2H, m), 3.24-3.17 (1H, m), 2.63-2.52 (1H, m), 2.01-1.90 (1H, m), 1.86-1.55 (3H, m) |

FIG. 34

| Ex. No. | NMR(ppm)<br>(*:300MHz, 270MHz) |
|---|---|
| 220 | $CDCl_3$*:8.30-8.25 (2H, m), 7.86-7.82 (1H, m), 7.78 (1H, d, J=9Hz), 7.54-7.48 (1H, m), 6.79-6.73 (2H, m), 5.25-5.17 (1H, m), 4.45-4.33 (2H, m), 3.79 (1H, d, J=12Hz), 3.64-3.47 (2H, m), 3.52 (1H, d, J=17Hz), 3.44-3.17 (3H, m), 2.72 (3H, s), 2.70-2.60 (1H, m), 2.01-1.93 (1H, m), 1.85-1.65 (3H, m) |
| 223 | $CDCl_3$*:8.31-8.24 (2H, m), 7.72-7.68 (1H, m), 7.54-7.45 (2H, m), 7.41-7.39 (1H, m), 6.69-6.64 (2H, m), 5.22-5.15 (1H, m), 4.48-4.34 (2H, m), 3.80 (1H, d, J=12Hz), 3.67 (1H, d, J=17Hz), 3.64-3.51 (2H, m), 3.43-3.25 (2H, m), 3.20 (1H, d, J=12Hz), 2.82-2.72 (1H, m), 1.99-1.89 (1H, m), 1.87-1.66 (3H, m) |
| 224 | $CDCl_3$*:8.30-8.25 (2H, m), 7.86 (1H, d, J=2Hz), 7.62 (1H, dd, J=2, 9Hz), 7.46 (1H, d, J=9Hz), 7.41-7.38 (1H, m), 6.69-6.63 (2H, m), 5.22-5.13 (1H, m), 4.48-4.40 (1H, m), 4.38 (1H, d, J=17Hz), 3.80 (1H, d, J=12Hz), 3.67 (1H, d, J=17Hz), 3.65-3.50 (2H, m), 3.43-3.15 (3H, m), 2.82-2.72 (1H, m), 1.98-1.88 (1H, m), 1.86-1.66 (3H, m) |
| 275 | $CDCl_3$*:8.30-8.24 (2H, m), 7.90-7.82 (3H, m), 7.48 (1H, dd, J=2, 9Hz), 6.68-6.63 (2H, m), 4.83-4.72 (1H, m), 4.37-4.28 (1H, m), 4.31 (1H, d, J=17Hz), 3.59 (1H, d, J=12Hz), 3.47 (1H, d, J=17Hz), 3.55-3.33 (4H, m), 3.22 (1H, d, J=12Hz), 2.53-2.43 (1H, m), 1.85-1.55 (5H, m) |
| 285 | $CDCl_3$*:8.30-8.23 (2H, m), 7.73-7.68 (1H, m), 7.53-7.44 (2H, m), 7.39 (1H, s), 6.70-6.63 (2H, m), 4.78-4.67 (1H, m), 4.45-4.32 (2H, m), 3.70-3.57 (2H, m), 3.55-3.32 (4H, m), 3.22 (1H, d, J=12Hz), 2.74-2.63 (1H, m), 1.85-1.57 (5H, m) |
| 337 | $CDCl_3$*:8.31-8.25 (2H, m), 7.90-7.82 (3H, m), 7.47 (1H, dd, J=2, 9Hz), 6.70-6.63 (2H, m), 4.37-4.18 (3H, m), 4.05-3.87 (2H, m), 3.73 (1H, d, J=12Hz), 3.48 (1H, d, J=17Hz), 3.40 (1H, d, J=12Hz), 2.95-2.72 (2H, m), 2.45 (1H, dd, J=9, 11Hz), 2.30 (3H, s), 2.00-1.87 (1H, m), 1.86-1.73 (1H, m), 1.58-1.49 (1H, m), 1.47-1.37 (1H, m) |
| 347 | $CDCl_3$*:8.29 (2H, dd, J=1, 5Hz), 7.72-7.68 (1H, m), 7.53-7.43 (2H, m), 7.39 (1H, d, J=1Hz), 6.67 (2H, dd, J=2, 5Hz), 4.40-4.20 (3H, m), 4.05-3.88 (2H, m), 3.77-3.70 (1H, m), 3.66 (1H, d, J=17Hz), 3.46-3.39 (1H, m), 2.95-2.73 (2H, m), 2.64 (1H, dd, J=9, 11Hz), 2.30 (3H, s), 2.01-1.88 (1H, m), 1.86-1.73 (1H, m), 1.57-1.39 (2H, m) |

FIG.35

| Ex. No. | NMR(ppm) (*:300MHz, 270MHz) |
|---|---|
| 388 | CDCl$_3$*:8.30-8.22 (2H, m), 7.28 (1H, s), 7.16-7.11 (1H, m), 7.03-6.97 (1H, m), 6.95-6.90 (1H, m), 6.68-6.62 (2H, m), 4.96-4.82 (2H, m), 4.32-4.18 (3H, m), 3.69 (1H, d, J=17Hz), 3.65-3.30 (6H, m), 3.41 (3H, s), 3.23 (1H, d, J=12Hz), 2.74 (1H, d, J=12Hz), 2.05-1.82 (2H, m), 1.73-1.57 (2H, m) |
| 399 | CDCl$_3$*:8.29-8.22 (2H, m), 7.90 (1H, d, J=2Hz), 7.88-7.84 (1H, m), 7.84 (1H, s), 7.51-7.45 (1H, m), 6.66-6.60 (2H, m), 4.39-4.30 (2H, m), 4.23 (1H, d, J=12Hz), 3.69-3.60 (2H, m), 3.50 (1H, d, J=17Hz), 3.50-3.26 (4H, m), 3.44 (3H, s), 3.23 (1H, d, J=12Hz), 2.43 (1H, d, J=12Hz), 2.05-1.82 (2H, m), 1.60-1.50 (2H, m) |
| 409 | CDCl$_3$*:8.30-8.22 (2H, m), 7.73-7.69 (1H, m), 7.56-7.45 (2H, m), 7.40 (1H, s), 6.67-6.61 (2H, m), 4.45-4.34 (2H, m), 4.25 (1H, d, J=11Hz), 3.73 (1H, d, J=17Hz), 3.63 (1H, d, J=10Hz), 3.59 (1H, d, J=10Hz), 3.41 (3H, s), 3.52-3.20 (5H, m), 2.63 (1H, d, J=12Hz), 2.05-1.82 (2H, m), 1.64-1.55 (2H, m) |
| 461 | CDCl$_3$*:8.24 (2H, d, J=6Hz), 7.92-7.82 (3H, m), 7.51-7.45 (1H, m), 6.62 (2H, d, J=6Hz), 4.33 (1H, d, J=17Hz), 4.21 (1H, d, J=12Hz), 4.16 (1H, d, J=12Hz), 3.74-3.68 (1H, m), 3.55-3.18 (6H, m), 3.45 (3H, s), 2.99 (1H, d, J=12Hz), 2.49 (1H, s), 2.38 (1H, d, J=12Hz), 1.92-1.70 (2H, m), 1.50-1.40 (2H, m) |
| 471 | CDCl$_3$*:8.28-8.23 (2H, m), 7.73-7.69 (1H, m), 7.55-7.45 (2H, m), 7.40-7.38 (1H, m), 6.67-6.60 (2H, m), 4.43-4.34 (1H, m), 4.27-4.20 (1H, m), 4.21 (1H, d, J=12Hz), 3.74-3.66 (1H, m), 3.67 (1H, d, J=10Hz), 3.50-3.20 (4H, m), 3.45 (1H, d, J=10Hz), 3.42 (3H, s), 3.05-2.97 (1H, m), 2.57 (1H, d, J=12Hz), 2.49 (1H, s), 1.93-1.71 (2H, m), 1.55-1.44 (2H, m) |
| 523 | CDCl$_3$*:8.27-8.23 (2H, m), 7.90-7.82 (3H, m), 7.50-7.45 (1H, m), 6.66-6.61 (2H, m), 4.37-4.28 (1H, m), 4.26-4.17 (2H, m), 3.98-3.63 (4H, m), 3.54-3.45 (1H, m), 3.38 (3H, s), 3.26-3.20 (1H, m), 2.89-2.69 (2H, m), 2.43-2.36 (1H, m), 2.38 (3H, s), 1.99-1.66 (3H, m), 1.20-1.11 (1H, m) |
| 533 | CDCl$_3$*:8.28-8.23 (2H, m), 7.72-7.68 (1H, m), 7.54-7.44 (2H, m), 7.39-7.37 (1H, m), 6.67-6.62 (2H, m), 4.42-4.33 (1H, m), 4.29-4.21 (1H, m), 4.26 (1H, d, J=12Hz), 3.98-3.77 (2H, m), 3.75-3.68 (1H, m), 3.71 (1H, d, J=10Hz), 3.60 (1H, d, J=10Hz), 3.35 (3H, s), 3.27-3.21 (1H, m), 2.91-2.69 (2H, m), 2.58 (1H, d, J=12Hz), 2.38 (3H, s), 1.99-1.69 (3H, m), 1.23-1.16 (1H, m) |

FIG. 36

| Ex. No. | NMR(ppm)<br>(*:300MHz, 270MHz) |
|---|---|
| 574 | CDCl$_3$*:8.30-8.25 (2H, m), 7.67-7.58 (2H, m), 7.46-7.36 (2H, m), 6.70-6.65 (2H, m), 5.24-5.16 (1H, m), 4.50-4.37 (1H, m), 4.37 (1H, d, J=17Hz), 3.81 (1H, d, J=12Hz), 3.70-3.51 (3H, m), 3.45-3.25 (2H, m), 3.20 (1H, d, J=12Hz), 2.82-2.73 (1H, m), 1.99-1.90 (1H, m), 1.87-1.65 (3H, m) |
| 580 | CDCl$_3$*:9.55 (1H, brs), 8.28 (2H, d, J=5Hz), 7.73 (1H, d, J=8Hz), 7.48 (1H, d, J=8Hz), 7.45-7.37 (1H, m), 7.32-7.21 (1H, m), 7.13 (1H, s), 6.66 (2H, d, J=5Hz), 5.20-5.12 (1H, m), 4.36-4.26 (2H, m), 3.76 (1H, d, J=11Hz), 3.64-3.48 (2H, m), 3.43 (1H, d, J=17Hz), 3.42-3.12 (3H, m), 2.54-2.44 (1H, m), 1.98-1.86 (1H, m), 1.82-1.60 (3H, m) |
| 600 | CDCl$_3$*:8.30-8.25 (2H, m), 7.54-7.47 (1H, m), 7.13-7.10 (1H, m), 6.95-6.92 (1H, m), 6.70-6.65 (2H, m), 6.36-6.28 (1H, m), 5.19 (1H, dd, J=4, 9Hz), 4.30-4.18 (2H, m), 3.84 (1H, d, J=12Hz), 3.64-3.53 (2H, m), 3.58 (1H, d, J=17Hz), 3.44-3.27 (2H, m), 3.22 (1H, d, J=12Hz), 2.73 (1H, dd, J=9, 12Hz), 2.01-1.92 (1H, m), 1.89-1.70 (3H, m) |
| 628 | CDCl$_3$*:8.30-8.24 (2H, m), 7.54-7.45 (1H, m), 7.14-7.09 (1H, m), 6.96-6.90 (1H, m), 6.70-6.63 (2H, m), 6.37-6.28 (1H, m), 4.80-4.66 (1H, m), 4.27-4.15 (2H, m), 3.64 (1H, d, J=12Hz), 3.58 (1H, d, J=17Hz), 3.56-3.35 (4H, m), 3.25 (1H, d, J=12Hz), 2.68-2.58 (1H, m), 1.90-1.60 (5H, m) |
| 656 | CDCl$_3$*:8.32-8.25 (2H, m), 7.49 (1H, d, J=15Hz), 7.13-7.09 (1H, m), 6.96-6.91 (1H, m), 6.71-6.65 (2H, m), 6.31 (1H, d, J=15Hz), 4.29-4.10 (3H, m), 4.05-3.90 (2H, m), 3.79-3.71 (1H, m), 3.59 (1H, d, J=17Hz), 3.52-3.43 (1H, m), 2.97-2.75 (2H, m), 2.58 (1H, dd, J=9, 12Hz), 2.29 (3H, s), 2.02-1.89 (1H, m), 1.87-1.73 (1H, m), 1.71-1.42 (2H, m) |
| 684 | CDCl$_3$*:8.30-8.23 (2H, m), 7.50 (1H, d, J=15Hz), 7.14-7.10 (1H, m), 6.96-6.92 (1H, m), 6.69-6.62 (2H, m), 6.31 (1H, d, J=15Hz), 4.30-4.18 (3H, m), 3.67-3.56 (3H, m), 3.52-3.30 (4H, m), 3.43 (3H, s), 3.24 (1H, d, J=12Hz), 2.62 (1H, d, J=12Hz), 2.05-1.83 (2H, m), 1.68-1.60 (2H, m) |
| 712 | CDCl$_3$*:8.30-8.23 (2H, m), 7.48 (1H, d, J=15Hz), 7.11 (1H, d, J=4Hz), 6.93 (1H, d, J=4Hz), 6.69-6.62 (2H, m), 6.31 (1H, d, J=15Hz), 4.25 (1H, d, J=12Hz), 4.22 (1H, d, J=17Hz), 4.07-4.01 (1H, m), 3.68 (1H, d, J=10Hz), 3.56 (1H, d, J=17Hz), 3.52-3.25 (4H, m), 3.47 (1H, d, J=10Hz), 3.43 (3H, s), 3.01 (1H, d, J=12Hz), 2.58-2.52 (1H, m), 2.48 (1H, s), 1.95-1.72 (2H, m), 1.57-1.50 (2H, m) |

FIG. 37

| Ex. No. | NMR(ppm) (*:300MHz, 270MHz) |
|---|---|
| 740 | CDCl₃*:8.29-8.24 (2H, m), 7.52-7.45 (1H, m), 7.11 (1H, d, J=4Hz), 6.93 (1H, d, J=4Hz), 6.68-6.64 (2H, m), 6.33-6.26 (1H, m), 4.32-4.17 (2H, m), 4.14-4.08 (1H, m), 3.99-3.81 (2H, m), 3.71 (1H, d, J=10Hz), 3.66-3.56 (1H, m), 3.62 (1H, d, J=10Hz), 3.38 (3H, s), 3.27-3.21 (1H, m), 2.95-2.71 (2H, m), 2.58-2.53 (1H, m), 2.37 (3H, s), 2.01-1.73 (3H, m), 1.30-1.21 (1H, m) |
| 759 | CDCl₃*:8.41-8.36 (1H, m), 8.27 (2H, dd, J=1, 5Hz), 8.06-7.93 (3H, m), 7.80-7.64 (3H, m), 6.65 (2H, dd, J=1, 5Hz), 5.24-5.17 (1H, m), 4.43-4.30 (2H, m), 3.75 (1H, d, J=12Hz), 3.62-3.47 (2H, m), 3.43-3.21 (2H, m), 3.31 (1H, d, J=17Hz), 3.18 (1H, d, J=12Hz), 2.48-2.38 (1H, m), 1.99-1.90 (1H, m), 1.82-1.60 (3H, m) |
| 760 | CDCl₃*:8.40-8.36 (1H, m), 8.30-8.24 (3H, m), 8.24-8.18 (1H, m), 8.06-8.01 (1H, m), 7.58 (1H, d, J=9Hz), 6.69-6.63 (2H, m), 5.24-5.17 (1H, m), 4.44-4.29 (2H, m), 3.80-3.73 (1H, m), 3.63-3.48 (2H, m), 3.42-3.23 (2H, m), 3.33 (1H, d, J=17Hz), 3.22-3.16 (1H, m), 2.54-2.45 (1H, m), 2.00-1.90 (1H, m), 1.84-1.58 (3H, m) |
| 761 | CDCl₃*:8.27 (2H, d, J=6Hz), 7.87 (1H, s), 7.66-7.60 (1H, m), 7.56-7.50 (1H, m), 7.43 (1H, s), 6.67 (2H, d, J=6Hz), 5.23-5.15 (1H, m), 4.50-4.33 (2H, m), 3.80 (1H, d, J=12Hz), 3.67 (1H, d, J=17Hz), 3.66-3.50 (2H, m), 3.45-3.24 (2H, m), 3.20 (1H, d, J=12Hz), 3.12 (1H, s), 2.83-2.72 (1H, m), 2.00-1.67 (4H, m) |
| 765 | CDCl₃*:8.38-8.34 (1H, m), 8.27 (2H, dd, J=2, 5Hz), 7.99-7.90 (3H, m), 7.82-7.76 (1H, m), 7.65-7.59 (1H, m), 6.65 (2H, dd, J=2, 5Hz), 4.80-4.69 (1H, m), 4.40-4.32 (1H, m), 4.32 (1H, d, J=16Hz), 3.59-3.28 (6H, m), 3.20 (1H, d, J=12Hz), 2.40-2.30 (1H, m), 1.85-1.50 (5H, m) |
| 769 | CDCl₃*:8.38-8.33 (1H, m), 8.31-8.24 (2H, m), 7.98-7.89 (3H, m), 7.81-7.76 (1H, m), 7.63-7.58 (1H, m), 6.70-6.62 (2H, m), 4.36-4.22 (3H, m), 4.04-3.85 (2H, m), 3.70 (1H, d, J=11Hz), 3.40-3.27 (2H, m), 2.94-2.70 (2H, m), 2.37-2.25 (1H, m), 2.30 (3H, s), 1.99-1.73 (2H, m), 1.65-1.49 (1H, m), 1.44-1.34 (1H, m) |
| 770 | CDCl₃*:8.39-8.35 (1H, m), 8.29-8.19 (4H, m), 8.05-8.00 (1H, m), 7.59 (1H, d, J=9Hz), 6.64-6.59 (2H, m), 4.41-4.32 (2H, m), 4.21 (1H, d, J=12Hz), 3.69-3.58 (2H, m), 3.49-3.18 (5H, m), 3.43 (3H, s), 3.37 (1H, d, J=17Hz), 2.34 (1H, d, J=12Hz), 2.03-1.81 (2H, m), 1.55-1.49 (2H, m) |

FIG. 38

| Ex. No. | NMR(ppm)<br>(*:300MHz, 270MHz) |
|---|---|
| 776 | DMSO-$d_6$*:13.25 (1H, s), 8.59 (1H, s), 8.28-8.17 (4H, m), 8.14-8.08 (1H, m), 7.88 (1H, dd, J=2, 9Hz), 7.80-7.68 (2H, m), 7.23 (2H, d, J=7Hz), 5.25-5.18 (1H, m), 4.23-4.14 (1H, m), 4.06 (1H, d, J=17Hz), 4.00-3.81 (2H, m), 3.71 (1H, d, J=12Hz), 3.62-3.35 (3H, m), 3.15 (1H, d, J=12Hz), 2.75-2.65 (1H, m), 2.31 (3H, s), 2.00-1.52 (4H, m) |
| 777 | DMSO-$d_6$*:13.22 (1H, s), 8.39-8.34 (1H, m), 8.25-8.15 (3H, m), 8.12-8.07 (1H, m), 7.63-7.57 (1H, m), 7.19 (2H, d, J=7Hz), 4.18-4.02 (3H, m), 3.92-3.28 (7H, m), 3.33 (3H, s), 3.20 (1H, d, J=12Hz), 2.82 (1H, d, J=11Hz), 2.30 (3H, s), 1.94-1.78 (2H, m), 1.70-1.48 (2H, m) |
| 778 | DMSO-$d_6$*:13.23 (1H, s), 8.26-8.18 (2H, m), 7.65-7.57 (1H, m), 7.52 (1H, d, J=4Hz), 7.26-7.19 (3H, m), 7.09-7.02 (1H, m), 4.24-4.17 (1H, m), 4.01-3.74 (5H, m), 3.62-3.47 (4H, m), 3.32 (3H, s), 3.26-3.20 (1H, m), 2.90-2.84 (1H, m), 2.30 (3H, s), 1.93-1.83 (2H, m), 1.71-1.60 (2H, m) |
| 779 | DMSO-$d_6$*:13.23 (1H, s), 8.28-8.15 (2H, m), 7.99-7.72 (3H, m), 7.67-7.57 (1H, m), 7.28-7.14 (2H, m), 4.23-4.03 (3H, m), 3.93-3.71 (3H, m), 3.67-3.15 (5H, m), 3.32 (3H, s), 3.07-2.97 (1H, m), 2.30 (3H, s), 1.98-1.77 (2H, m), 1.70-1.53 (2H, m) |
| 780 | DMSO-$d_6$*:13.23 (1H, s), 8.27-8.18 (2H, m), 7.52-7.46 (1H, m), 7.50 (1H, s), 7.26-7.20 (2H, m), 7.12 (1H, dd, J=2, 8Hz), 7.08-7.06 (1H, m), 5.02 (2H, s), 4.20 (1H, d, J=12Hz), 4.05-3.75 (5H, m), 3.65-3.45 (4H, m), 3.31 (3H, s), 3.23 (1H, d, J=12Hz), 3.03 (1H, d, J=11Hz), 2.29 (3H, s), 2.00-1.55 (4H, m) |

FIG. 39

<TABLE A>

COORDINATES OF THE ACTIVE CENTER SITES IN THE CRYSTAL STRUCTURE OF COMPOUND A - FXA COMPLEX ARE SHOWN BELOW IN PDB FORMAT

| ① | ② | ③ | ④ | ⑤ | ⑥ | ⑦ | ⑧ | ⑨ | ⑩ |
|---|---|---|---|---|---|---|---|---|---|
| ATOM | 784 | N | LYS | 96 | 4.741 | 10.202 | 10.448 | 1.00 | 23.85 |
| ATOM | 785 | H | LYS | 96 | 5.064 | 9.293 | 10.312 | 1.00 | 0.00 |
| ATOM | 786 | CA | LYS | 96 | 4.804 | 11.268 | 9.454 | 1.00 | 22.65 |
| ATOM | 787 | CB | LYS | 96 | 5.745 | 10.872 | 8.307 | 1.00 | 27.27 |
| ATOM | 788 | CG | LYS | 96 | 6.091 | 9.385 | 8.228 | 1.00 | 30.35 |
| ATOM | 789 | CD | LYS | 96 | 7.164 | 9.009 | 9.239 | 1.00 | 29.56 |
| ATOM | 790 | CE | LYS | 96 | 7.405 | 7.504 | 9.282 | 1.00 | 32.56 |
| ATOM | 791 | NZ | LYS | 96 | 6.242 | 6.736 | 9.818 | 1.00 | 28.13 |
| ATOM | 792 | HZ1 | LYS | 96 | 5.404 | 6.920 | 9.230 | 1.00 | 0.00 |
| ATOM | 793 | HZ2 | LYS | 96 | 6.041 | 7.047 | 10.791 | 1.00 | 0.00 |
| ATOM | 794 | HZ3 | LYS | 96 | 6.459 | 5.720 | 9.815 | 1.00 | 0.00 |
| ATOM | 795 | C | LYS | 96 | 3.431 | 11.693 | 8.910 | 1.00 | 20.65 |
| ATOM | 796 | O | LYS | 96 | 3.285 | 12.797 | 8.388 | 1.00 | 16.33 |
| ATOM | 797 | N | GLU | 97 | 2.422 | 10.839 | 9.093 | 1.00 | 19.10 |
| ATOM | 798 | H | GLU | 97 | 2.641 | 10.040 | 9.589 | 1.00 | 0.00 |
| ATOM | 799 | CA | GLU | 97 | 1.066 | 11.119 | 8.610 | 1.00 | 19.57 |
| ATOM | 800 | CB | GLU | 97 | 0.233 | 9.842 | 8.507 | 1.00 | 18.38 |
| ATOM | 801 | CG | GLU | 97 | 0.703 | 8.698 | 9.374 | 1.00 | 29.43 |
| ATOM | 802 | CD | GLU | 97 | 1.871 | 7.943 | 8.757 | 1.00 | 39.21 |
| ATOM | 803 | OE1 | GLU | 97 | 2.967 | 7.943 | 9.362 | 1.00 | 48.48 |
| ATOM | 804 | OE2 | GLU | 97 | 1.693 | 7.350 | 7.666 | 1.00 | 41.77 |
| ATOM | 805 | C | GLU | 97 | 0.309 | 12.140 | 9.438 | 1.00 | 19.94 |
| ATOM | 806 | O | GLU | 97 | -0.542 | 12.860 | 8.929 | 1.00 | 15.85 |
| ATOM | 807 | N | THR | 98 | 0.604 | 12.181 | 10.728 | 1.00 | 21.36 |
| ATOM | 808 | H | THR | 98 | 1.261 | 11.557 | 11.087 | 1.00 | 0.00 |
| ATOM | 809 | CA | THR | 98 | -0.056 | 13.124 | 11.626 | 1.00 | 21.20 |
| ATOM | 810 | CB | THR | 98 | -0.611 | 12.419 | 12.855 | 1.00 | 20.12 |
| ATOM | 811 | OG1 | THR | 98 | 0.473 | 11.796 | 13.553 | 1.00 | 25.14 |
| ATOM | 812 | HG1 | THR | 98 | 0.192 | 11.011 | 14.047 | 1.00 | 0.00 |
| ATOM | 813 | CG2 | THR | 98 | -1.640 | 11.363 | 12.458 | 1.00 | 26.75 |
| ATOM | 814 | C | THR | 98 | 0.947 | 14.110 | 12.156 | 1.00 | 19.21 |
| ATOM | 815 | O | THR | 98 | 0.591 | 15.212 | 12.538 | 1.00 | 22.96 |
| ATOM | 816 | N | TYR | 99 | 2.209 | 13.691 | 12.171 | 1.00 | 18.62 |
| ATOM | 817 | H | TYR | 99 | 2.395 | 12.809 | 11.804 | 1.00 | 0.00 |
| ATOM | 818 | CA | TYR | 99 | 3.304 | 14.486 | 12.711 | 1.00 | 17.73 |
| ATOM | 819 | CB | TYR | 99 | 3.410 | 15.846 | 12.010 | 1.00 | 14.99 |
| ATOM | 820 | CG | TYR | 99 | 4.440 | 15.851 | 10.912 | 1.00 | 14.90 |
| ATOM | 821 | CD1 | TYR | 99 | 5.423 | 16.839 | 10.848 | 1.00 | 15.28 |
| ATOM | 822 | CE1 | TYR | 99 | 6.420 | 16.804 | 9.870 | 1.00 | 17.93 |
| ATOM | 823 | CD2 | TYR | 99 | 4.477 | 14.828 | 9.968 | 1.00 | 18.54 |
| ATOM | 824 | CE2 | TYR | 99 | 5.464 | 14.786 | 8.993 | 1.00 | 25.43 |
| ATOM | 825 | CZ | TYR | 99 | 6.432 | 15.771 | 8.954 | 1.00 | 25.32 |
| ATOM | 826 | OH | TYR | 99 | 7.412 | 15.709 | 7.995 | 1.00 | 32.89 |
| ATOM | 827 | HH | TYR | 99 | 7.202 | 15.004 | 7.373 | 1.00 | 0.00 |
| ATOM | 828 | C | TYR | 99 | 3.098 | 14.642 | 14.220 | 1.00 | 18.17 |
| ATOM | 829 | O | TYR | 99 | 3.565 | 15.592 | 14.844 | 1.00 | 21.63 |
| ATOM | 1577 | N | PHE | 174 | -4.467 | 21.058 | 8.884 | 1.00 | 13.87 |
| ATOM | 1578 | H | PHE | 174 | -4.036 | 21.860 | 9.243 | 1.00 | 0.00 |
| ATOM | 1579 | CA | PHE | 174 | -4.243 | 19.756 | 9.527 | 1.00 | 14.33 |
| ATOM | 1580 | CB | PHE | 174 | -2.773 | 19.378 | 9.454 | 1.00 | 8.22 |
| ATOM | 1581 | CG | PHE | 174 | -2.290 | 19.047 | 8.090 | 1.00 | 4.53 |
| ATOM | 1582 | CD1 | PHE | 174 | -2.151 | 17.728 | 7.701 | 1.00 | 2.00 |
| ATOM | 1583 | CD2 | PHE | 174 | -1.861 | 20.046 | 7.229 | 1.00 | 8.32 |
| ATOM | 1584 | CE1 | PHE | 174 | -1.582 | 17.407 | 6.477 | 1.00 | 4.74 |
| ATOM | 1585 | CE2 | PHE | 174 | -1.288 | 19.729 | 6.002 | 1.00 | 8.59 |
| ATOM | 1586 | CZ | PHE | 174 | -1.148 | 18.407 | 5.632 | 1.00 | 11.56 |

FIG. 40

CONTINUED FROM <TABLE A>

| | | | | | | | | |
|---|---|---|---|---|---|---|---|---|
| ATOM | 1587 | C | PHE | 174 | -4.654 | 19.705 | 11.000 | 1.00 16.38 |
| ATOM | 1588 | O | PHE | 174 | -4.788 | 20.738 | 11.654 | 1.00 20.64 |
| ATOM | 1745 | N | ASP | 189 | 8.408 | 33.948 | 10.783 | 1.00 12.09 |
| ATOM | 1746 | H | ASP | 189 | 9.304 | 34.162 | 10.443 | 1.00 0.00 |
| ATOM | 1747 | CA | ASP | 189 | 8.045 | 32.569 | 11.126 | 1.00 14.13 |
| ATOM | 1748 | CB | ASP | 189 | 7.060 | 32.074 | 10.052 | 1.00 18.27 |
| ATOM | 1749 | CG | ASP | 189 | 6.299 | 30.818 | 10.447 | 1.00 29.21 |
| ATOM | 1750 | OD1 | ASP | 189 | 6.899 | 29.872 | 11.005 | 1.00 26.93 |
| ATOM | 1751 | OD2 | ASP | 189 | 5.077 | 30.767 | 10.152 | 1.00 28.08 |
| ATOM | 1752 | C | ASP | 189 | 9.333 | 31.731 | 11.053 | 1.00 14.52 |
| ATOM | 1753 | O | ASP | 189 | 10.370 | 32.219 | 10.606 | 1.00 17.15 |
| ATOM | 1754 | N | ALA | 190 | 9.301 | 30.508 | 11.571 | 1.00 10.01 |
| ATOM | 1755 | H | ALA | 190 | 8.522 | 30.238 | 12.091 | 1.00 0.00 |
| ATOM | 1756 | CA | ALA | 190 | 10.453 | 29.620 | 11.470 | 1.00 5.72 |
| ATOM | 1757 | CB | ALA | 190 | 10.325 | 28.473 | 12.450 | 1.00 9.56 |
| ATOM | 1758 | C | ALA | 190 | 10.396 | 29.112 | 10.025 | 1.00 5.82 |
| ATOM | 1759 | O | ALA | 190 | 9.799 | 29.761 | 9.186 | 1.00 9.42 |
| ATOM | 1760 | N | CYS | 191 | 10.988 | 27.960 | 9.728 | 1.00 3.41 |
| ATOM | 1761 | H | CYS | 191 | 11.414 | 27.439 | 10.437 | 1.00 0.00 |
| ATOM | 1762 | CA | CYS | 191 | 10.979 | 27.440 | 8.360 | 1.00 6.67 |
| ATOM | 1763 | C | CYS | 191 | 11.864 | 26.196 | 8.255 | 1.00 5.52 |
| ATOM | 1764 | O | CYS | 191 | 12.375 | 25.715 | 9.277 | 1.00 6.15 |
| ATOM | 1765 | CB | CYS | 191 | 11.469 | 28.518 | 7.387 | 1.00 8.63 |
| ATOM | 1766 | SG | CYS | 191 | 11.102 | 28.223 | 5.629 | 1.00 18.50 |
| ATOM | 1767 | N | GLN | 192 | 12.098 | 25.713 | 7.033 | 1.00 5.87 |
| ATOM | 1768 | H | GLN | 192 | 11.679 | 26.167 | 6.270 | 1.00 0.00 |
| ATOM | 1769 | CA | GLN | 192 | 12.925 | 24.515 | 6.820 | 1.00 10.96 |
| ATOM | 1770 | CB | GLN | 192 | 13.086 | 24.254 | 5.331 | 1.00 17.72 |
| ATOM | 1771 | CG | GLN | 192 | 13.700 | 22.910 | 5.018 | 1.00 32.49 |
| ATOM | 1772 | CD | GLN | 192 | 14.143 | 22.802 | 3.575 | 1.00 41.58 |
| ATOM | 1773 | OE1 | GLN | 192 | 15.327 | 22.950 | 3.264 | 1.00 44.38 |
| ATOM | 1774 | NE2 | GLN | 192 | 13.194 | 22.551 | 2.678 | 1.00 43.85 |
| ATOM | 1775 | HE21 | GLN | 192 | 12.259 | 22.433 | 2.903 | 1.00 0.00 |
| ATOM | 1776 | HE22 | GLN | 192 | 13.527 | 22.509 | 1.763 | 1.00 0.00 |
| ATOM | 1777 | C | GLN | 192 | 14.316 | 24.525 | 7.478 | 1.00 7.56 |
| ATOM | 1778 | O | GLN | 192 | 14.974 | 25.563 | 7.548 | 1.00 2.44 |
| ATOM | 1779 | N | GLY | 193 | 14.761 | 23.372 | 7.964 | 1.00 8.11 |
| ATOM | 1780 | H | GLY | 193 | 14.237 | 22.555 | 7.869 | 1.00 0.00 |
| ATOM | 1781 | CA | GLY | 193 | 16.064 | 23.313 | 8.603 | 1.00 9.56 |
| ATOM | 1782 | C | GLY | 193 | 16.035 | 23.720 | 10.065 | 1.00 11.52 |
| ATOM | 1783 | O | GLY | 193 | 16.889 | 23.315 | 10.843 | 1.00 15.90 |
| ATOM | 1784 | N | ASP | 194 | 15.080 | 24.571 | 10.431 | 1.00 12.53 |
| ATOM | 1785 | H | ASP | 194 | 14.493 | 24.947 | 9.749 | 1.00 0.00 |
| ATOM | 1786 | CA | ASP | 194 | 14.915 | 24.987 | 11.814 | 1.00 7.55 |
| ATOM | 1787 | CB | ASP | 194 | 13.908 | 26.131 | 11.915 | 1.00 2.00 |
| ATOM | 1788 | CG | ASP | 194 | 14.475 | 27.465 | 11.459 | 1.00 2.00 |
| ATOM | 1789 | OD1 | ASP | 194 | 13.728 | 28.235 | 10.814 | 1.00 4.12 |
| ATOM | 1790 | OD2 | ASP | 194 | 15.651 | 27.765 | 11.761 | 1.00 7.76 |
| ATOM | 1791 | C | ASP | 194 | 14.402 | 23.791 | 12.621 | 1.00 9.73 |
| ATOM | 1792 | O | ASP | 194 | 14.536 | 23.750 | 13.840 | 1.00 12.71 |
| ATOM | 1793 | N | SER | 195 | 13.804 | 22.823 | 11.938 | 1.00 6.99 |
| ATOM | 1794 | H | SER | 195 | 13.748 | 22.953 | 10.974 | 1.00 0.00 |
| ATOM | 1795 | CA | SER | 195 | 13.264 | 21.625 | 12.589 | 1.00 10.57 |
| ATOM | 1796 | CB | SER | 195 | 12.968 | 20.532 | 11.555 | 1.00 10.36 |
| ATOM | 1797 | OG | SER | 195 | 11.748 | 20.787 | 10.868 | 1.00 8.45 |
| ATOM | 1798 | HG | SER | 195 | 11.756 | 21.696 | 10.548 | 1.00 0.00 |
| ATOM | 1799 | C | SER | 195 | 14.136 | 21.054 | 13.707 | 1.00 8.30 |
| ATOM | 1800 | O | SER | 195 | 15.298 | 20.752 | 13.486 | 1.00 13.26 |
| ATOM | 1965 | N | VAL | 213 | 10.619 | 22.878 | 17.479 | 1.00 8.87 |
| ATOM | 1966 | H | VAL | 213 | 11.529 | 23.087 | 17.805 | 1.00 0.00 |

FIG. 41

CONTINUED FROM <TABLE A>

| | | | | | | | | |
|---|---|---|---|---|---|---|---|---|
| ATOM | 1967 | CA | VAL | 213 | 10.217 | 23.245 | 16.105 | 1.00 3.61 |
| ATOM | 1968 | CB | VAL | 213 | 11.363 | 23.956 | 15.352 | 1.00 4.20 |
| ATOM | 1969 | CG1 | VAL | 213 | 11.061 | 24.047 | 13.872 | 1.00 2.00 |
| ATOM | 1970 | CG2 | VAL | 213 | 11.554 | 25.346 | 15.896 | 1.00 2.00 |
| ATOM | 1971 | C | VAL | 213 | 9.808 | 21.980 | 15.336 | 1.00 5.71 |
| ATOM | 1972 | O | VAL | 213 | 10.634 | 21.095 | 15.120 | 1.00 2.00 |
| ATOM | 1973 | N | SER | 214 | 8.540 | 21.914 | 14.921 | 1.00 8.94 |
| ATOM | 1974 | H | SER | 214 | 7.946 | 22.664 | 15.112 | 1.00 0.00 |
| ATOM | 1975 | CA | SER | 214 | 8.004 | 20.737 | 14.221 | 1.00 8.85 |
| ATOM | 1976 | CB | SER | 214 | 6.839 | 20.152 | 15.020 | 1.00 10.34 |
| ATOM | 1977 | OG | SER | 214 | 6.380 | 18.937 | 14.453 | 1.00 8.56 |
| ATOM | 1978 | HG | SER | 214 | 5.666 | 18.601 | 15.008 | 1.00 0.00 |
| ATOM | 1979 | C | SER | 214 | 7.592 | 20.874 | 12.744 | 1.00 12.05 |
| ATOM | 1980 | O | SER | 214 | 8.239 | 20.305 | 11.862 | 1.00 14.40 |
| ATOM | 1981 | N | TRP | 215 | 6.490 | 21.567 | 12.478 | 1.00 14.50 |
| ATOM | 1982 | H | TRP | 215 | 5.987 | 21.982 | 13.213 | 1.00 0.00 |
| ATOM | 1983 | CA | TRP | 215 | 6.011 | 21.750 | 11.101 | 1.00 11.54 |
| ATOM | 1984 | CB | TRP | 215 | 5.193 | 20.536 | 10.632 | 1.00 11.75 |
| ATOM | 1985 | CG | TRP | 215 | 3.961 | 20.290 | 11.450 | 1.00 12.42 |
| ATOM | 1986 | CD2 | TRP | 215 | 2.631 | 20.752 | 11.174 | 1.00 18.81 |
| ATOM | 1987 | CE2 | TRP | 215 | 1.811 | 20.311 | 12.230 | 1.00 16.79 |
| ATOM | 1988 | CE3 | TRP | 215 | 2.051 | 21.492 | 10.133 | 1.00 25.81 |
| ATOM | 1989 | CD1 | TRP | 215 | 3.891 | 19.611 | 12.617 | 1.00 12.16 |
| ATOM | 1990 | NE1 | TRP | 215 | 2.607 | 19.618 | 13.097 | 1.00 17.72 |
| ATOM | 1991 | HE1 | TRP | 215 | 2.296 | 19.183 | 13.914 | 1.00 0.00 |
| ATOM | 1992 | CZ2 | TRP | 215 | 0.441 | 20.585 | 12.285 | 1.00 16.94 |
| ATOM | 1993 | CZ3 | TRP | 215 | 0.688 | 21.767 | 10.185 | 1.00 25.39 |
| ATOM | 1994 | CH2 | TRP | 215 | -0.101 | 21.310 | 11.259 | 1.00 22.37 |
| ATOM | 1995 | C | TRP | 215 | 5.167 | 23.007 | 10.918 | 1.00 14.86 |
| ATOM | 1996 | O | TRP | 215 | 4.957 | 23.789 | 11.854 | 1.00 14.41 |
| ATOM | 1997 | N | GLY | 216 | 4.675 | 23.173 | 9.695 | 1.00 16.84 |
| ATOM | 1998 | H | GLY | 216 | 4.881 | 22.520 | 8.995 | 1.00 0.00 |
| ATOM | 1999 | CA | GLY | 216 | 3.850 | 24.316 | 9.345 | 1.00 17.38 |
| ATOM | 2000 | C | GLY | 216 | 3.471 | 24.237 | 7.880 | 1.00 20.21 |
| ATOM | 2001 | O | GLY | 216 | 3.922 | 23.333 | 7.173 | 1.00 20.21 |
| ATOM | 2002 | N | GLU | 217 | 2.587 | 25.129 | 7.440 | 1.00 19.61 |
| ATOM | 2003 | H | GLU | 217 | 2.216 | 25.764 | 8.085 | 1.00 0.00 |
| ATOM | 2004 | CA | GLU | 217 | 2.153 | 25.176 | 6.042 | 1.00 12.11 |
| ATOM | 2005 | CB | GLU | 217 | 0.645 | 25.351 | 5.953 | 1.00 6.63 |
| ATOM | 2006 | CG | GLU | 217 | -0.079 | 24.049 | 6.207 | 1.00 20.42 |
| ATOM | 2007 | CD | GLU | 217 | -1.531 | 24.228 | 6.510 | 1.00 23.62 |
| ATOM | 2008 | OE1 | GLU | 217 | -2.230 | 25.085 | 6.031 | 1.00 24.43 |
| ATOM | 2009 | OE2 | GLU | 217 | -1.975 | 23.500 | 7.521 | 1.00 28.17 |
| ATOM | 2010 | C | GLU | 217 | 2.897 | 26.300 | 5.348 | 1.00 11.70 |
| ATOM | 2011 | O | GLU | 217 | 2.504 | 27.469 | 5.400 | 1.00 6.58 |
| ATOM | 2012 | N | GLY | 218 | 4.013 | 25.919 | 4.738 | 1.00 11.12 |
| ATOM | 2013 | H | GLY | 218 | 4.256 | 24.974 | 4.781 | 1.00 0.00 |
| ATOM | 2014 | CA | GLY | 218 | 4.865 | 26.877 | 4.065 | 1.00 15.66 |
| ATOM | 2015 | C | GLY | 218 | 5.754 | 27.559 | 5.090 | 1.00 12.39 |
| ATOM | 2016 | O | GLY | 218 | 6.206 | 26.925 | 6.034 | 1.00 15.04 |
| ATOM | 2017 | N | CYS | 220 | 6.020 | 28.842 | 4.900 | 1.00 9.76 |
| ATOM | 2018 | H | CYS | 220 | 5.639 | 29.259 | 4.101 | 1.00 0.00 |
| ATOM | 2019 | CA | CYS | 220 | 6.833 | 29.599 | 5.838 | 1.00 9.17 |
| ATOM | 2020 | C | CYS | 220 | 6.352 | 31.034 | 5.783 | 1.00 13.52 |
| ATOM | 2021 | O | CYS | 220 | 6.480 | 31.710 | 4.759 | 1.00 15.23 |
| ATOM | 2022 | CB | CYS | 220 | 8.336 | 29.530 | 5.506 | 1.00 9.55 |
| ATOM | 2023 | SG | CYS | 220 | 9.098 | 27.875 | 5.612 | 1.00 10.99 |
| ATOM | 2092 | N | GLY | 226 | 3.145 | 28.841 | 13.069 | 1.00 12.64 |
| ATOM | 2093 | H | GLY | 226 | 3.142 | 29.684 | 13.567 | 1.00 0.00 |
| ATOM | 2094 | CA | GLY | 226 | 4.219 | 27.901 | 13.325 | 1.00 7.11 |

FIG. 42

CONTINUED FROM <TABLE A>

| | | | | | | | | |
|---|---|---|---|---|---|---|---|---|
| ATOM | 2095 | C | GLY | 226 | 3.728 | 26.832 | 14.287 | 1.00 2.00 |
| ATOM | 2096 | O | GLY | 226 | 3.203 | 27.151 | 15.355 | 1.00 2.00 |
| ATOM | 2097 | N | ILE | 227 | 3.858 | 25.569 | 13.899 | 1.00 2.00 |
| ATOM | 2098 | H | ILE | 227 | 4.255 | 25.373 | 13.019 | 1.00 0.00 |
| ATOM | 2099 | CA | ILE | 227 | 3.416 | 24.465 | 14.748 | 1.00 8.14 |
| ATOM | 2100 | CB | ILE | 227 | 2.711 | 23.360 | 13.916 | 1.00 10.97 |
| ATOM | 2101 | CG2 | ILE | 227 | 2.093 | 22.318 | 14.848 | 1.00 12.70 |
| ATOM | 2102 | CG1 | ILE | 227 | 1.662 | 23.971 | 12.978 | 1.00 10.26 |
| ATOM | 2103 | CD1 | ILE | 227 | 0.580 | 24.750 | 13.683 | 1.00 5.42 |
| ATOM | 2104 | C | ILE | 227 | 4.593 | 23.829 | 15.500 | 1.00 8.86 |
| ATOM | 2105 | O | ILE | 227 | 5.455 | 23.179 | 14.902 | 1.00 14.80 |
| ATOM | 2106 | N | TYR | 228 | 4.632 | 24.017 | 16.811 | 1.00 9.76 |
| ATOM | 2107 | H | TYR | 228 | 3.915 | 24.543 | 17.234 | 1.00 0.00 |
| ATOM | 2108 | CA | TYR | 228 | 5.701 | 23.457 | 17.628 | 1.00 5.66 |
| ATOM | 2109 | CB | TYR | 228 | 6.321 | 24.544 | 18.502 | 1.00 3.07 |
| ATOM | 2110 | CG | TYR | 228 | 6.709 | 25.806 | 17.775 | 1.00 2.00 |
| ATOM | 2111 | CD1 | TYR | 228 | 5.745 | 26.627 | 17.220 | 1.00 6.58 |
| ATOM | 2112 | CE1 | TYR | 228 | 6.085 | 27.801 | 16.566 | 1.00 8.20 |
| ATOM | 2113 | CD2 | TYR | 228 | 8.042 | 26.192 | 17.667 | 1.00 2.00 |
| ATOM | 2114 | CE2 | TYR | 228 | 8.397 | 27.372 | 17.017 | 1.00 4.75 |
| ATOM | 2115 | CZ | TYR | 228 | 7.407 | 28.171 | 16.464 | 1.00 7.14 |
| ATOM | 2116 | OH | TYR | 228 | 7.726 | 29.323 | 15.773 | 1.00 17.75 |
| ATOM | 2117 | HH | TYR | 228 | 8.674 | 29.467 | 15.777 | 1.00 0.00 |
| ATOM | 2118 | C | TYR | 228 | 5.182 | 22.342 | 18.535 | 1.00 5.39 |
| ATOM | 2119 | O | TYR | 228 | 4.005 | 22.311 | 18.874 | 1.00 8.14 |
| ATOM | 2750 | C | M32 | 300 | 8.267 | 25.094 | 7.801 | 1.00 25.03 |
| ATOM | 2751 | C1 | M32 | 300 | 8.858 | 23.853 | 7.444 | 1.00 25.98 |
| ATOM | 2752 | C2 | M32 | 300 | 8.379 | 24.441 | 10.246 | 1.00 20.98 |
| ATOM | 2753 | C3 | M32 | 300 | 8.980 | 23.178 | 9.869 | 1.00 24.37 |
| ATOM | 2754 | C4 | M32 | 300 | 9.212 | 22.895 | 8.505 | 1.00 29.21 |
| ATOM | 2755 | C5 | M32 | 300 | 8.010 | 25.433 | 9.161 | 1.00 22.21 |
| ATOM | 2756 | CL1 | M32 | 300 | 7.230 | 26.454 | 13.601 | 1.00 25.81 |
| ATOM | 2757 | C6 | M32 | 300 | 7.411 | 26.704 | 9.530 | 1.00 19.62 |
| ATOM | 2758 | C7 | M32 | 300 | 8.120 | 24.794 | 11.600 | 1.00 21.01 |
| ATOM | 2759 | C8 | M32 | 300 | 7.183 | 26.988 | 10.884 | 1.00 18.60 |
| ATOM | 2760 | C9 | M32 | 300 | 7.533 | 26.044 | 11.925 | 1.00 19.36 |
| ATOM | 2761 | S | M32 | 300 | 9.015 | 23.469 | 5.780 | 1.00 17.20 |
| ATOM | 2762 | O | M32 | 300 | 9.071 | 24.779 | 4.968 | 1.00 16.38 |
| ATOM | 2763 | O1 | M32 | 300 | 10.242 | 22.582 | 5.534 | 1.00 17.25 |
| ATOM | 2764 | C10 | M32 | 300 | 5.199 | 22.312 | 4.491 | 1.00 27.00 |
| ATOM | 2765 | O2 | M32 | 300 | 4.122 | 22.777 | 4.126 | 1.00 32.92 |
| ATOM | 2766 | C11 | M32 | 300 | 6.360 | 23.283 | 4.882 | 1.00 23.85 |
| ATOM | 2767 | N | M32 | 300 | 7.627 | 22.680 | 5.299 | 1.00 22.06 |
| ATOM | 2768 | C12 | M32 | 300 | 6.769 | 20.390 | 5.043 | 1.00 32.04 |
| ATOM | 2769 | C13 | M32 | 300 | 7.755 | 20.001 | 3.914 | 1.00 39.28 |
| ATOM | 2770 | O3 | M32 | 300 | 7.210 | 19.046 | 2.977 | 1.00 47.51 |
| ATOM | 2771 | C14 | M32 | 300 | 7.939 | 18.829 | 1.852 | 1.00 48.79 |
| ATOM | 2772 | C15 | M32 | 300 | 7.490 | 21.418 | 5.984 | 1.00 25.44 |
| ATOM | 2773 | N1 | M32 | 300 | 5.477 | 20.938 | 4.593 | 1.00 29.98 |
| ATOM | 2774 | C16 | M32 | 300 | 4.491 | 19.869 | 4.670 | 1.00 30.81 |
| ATOM | 2775 | C17 | M32 | 300 | 0.442 | 15.501 | 8.992 | 1.00 49.84 |
| ATOM | 2776 | N2 | M32 | 300 | 2.584 | 18.058 | 7.186 | 1.00 41.26 |
| ATOM | 2777 | C18 | M32 | 300 | 1.691 | 17.430 | 8.145 | 1.00 44.57 |
| ATOM | 2778 | C19 | M32 | 300 | 1.309 | 16.052 | 8.031 | 1.00 46.32 |
| ATOM | 2779 | C20 | M32 | 300 | 2.968 | 19.503 | 7.333 | 1.00 38.25 |
| ATOM | 2780 | C21 | M32 | 300 | 1.145 | 18.166 | 9.257 | 1.00 43.40 |
| ATOM | 2781 | C22 | M32 | 300 | 3.160 | 17.297 | 6.016 | 1.00 39.49 |
| ATOM | 2782 | C23 | M32 | 300 | 5.033 | 19.081 | 5.868 | 1.00 36.22 |
| ATOM | 2783 | O4 | M32 | 300 | 6.468 | 19.227 | 5.792 | 1.00 37.50 |
| ATOM | 2784 | C24 | M32 | 300 | 4.489 | 19.666 | 7.202 | 1.00 33.76 |
| ATOM | 2785 | N3 | M32 | 300 | -0.065 | 16.209 | 10.032 | 1.00 49.11 |
| ATOM | 2786 | C25 | M32 | 300 | 0.286 | 17.511 | 10.160 | 1.00 45.71 |
| ATOM | 2787 | C26 | M32 | 300 | 4.673 | 17.567 | 5.876 | 1.00 35.53 |

END

Human Factor Xa (Des-Gla domain)

Human Factor Xa (Des-Gla domain)—Compound A

Factor Xa Active Site

Factor Xa Active Site occupied Compound A

Stereo View
Factor Xa Active Site occupied Compound A

FIG. 48

①CHYMOTRYPSIN NO. IN 1FAX STRUCTURE
②AMINO ACID SEQUENCE OF THE SERINE PROTEASE DOMAIN IN FXA
③SERIAL NO. OF THE RESIDUES OF THE SERINE PROTEASE DOMAIN IN FXA

| ① | ② | ③ | ① | ② | ③ | ① | ② | ③ | ① | ② | ③ | ① | ② | ③ |
|---|---|---|---|---|---|---|---|---|---|---|---|---|---|---|
| 16 | ILE | 1 | 67 | ARG | 53 | 119 | ALA | 105 | 169 | LYS | 157 | 220 | CYS | 209 |
| 17 | VAL | 2 | 68 | VAL | 54 | 120 | PRO | 106 | 170 | LEU | 158 | 221 | ALA | 210 |
| 18 | GLY | 3 | 69 | GLY | 55 | 121 | ALA | 107 | 171 | SER | 159 | 222 | ARG | 211 |
| 19 | GLY | 4 | 70 | ASP | 56 | 122 | CYS | 108 | 172 | SER | 160 | 223 | LYS | 212 |
| 20 | GLN | 5 | 71 | ARG | 57 | 123 | LEU | 109 | 173 | SER | 161 | 223A | GLY | 213 |
| 21 | GLU | 6 | 72 | ASN | 58 | 124 | PRO | 110 | 174 | PHE | 162 | 224 | LYS | 214 |
| 22 | CYS | 7 | 73 | THR | 59 | 124A | GLU | 111 | 175 | ILE | 163 | 225 | TYR | 215 |
| 23 | LYS | 8 | 74 | ALA | 60 | 125 | ARG | 112 | 176 | ILE | 164 | 226 | GLY | 216 |
| 24 | ASP | 9 | 75 | ALA | 61 | 126 | ASP | 113 | 177 | THR | 165 | 227 | ILE | 217 |
| 25 | GLY | 10 | 76 | GLU | 62 | 127 | TRP | 114 | 178 | GLN | 166 | 228 | TYR | 218 |
| 26 | GLU | 11 | 77 | GLU | 63 | 128 | ALA | 115 | 179 | ASN | 167 | 229 | THR | 219 |
| 27 | CYS | 12 | 78 | GLY | 64 | 129 | GLU | 116 | 180 | MET | 168 | 230 | LYS | 220 |
| 28 | PRO | 13 | 79 | GLY | 65 | 130 | SER | 117 | 181 | PHE | 169 | 231 | VAL | 221 |
| 29 | TRP | 14 | 80 | GLU | 66 | 131 | THR | 118 | 182 | CYS | 170 | 232 | THR | 222 |
| 30 | GLN | 15 | 81 | ALA | 67 | 131A | LEU | 119 | 183 | ALA | 171 | 233 | ALA | 223 |
| 31 | ALA | 16 | 82 | VAL | 68 | 131B | MET | 120 | 184 | GLY | 172 | 234 | PHE | 224 |
| 32 | LEU | 17 | 83 | HIS | 69 | 132 | THR | 121 | 185 | TYR | 173 | 235 | LEU | 225 |
| 33 | LEU | 18 | 84 | GLU | 70 | 133 | GLN | 122 | 185A | ASP | 174 | 236 | LYS | 226 |
| 34 | ILE | 19 | 85 | VAL | 71 | 134 | LYS | 123 | 185B | THR | 175 | 237 | TRP | 227 |
| 35 | ASN | 20 | 86 | GLU | 72 | 135 | THR | 124 | 186 | LYS | 176 | 238 | ILE | 228 |
| 36 | GLU | 21 | 87 | VAL | 73 | 136 | GLY | 125 | 187 | GLN | 177 | 239 | ASP | 229 |
| 37 | GLU | 22 | 88 | VAL | 74 | 137 | ILE | 126 | 188 | GLU | 178 | 240 | ARG | 230 |
| 38 | ASN | 23 | 89 | ILE | 75 | 138 | VAL | 127 | 189 | ASP | 179 | 241 | SER | 231 |
| 39 | GLU | 24 | 90 | LYS | 76 | 139 | SER | 128 | 190 | ALA | 180 | 242 | MET | 232 |
| 40 | GLY | 25 | 91 | HIS | 77 | 140 | GLY | 129 | 191 | CYS | 181 | 243 | LYS | 233 |
| 41 | PHE | 26 | 92 | ASN | 78 | 141 | PHE | 130 | 192 | GLN | 182 | 244 | THR | 234 |
| 42 | CYS | 27 | 93 | ARG | 79 | 142 | GLY | 131 | 193 | GLY | 183 | | | |
| 43 | GLY | 28 | 94 | PHE | 80 | 143 | ARG | 132 | 194 | ASP | 184 | | | |
| 44 | GLY | 29 | 95 | THR | 81 | 144 | THR | 133 | 195 | SER | 185 | | | |
| 45 | THR | 30 | 96 | LYS | 82 | 145 | HIS | 134 | 196 | GLY | 186 | | | |
| 46 | ILE | 31 | 97 | GLU | 83 | 147 | GLU | 135 | 197 | GLY | 187 | | | |
| 47 | LEU | 32 | 98 | THR | 84 | 148 | LYS | 136 | 198 | PRO | 188 | | | |
| 48 | SER | 33 | 99 | TYR | 85 | 149 | GLY | 137 | 199 | HIS | 189 | | | |
| 49 | GLU | 34 | 100 | ASP | 86 | 150 | ARG | 138 | 200 | VAL | 190 | | | |
| 50 | PHE | 35 | 101 | PHE | 87 | 151 | GLN | 139 | 201 | THR | 191 | | | |
| 51 | TYR | 36 | 102 | ASP | 88 | 152 | SER | 140 | 202 | ARG | 192 | | | |
| 52 | ILE | 37 | 103 | ILE | 89 | 153 | THR | 141 | 203 | PHE | 193 | | | |
| 53 | LEU | 38 | 104 | ALA | 90 | 154 | ARG | 142 | 204 | LYS | 194 | | | |
| 54 | THR | 39 | 105 | VAL | 91 | 155 | LEU | 143 | 205 | ASP | 195 | | | |
| 55 | ALA | 40 | 106 | LEU | 92 | 156 | LYS | 144 | 206 | THR | 196 | | | |
| 56 | ALA | 41 | 107 | ARG | 93 | 157 | MET | 145 | 207 | TYR | 197 | | | |
| 57 | HIS | 42 | 108 | LEU | 94 | 158 | LEU | 146 | 208 | PHE | 198 | | | |
| 58 | CYS | 43 | 109 | LYS | 95 | 159 | GLU | 147 | 209 | VAL | 199 | | | |
| 59 | LEU | 44 | 110 | THR | 96 | 160 | VAL | 148 | 210 | THR | 200 | | | |
| 60 | TYR | 45 | 111 | PRO | 97 | 161 | PRO | 149 | 211 | GLY | 201 | | | |
| 61 | GLN | 46 | 112 | ILE | 98 | 162 | TYR | 150 | 212 | ILE | 202 | | | |
| 61A | ALA | 47 | 113 | THR | 99 | 163 | VAL | 151 | 213 | VAL | 203 | | | |
| 62 | LYS | 48 | 114 | PHE | 100 | 164 | ASP | 152 | 214 | SER | 204 | | | |
| 63 | ARG | 49 | 115 | ARG | 101 | 165 | ARG | 153 | 215 | TRP | 205 | | | |
| 64 | PHE | 50 | 116 | MET | 102 | 166 | ASN | 154 | 216 | GLY | 206 | | | |
| 65 | LYS | 51 | 117 | ASN | 103 | 167 | SER | 155 | 217 | GLU | 207 | | | |
| 66 | VAL | 52 | 118 | VAL | 104 | 168 | CYS | 156 | 218 | GLY | 208 | | | |

TRICYCLIC COMPOUND HAVING SPIRO UNION

This application is a continuation-in-part of PCT application no. PCT/JP00/04374 filed on Jun. 30, 2000, which designated the United States and on which priority is claimed under 35 U.S.C. §120. This application further claims priority under 35 U.S.C. §119 to Japanese applications H11-222883 filed on Jun. 30, 1999 and 2000-399998 filed on Dec. 28, 2000 The entire contents of these applications are hereby incorporated by reference.

TECHNICAL FIELD

This invention relates to orally administrable tricyclic compounds having spiro union or its salts thereof that are useful as pharmaceuticals, particularly as an inhibitor of activated blood coagulation factor X (hereunder referred to as FXa), and which exhibit potent anticoagulation action.

This invention also relates to a drug designing methods by means of molecular design for creating a compound, which exhibits inhibitory activity for FXa.

BACKGROUND TECHNOLOGY

With the westernization of the life style and the increasing number of aged people, ischemic heart diseases and other pathology of heart and blood vessels are increasing year after year. In particular, increase of vascular occlusive diseases such as myocardial infarction, cerebral thrombosis, pulmonary embolism, and peripheral arterial and venous occlusive disease is increasing each year and treatment of such diseases has become a serious social issue. In the treatment and prevention of the thrombosis, anticoagulation therapy has been playing an important role in internal medicine together with anti-platelet therapy and thrombolytic therapy. For the treatment and prevention of thrombosis, safety that permits long-term drug administration and the development of a positive and appropriate anticoagulant activity are essential. Heretofore, anticoagulants such as warfarin and heparin have been used in order to prevent and treat thrombosis due to hypercoagulability. However, such use of the anticoagulants has been pointed to be associated with various demerits including the risk of bleeding and interactions with other drugs. Warfarin is extensively used in the world as the solo peroral anticoagulant. However, due to its characteristics based on the mechanism of action, the concentration range for the development of efficacy is narrow and yet it takes long to develop efficacy and the half-life in blood is as long as 36 hours; what is more, for several reasons such as the great individual difference of effective dose, it is difficult to control the anticoagulability of warfarin (N. Eng. J. Med. 324 (26) 1865–1875, 1991) and frequent monitoring is required in order to prevent bleeding as a side effect. In addition, warfarin also has many other side effects such as nausea, vomiting, diarrhea, and alopecia; thus, warfarin is a drug that involves considerable difficulty in clinical use. On the other hand, heparin is extensively used in the world as an intravenously administrable anticoagulant. However, since it is a direct inhibitor of thrombin, heparin has a high risk of bleeding and needs as frequent monitoring as warfarin; what is more, due to its characteristics based on the mechanism of action, adequate coagulation inhibiting effect is not expected at a lowered antithrombin III level; thus, heparin is a drug that involves considerable difficulty in clinical use. In view of such situation, improved anticoagulants have been desired that has none of the defects inherent in warfarin and heparin.

The blood coagulation cascade is a chain reaction involving limited protein hydrolysis triggered by activation of the extrinsic coagulation cascade or the intrinsic coagulation cascade, and once the cascade is activated, the reaction is amplifies like an avalanche. Since the final stage of the blood coagulation cascade is thrombin-mediated conversion of fibrinogen to fibrin, efforts have recently been made to develop thrombin inhibitors; however, drugs that directly inhibit thrombin are known to increase the risk of bleeding. In addition, they have low bioavailability in oral administration; therefore no thrombin inhibitor, which can be orally administered, has been introduced into market.

FXa is a key enzyme, which is located in the upstream of the thrombin in the coagulation cascade, and also at the point of convergence between the extrinsic and the intrinsic coagulation cascade. One molecule of FXa is known to produce about a hundred molecules of thrombin per minute. Therefore, an FXa inhibitor can potentially inhibit the coagulation cascade more efficiently than a thrombin inhibitor (Thrombosis Research, vol. 19, pages 339–349, 1980; Mebio vol. 14, No. 8, 1997).

Compounds that exhibit FXa inhibiting actions have been disclosed in several patents, among which Japanese Patent Application Laid-Opened No.208946/1993 and WO96/16940 disclose aromatic amidine derivatives, and in particular, amidinonaphthyl derivatives, and WO97/38984 and the like disclose cyclic urea compounds having an aminodiphenyl group. However, these compounds are still in the process of development and none have been commercialized to date.

These compounds also suffer from low bioavailability in oral administration, and there is good room of improvement in separating the thrombin inhibitory action and the trypsin inhibitory action from the FXa inhibitory action. In addition, there is apprehension that these compounds are associated with decrease of blood pressure, respiratory insufficiency, and other side effects induced by the amidino group.

With regard to the compound of Japanese Patent Application Laid-Opened No. 208946/1993, use of this compound as a preventive and therapeutic agent for influenza virus is disclosed. The activity of this agent to inhibit the influenza virus propagation is based on the FXa inhibitory action.

Compounds having an aminoheterocyclic group typified by 1-(4-pyridyl)piperidin-4-yl group can be used as FXa inhibitor; for example, disclosed in prior art references including WO96/10022, WO97/28129, WO97/29104, WO98/21188, WO98/54164, WO99/06371, and WO99/09027.

These compounds have been developed for the purpose of providing an FXa inhibitor, which is effective in oral absorption. However, low molecular weight FXa inhibitors are still under development and no drug of low molecular weight FXa inhibitors has been commercialized.

In the development of pharmaceutical products, the desired pharmacological activity is not the sole requirement. Another requirement is that strict criteria be met in various aspects including absorption, distribution, metabolism and excretion, and the like. For example, the drugs are required to pass various examinations for drug interaction, desensitization or tolerance, absorption from digestive tract in the oral administration, transfer rate to small intestine, absorption rate and first pass effect, organ barrier, protein binding, induction of drug metabolizing enzyme, excretion pathway and clearance from body, administration method (site, method, and purpose of administration), and the like, and a drug meeting all such requirements are seldom discovered.

The anticoagulants also share such general challenge of the drug development.

In the case of the FXa inhibitor, circumvention of the problem of the side effects associated with the oral administration of the warfarin as well as risk of bleeding based on the thrombin inhibition as found in the case of heparin whose administration is only accomplished by intravenous injection is required.

When the FXa inhibitor is constructed by molecular designing method, condition of the binding between the FXa and the FXa inhibitor has great significance. In the three-dimensional structure of FXa, active site of the FXa is formed in the structure characteristic to a chymotrypsin-like serine protease.

The active center of a serine protease is formed from a plurality of pockets called subsites, and it is known that substantially all of the inhibitors which do not form covalent bond with Ser195 residue bind to these pockets. Among such pockets, S1 pocket is believed to be the most important in the serine protease in the binding with the substrate, or in the development of the substrate selectivity.

S1 site is also believed to be the most important in the serine protease inhibitor for the development of the inhibitory activity and the enzyme selectivity. The residue which is generally believed to be the most important for the substrate specificity in the S1 pocket is the residue corresponding to chymotrypsin No. 189, and FXa has Asp (Asp189) as this residue and the inside of the pocket is believed to be negatively charged.

However, this is also the case in serine proteases other than the FXa, namely, in trypsin, thrombin, protein C, tissue plasminogen activator, and the like, and such resemblance is one cause of difficulty in enzyme specificity in FXa inhibitor. The substrate specificity of the entire enzyme is determined by structural difference of the subsite such as S3 pocket in addition to the structural difference of S1, and designing of an inhibitor selective for FXa can be accomplished by using such structural difference.

With regard to the binding state between the FXa and the FXa inhibitor, there has been only the report for specific compounds (DX-9065a and FX-2212a) by X-ray crystallographic analysis.

In DX-9065a, amidino group is bound to S1 pocket of the FXa, and in particular, Asp189 and the amidino group are firmly bound to each other by electrostatic interaction and hydrogen bonds. This is the binding manner commonly known in trypsin inhibitors and thrombin inhibitors.

It has also been found out for FX-2212a that the amidino group is bound to the S1 pocket of the FXa by the similar known binding manner (J. Biol. Chem. 1996 Nov. 22; 271(47):29988–92 Brandstetter H. et al., Proc. Natl. Acad. Sci. USA (1998) Jun. 9; 95(12):6630–5 Kamata K. et al.).

However, DX-9065a and FX-2212a are insufficient in their efficacy in oral administration, and there was also apprehension for the side effects induced by amidino group and guanidino group. In the meanwhile, it has not been even found out for the FXa inhibitors having other structure whether such X-ray crystallographic analysis is possible, and the binding state with the FXa was not at all found out.

Accordingly, despite the recognition of the usefulness of the amidino group and the guanidino group, there has been no indication as to what structure should be focused in the effort of searching or developing the FXa inhibitor of different type wherein such defects have been improved since no clue has been provided from the information on interaction based on the crystal structure data of such complex of the FXa with known FXa inhibitory compound, and the structural clue has been sincerely awaited.

DISCLOSURE OF THE INVENTION

In view of such situation, there is a demand for an anticoagulant drug which exhibits high safety and excellent effectivity, and which is easy to use. To be more specific, there is a high demand for an anticoagulant which can be orally administered to human and other mammals, and in particular, which can be readily used in clinical practice, and which has realized at least one of avoidance of interaction with other drugs, reduced side effects including reduced risk of bleeding, improved dose response, and the like.

In addition, in the search and development of an FXa inhibitor, there is a high demand for proposal of a pharmacophore (pharmacophore:parameter in the molecular design which can be used in the discovery of the inhibitor by means of computer-aided drug design) which can be used in the discovery of drugs of the type different from DX-9065a and the like which exhibit same type of bonding as the trypsin inhibitor and the thrombin inhibitor, and which is useful in the association state between the FXa and the FXa inhibitor to give an important indication.

It should be noted that use of such parameter will enable, for example, in the course of discovering the FXa inhibitory compounds which do not have amidino group or guanidino group, computer-aided construction and search of search parameter for the inhibitory compound; conversion into a compound which can serve as a drug comprising a protein substrate for FXa; departure from known skeleton of the FXa inhibitory compounds exhibiting side effects; de novo design based on the novel pharmacophore; and change of the specificity based on the new parameter owned by the inhibitor for serine protease other than FXa; and the like.

The inventors of the present invention conducted an intensive study in order to solve the problems as described above and to provide a compound which has excellent FXa inhibitory action, and found that the compound of formula (I) having spiro skeleton exhibits remarkably excellent FXa inhibitory action. The present invention has been completed on the bases of such finding.

The inventors of the present invention also succeeded in producing the crystal of the complex of the FXa inhibitor of the present invention and the FXa, and found an important pharmacophore useful in discovering the FXa inhibitor of the type which is different from DX-9065a and the like through the analysis of such crystal. The present invention has been completed also on the basis of such finding.

BRIEF DESCRIPTION OF THE DRAWINGS

FIG. 1 is a view showing structural formulae of the compounds of the present invention.

FIG. 2 is a view showing structural formulae of the compounds of the present invention.

FIG. 3 is a view showing structural formulae of the compounds of the present invention.

FIG. 4 is a view showing structural formulae of the compounds of the present invention.

FIG. 5 is a view showing structural formulae of the compounds of the present invention.

FIG. 6 is a view showing structural formulae of the compounds of the present invention.

FIG. 7 is a view showing structural formulae of the compounds of the present invention.

FIG. 8 is a view showing structural formulae of the compounds of the present invention.

FIG. 9 is a view showing structural formulae of the compounds of the present invention.

FIG. 10 is a view showing structural formulae of the reference compounds B and C.

FIG. 21 is a view showing physical property data (NMR spectrum) of the compounds of the present invention.

FIG. 22 is a view showing physical property data (NMR spectrum) of the compounds of the present invention.

FIG. 23 is a view showing physical property data (NMR spectrum) of the compounds of the present invention.

FIG. 24 is a view showing physical property data (NMR spectrum) of the compounds of the present invention.

FIG. 25 is a view showing physical property data (NMR spectrum) of the compounds of the present invention.

FIG. 26 is a view showing physical property data (NMR spectrum) of the compounds of the present invention.

FIG. 27 is a view showing physical property data (NMR spectrum) of the compounds of the present invention.

FIG. 28 is a view showing physical property data (NMR spectrum) of the compounds of the present invention.

FIG. 29 is a view showing physical property data (NMR spectrum) of the compounds of the present invention.

FIG. 30 is a view showing physical property data (NMR spectrum) of the compounds of the present invention.

FIG. 31 is a view showing physical property data (NMR spectrum) of the compounds of the present invention.

FIG. 32 is a view showing physical property data (NMR spectrum) of the compounds of the present invention.

FIG. 33 is a view showing physical property data (NMR spectrum) of the compounds of the present invention.

FIG. 34 is a view showing physical property data (NMR spectrum) of the compounds of the present invention.

FIG. 35 is a view showing physical property data (NMR spectrum) of the compounds of the present invention.

FIG. 36 is a view showing physical property data (NMR spectrum) of the compounds of the present invention.

FIG. 37 is a view showing physical property data (NMR spectrum) of the compounds of the present invention.

FIG. 38 is a view showing physical property data (NMR spectrum) of the compounds of the present invention.

FIG. 39 is a view showing physical property data (X ray chart table) of the compounds of the present invention.

FIG. 40 is a view showing physical property data (X ray chart table) of the compounds of the present invention.

FIG. 41 is a view showing physical property data (X ray chart table) of the compounds of the present invention.

FIG. 42 is a view showing physical property data (X ray chart table) of the compounds of the present invention.

FIG. 48 is a view of the table showing serial Nos. of the residues of serine protease domain of FXa corresponding to the chymotrypsin Nos. in the amino acid sequence of the serine protease domain of FXa.

BEST EMBODIMENTS FOR CARRYING OUT THE INVENTION

Figure 11:
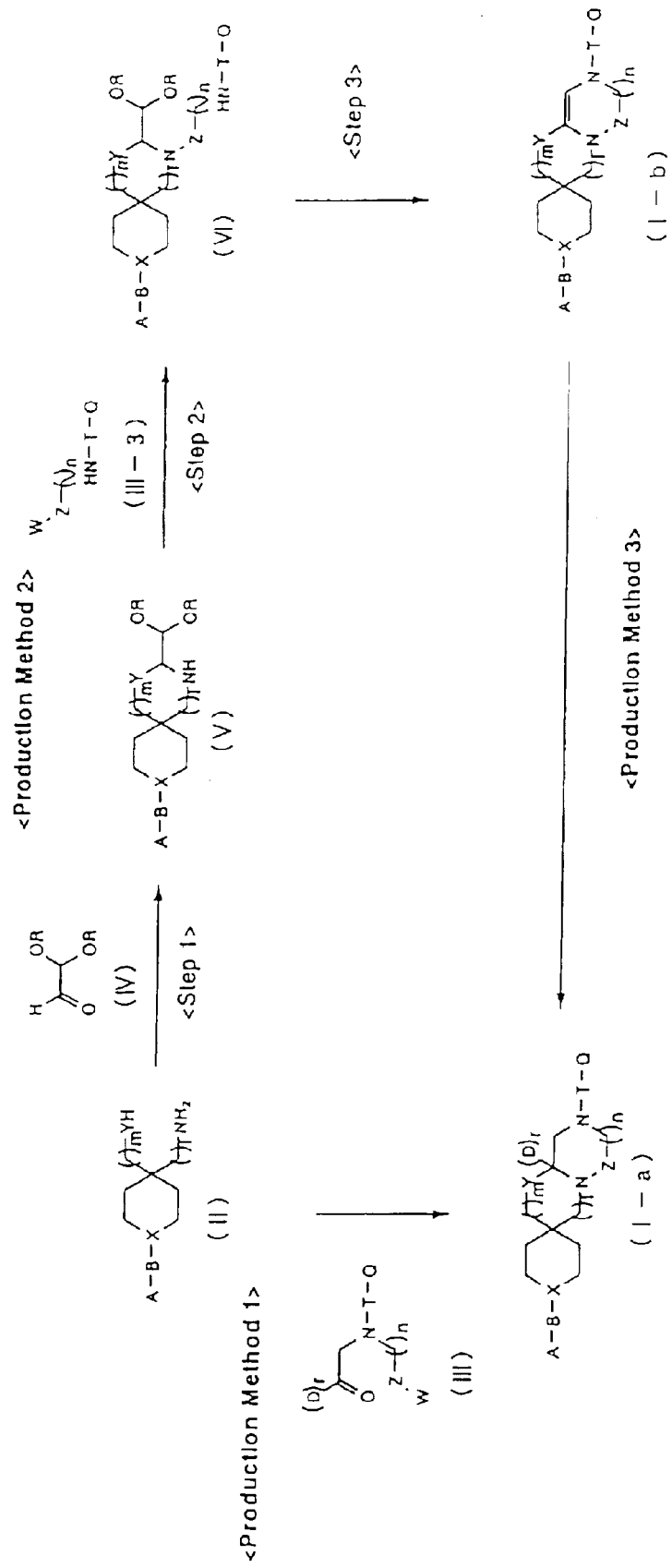
FIG. 11 is a view showing synthesis route of the compound of the present invention.
Figure 12:
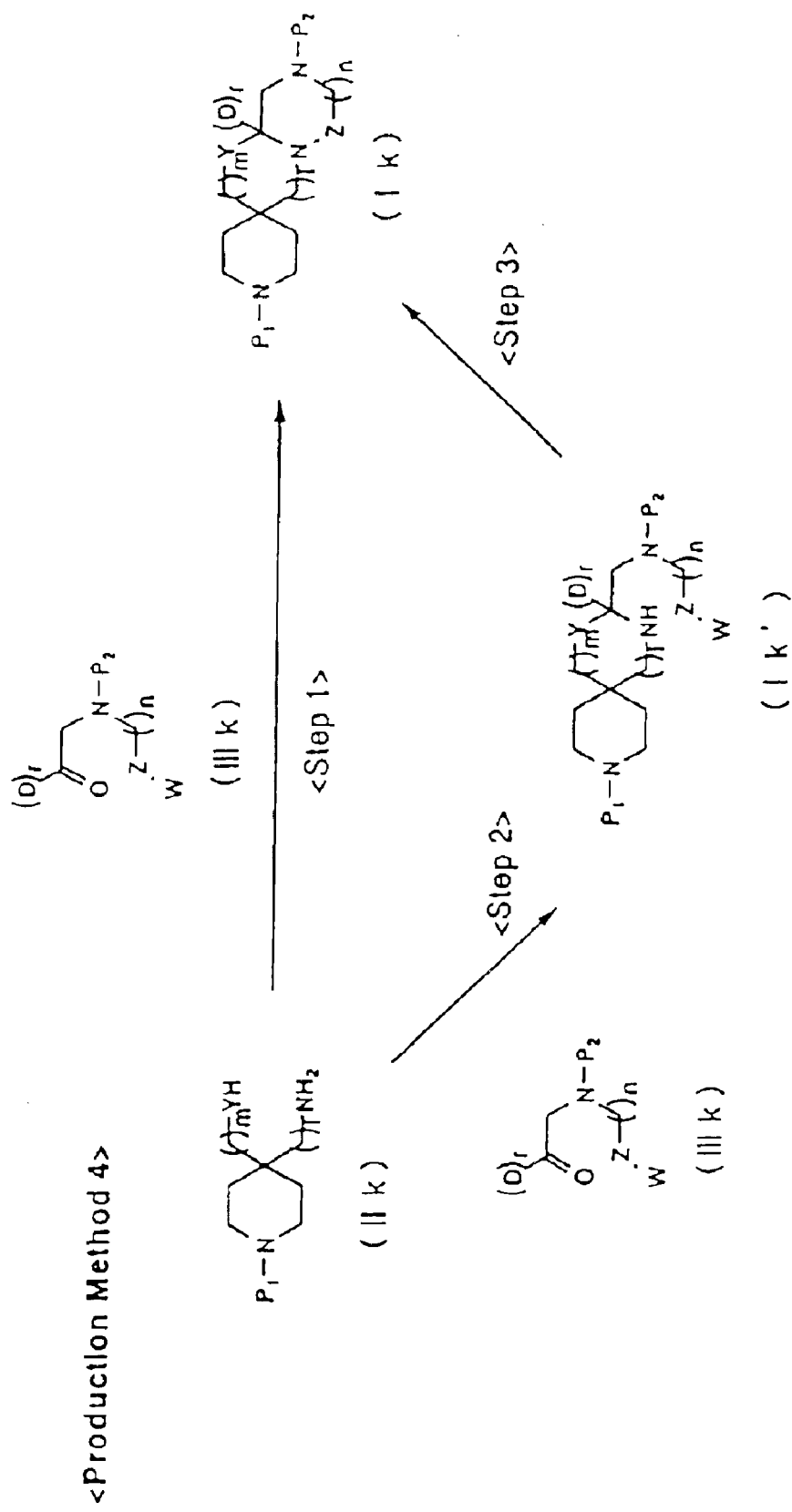
FIG. 12 is a view showing synthesis route of the compound of the present invention.
Figure 13:
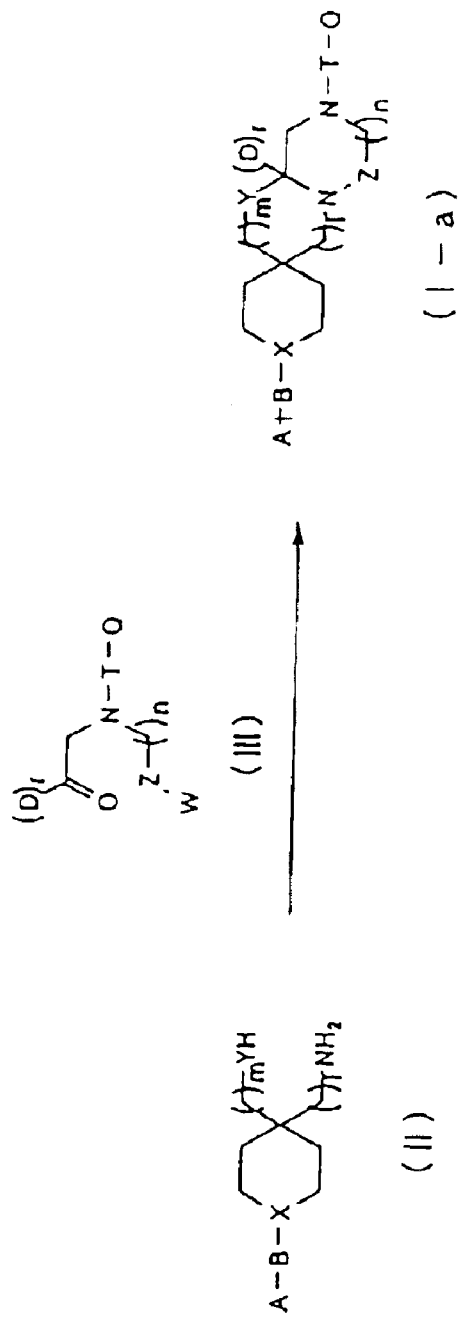
FIG. 13 is a view showing synthesis route of the compound of the present invention.
Figure 14:
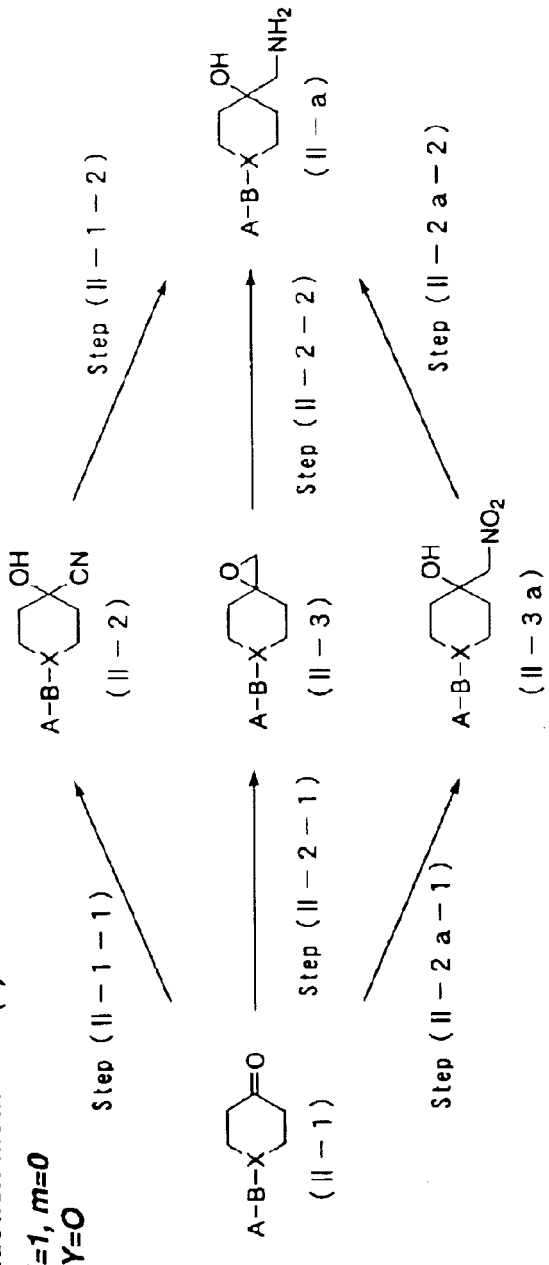
FIG. 14 is a view showing synthesis route of the compound of the present invention.
Figure 15A:
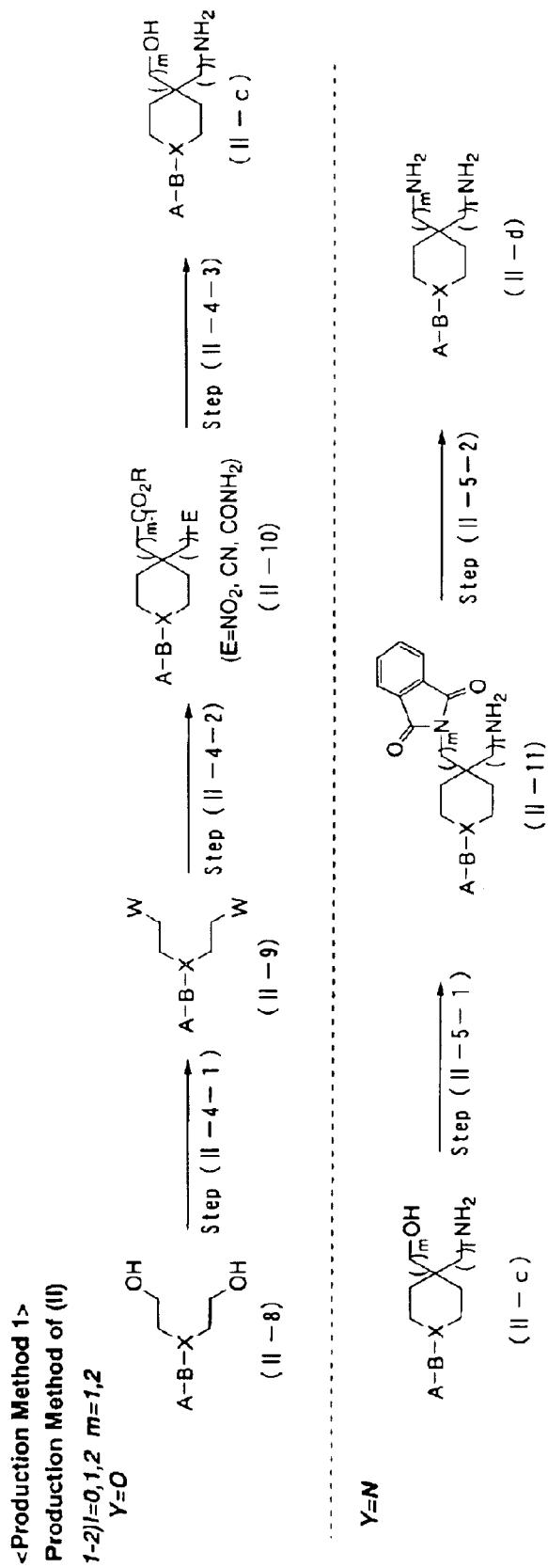
FIGS. 15A and 15B are views showing synthesis route of the compound of the present invention.
Figure 15B:
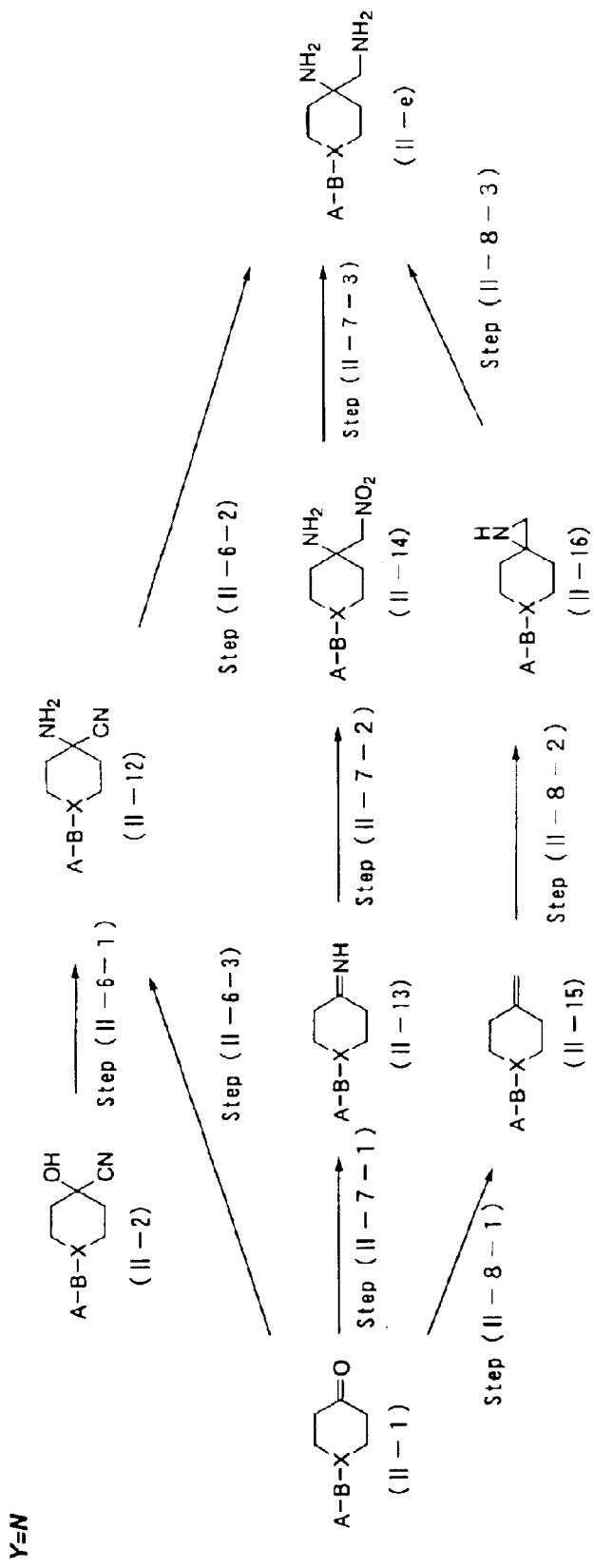
Figure 16:
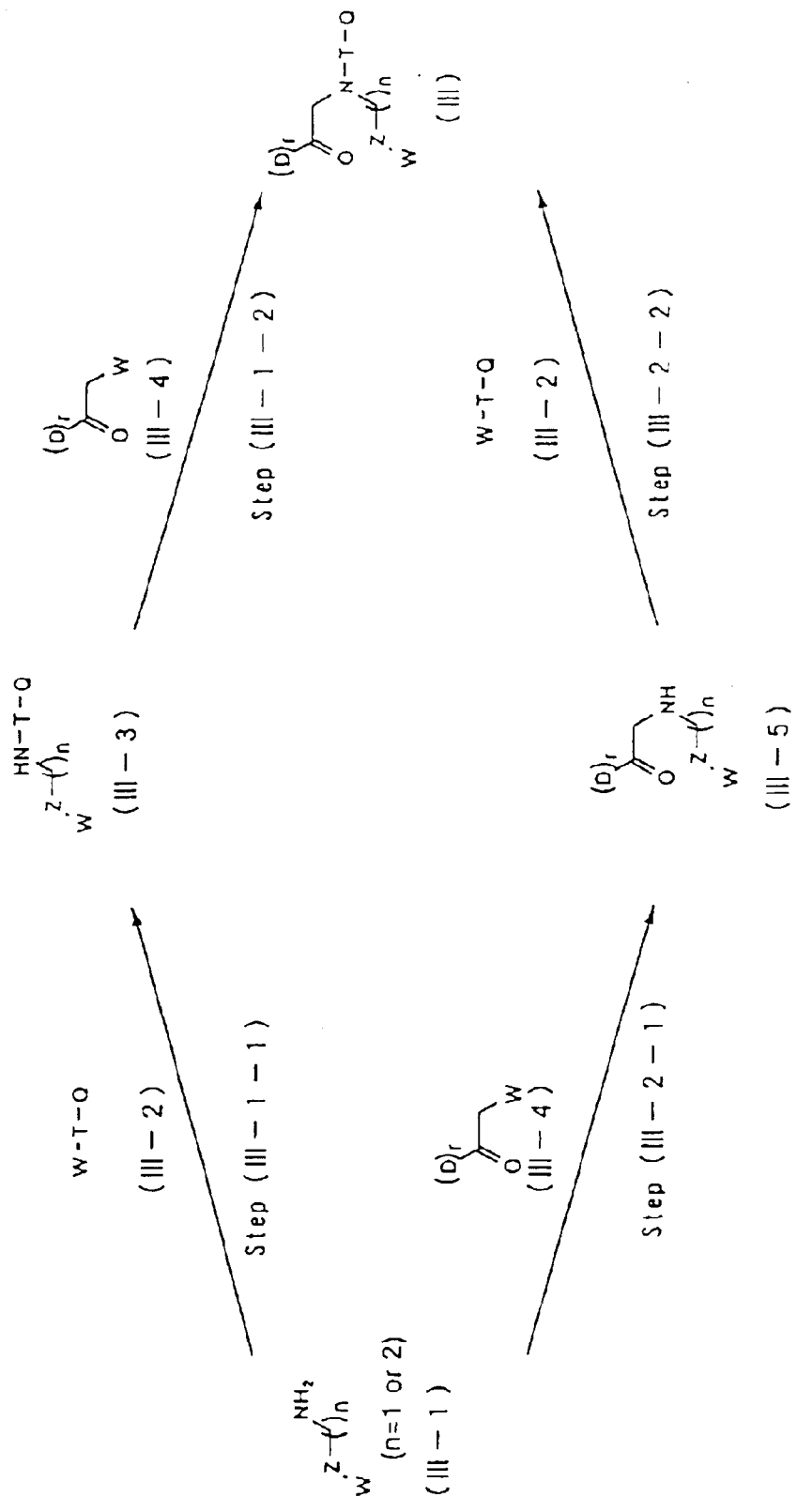
FIG. 16 is a view showing synthesis route of the compound of the present invention.
Figure 17:
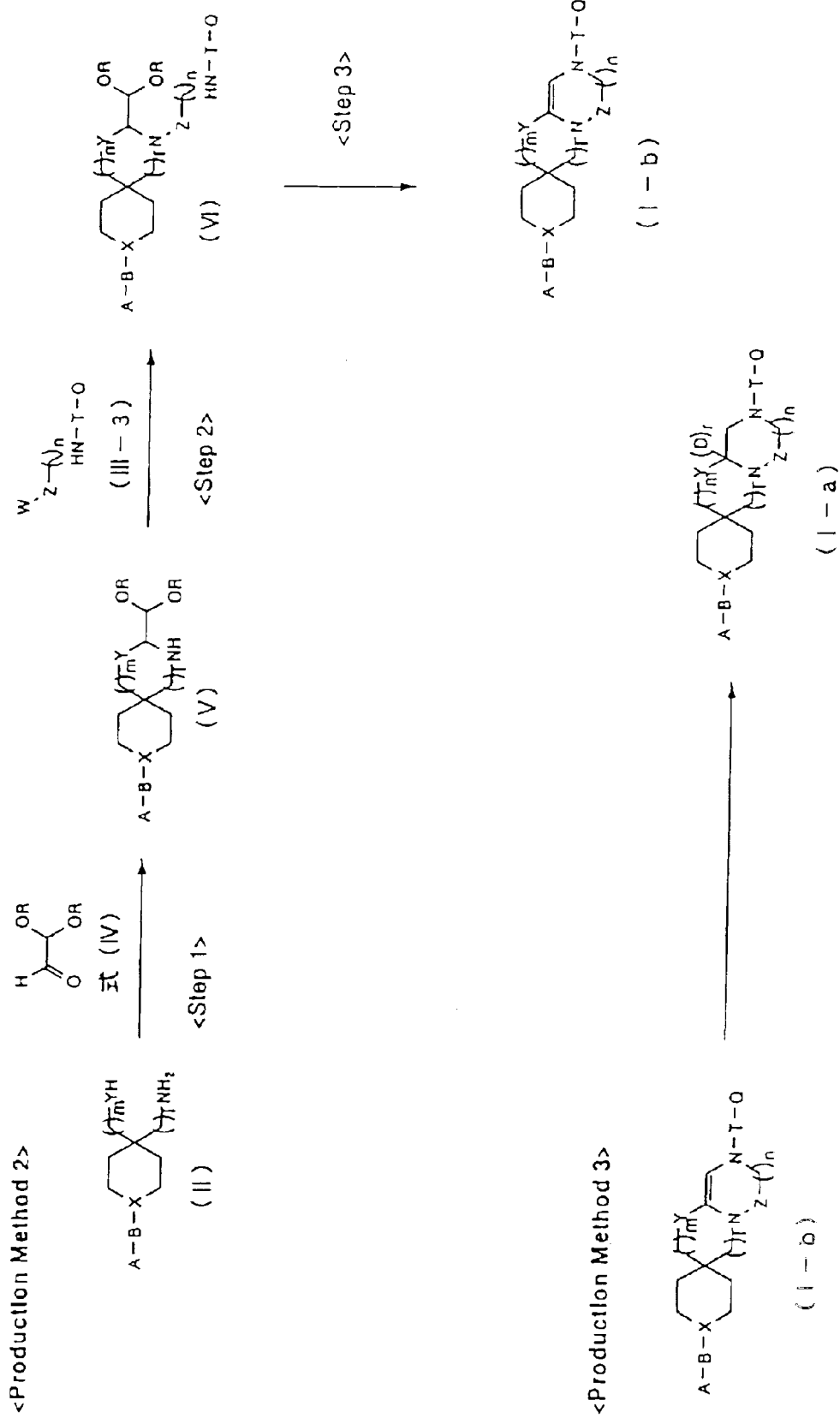
FIG. 17 is a view showing synthesis route of the compound of the present invention.
Figure 18:
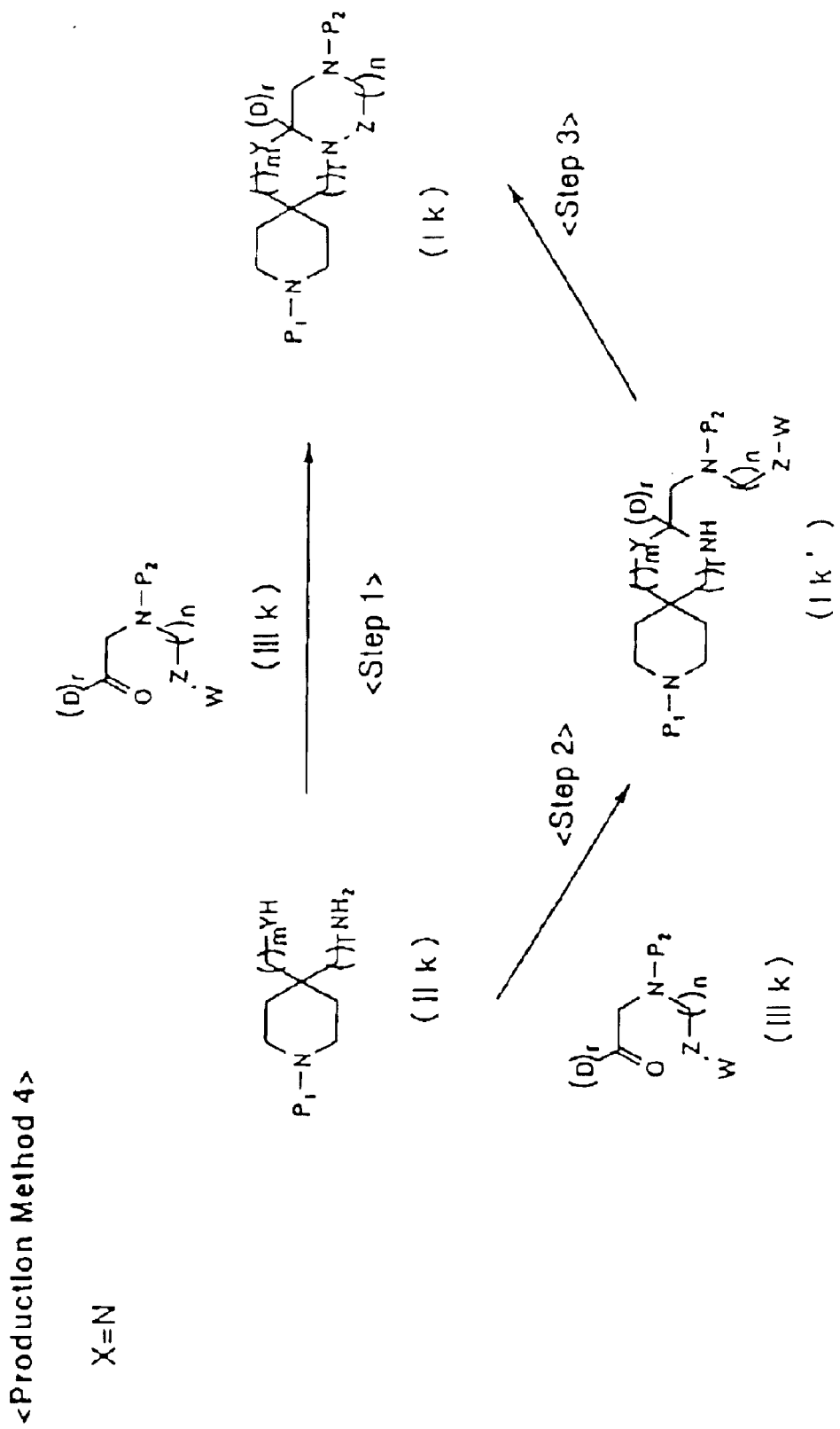
FIG. 18 is a view showing synthesis route of the compound of the present invention.
Figure 19:
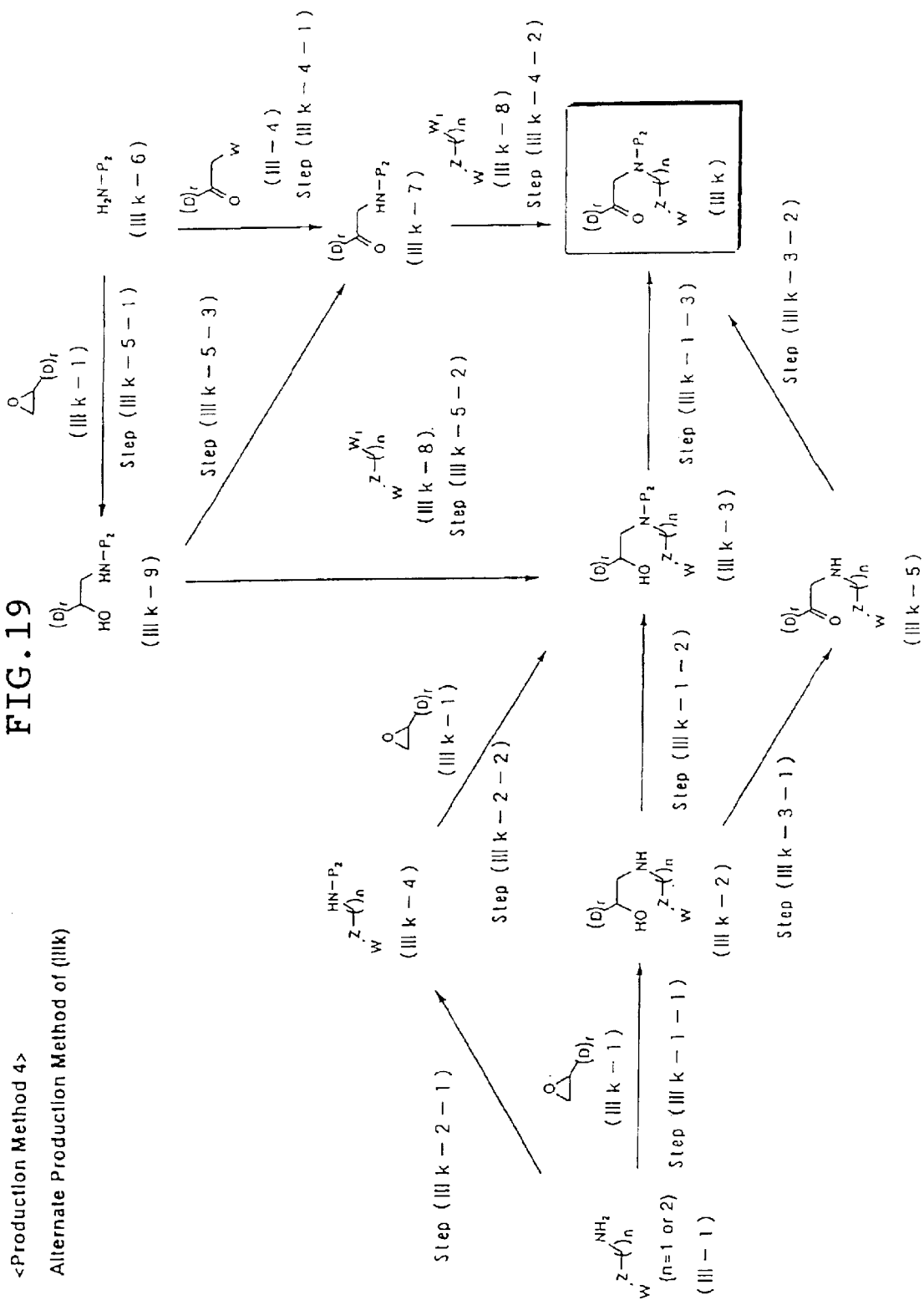
FIG. 19 is a view showing synthesis route of the compound of the present invention.
Figure 20:
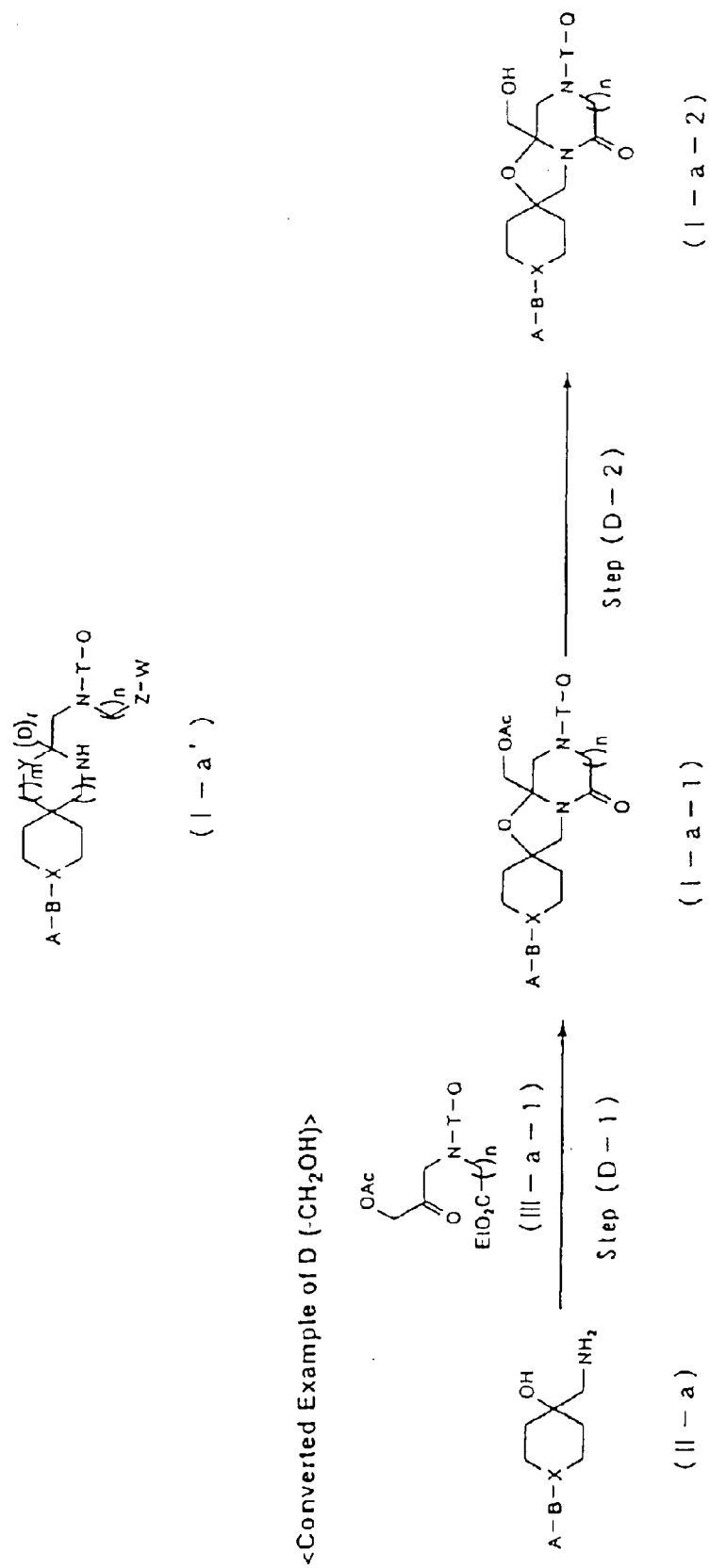
FIG. 20 is a view showing synthesis route of the compound of the present invention.

Next, the present invention is described in detail. The present invention relates to a tricyclic compound having spiro union as represented by formula (I) which will be described below, intermediates thereof, and pharmacophores which are useful in molecule design of a FXa inhibitor.

Various embodiments of the present invention are described in the following. In the compound of the present invention, "$C_{1-6}$", for example, means that "the group is a straight chain or branched group containing 1 to 6 carbon atoms" unless otherwise noted. In the case of a cyclic group, "$C_{1-6}$" denotes "the number of ring member carbon atoms".

The compound of formula (I) and the compound of formula (I') according to the present invention are not particularly limited for their molecular weight. The molecular weight, however, is preferably up to 1000, and more preferably up to 700 (and otherwise stated, the total number of carbon atoms constituting the compound is less than 40). Such limitation of molecular weight is routinely employed for identifying the structure of the compound as a major limiting factor in addition to the pharmacologically characteristic basic skeleton in recent drug design. In particular, the molecular weight is preferably limited to the range of up to 1000 when oral absorptivity of the drug is taken into consideration.

[1] First Aspect of the Invention

The compound of this invention is represented by formula (I) or its pharmaceutically acceptable salt.

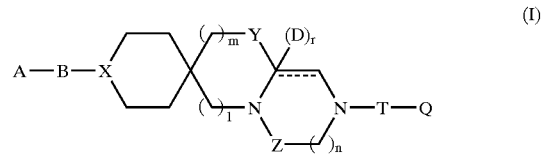

(I)

In the formula, A is a hydrogen atom, or a group selected from (1) a saturated or unsaturated five- or six-membered cyclic hydrocarbon group, or a saturated or unsaturated five- or six-membered heterocyclic group, (2) an amino group, and (3) an imidoyl group (wherein the groups of (1) to (3) are optionally substituted);

B is a single bond, a carbonyl group, —S(O)$_x$—, or an optionally substituted C$_{1-2}$ alkylene group;

D is a hydrogen atom, —CO—R$_5$ (wherein R$_5$ is hydrogen atom or a substituent), or an optionally substituted C$_{1-6}$ alkyl group;

X is a nitrogen atom or a methine group optionally substituted with group A'-B'- (wherein A' represents a group selected from those defined for A, and B' represents a group selected from those defined for B);

Y is an oxygen atom, —S(O)$_y$—, or an optionally substituted imino group (—NH—);

Z is a methylene group, a carbonyl group, or a thiocarbonyl group;

T is —S(O)$_z$—, a carbonyl group, or an optionally substituted C$_{1-2}$ alkylene group;

Q is a hydrocarbon group or a heterocyclic group, which are optionally substituted;

l, m, n, x, y, and z are independently an integer selected from 0, 1 and 2 with the proviso that l and m are not simultaneously 0; and r is an integer of 0 or 1; and the three rings (the ring containing X, the ring containing Y, and the ring containing Z) are independently optionally substituted; and the bond indicated by the broken line and the solid line in the ring containing Z is single bond or double bond (when r is 0).

Various groups included in the formula (I) are described in detail.

[1-1] In the compound of formula (I), Q is a hydrocarbon group or a heterocyclic group, and these groups may optionally have substituents. Exemplary "hydrocarbon groups" within the definition of Q include aliphatic hydrocarbon groups, alicyclic hydrocarbon groups, and aryl groups, and the preferred is an aryl group.

Exemplary "aliphatic hydrocarbon groups" include straight- or branched-chain hydrocarbon groups, for example, alkyl groups, alkenyl groups, alkynyl groups, and the like.

Exemplary "alkyl groups" include C$_{1-10}$ (and more preferably C$_{1-6}$) alkyl groups, for example, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-hexyl, 1-methyl-heptyl, and n-nonyl.

Exemplary "alkenyl groups" include C$_{2-6}$ alkenyl groups, for example, vinyl, allyl, isopropenyl, 2-methylallyl, butenyl, pentenyl, and hexenyl.

Exemplary "alkynyl groups" include C$_{2-6}$ alkynyl groups, for example, ethinyl, 1-propinyl, 2-propinyl, butinyl, pentynyl, and hexinyl.

Exemplary "alicyclic hydrocarbon groups" include saturated and unsaturated alicyclic hydrocarbon groups, for example, cycloalkyl group, cycloalkenyl group, and cycloalkanedienyl group.

Exemplary "cycloalkyl groups" include C$_{3-9}$ cycloalkyl groups, for example, cyclopropyl, cyclobutyl, cyclopentyl, cyclohexyl, cycloheptyl, cyclooctyl, and cyclononyl. Exemplary "cycloalkenyl groups" include C$_{3-6}$ cycloalkenyl groups, for example, 1-cyclopropen-1-yl, 1-cyclobuten-1-yl, 1-cyclopenten-1-yl, 2-cyclopenten-1-yl, 3-cyclopenten-1-yl, and 1-cyclohexen-1-yl.

Exemplary "cycloalkanedienyl groups" include C$_{4-6}$ cycloalkanedienyl groups, for example, 2,4-cyclopentadien-1-yl and 2,5-cyclohexadien-1-yl.

Exemplary "aryl groups" include C$_{6-14}$ aryl groups, for example, phenyl, naphthyl, biphenylyl, 2-anthryl, phenanthryl, acenaphthyl, and 5,6,7,8-tetrahydronaphthalenyl(2-yl), and among these, the preferred are phenyl, 2-naphthyl, and 1-naphthyl.

Exemplary heterocyclic groups of the "optionally substituted heterocyclic groups" in Q include aromatic heterocyclic groups, and saturated and unsaturated non-aromatic heterocyclic groups. Exemplary such heterocyclic groups include those having a five- to fourteen-membered ring, and preferably, a five- to twelve-membered ring containing at least one heteroatom (preferably 1 to 4 heteroatoms) selected from N, O and S in addition to the carbon atoms.

Exemplary "aromatic heterocyclic groups" include monocyclic and fused heterocyclic groups. Preferable monocyclic aromatic heterocyclic groups are those containing 5 to 6 ring members, for example, pyrolyl, furyl, thienyl, oxazolyl, imidazolyl, oxazolyl, isooxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,2,5-triazinyl, 1,3,5-triazinyl, and thiadiazinyl.

Preferable fused aromatic heterocyclic groups are those containing 8 to 12 ring members, for example, monovalent groups formed by condensation of the five- or six-membered aromatic ring as described above with 1 or a plurality of (preferably 1 to 2) aromatic rings (for example, benzene ring) followed by removal of hydrogen atom at an arbitrary position from the thus formed ring.

Exemplary such groups include indolyl, isoindolyl, 1H-indazolyl, benzofuranyl (-2-yl), isobenzofuranyl, benzothienyl (-2-yl), isobenzothienyl, benzindazolyl, benzoxazolyl (-2-yl), 1,2-benzoisoxazolyl, benzothiazolyl (-2-yl), 1,2-benzoisothiazolyl, 2H-benzopyranyl (-3-yl), (1H-) benzimidazolyl (-2-yl), 1H-benzotriazolyl, 4H-1,4-benzoxazinyl, 4H-1,4-benzothiazinyl, quinolyl, isoquinolyl, cinnolinyl, quinazolinyl, quinoxalinyl, phthalazinyl, naphthylizinyl, purinyl, pteridinyl, carbazolyl, carbolinyl, acridinyl, phenoxazinyl, phenothiazinyl, phenazinyl, phenoxazinyl, thianthrenyl, phenanthridinyl, phenanthrolinyl, indolizinyl, (4,5,6,7-) tetrahydrothiazolo[5,4-c]pyridyl (-2-yl), (4,5,6,7-) tetrahydrothieno[3,2-c] pyridyl, (1,2,3,4-) tetrahydroisoquinolyl (-6-yl), thiazolo[5,4-c]pyridyl (-2-yl), pyrolo[1,2-b]pyridazinyl, pyrazo[1,5-a] pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl (Preferred Embodiments are Indicated in the Bracket).

Exemplary "non-aromatic heterocyclic groups" include three- to eight-membered saturated and unsaturated non-aromatic heterocyclic groups, for example, azetidinyl, oxilanyl, oxetanyl, thietanyl, pyrolidinyl, tetrahydrofuryl, thiolanyl, pyrazolinyl, pyrazolidinyl, pyperidyl, tetrahydropyranyl, pyperadinyl, morpholinyl, thiomorpholinyl, and quinuclidinyl.

Exemplary "substituents" of the "optionally substituted hydrocarbon group" or the "optionally substituted heterocyclic group" in Q include (a) alkyl, alkenyl, alkynyl, aryl, cycloalkyl, and cycloalkenyl, (b) heterocyclic groups, (c) amino, (d) imidoyl, amidino, hydroxyl, thiol, and oxo, (e) halogen atoms such as fluorine, chlorine, bromine, and iodine, cyano, and nitro, (f) carboxyl, and (g) carbamoyl, thiocarbamoyl, sulfonyl, sulfinyl, sulfide and acyl. Of the (a) to (g) as described above, the groups excluding (e) may further comprise a substituent.

The "optionally substituted hydrocarbon group" and the "optionally substituted heterocyclic group" in Q may be arbitrarily substituted with 1 to 5 such substituents. Such substituents (a) to (f) are described in further detail.

(a) The alkyl, alkenyl, alkynyl, aryl, cycloalkyl, and cycloalkenyl groups may be any of the "alkyl groups", "alkenyl groups", "alkynyl groups", "aryl groups", "cycloalkyl groups" and "cycloalkenyl groups" mentioned as examples of the "hydrocarbon group" for Q, and the preferred are $C_{1-6}$ alkyl groups, $C_{2-6}$ alkenyl groups, $C_{2-6}$ alkynyl groups, $C_{6-14}$ aryl groups, $C_{3-7}$ cycloalkyl groups and $C_{3-6}$ cycloalkenyl groups.

These groups may further include an optional substituent RI (wherein RI represents a group selected from $C_{1-6}$ alkoxy, $C_{1-6}$ alkoxycarbonyl, carboxyl, carbamoyl which is optionally mono- or di-substituted with a $C_{1-6}$ alkyl, halogen, $C_{1-6}$ alkyl, halogenated $C_{1-6}$ alkyl, amino which is optionally mono- or di-substituted with a $C_{1-6}$ alkyl, $C_{2-6}$ alkenoylamino, nitro, hydroxyl, oxo, cyano, and amidino).

(b) The heterocyclic group may be any of the "aromatic heterocyclic groups" and "non-aromatic heterocyclic groups" mentioned as examples of the "heterocyclic group" for Q, and the preferred are (i) "five- or six-membered, monocyclic aromatic heterocyclic groups", (ii) "eight- to twelve-membered, fused, aromatic heterocyclic groups", and (iii) "three- to eight-membered, saturated or unsaturated, non-aromatic heterocyclic groups", which contain 1 to 4 heteroatoms selected from nitrogen atom, oxygen atom and sulfur atom in addition to the carbon atoms.

These groups may further include an optional substituent RII (wherein RII represents a group selected from $C_{1-6}$ alkyl groups, $C_{1-6}$ alkanoyl groups, and benzoyl group).

(c) The "optionally substituted amino group" may be, for example, amino group which is optionally mono- or di-substituted with substituent RIII (wherein RIII represents a group selected from $C_{1-6}$ alkyl, $C_{1-6}$ alkanoyl, $C_{2-6}$ alkenoyl, benzoyl, and $C_{1-6}$ alkoxycarbonyl which is optionally substituted with 1 to 5 halogen atoms), or three- to eight-membered monocyclic amino group which is optionally substituted with a group selected from $C_{1-6}$ alkyl, $C_{7-10}$ aralkyl and $C_{6-10}$ aryl.

(d) Exemplary substituents in the "optionally substituted imidoyl group, the optionally substituted amidino group, the optionally substituted hydroxyl group, and the optionally substituted thiol group" include RIII (RIII represents a group selected from $C_{1-6}$ alkyl, $C_{1-6}$ alkanoyl, $C_{2-6}$ alkenoyl, benzoyl, and $C_{1-6}$ alkoxycarbonyl which is optionally substituted with 1 to 5 halogen atoms) described in (c). Therefore, examples of (d) include $C_{1-6}$ alkylimidoyl groups, formimidoyl group or amidino group, benzyloxy group, $C_{1-6}$ alkanoyloxy groups, and oxo group.

(e) Halogen atoms such as fluorine, chlorine, bromine, and iodine, cyano group, and nitro group.

(f) The "optionally substituted carboxyl groups" include carboxyl group, $C_{1-6}$ alkoxycarbonyl groups, $C_{7-12}$ aryloxycarbonyl groups, and $C_{6-10}$ aryl-$C_{1-4}$ alkoxycarbonyl groups, and the aryl group in such (f) is optionally substituted with substituent RIV. RIV represents amino group which is mono- or di-substituted with substituent RII (wherein RII represents a $C_{1-6}$ alkyl group, a $C_{1-6}$ alkanoyl group, or benzoyl group) of (b); halogen atom; hydroxyl group; nitro group; cyano group; a $C_{1-6}$ alkyl group which is optionally substituted with 1 to 5 halogen atoms; or an alkoxy group which is optionally substituted with 1 to 5 halogen atoms.

(g) The "optionally substituted carbamoyl group, the optionally substituted thiocarbamoyl group, the optionally substituted sulfonyl, the optionally substituted sulfinyl, the optionally substituted sulfide and the optionally substituted acyl group" are, for example, the groups represented by —CONRgRg', —CSNRgRg', —SO$_y$—Rg, or —CO—Rg, wherein:

Rg represents hydrogen atom or substituent RV (wherein RV represents $C_{1-6}$ alkyl, $C_{3-6}$ cycloalkyl, $C_{6-10}$ aryl, $C_{7-10}$ aralkyl, or a heterocyclic group, and the heterocyclic group is a heterocyclic group containing 1 to 4 heteroatoms selected from oxygen atom, sulfur atom, and nitrogen atom in addition to the carbon atoms which is any one of (i) a five- or six-membered monocyclic aromatic heterocyclic group, (ii) an eight- to twelve-membered fused aromatic heterocyclic group, and (iii) a three- to eight-membered saturated or unsaturated non-aromatic heterocyclic group, and the alkyl, the cycloalkyl, the aryl, the aralkyl, or the heterocyclic group is optionally further substituted with substituent RIV of (f));

Rg' is hydrogen atom or a group selected from $C_{1-6}$ alkyl groups, $C_{3-6}$ cycloalkyl groups, and $C_{7-10}$ aralkyl groups; and y is 0, 1, or 2.

In the compound of the formula (I), Q is preferably as described below.

[1-1-a] Examples of the "optionally substituted hydrocarbon group" or the "optionally substituted heterocyclic group" include:

(1) $C_{1-10}$ alkyl groups; (2) $C_{2-6}$ alkenyl groups; (3) $C_{2-6}$ alkynyl groups; (4) $C_{3-9}$ cycloalkyl groups; (5) $C_{3-6}$ cycloalkenyl groups; (6) $C_{4-6}$ cycloalkanedienyl groups; (7) $C_{6-14}$ aryl groups; and (8) (i) "five- or six-membered, monocyclic aromatic heterocyclic groups", (ii) "eight- to twelve-membered, fused aromatic heterocyclic groups", and (iii) "three- to eight-membered, saturated or unsaturated, non-aromatic heterocyclic groups", which contain 1 to 4 heteroatoms selected from nitrogen atom, oxygen atom and sulfur atom in addition to the carbon atoms, and each group of the above (1) to (8) may be either unsubstituted or substituted with 1 to 5 substituents of the class selected from (a-1) to (g-1) as described below.

The classes are:

(a-1): $C_{1-6}$ alkyl groups, $C_{2-6}$ alkenyl groups, $C_{2-6}$ alkynyl groups, $C_{6-14}$ aryl groups, $C_{3-7}$ cycloalkyl groups, and $C_{3-6}$ cycloalkenyl groups. These substituents are optionally further substituted with substituent RI (wherein RI represents a group selected from $C_{1-6}$ alkoxy; $C_{1-6}$ alkoxycarbonyl; carboxyl; carbamoyl which is optionally mono- or di-substituted with a $C_{1-6}$ alkyl; a halogen; $C_{1-6}$ alkyl; halogenated $C_{1-6}$ alkyl; amino which is optionally mono- or di-substituted with a $C_{1-6}$ alkyl; $C_{2-6}$ alkenoylamino; nitro; hydroxy; oxo; cyano; and amidino).

(b-1): a heterocyclic group containing 1 to 4 heteroatoms selected from oxygen atom, sulfur atom, and nitrogen atom in addition to the carbon atoms which is any one of (i) a "five- or six-membered, monocyclic aromatic heterocyclic group", (ii) an "eight- to twelve-membered, fused aromatic heterocyclic group", and (iii) a "three- to eight-membered, saturated or unsaturated, non-aromatic heterocyclic group". These heterocyclic groups are optionally further substituted with RII (wherein RII represents a group selected from $C_{1-6}$ alkyl, $C_{1-6}$ alkanoyl, and benzoyl).

(c-1): an amino group which is optionally substituted with substituent RIII (wherein RIII represents a group selected from $C_{1-6}$ alkyl, $C_{1-6}$ alkanoyl, $C_{2-6}$ alkenoyl, benzoyl, and C$_{1-6}$ alkoxycarbonyl which is optionally substituted with 1 to 5 halogen atoms), and a three- to eight-membered monocyclic amino group which is optionally substituted with a group selected from C$_{1-6}$ alkyl, C$_{7-10}$ aralkyl and C$_{6-10}$ aryl.

(d-1): an imidoyl group, an amidino group, a hydroxyl group, and a thiol group. These substituents are optionally substituted with groups selected from substituents RIII as described above in the (c-1).

(e-1): a halogen atom such as fluorine, chlorine, bromine, and iodine, a cyano group, and a nitro group.

(f-1): a carboxyl group, a C$_{1-6}$ alkoxycarbonyl group, a C$_{7-12}$ aryloxycarbonyl group and a C$_{6-10}$ aryl-C$_{1-4}$ alkoxycarbonyl group; and the aryl group in such (f-1) is optionally substituted with substituent RIV' (wherein RIV' represents amino which is optionally mono- or di-substituted with groups selected from RIII as described above in the (c-1); C$_{1-6}$ alkyl or C$_{1-6}$ alkoxy which is optionally substituted with 1 to 5 halogen atoms; a halogen atom; hydroxyl; nitro; and cyano).

(g-1): a group —CONRgRg', —CSNRgRg', —CO—Rg and —SO$_y$—Rg wherein:

Rg represents a hydrogen atom or a substituent RV (wherein RV represents C$_{1-6}$ alkyl, C$_{3-6}$ cycloalkyl, C$_{6-10}$ aryl, C$_{7-10}$ aralkyl, or a heterocyclic group, and the heterocyclic group is a heterocyclic group containing 1 to 4 heteroatoms selected from oxygen atom, sulfur atom, and nitrogen atom in addition to the carbon atoms which is any one of (i) a five- or six-membered monocyclic aromatic heterocyclic group, (ii) an eight- to twelve-membered fused aromatic heterocyclic group, and (iii) a three- to eight-membered, saturated or unsaturated, non-aromatic heterocyclic group, and the alkyl, the cycloalkyl, the aryl, the aralkyl, or the heterocyclic group is optionally further substituted with substituent RIV as described in the (f-1));

Rg' is a hydrogen atom or a group selected from C$_{1-6}$ alkyl groups, C$_{3-6}$ cycloalkyl groups, and C$_{7-10}$ aralkyl groups; and y is 0, 1, or 2.

In the groups shown in (a-1) to (g-1) as described above, the "most preferable groups" are substituents including C$_{1-6}$ alkyl, C$_{2-6}$ alkenyl, C$_{2-6}$ alkynyl, halogen atom, halogenated C$_{1-6}$ alkyl, cyano, amino, hydroxyl, carbamoyl, C$_{1-6}$ alkoxy, C$_{2-6}$ alkenyloxy, C$_{2-6}$ alkynyloxy, C$_{1-6}$ alkylthio, C$_{1-6}$ alkylsulfinyl, C$_{1-6}$ alkylsulfonyl, mono/di C$_{1-6}$ alkylamino, C$_{1-6}$ alkoxycarbonyl, C$_{2-6}$ alkanoyl, C$_{2-6}$ alkanoylamino, hydroxy-C$_{1-6}$ alkyl, C$_{1-6}$ alkoxy-C$_{1-6}$ alkyl, carboxy-C$_{1-6}$ alkyl, C$_{1-6}$ alkoxycarbonyl-C$_{1-6}$ alkyl, carbamoyl-C$_{1-6}$ alkyl, N-(C$_{1-6}$)alkylcarbamoyl-C$_{1-6}$ alkyl, N,N-di C$_{1-6}$ alkylcarbamoyl-C$_{1-6}$ alkyl, phenyl, phenoxy, phenylthio, phenylsulfinyl, phenylsulfonyl, benzyl, and benzoyl, and the aromatic ring in these substituents may be substituted with 1 to 3 substituents selected from halogen atoms, trifluoromethyl, cyano, hydroxyl, amino, nitro, carboxyl, carbamoyl, C$_{1-6}$ alkyl, C$_{1-6}$ alkoxy, mono/di C$_{1-6}$ alkylamino, di-C$_{1-6}$ alkylcarbamoyl, C$_{1-6}$ alkoxycarbonyl, N-C$_{1-6}$ alkylcarbamoyl, N,N-di C$_{1-6}$ alkylcarbamoyl, and C$_{2-6}$ alkenoylamino.

[1-1-b] Preferably, Q is (1) a C$_{1-6}$ alkyl group, (2) a C$_{2-6}$ alkenyl group, (7) a C$_{6-14}$ aryl group, or (8) (i) a five- or six-membered, monocyclic aromatic heterocyclic group, (ii) an eight- to twelve-membered, fused aromatic heterocyclic group, or (iii) a three- to eight-membered, saturated or unsaturated, non-aromatic heterocyclic group, which contains 1 to 4 heteroatoms selected from nitrogen atom, oxygen atom and sulfur atom in addition to the carbon atoms, and each group in (1), (2), (7) and (8) is optionally mono- or di-substituted at an arbitrary position with the substituent of the class selected from [1-1] (a-1) to (g-1) (and most preferably, from those listed as "particularly preferable groups").

[1-1-c] More preferably, Q is (1') or (2'): a C$_{1-6}$ alkyl group (most preferably a C$_{1-2}$ alkyl group) or a C$_{2-6}$ alkenyl group (most preferably a C$_2$ alkenyl group) substituted with a substituent selected from substituent (a-1): a C$_{6-14}$ aryl group and substituent (b-1): an aromatic group selected from (i) five- or six-membered monocyclic aromatic heterocyclic groups and (ii) eight- to twelve-membered fused aromatic heterocyclic groups, which contain 1 to 4 heteroatoms selected from nitrogen atom, oxygen atom and sulfur atom in addition to the carbon atoms; or (7'): a C$_{6-14}$ aryl group which is optionally substituted with 1 to 2 halogen atoms; or (8'): a heterocyclic group which is (i) a five- or six-membered, monocyclic, aromatic heterocyclic group, (ii) an eight- to twelve-membered, fused aromatic heterocyclic group, or (iii) a three- to eight-membered, saturated or unsaturated, non-aromatic heterocyclic group, which contains 1 to 4 heteroatoms selected from nitrogen atom, oxygen atom and sulfur atom in addition to the carbon atoms, and wherein the carbon atoms are mono- or di-substituted with a halogen atom.

The aromatic ring in the above substituent (1') or (2') is optionally substituted with 1 to 3 substituents selected from halogen atoms, trifluoromethyl, cyano, hydroxyl, amino, nitro, carboxyl, carbamoyl, C$_{1-6}$ alkyl, C$_{1-6}$ alkoxy, mono/di C$_{1-6}$ alkylamino, di C$_{1-6}$ alkylcarbamoyl, C$_{1-6}$ alkoxycarbonyl, N-C$_{1-6}$ alkylcarbamoyl, N,N-di 1–6 alkylcarbamoyl and C$_{2-6}$ alkenoylamino.

The aromatic ring in the substituents (7') and (8') is also optionally mono- or di-substituted at arbitrary position with the substituent of the class selected from [1-1] (a-1) to (g-1) (and most preferably, from those listed as "particularly preferable groups").

[1-1-d] Still more preferably, Q is benzyl group, phenethyl group, styryl group, 1-naphthyl group, 2-naphthyl group, benzofuran-2-yl group, benzo[b]thien-2-yl group, indolyl-2-yl group, quinolin-3-yl group, quinolin -6-yl, 1H-benzimidazol-2-yl group, benzoxazol-2-yl group, benzothiazol-2-yl group, 2H-benzopyran-3-yl group, 4-vinylphenyl group, 4-benzenesulfonyl-thiophen-2-yl group, or 5-(2-pyridyl)thiophen-2-yl group, 2-(thiophen-2-yl)ethenyl group, 5-ethynylbenzo[b]furan-2-yl group, and the aromatic ring in such group is optionally mono- or di-substituted with halogen atom (most preferably chlorine atom or bromine atom) or a C$_{1-6}$ alkyl group (most preferably methyl group).

[1-2] In the compound of formula (I), A is hydrogen atom; or (1) an optionally substituted, saturated or unsaturated, five- or six-membered, cyclic hydrocarbon group, or an optionally substituted, saturated or unsaturated, five- or six-membered, heterocyclic group, (2) an optionally substituted amino group, or (3) an optionally substituted imidoyl group.

[1-2-a] In the (1) optionally substituted, saturated or unsaturated, five- or six-membered, cyclic hydrocarbon group, or optionally substituted, saturated or unsaturated, five- or six-membered, heterocyclic group, the "saturated or unsaturated, five- or six-membered, cyclic hydrocarbon group" corresponds to those containing 5 or 6 carbon atoms in the cyclic hydrocarbon groups listed as "alicyclic hydrocarbon groups" and "aryl groups" in Q. Examples are cyclopentyl, cyclohexyl, cycloheptyl, cyclopentenyl, cyclopentadienyl, cyclohexadienyl, and phenyl.

Exemplary "saturated or unsaturated, five- or six-membered, heterocyclic groups" are five- or six-membered, monocyclic groups in the heterocyclic groups shown in "aromatic heterocyclic groups, and saturated or unsaturated, non-aromatic heterocyclic groups" in Q. The heterocyclic groups contain at least one (and preferably 1 to 4) heteroatom selected from N, O, and S in addition to the carbon atoms.

To be more specific, exemplary "non-aromatic heterocyclic groups" include azetidinyl, oxilanyl, oxetanyl, thietanyl, pyrolidinyl, tetrahydrofuryl, thiolanyl, pyrazolinyl, pyrazolidinyl, pyperidyl, tetrahydropyranyl, pyperadinyl, morpholinyl, thiomorpholinyl, and quinuclidinyl, and exemplary "aromatic heterocyclic groups" include pyrolyl, furyl, thienyl, oxazolyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,2,5-triazinyl, 1,3,5-triazinyl, and thiadiazinyl.

The ring in A is optionally further substituted with 1 to 3 subustituents Rq (wherein Rq is any of substituents (1) to (8) of Q which is optionally substituted with any of substituents (a) to (f)) Alternatively, the ring in A is optionally mono- or di-substituted with a group selected from:

R1 (wherein R1 is any group selected from group A (hydrogen atom, halogen atoms, trifluoromethyl group, trifluoromethoxy group, carboxyl group, carbamoyl group, sulfamonyl group, amino group, cyano group, nitro group, lower alkanoyl groups, lower alkoxy groups, lower alkoxycarbonyl groups, lower alkylsulfonyl groups, lower alkylsulfinyl groups, mono- or di-substituted lower alkylamino groups, cyclic amino groups, lower alkanoylamino groups, phenyl group, phenoxy group, benzyloxy group, benzoyl group, mercapto group, lower alkylthio groups, lower alkylthiocarbonyl groups, hydroxy group, and mono- or di-substituted lower alkylamino carbonyl groups); oxygen atom which forms N-oxide group with a cyclic nitrogen atom; and lower alkyl groups, lower alkoxy groups, lower alkenyl groups, phenyl group, five- or six-membered heterocyclic groups which are optionally substituted at an arbitrary number of positions with the substituent of group A).

[1-2-b] Examples of the optionally substituted amino group of (2) are amino groups optionally mono- or di-substituted with substituent RVII (wherein RVII is a $C_{1-10}$ alkyl group, a formimide group, an acetimidoyl group, a $C_{2-6}$ alkenyl group, a $C_{3-6}$ cycloalkenyl group, a $C_{3-9}$ cycloalkyl group, a $C_{4-6}$ cycloalkanedienyl group, or a $C_{6-14}$ aryl group). It should be noted that the cyclic amino group is included within the "saturated or unsaturated, five- or six-membered heterocyclic groups" of [1-2-a] (1).

[1-2-c] Examples of the optionally substituted imidoyl group of (3) include group: —C(RVII')=N—RVII"

(wherein RVII' and RVII" are the same or different and arbitrarily selected from a hydrogen atom and the substituent RVII as described above in (2)).

It should be noted that the cyclic imidoyl group is included within [1-2-a] (1) "unsaturated, five- or six-membered, heterocyclic groups".

More preferably, A is a hydrogen atom; or [1-2-a1] a five-membered, aromatic, monocyclic heterocyclic group which may contain 1 to 4 nitrogen atoms or 1 to 3 oxygen atoms or sulfur atoms in addition to the carbon atoms, or the following group:

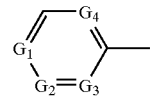

wherein $G_1$, $G_2$, $G_3$, and $G_4$ are independently CH or N, and all rings are optionally mono- or di-substituted with any of the (a) to (g) as described above;

[1-2-b1] an amino group which is optionally mono- or di-substituted with a $C_{1-10}$ alkyl group or a $C_{6-14}$ aryl group, a formimidoyl-amino group, or an acetimidoyl amino group; or [1-2-c1] group: —N(Ra")—C(Ra')=N—Ra or group: —C(Ra')=N—Ra (wherein, in each group, Ra" is a hydrogen atom or a $C_{1-6}$ alkyl group;

Ra' is a hydrogen atom; a $C_{1-6}$ alkyl group; a $C_{1-6}$ alkanoyl group; a benzoyl group; an amino group which is optionally mono- or di-substituted with a group selected from a $C_{1-6}$ alkyl, a $C_{1-6}$ alkanoyl or a benzoyl; or a $C_{1-6}$ alkoxy group; and Ra is a hydrogen atom, a $C_{1-6}$ alkyl group, a $C_{1-6}$ alkanoyl group, or benzoyl group), or alternatively, —C(Ra')=N—Ra moiety in each group may form:

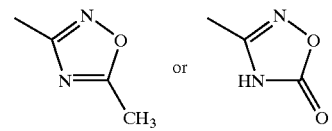

[1-3] In the compound of formula (I), B is [1-3-a] a single bond, a carbonyl group, —S(O)$_x$— (wherein x is typically 0 to 2, and preferably 2), or an optionally substituted $C_{1-2}$ alkylene group (which is typically substituted with an optionally halogenated $C_{1-6}$ alkyl group or an optionally halogenated $C_{1-6}$ alkoxy group),

[1-3-b] preferably a single bond, a carbonyl group, or —SO$_2$—, and

[1-3-c] more preferably a single bond.

[1-4] In the compound of formula (I), D is [1-4-a] a hydrogen atom, a group —CO—R$_5$ (wherein R$_5$ is hydrogen atom or a substituent), or an optionally substituted $C_{1-6}$ alkyl group (preferably a $C_{1-6}$ alkyl group optionally substituted with R$_{15}$ as described below)

R$_5$ is preferably a hydrogen atom; a hydroxyl group; a $C_{1-6}$ alkyl group; a $C_{1-6}$ alkoxy group; a $C_{1-6}$ alkoxycarbonylalkyl group; a phenoxy group or a benzyloxy group each of which is optionally substituted with a $C_{1-6}$ alkyl, a $C_{1-6}$ alkoxy, or a halogen atom; or an optionally substituted amino group, and in particular, a group —NR$_6$R$_7$ (wherein R$_6$ and R$_7$ are independently hydrogen atom, a $C_{1-6}$ alkyl, a $C_{4-7}$ cycloalkyl, or a $C_{2-6}$ alkenyl; or R$_6$ and R$_7$ may together form a five- to seven-membered heterocyclic ring with the nitrogen atom to which R$_6$ and R$_7$ are binding, the heterocyclic ring optionally further comprising 1 or 2 heteroatoms selected from N, S, and O); and such substituent R$_5$ is optionally further substituted with a group selected from hydroxyl, amino, carboxyl, $C_{1-6}$ alkoxycarbonyl, oxo, $C_{1-6}$ alkyl, hydroxy-$C_{1-6}$ alkyl, $C_{1-6}$ alkoxy-$C_{1-6}$ alkyl, carboxy $C_{1-6}$ alkyl, $C_{1-6}$ alkyl-$C_{1-6}$ alkoxycarbonyl, and carbamoyl $C_{1-6}$ alkoxy).

[1-4-b] More preferably, D is a hydrogen atom; or
1) a group selected from a carboxyl group; a $C_{1-6}$ alkylcarbonyl group; a $C_{1-6}$ alkoxycarbonyl group; a $C_{1-6}$ alkoxycarbonylalkylcarbonyl group; a phenoxycarbonyl group optionally substituted with a $C_{1-6}$ alkyl, a $C_{1-6}$ alkoxy, or a halogen atom; a benzyloxycarbonyl group optionally substituted with a $C_{1-6}$ alkyl, a $C_{1-6}$ alkoxy, or a halogen atom;

2) a carbamoyl group which is optionally mono- or di-substituted with a $C_{1-6}$ alkyl; a $C_{1-6}$ alkoxycarbamoyl group; a $C_{1-6}$ alkoxycarbonylalkylcarbamoyl group; a cyclic amino carbonyl group optionally substituted with oxo, hydroxyl, amino, or carboxyl (and in particular, a pyrrolidin-1-ylcarbonyl group, a piperidin-1-ylcarbonyl, a piperazin-1-ylcarbonyl, a 4-morpholinocarbonyl, a thiomorpholinocarbonyl, or a 1,1-dioxo-4-thiomorpholinocarbonyl); a N-phenylcarbamoyl group; or a group selected from the groups represented by —CONH(CH$_2$)$_p$S(O)$_q$R$_{10}$ and —CONH(CH$_2$)$_t$ NR$_{11}$R$_{12}$ (wherein R$_{10}$, R$_{11}$ and R$_{12}$ are independently a hydrogen atom, a $C_{1-6}$ alkyl group, a phenyl group, or a $C_1$-6 alkylphenyl group; p is an integer of 0 to 4; q is an integer of 0 to 2; and t is an integer of 1 to 4); or 3) a $C_{1-6}$ alkyl group (preferably methyl or ethyl) optionally substituted with R$_{15}$ (wherein R$_{15}$ represents a carboxyl group; a $C_{1-6}$ alkoxycarbonyl group; hydroxyl group; a $C_{1-6}$ alkoxy group; a C$_1$6 alkanoyloxy group; an amino group; a mono- or di-substituted $C_{1-6}$ alkylamino group; a $C_{1-6}$ alkanoylamino group; a $C_{1-6}$ alkylsulfonylamino group; a five- or six-membered cyclic amino group optionally substituted with oxo, hydroxyl, amino, or carboxyl (and in particular, a pyrrolidin-1-yl, a piperidin-1-yl, a piperazin-1-yl, a 4-morpholino, a thiomorpholino, or a 1,1-dioxo-4-thiomorpholino); or a N-hydroxyimino group (an aldoxime group)).

[1-4-c] Still more preferably, D is a hydrogen atom; or
1) a group selected from a carboxyl group, a $C_{1-2}$ alkylcarbonyl group, a $C_{1-2}$ alkoxycarbonyl group, and a $C_{1-2}$ alkoxycarbonylalkylcarbonyl group; or a group selected from a phenoxycarbonyl group which is optionally substituted with a $C_{1-2}$ alkyl, a $C_{1-2}$ alkoxy, or a halogen atom, or a benzyloxycarbonyl group which is optionally substituted with a $C_{1-2}$ alkyl, a $C_{1-2}$ alkoxy, or a halogen atom;

2) a carbamoyl group which is optionally mono- or di-substituted with a $C_{1-2}$ alkyl; a $C_{1-2}$ alkoxycarbamoyl group; a $C_{1-2}$ alkoxycarbonylalkylcarbamoyl group; a cyclic amino carbonyl group which is optionally substituted with oxo, hydroxyl, amino or carboxyl (and in particular, a pyrrolidin-1-ylcarbonyl group, a piperidin-1-ylcarbonyl, a piperazin-1-ylcarbonyl, a 4-morpholino carbonyl group, a thiomorpholino carbonyl group, or a 1,1-dioxo-4-thiomorpholino carbonyl group); or 3) a methyl group or an ethyl group optionally substituted with R$_{15}$' (wherein R$_{15}$' represents a carboxyl group; a $C_{1-2}$ alkoxycarbonyl group; a hydroxyl group; a $C_{1-2}$ alkoxy group; a $C_{1-3}$ alkanoyloxy group; an amino group; a mono- or di-substituted $C_{1-2}$ alkylamino group; a $C_{1-2}$ alkanoylamino group; a pyrrolidin-1-yl group, a piperidin-1-yl group, a piperazin-1-yl group, a 4-morpholino group, a thiomorpholino group or a 1,1-dioxo-4-thiomorpholino group, each of which is optionally substituted with oxo, hydroxyl, amino or carboxyl).

[1-5] In formula (I), X is
[1-5-a] a methine group optionally substituted with A'-B' (wherein A' is a group selected from those defined for A and B' is a group selected from those defined for B), or nitrogen atom, and

[1-5-b] preferably a methine group or a nitrogen atom, and
[1-5-c] more preferably a nitrogen atom.
[1-6] In formula (I), Y is
[1-6-a] an oxygen atom, —S(O)$_y$— (wherein y is an integer of 0 to 2), or an optionally substituted imino group (—NH—) wherein the substituent for the imino group is 1) —CO—R$_5$ (wherein R$_5$ is a group selected from those as defined above); 2) a $C_{1-6}$ alkyl group optionally substituted with R$_{15}$ (wherein R$_{15}$ is a group selected from those as defined above); 3) a $C_{1-6}$ alkyl, $C_{1-6}$ alkoxy or phenyl group which is optionally substituted with a halogen atom; or 4) a N-oxide group, as described for D in [4].
[1-6-b] Preferably, Y is an oxygen atom, or
[1-6-c] alternatively, —S(O)$_y$— (wherein y is an integer of 0 to 2, and preferably 0), or
[1-6-d] an unsubstituted imino group (—NH—).
[1-7] In formula (I), Z is
[1-7-a] a methylene group, a carbonyl group, or a thiocarbonyl group, and
[1-7-b] preferably a carbonyl group.
[1-8] In formula (I), T is
[1-8-a] —S(O)$_z$— (wherein z is an integer of 0 to 2, and preferably 2), carbonyl group, or an optionally substituted $C_{1-2}$ alkylene group (in particular, $C_{1-2}$ alkylene group optionally substituted with an optionally halogenated $C_{1-6}$ alkyl group or an optionally halogenated $C_{1-6}$ alkoxy group), and
[1-8-b] preferably, —SO$_2$— or —CH$_2$—.
[1-9] In formula (I), l, m, and n are
[1-9-a] independently an integer selected from 0, 1 and 2 with the proviso that l and m are not simultaneously 0, and
[1-9-b] more preferably, l is 1; m is 0 or 1; and n is 1.
[1-10] In formula (I), r is 0 or 1. The bond indicated by the broken line and the solid line is a single bond or a double bond (when r is 0).
[1-11] Exemplary substitutents of the ring containing X, the ring containing Y, and the ring containing Z include an oxo group (=O); a hydroxyimino group (=N~OH); an alkoxyimino groups (=N~ORi wherein Ri is a $C_{1-6}$ alkyl groups optionally substituted with a substituent which is preferably a group selected from halogen, hydroxyl, and carboxyl); and groups shown for D in [1–4], and the preferable substituents are an oxo group, a hydroxyl group, a carboxyl group, a halogen atoms, a $C_{1-6}$ alkyl groups, a $C_{2-6}$ alkenyl groups, and a $C_{2-6}$ alkynyl groups. Among these, the $C_{1-6}$ alkyl groups, the $C_{2-6}$ alkenyl groups, and the $C_{2-6}$ alkynyl group are optionally further substituted with substituent RI (wherein RI represents a group selected from $C_{1-6}$ alkoxy; $C_{1-6}$ alkoxycarbonyl; carboxyl; carbamoyl optionally mono- or di-substituted with $C_{1-6}$ alkyl; halogen; $C_{1-6}$ alkyl; halogenated $C_{1-6}$ alkyl; amino optionally mono- or di-substituted with a $C_{1-6}$ alkyl; $C_{2-6}$ alkenoyl amino; nitro; hydroxyl; oxo; cyano; and amidino). Particularly preferable substituents are an oxo group, a $C_{1-6}$ alkoxy groups, and a carboxyl group.
Preferably,
[1-11-a] the substituent of the ring containing X is preferably an oxo group, a hydroxyl group, a lower alkyl group, or a lower alkoxyalkyl group;
[1-11-b] the substituent of the ring containing Y is preferably an oxo group, a hydroxyimino group, or a substituted alkoxyimino group (=N~ORi wherein Ri is a $C_{1-6}$ alkyl group optionally substituted with a substituent which is preferably selected from halogen, hydroxyl, and carboxy); and
[1-11-c] the substituent of the ring containing Z is preferably an oxo group, a hydroxyimino group, or a substituted alkoxyimino group (=N~ORi wherein Ri is a $C_{1-6}$ alkyl group optionally substituted with a substituent which is preferably selected from halogen, hydroxyl, and carboxy), and the position of the substitution includes replacement of the carbonyl defined as Z with the hydroxyimino group or the substituted alkoxyimino group.

With regard to the compounds of formula (I), the preferable compounds may be defined by arbitrary combinations of the [1-1] to [1-11] as described above. Examples of the compounds of such combination are shown below in [1-12].

[1-12]

In formula (I),

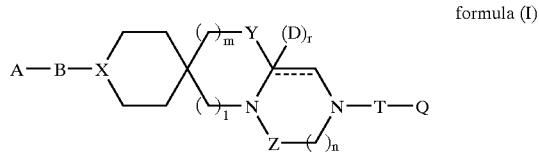

formula (I)

Q is (1) a $C_{1-10}$ alkyl group; (2) a $C_{2-6}$ alkenyl group; (3) a $C_{2-6}$ alkynyl group; (4) a $C_{3-9}$ cycloalkyl group; (5) a $C_{3-6}$ cycloalkenyl group; (6) a $C_{4-6}$ cycloalkadienyl group; (7) a $C_{6-14}$ aryl group; or (8) a heterocyclic group containing 1 to 4 heteroatoms selected from oxygen atom, sulfur atom and nitrogen atom in addition to the carbon atoms which is (i) a five- or six-membered, monocyclic aromatic heterocyclic group, (ii) an eight- to twelve-membered, fused aromatic heterocyclic group, or (iii) a three- to eight-membered, saturated or unsaturated, non-aromatic heterocyclic group; and each group of the above (1) to (8) is either unsubstituted or substituted at 1 to 5 arbitrary positions with a substituent of the class selected from (a) to (g) as described below:

(a) $C_{1-6}$ alkyl groups, $C_{2-6}$ alkenyl groups, $C_{2-6}$ alkynyl groups, $C_{1-6}$ alkoxy groups and $C_{6-14}$ aryl groups, at least one of which is optionally further substituted with substituent RI (wherein RI represents a $C_{1-6}$ alkoxy group, a halogen, a $C_{1-6}$ alkyl group, an amino group, a hydroxyl group, a cyano group or an amidino group);

(b) a heterocyclic group containing 1 to 4 heteroatoms selected from oxygen atom, sulfur atom and nitrogen atom in addition to the carbon atoms which is (i) a five- or six-membered, monocyclic aromatic heterocyclic group, (ii) an eight- to twelve-membered, fused aromatic heterocyclic group, or (iii) a three- to eight-membered, saturated or unsaturated, non-aromatic heterocyclic groups; wherein the heterocyclic groups are optionally further substituted with a substituent RII (wherein RII represents a $C_{1-6}$ alkyl group, a $C_{1-6}$ alkanoyl group, a halogen , or a benzoyl group);

(c) an amino group optionally substituted with a substituent selected from substituents RIII (wherein RIII represents a $C_{1-6}$ alkyl group, a $C_{1-6}$ alkanoyl group, a benzoyl group, or an optionally halogenated $C_{1-6}$ alkoxycarbonyl group, a $C_{1-6}$ alkyl imidoyl group, a formimidoyl group, or an amidino group);

(d) an imidoyl group, an amidino group, a hydroxyl group and a thiol group which are optionally further substituted with a group selected from $C_{1-6}$ alkyl groups, $C_{1-6}$ alkanoyl groups, a benzoyl group and optionally halogenated $C_{1-6}$ alkoxycarbonyl groups;

(e) a halogen atom, a cyano group and a nitro group;

(f) a carboxyl group, a $C_{1-6}$ alkoxycarbonyl groups, a $C_{7-12}$ aryloxycarbonyl groups, and a $C_{6-10}$ aryl-$C_{1-4}$ alkoxycarbonyl group wherein the aryl group in such substituents is optionally further substituted with substituent RIV (wherein RIV represents hydroxyl, amino group optionally mono- or di-substituted with a group selected from substituents RIII of (c) as described above, a halogen atom, a nitro group, a cyano group, a $C_{1-6}$ alkyl group which is optionally substituted with 1 to 5 halogen atoms, or an alkoxy group which is optionally substituted with 1 to 5 halogen atoms); and (g) —CO—RV wherein RV represents a $C_{1-6}$ alkyl group, a $C_{3-6}$ cycloalkyl group, a $C_{6-10}$ aryl group, a $C_{7-10}$ aralkyl group, or a heterocyclic group, and the heterocyclic group is the one containing 1 to 4 heteroatoms selected from oxygen atom, sulfur atom and nitrogen atom in addition to the carbon atoms which is (i) a five- or six-membered, monocyclic aromatic heterocyclic group, (ii) an eight- to twelve-membered, fused aromatic heterocyclic group, or (iii) a three- to eight-membered, saturated or unsaturated, non-aromatic heterocyclic group;

T is —S(O)$_z$— (wherein z is an integer of 0 to 2, and preferably 2), a carbonyl group, or an optionally substituted $C_{1-2}$ alkylene group (and in particular, a $C_{1-2}$ alkylene group which is optionally substituted with an optionally halogenated $C_{1-6}$ alkyl group or an optionally halogenated $C_{1-6}$ alkoxy group); and preferably —SO$_2$— or —CH$_2$—;

A is a hydrogen atom, or (1) a five- or six-membered, aromatic or non-aromatic, monocyclic heterocyclic group which may contain 1 to 4 nitrogen atoms or 1 to 3 oxygen atoms or sulfur atoms in addition to the carbon atoms; wherein the ring is optionally further substituted with the substituent of (a) to (d), below:

(a) a halogen atom; (b) an amino group; (c) a $C_{1-6}$ alkyl group optionally substituted with a substituent selected from halogen, amino, carboxyl and hydroxy; and (d) a carboxyl group, a $C_{1-6}$ alkoxycarbonyl group, a $C_{7-12}$ aryloxycarbonyl group, and a $C_{1-6}$ aryl-$C_{1-4}$ alkoxycarbonyl group, wherein the aryl is optionally substituted with substituent RIV (wherein RIV represents hydroxyl; an amino group optionally mono- or di-substituted with substituent RII (a group selected from $C_{1-6}$ alkyl, $C_{1-6}$ alkanoyl, and benzoyl); a halogen atom; a nitro group; a cyano group; a $C_{1-6}$ alkyl group optionally substituted with 1 to 5 halogen atoms; or an alkoxy group which is optionally substituted with 1 to 5 halogen atoms);

(2) an amino group optionally mono- or di-substituted with a $C_{1-10}$ alkyl group or a $C_{6-14}$ aryl group; or (3) a group: —N(Ra")—C(Ra')=N—Ra or a group: —C(Ra')=N—Ra wherein Ra" is a hydrogen atom or a $C_{1-6}$ alkyl group;

Ra' is a hydrogen atom, a $C_{1-6}$ alkyl group, a $C_{1-6}$ alkanoyl group, a benzoyl group, an amino group mono- or di-substituted with a group selected from $C_{1-6}$ alkyl, $C_{1-6}$ alkanoyl and benzoyl, or a $C_{1-6}$ alkoxy group; and Ra is a hydrogen atom, a $C_{1-6}$ alkyl group, a $C_{1-6}$ alkanoyl group, or a benzoyl group; or alternatively the —C(Ra')=N—Ra moiety in each group may form

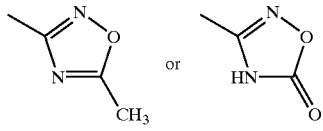

B is a single bond, —SO$_2$—, or an optionally substituted $C_{1-2}$ alkylene;

D is a hydrogen atom; a group —CO—R$_5$ (wherein R$_5$ is hydrogen atom or a substituent); or an optionally substituted $C_{1-6}$ alkyl group (and preferably a $C_{1-6}$ alkyl group optionally substituted with R$_{15}$ as described below); wherein R$_5$ is preferably a hydrogen atom, hydroxyl, a $C_{1-6}$ alkyl, a $C_{1-6}$ alkoxy, a $C_{1-6}$ alkoxycarbonylalkyl, or an optionally substituted amino group, and in particular, group —NR$_6$R$_7$ (wherein R$_6$ and R$_7$ are independently hydrogen atom, a $C_{1-6}$ alkyl, a $C_{4-7}$ cycloalkyl, or a $C_{2-6}$ alkenyl; or $R_6$ and $R_7$ may together form a five- to seven-membered heterocyclic ring with the nitrogen atom to which $R_6$ and $R_7$ are binding, the heterocyclic ring optionally further comprising 1 or 2 heteroatoms selected from N, S, and O); wherein the substituent $R_5$ is optionally further substituted with a group selected from hydroxyl, amino, carboxyl, $C_{1-6}$ alkoxycarbonyl, OXO, $C_{1-6}$ alkyl, hydroxy-$C_{1-6}$ alkyl, $C_{1-6}$ alkoxy-$C_{1-6}$ alkyl, carboxy-$C_{1-6}$ alkyl, $C_{1-6}$ alkyl-$C_{1-6}$ alkoxycarbonyl, and carbamoyl-$C_{1-6}$ alkoxy; and D is more preferably a hydrogen atom; or 1) a group selected from carboxyl group, $C_{1-6}$ alkylcarbonyl groups, $C_{1-6}$ alkoxycarbonyl groups, and $C_{1-6}$ alkoxycarbonylalkylcarbonyl groups;

2) a carbamoyl group mono- or di-substituted with a $C_{1-6}$ alkyl; a $C_{1-6}$ alkoxycarbamoyl group; a $C_{1-6}$ alkoxycarbonylalkylcarbamoyl group; a cyclic amino carbonyl group optionally substituted with oxo, hydroxyl, amino, or carboxyl (and in particular, pyrrolidin-1-ylcarbonyl group, piperidin-1-ylcarbonyl, piperazin-1-ylcarbonyl, 4-morpholinocarbonyl, thiomorpholinocarbonyl, or 1,1-dioxo-4-thiomorpholinocarbonyl); N-phenylcarbamoyl group; or a group selected from the groups represented by —CONH(CH$_2$)$_p$S(O)$_q$R$_{10}$ and —CONH(CH$_2$)$_t$NR$_{11}$R$_{12}$ (wherein $R_{10}$, $R_{11}$ and $R_{12}$ are independently hydrogen atom, a $C_{1-6}$ alkyl group, phenyl group, or a $C_{1-6}$ alkylphenyl group; p is an integer of 0 to 4; q is an integer of 0 to 2; and t is an integer of 1 to 4); or 3) a $C_{1-6}$ alkyl group (preferably methyl or ethyl) optionally substituted with $R_{15}$ (wherein $R_{15}$ represents a carboxyl group; a $C_{1-6}$ alkoxycarbonyl group; a hydroxyl group; a $C_{1-6}$ alkoxy group; a $C_{1-6}$ alkanoyloxy group; an amino group; a mono- or di-substituted $C_{1-6}$ alkylamino group; a $C_{1-6}$ alkanoylamino group; a $C_{1-6}$ alkylsulfonylamino group; a five- or six-membered cyclic amino group which is optionally substituted with oxo, hydroxyl, amino or carboxyl (and in particular, a pyrrolidin-1-yl, a piperidin-1-yl, a piperazin-1-yl, a 4-morpholino, a thiomorpholino, or a 1,1-dioxo-4-thiomorpholino); a N-hydroxyimino group (an aldoxime group));

X is CH or N;

Y is oxygen atom, —S(O)$_y$— (wherein y is an integer of 0 to 2, and preferably 0), or NH;

Z is a methylene group, a carbonyl group, or a thiocarbonyl group (and preferably a carbonyl group); and l, m, and n are independently an integer selected from 0, 1 and 2 with the proviso that l and m are not simultaneously 0; and r is an integer of 0 or 1, and the bond indicated by the broken line and the solid line is a single bond or a double bond (when r is 0).

[1-13]

A more preferable compound within the range as described above is the compound represented by formula (Im):

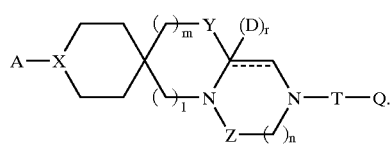

(Im)

In formula (Im), X, Y, Z, D, Q, l, m, n, and r are as defined for [1-12]; T is —SO$_2$— or —CH$_2$—; and A is a five-membered aromatic monocyclic heterocyclic group which may contain 1 to 4 nitrogen atoms or 1 to 3 oxygen atoms or sulfur atoms in addition to the carbon atoms (and in particular,

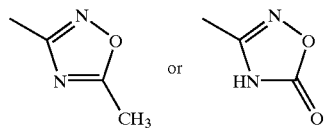

or the group:

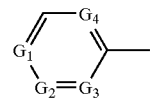

wherein $G_1$, $G_2$, $G_3$, and $G_4$ are independently CH or N, and preferably, at least one of the $G_1$, $G_2$, $G_3$, and $G_4$ is N. The more preferred are those wherein $G_1$ is N, and $G_2$, $G_3$, and $G_4$ are CH; $G_2$ is N, and $G_1$, $G_3$, and $G_4$ are CH; $G_3$ is N, and $G_1$, $G_2$, and $G_4$ are CH; $G_1$ and $G_2$ are N, and $G_3$ and $G_4$ are CH; $G_1$ and $G_3$ are N, and $G_2$ and $G_4$ are CH; $G_1$, $G_2$, and $G_4$ are N, and $G_3$ is CH; and $G_1$, $G_3$, and $G_4$ are N, and $G_2$ is CH; and the still more preferred are those wherein $G_1$ is N, and $G_2$, $G_3$, and $G_4$ are CH; $G_1$ and $G_3$ are N, and $G_2$ and $G_4$ are CH; and $G_1$, $G_3$ and $G_4$ are N, and $G_2$ is CH.

Exemplary groups are 4-pyridyl, 3-pyridyl, 2-pyridyl, 4-pyrimidinyl, 3-pyrimidinyl, and 4-pyridazinyl, and the preferred are 4-pyridyl and 4-pyrimidinyl.

It should be noted that, although N-oxide can be formed by the N at any of the $G_1$ to $G_4$, N-oxide at $G_1$ is preferable (and in particular, the one wherein at least $G_1$ is N is preferable). In addition, all of the five- or six-membered rings are optionally mono- or di-substituted by any of the substituents (a) to (d) as described for A.

Among these, A is preferably unsubstituted 4-pyridyl group or 4-pyridyl group mono-substituted with a halogen atom, amino group, methyl group, ethyl group, hydroxyl group, or hydroxymethyl group; and most preferably unsubstituted 4-pyridyl group.

Exemplary preferable compounds are:
1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(hydroxymethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(ethoxycarbonylmethoxymethyl)-7-oxa-1'-(4-pyridyl) spiro[bicyclo[4.3.0]nonane-8,4'-piperidin]-2-one;

6-(acetoxymethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-7-oxa-1'-(4-pyrimidinyl)spiro[bicyclo[4.3.0]nonane-8,4'-piperidin]-2-one;

1,4-diaza-4-((E)-4-chlorostyrylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(2-methoxyethoxymethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one methanesulfone;

(−)-1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(methoxycarbonyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(isopropoxycarbonyl)-7-oxa-1'-(4-pyridyl) spiro[bicyclo[4.3.0]nonane-8,4'-piperidin]-2-one;

(−)-1,4-diaza-4-(6-chloronaphthalen-2-ylsulfonyl)-7-oxa-6-(propoxycarbonyl)-1'-(4-pyridyl)spiro[bicyclo[4.3.0]nonane-8,4'-piperidin]-2-one;

(−)-6-(allyloxycarbonyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(2-methoxyethoxycarbonyl)-7-oxa-1'-(4-pyridyl)spiro[bicyclo[4.3.0]nonane-8,4'-piperidin]-2-one;

(−)-1,4-diaza-6-(t-butoxycarbonyl)-4-(6-chloronaphthalen-2-ylsulfonyl)-7-oxa-1'-(4-pyridyl)spiro[bicyclo[4.3.0]nonane-8,4'-piperidin]-2-one;

ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine]-6-carboxylate;

(+)-ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine]-6-carboxylate;

(−)-ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine]-6-carboxylate;

4-[1,4-diaza-4-(6-chloronaphthalen-2-ylsulfonyl)-6-(methoxymethyl)-7-oxa-2-oxospiro[bicyclo[4.3.0]nonane-8,4'-piperidin]-1'-yl]pyridine 1-oxide;

1'-acetimidoyl-1,4-diaza-4-(6-chloronaphthalen-2-ylsulfonyl)-7-oxaspiro[bicyclo[4.3.0]nonane-8,4'-piperidin]-2-one;

6-(aminomethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(ethoxycarbonylaminomethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(morpholinomethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-methyl-7-oxa-1'-(4-pyridyl)spiro[bicyclo[4.3.0]nonane-8,4'-piperidin]-2-one;

ammonium 4-[1,4-diaza-4-(6-chloronaphthalen-2-ylsulfonyl)-7-oxa-2-oxo-1'-(4-pyridyl)spiro[bicyclo[4.3.0]nonane-8,4'-piperidin]-6-yl]butylate;

1,4,7-triaza-4-(6-chloronaphthalen-2-ylsulfonyl)-6-(methoxymethyl)-7-methyl-1'-(4-pyridyl)spiro[bicyclo[4.3.0]nonane-8,4'-piperidin]-2-one;

1,4,7-triaza-4-(6-chloronaphthalen-2-ylsulfonyl)-6-(methoxymethyl)-1'-(4-pyridyl)spiro[bicyclo[4.3.0]nonane-8,4'-piperidin]-2-one;

(−)-1,4,7-triaza-4-(6-chloronaphthalen-2-ylsulfonyl)-6-(methoxymethyl)-1'-(4-pyridyl)spiro[bicyclo[4.3.0]nonane-8,4'-piperidin]-2-one;

1,4-diaza-4-(7-chloro-2H-benzopyran-3-ylsulfonyl)-(6-methoxymethyl)-7-oxa-1'-(4-pyridyl)spiro[bicyclo[4.3.0]nonane-8,4'-piperidin]-2-one;

1,4-diaza-4-(7-chloro-2H-benzopyran-3-ylmethyl)-(6-methoxymethyl)-7-oxa-1'-(4-pyridyl)spiro[bicyclo[4.3.0]nonane-8,4'-piperidin]-2-one;

1,4-diaza-4-(6-chlorobenzothiophen-2-ylsulfonyl)-(6-methoxymethyl)-7-oxa-1'-(4-pyridyl)spiro[bicyclo[4.3.0]nonane-8,4'-piperidin]-2-one;

1,4-diaza-4-(6-chlorobenzothiophen-2-ylmethyl)-(6-methoxymethyl)-7-oxa-1'-(4-pyridyl)spiro [bicyclo [4.3.0]nonane-8,4'-piperidin]-2-one;

1,4-diaza-4-(5-chlorobenzofuran-2-ylsulfonyl)-(6-methoxymethyl)-7-oxa-1'-(4-pyridyl)spiro[bicyclo[4.3.0]nonane-8,4'-piperidin]-2-one;

1,4-diaza-4-(5-chlorobenzofuran-2-ylmethyl)-(6-methoxymethyl)-7-oxa-1'-(4-pyridyl)spiro [bicyclo [4.3.0]nonane-8,4'-piperidin]-2-one;

1,4-diaza-4-(6-chlorobenzofuran-2-ylsulfonyl)-(6-methoxymethyl)-7-oxa-1'-(4-pyridyl)spiro[bicyclo[4.3.0]nonane-8,4'-piperidin]-2-one;

1,4-diaza-4-(2H-benzopyran-3-sulfonyl)-7-oxa-1'-(4-pyridyl)spiro [bicyclo[4.3.0]nonane-8,4'-piperidin]-2-one;

1,4-diaza-4-(7-chloro-2H-benzopyran-3-sulfonyl)-7-oxa-1'-(4-pyridyl)spiro[bicyclo[4.3.0]nonane-8,4'-piperidin]-2-one;

1,4-diaza-4-(benzo[b]thiophen-2-ylsulfonyl)-7-oxa-1'-(4-pyridyl)spiro[bicyclo[4.3.0]nonane-8,4'-piperidin]-2-one;

1,4-diaza-4-(5-fluorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(5-chlorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(6-chlorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(6-chloro-5-fluorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(5-chloro-3-methylbenzo[b]thiophen-2-ylsulfonyl)-7-oxa-1'-(4-pyridyl)spiro[bicyclo[4.3.0]nonane-8,4'-piperidin]-2-one;

1,4-diaza-4-(5-chlorobenzo[b]furan-2-ylsulfonyl)-7-oxa-1'-(4-pyridyl)spiro[bicyclo[4.3.0]nonane-8,4'-piperidin]-2-one;

1,4-diaza-4-(5-bromobenzo[b]furan-2-ylsulfonyl)-7-oxa-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-1'-(4-pyridyl)spiro[bicyclo[4.3.0]nonane-8,4'-piperidin]-2-one;

1,4,7-triaza-4-(5-chlorobenzo[b]furan-2-ylsulfonyl)-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-7-methyl-1'-(4-pyridyl)spiro[bicyclo[4.3.0]nonane-8,4'-piperidin]-2-one;

1,4,7-triaza-4-(5-chlorobenzo[b]furan-2-ylsulfonyl)-7-methyl-1'-(4-pyridyl)spiro[bicyclo[4.3.0]nonane-8,4'-piperidin]-2-one;

1,4-diaza-4-(7-chloro-2H-benzopyran-3-sulfonyl)-6-(methoxymethyl)-7-oxa-1'-(4-pyridyl)spiro[bicyclo[4.3.0]nonane-8,4'-piperidin]-2-one;

1,4-diaza-4-(6-chlorobenzo[b]thiophen-2-ylsulfonyl)-6-(methoxymethyl)-7-oxa-1'-(4-pyridyl)spiro[bicyclo[4.3.0]nonane-8,4'-piperidin]-2-one;

1,4-diaza-4-(5-chlorobenzo[b]furan-2-ylsulfonyl)-6-(methoxymethyl)-7-oxa-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-6-(methoxymethyl)-1'-(4-pyridyl)spiro[bicyclo[4.3.0]nonane-8,4'-piperidin]-2-one;

1,4,7-triaza-4-(5-chlorobenzo[b]furan-2-ylsulfonyl)-6-(methoxymethyl)-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-6-(methoxymethyl)-7-methyl-1'-(4-pyridyl)spiro[bicyclo[4.3.0]nonane-8,4'-piperidin]-2-one;

1,4,7-triaza-4-(5-chlorobenzo[b]furan-2-ylsulfonyl)-6-(methoxymethyl)-7-methyl-1'-(4-pyridyl)spiro[bicyclo[4.3.0]nonane-8,4'-piperidin]-2-one;

1,4-diaza-4-(6-chlorobenzo[b]furan-2-ylsulfonyl)-7-oxa-1'-(4-pyridyl)spiro[bicyclo[4.3.0]nonane-8,4-piperidin]-2-one;

1,4-diaza-4-(indol-2-ylsulfonyl)-7-oxa-1'-(4-pyridyl)spiro[bicyclo[4.3.0]nonane-8,4'-piperidin]-2-one;

1,4-diaza-4-[2-(5-chlorothiophen-2-yl)ethenesulfonyl]-7-oxa-1'-(4-pyridyl)spiro[bicyclo[4.3.0]nonane-8,4'-piperidin]-2-one;

1,4,7-triaza-4-[2-(5-chlorothiophen-2-yl)ethenesulfonyl]-1'-(4-pyridyl)spiro[bicyclo[4.3.0]nonane-8,4'-piperidin]-2-one;

1,4,7-triaza-4-[2-(5-chlorothiophen-2-yl)ethenesulfonyl]-7-methyl-1'-(4-pyridyl)spiro[bicyclo[4.3.0]nonane-8,4'-piperidin]-2-one;

1,4-diaza-4-[2-(5-chlorothiophen-2-yl)ethenesulfonyl]-6-(methoxymethyl)-7-oxa-1'-(4-pyridyl)spiro[bicyclo[4.3.0]nonane-8,4'-piperidin]-2-one;

1,4,7-triaza-4-[2-(5-chlorothiophen-2-yl)ethenesulfonyl]-6-(methoxymethyl)-1'-(4-pyridyl)spiro[bicyclo[4.3.0]nonane-8,4'-piperidin]-2-one;

1,4,7-triaza-4-[2-(5-chlorothiophen-2-yl)ethenesulfonyl]-6-(methoxymethyl)-7-methyl-1'-(4-pyridyl)spiro[bicyclo[4.3.0]nonane-8,4'-piperidin]-2-one;

1,4-diaza-4-(naphthalen-2-ylsulfonyl)-7-oxa-1'-(4-pyridyl)spiro[bicyclo[4.3.0]nonane-8,4'-piperidin]-2-one;

1,4-diaza-4-(2-chloroquinolin-6-ylsulfonyl)-7-oxa-1'-(4-pyridyl)spiro[bicyclo[4.3.0]nonane-8,4'-piperidin]-2-one;

1,4-diaza-4-(5-ethynylbenzo[b]furan-2-ylsulfonyl)-7-oxa-1'-(4-pyridyl)spiro[bicyclo[4.3.0]nonane-8,4'-piperidin]-2-one;

1,4,7-triaza-4-(6-chloronaphthalen-2-ylsulfonyl)-1'-(4-pyridyl)spiro[bicyclo[4.3.0]nonane-8,4'-piperidin]-2-one;

1,4,7-triaza-4-(6-chloronaphthalen-2-ylsulfonyl)-7-methyl-1'-(4-pyridyl)spiro[bicyclo[4.3.0]nonane-8,4'-piperidin]-2-one, and 1,4-diaza-4-(2-chloroquinolin-6-ylsulfonyl)-6-(methoxymethyl)-7-oxa-1'-(4-pyridyl)spiro[bicyclo[4.3.0]nonane-8,4'-piperidin]-2-one; and (+) or (−)optical isomers of such compounds, and their pharmaceutically acceptable salts (for example, methanesulfonate (mono-salt or di-salt).

[2] Second aspect of the present invention is a pharmaceutical composition characterized by its inclusion of the compound represented by formula (I) or its pharmaceutically acceptable salt as an effective component.

[2-a] More specifically, the pharmaceutical composition is
1) an anticoagulant; or a prophylactic and/or therapeutic agent for diseases induced by thrombosis or embolism;
2) a prophylactic and/or therapeutic agent for diseases wherein an anticoagulant is effective; or a prophylactic and/or therapeutic agent for diseases wherein inhibition of FXa is effective;
3) a prophylactic agent for enbolism associated with atrial fibrillation/artificial valve or valvular heart disease (and preferably, a prophylactic agent for onset of cerebral embolism associated with these diseases); or a prophylactic and/or therapeutic agent for (and in particular, a prophylactic agent for recurrence of) transient ischemic attack; or
4) a prophylactic and/or therapeutic agent for DIC; a prophylactic and/or therapeutic agent for influenza virus infection; or a prophylactic and/or therapeutic agent for deep vein thrombosis.

[3] Third aspect of the present invention is a FXa inhibitor characterized by its inclusion of the compound represented by formula (I) or its pharmaceutically acceptable salt.

[3-a] More specifically, the FXa inhibitor is an inhibitor specific for FXa characterized by its inclusion of the compound represented by formula (I) or its pharmaceutically acceptable salt as an effective component; a FXa inhibitor which can be orally administered; and an inhibitor specific for FXa which can be orally administered.

[3-b] The FXa inhibitor is a reagent characterized by its use of the compound represented by formula (I) or its pharmaceutically acceptable salt. Exemplary such reagents include a reagent for diagnosing abnormality of blood coagulation in a mammal wherein the FXa inhibitory action is utilized; a reagent for use in physiological experiments wherein quantitative FXa inhibitory action is utilized.

[4] Fourth aspect of the present invention is the compound represented by formula (V):

$$A-B-X\diagdown\diagup_{\substack{(\ )_m-Y\\(\ )_1-NH}}\diagdown\diagup\begin{matrix}OR\\OR\end{matrix} \quad (V)$$

(wherein A, B, X, Y, l, and m and the preferred embodiments are as defined above for the formula (I); the ring containing X and the ring containing Y are independently optionally substituted; R is hydrogen atom, $C_{1-6}$ alkyl, $C_{1-6}$ alkoxy, or a $C_{1-6}$ alkyl group optionally substituted with hydroxyl or a halogen atom, or the two R may together represent a $C_{2-4}$ alkylene group which is optionally substituted with $C_{1-6}$ alkyl, $C_{1-6}$ alkoxy, hydroxyl, or a halogen atom.)

The compound of formula (V) is a novel compound useful as an intermediate in the synthesis of the compound of formula (I). It should be noted that the preferable range for A, B, X, Y, l, and m are as described above for the preferable embodiments of the formula (I). R is preferably methyl group, ethyl group, 1,2-ethylene group, or 1,3-propylene group.

[5] Fifth aspect of the present invention is the compound of formula (VI):

$$A-B-X\diagdown\diagup_{\substack{(\ )_m-Y\\(\ )_1-N\\Z-(\ )_n\\HN-T-Q}}\diagdown\diagup\begin{matrix}OR\\OR\end{matrix} \quad (VI)$$

(wherein A, B, X, Y, Z, T, Q, l, m, and n and the preferred embodiments are as defined above for the formula (I); the ring containing X and the ring containing Y are independently optionally substituted; the alkylene group which binds to Z when n is 1 or more is optionally substituted; R is hydrogen atom, a $C_{1-6}$ alkyl, a $C_{1-6}$ alkoxy, or a $C_{1-6}$ alkyl group optionally substituted with hydroxyl or a halogen atom, or the two R may together represent a $C_{1-6}$ alkyl, a $C_{1-6}$ alkoxy, a $C_{2-4}$ alkylene group optionally substituted with hydroxyl or a halogen atom.)

The compound of formula (VI) is also a novel compound useful as an intermediate in the synthesis of the compound of formula (I). It should be noted that the preferable range for A, B, X, Y, l, and m are as described above for the preferable embodiments of the formula (I). R is preferably methyl group, ethyl group, 1,2-ethylene group, or 1,3-propylene group.

[6] Sixth aspect of the present invention is the compound of formula (Ik):

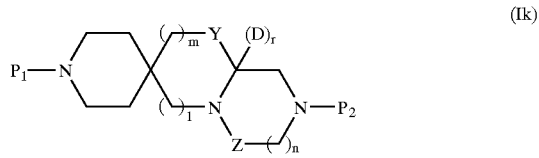

(wherein P₁ and P₂ are independently hydrogen atom or a protective group for the imino group; Y, Z, D, l, m, n, and r and the preferred embodiments are as defined above for the formula (I); and the three rings are independently optionally substituted) Exemplary imino protective groups are aralkyl groups such as benzyl group; acyl groups such as acetyl group; alkoxycarbonyl groups such as benzyloxycarbonyl and t-butoxycarbonyl; as well as the imino protective groups described in comprehensive volumes such as Protective Groups in Organic Synthesis, Second edition, 1991, John Wiley & Sons, Inc.

[7] Seventh aspect of the present invention is the compound of formula (I-a'):

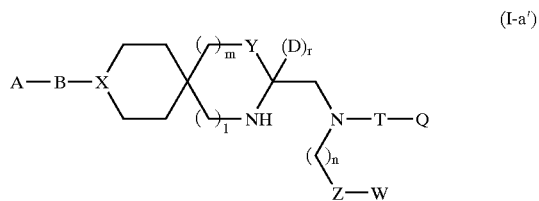

(wherein A, B, D, X, Y, Z, Q, T, l, m, n, and r and the preferred embodiments are as defined above for the formula (I); W is a leaving group or a group convertible into a leaving group; the ring containing X and the ring containing Y are independently optionally substituted; and the alkylene group which binds to Z when n is 1 or more is optionally substituted). Exemplary leaving groups are halogen atoms; acyloxy groups such as acetyloxy; and substituted sulfonyloxy groups such as methanesulfonyloxy and p-toluenesulfonyloxy groups, and if necessary, a general textbook on organic chemistry may be referred for other examples.

[8] Eighth aspect of the present invention is a compound exhibiting FXa inhibitory activity which has a partial structure represented by formula (I″) in its molecule, and the salt thereof.

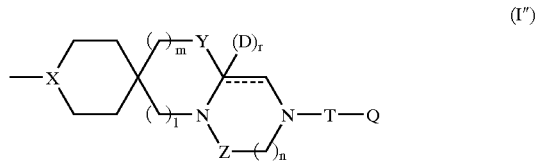

(In the formula, —X= is —CH= or —N=; the three rings, namely, the ring containing X, the ring containing Y, and the ring containing Z are independently optionally substituted; and Y. Z, D, T, Q, l, m, n, and r and the preferred embodiments are as defined above for the formula (I)).

The partial structure represented by formula (I″) is a novel partial structure which plays an important role when the compound develops its FXa inhibitory activity.

[9] Ninth aspect of the present invention is a compound exhibiting FXa inhibitory activity which has a partial structure represented by formula (I‴) in its molecule, and the salt thereof.

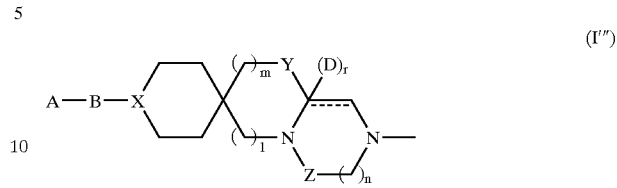

(In the formula, X is methine group or nitrogen atom; the three rings, namely, the ring containing X, the ring containing Y, and the ring containing Z are independently optionally substituted; and A, B, Y, Z, D, l, m, n, and r and the preferred embodiments are as defined above for the formula (I)).

The partial structure represented by formula (I‴) is a novel partial structure which plays an important role when the compound develops its FXa inhibitory activity.

[10] Tenth aspect of the present invention is

[10-a] a compound having FXa inhibitory activity represented by the formula (I') or its pharmaceutically acceptable salt:

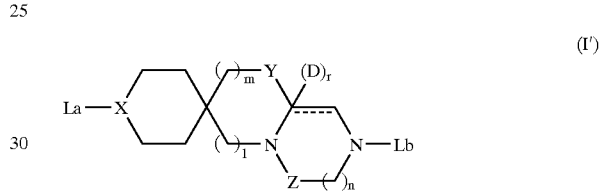

wherein D is hydrogen atom, —CO—R₅ (wherein R₅ is hydrogen atom or a substituent), or an optionally substituted $C_{1-6}$ alkyl group, X is a methine group or a nitrogen atom;

Y is an oxygen atom, —S(O)$_y$—, or an optionally substituted imino group (—NH—);

the ring containing Y may optionally have an oxo group as a substituent;

Z is a methylene group, a carbonyl group, or a thiocarbonyl group;

l, m, n, and y are independently an integer selected from 0, 1 and 2, with the proviso that l and m are not simultaneously 0, and r is an integer of 0 or 1;

the bond indicated by the broken line and the solid line represents a single bond or a double bond (when r is 0); and La and Lb are groups involved in the binding of the compound of the formula (I') to the FXa, wherein La represents a group having a basic moiety which associates with S3 pocket of FXa [a space formed at least by amino residues Trp215, Phe174, Tyr99, Thr98, Glu97, and Lys96], and Lb represents a group having a hydrophobic moiety which binds to S1 pocket of FXa [a space formed at least by amino acid residues Val213, Ser214, Trp215, Gly216, Glu217, Gly218, Cys220, Asp189, Ala190, Cys191, Gln192, Gly193, Asp194, Ser195, Gly226, Ile227, and Tyr228], and which interacts with the Tyr228 side chain in the S1 pocket but which does not form a covalent bond with Ser195 in the active center. (The amino acid No. of the FXa is indicated by chymotrypsin No. used in Protein Data Bank (PDB), Registration ID: 1FAX (J. Biol. Chem. 1996 Nov. 22; 271(47): 29988–92)).

The amino acid No. of the FXa corresponding to the chymotrypsin No. is shown in FIG. 48 in the form of a table.

[10-b] Preferably, the compound of formula (I') is the one wherein, when the compound of formula (I') binds to the FXa, the interaction of the Lb with the Tyr228 is an interaction mediated by the halogen atom, methyl group, ethyl group, or methoxy group (preferably chlorine atom or bromine atom) constituting a part of the hydrophobic moiety of the Lb. A preferable example of Lb is a group represented by the combination of Q in [1-1-d] and T in [1-8-a].

[10-c] More preferably, the compound of formula (I') is the one wherein, when the hydrophobic moiety of the Lb interacts with the Tyr228 in the binding of the compound of formula (I') to the FXa, the distance between the centroid (the coordinate obtained by calculating the average for each of X, Y, and Z coordinates of all heavy atoms included in the partial structure; hereinafter simply referred to as centroid) of the hydrophobic moiety of the Lb and the centroid of the Tyr228 side chain is within the range of 6.9 to 7.9 Å.

[10-d] The compound is also a FXa inhibitory compound which further satisfies at least one of, more preferably at least two of the following conditions 1) to 4) in addition to the [10-a] to [10-c] as described above.

1) When the compound binds to the FXa, the hydrophobic moiety of the Lb does not either partly or entirely undergo an electrostatic interaction with the Asp189 of the S1 pocket.

2) When the compound binds to the FXa, position of the centroid of the hydrophobic moiety of the Lb satisfies in the S1 pocket at least two of the following conditions that such position is:
  i) at a distance of 3.6 to 4.6 Å from the Cys191 backbone $C_\alpha$ atom;
  ii) at a distance of 6.2 to 7.2 Å from the Ser195 backbone $C_\alpha$ atom;
  iii) at a distance of 5.5 to 6.5 Å from the Ser214 backbone $C_\alpha$ atom;
  iv) at a distance of 3.6 to 4.6 Å from the Trp215 backbone $C_\alpha$ atom;
  v) at a distance of 6.7 to 7.7 Å from the Glu217 backbone $C_\alpha$ atom; and
  vi) at a distance of 5.8 to 6.8 Å from the Cys220 backbone $C_\alpha$ atom.

3) When the compound binds to the FXa, position of the centroid of the partial structure including the basic moiety of the La satisfies in the S3 pocket at least two of the following conditions that such position is:
  i) at a distance of 4.1 to 5.5 Å from the Tyr99 side chain centroid;
  ii) at a distance of 3.1 to 4.5 Å from the Phe174 side chain centroid;
  iii) at a distance of 4.1 to 5.5 Å from the Trp215 side chain centroid;
  iv) at a distance of 4.1 to 6.3 Å from the Lys96 backbone carbonyl oxygen atom; and
  v) at a distance of 3.5 to 5.1 Å from the Glu97 backbone carbonyl oxygen atom.

4) La has an optionally substituted, five- to six-membered, aromatic monocyclic heterocyclic group.

[11] Eleventh aspect of the present invention is a compound exhibiting FXa inhibitory activity which fulfills the binding conditions of any one of embodiments [10-a] to [10-d] when the compound has formed a complex with the FXa and the complex is in its crystalline state; and preferably, the compound is the one which satisfies the binding condition of [10-d].

[12] Twelfth aspect of the present invention is a compound which satisfies all of the following conditions:
  (1) the compound has a group including a basic moiety which associates with the S3 pocket of the Fxa [a space formed at least by amino residues Trp215, Phe174, Tyr99, Thr98, Glu97, and Lys96] when the complex of the compound with the FXa is in its crystalline state;
  (2) the compound has a hydrophobic moiety which binds to the S1 pocket of FXa [a space formed at least by amino acid residues Val213, Ser214, Trp215, Gly216, Glu217, Gly218, Cys220, Asp189, Ala190, Cys191, Gln192, Gly193, Asp194, Ser195, Gly226, Ile227, and Tyr228] when the complex of the compound with the FXa is in its crystalline state;
  (3) said hydrophobic moiety interacts with the Tyr228 side chain in the S1 pocket, but does not covalently bond to the Ser195 in the active center when the complex of the compound with the FXa is in its crystalline state; and
  (4) the compound has FXa inhibitory activity.

[13] Thirteenth aspect of the present invention is a composition characterized by its inclusion of at least one compound according to eighth to twelfth aspect of the invention or its salt as an effective component. Such composition has FXa inhibitory activity, and therefore, the composition is on one hand useful as a prophylactic or therapeutic agent for the diseases described in the second aspect, and on the other hand as a FXa inhibitor described in the third aspect.

[14] Fourteenth aspect of the present invention is a pharmaceutical composition characterized by its inclusion of at least one compound according to eighth to twelfth aspect of the invention as an effective component.

[15] Fifteenth aspect of the present invention is a method for inhibiting FXa characterized in that the method comprises administration of the pharmaceutical composition according to the fourteenth aspect of the invention to a mammal requiring the FXa inhibition. The method is preferably the one characterized by that the administration is accomplished by oral administration.

[16] Sixteenth aspect of the present invention is a crystal of the complex of at least one compound according to eighth to twelfth aspect of the invention or its salt with FXa.

It should be noted that, with regard to the FXa inhibitory activity mentioned in the [10] to [16], $IC_{50}$ of up to 1 µM, preferably up to 0.5 µM, more preferably up to 0.1 µM, and most preferably up to 0.01 µM in a bioassay for FXa can be added as a preferable option.

[17] Seventeenth aspect of the present invention is:

[17-a] a pharmacophore which is useful in identifying or designing an inhibitor which competitively binds to active site of the FXa or its fragment, and which satisfies all of the (a) to (c):
  (a) it is the three-dimensional structural parameter which defines the binding mode when the inhibitor binds to S1 pocket of the FXa by its hydrophobic moiety, and which induces the interaction with the Tyr228 side chain in the S1 pocket;
  (b) it is the three-dimensional structural parameter defining the binding mode when the inhibitor binds to S3 pocket of FXa by its basic moiety; and
  (c) the inhibitor does not covalently bond to Ser195 in the active center.

It should be noted that amino acid No. of the FXa is indicated by chymotrypsin No. used in Protein Data Bank (PDB), Registration ID: 1FAX (J. Biol. Chem. 1996 Nov. 22; 271(47): 29988-92).

The structure of the part of the compound which binds to the S1 pocket defined by the pharmacophore of the present invention is clearly different from the structure of the part reported for the prior art DX-9065a and the like in that the interaction with the Tyr228 is necessary, and that the electrostatic interaction with the Asp189 is not the prerequisite.

[17-b] a pharmacophore of [17-a] wherein
[17-b1] the interaction with the Tyr228 is an interaction mediated by the halogen atom, methyl group, ethyl group, or methoxy group (preferably chlorine atom or bromine atom) constituting a part of the hydrophobic moiety;
[17-b2] in the interaction with Tyr228, the distance between the centroid of the hydrophobic moiety and the centroid of the Tyr228 side chain is within the range of 6.9 to 7.9 Å;
[17-b3] the pharmacophore satisfies at least one of the following conditions 1) to 3):
  1) when the compound binds to the FXa, the hydrophobic moiety does not either partly or entirely undergo an electrostatic interaction with the Asp189 of the S1 pocket;
  2) when the compound binds to the FXa, position of the centroid of the hydrophobic moiety satisfies in the S1 pocket at least two of the following conditions that such position is:
    i) at a distance of 3.6 to 4.6 Å from the Cys191 backbone $C_\alpha$ atom;
    ii) at a distance of 6.2 to 7.2 Å from the Ser195 backbone $C_\alpha$ atom;
    iii) at a distance of 5.5 to 6.5 Å from the Ser214 backbone $C_\alpha$ atom;
    iv) at a distance of 3.6 to 4.6 Å from the Trp215 backbone $C_\alpha$ atom;
    v) at a distance of 6.7 to 7.7 Å from the Glu217 backbone $C_\alpha$ atom; and
    vi) at a distance of 5.8 to 6.8 Å from the Cys220 backbone $C_\alpha$ atom; and
  3) when the compound binds to the FXa, centroid position of the partial structure including the basic moiety of the La satisfies in the S3 pocket at least two of the following conditions that such position is:
    i) at a distance of 4.1 to 5.5 Å from the Tyr99 side chain centroid;
    ii) at a distance of 3.1 to 4.5 Å from the Phe174 side chain centroid;
    iii) at a distance of 4.1 to 5.5 Å from the Trp215 side chain centroid;
    iv) at a distance of 4.1 to 6.3 Å from the Lys96 backbone carbonyl oxygen atom; and
    v) at a distance of 3.5 to 5.1 Å from the Glu97 backbone carbonyl oxygen atom; or
[17-b4] the pharmacophore satisfies all of the conditions 1) to 3) in [17-b3].
[18] Eighteenth aspect of the present invention is [18-a] a method for identifying or designing an inhibitor which competitively binds to an active site of FXa or its fragment, wherein the inhibitor is screened by providing three-dimensional structural information of the active site to a computer system; identifying a compound which is assumed to bind to the FXa in a manner satisfying all of the conditions that:
  (a) the compound associates with S1 pocket by its hydrophobic moiety and the moiety interacts with Tyr228,
  (b) the compound associates with the inside of S3 pocket of the active site by its basic moiety, and
  (c) the compound does not bind covalently with Ser195; and
subjecting the compound to a biological assay which is capable of measuring FXa inhibitory activity to thereby determine whether the compound exhibits FXa inhibitory activity in the assay; and
[18-b] preferably, an inhibitor identification method within the scope of the aspect [18-a] characterized in that the method comprises: providing a computer system with the three-dimensional structural information of the FXa molecule containing the active site defined by coordinates of Table A (FIGS. 39 to 42) as described below; depicting the three-dimensional structure of the active site in the computer system; overlaying the three-dimensional structure of a test compound on the three-dimensional structure of the active site such that the three-dimensional structure of the test compound is arranged to meet all of the following conditions that:
  (a) the hydrophobic moiety is arranged in the S1 pocket so that the hydrophobic moiety can interact with the Tyr228;
  (b) the basic moiety is arranged in the S3 pocket; and
  (c) the compound does not bind covalently with the Ser195; evaluating whether the three-dimensional structure of the test compound spatially fits with the active site; preparing a test compound which spatially fits with the active site; and subjecting the test compound to a biological assay which is capable of measuring FXa inhibitory activity to thereby determine whether the test compound exhibits FXa inhibitory activity in the assay; or
[18-c] alternatively, a drug designing method characterized in that an evaluation is conducted on a computer by using the three-dimensional structural information of the FXa or its fragment for a compound which satisfies the following association conditions:
  (a) the compound associates with the S1 pocket by its hydrophobic moiety, and the moiety interacts with the Tyr228;
  (b) the compound associates with the inside of the S3 pocket by its basic moiety; and
  (c) the compound does not bind covalently with Ser195; or
[18-d] a method within the scope of the aspects [18-a] to [18-c] which is:
[18-d1] a method for conducting identification or molecular design on the bases of the condition that interaction with the Tyr228 is mediated by the halogen atom, methyl group, ethyl group, or methoxy group (preferably chlorine atom or bromine atom) constituting a part of the hydrophobic moiety; or
[18-d2] a method for conducting identification or molecular design on the bases of the condition that, in the interaction with the Tyr228, the distance between the centroid of the hydrophobic moiety and the centroid of the Tyr228 side chain is within the range of 6.9 to 7.9 Å; or
[18-d3] a method for conducting identification or molecular design of a FXa inhibitory compound which satisfies at least one of the following conditions 1) to 3):
  1) when the compound binds to the FXa, the hydrophobic moiety does not either partly or entirely undergo an electrostatic interaction with the Asp189 of the S1 pocket;
  2) when the compound binds to the FXa, centroid position of the hydrophobic moiety satisfies in the S1 pocket at least two of the following conditions that such position is:
    i) at a distance of 3.6 to 4.6 Å from the Cys191 backbone $C_\alpha$ atom;
    ii) at a distance of 6.2 to 7.2 Å from the Ser195 backbone $C_\alpha$ atom;
    iii) at a distance of 5.5 to 6.5 Å from the Ser214 backbone $C_\alpha$ atom;
    iv) at a distance of 3.6 to 4.6 Å from the Trp215 backbone $C_\alpha$ atom;
    v) at a distance of 6.7 to 7.7 Å from the Glu217 backbone $C_\alpha$ atom; and
    vi) at a distance of 5.8 to 6.8 Å from the Cys220 backbone $C_\alpha$ atom; and
  3) when the compound binds to the FXa, centroid position of the partial structure including the basic moiety of the La satisfies in the S3 pocket at least two of the following conditions that such position is:

i) at a distance of 4.1 to 5.5 Å from the Tyr99 side chain centroid;

ii) at a distance of 3.1 to 4.5 Å from the Phe174 side chain centroid;

iii) at a distance of 4.1 to 5.5 Å from the Trp215 side chain centroid;

iv) at a distance of 4.1 to 6.3 Å from the Lys96 backbone carbonyl oxygen atom; and v) at a distance of 3.5 to 5.1 Å from the Glu97 backbone carbonyl oxygen atom; or

[18-d4] a method for conducting the identification or the molecular design within the scope of the aspect [18-d3] on the condition that all of the conditions 1) to 3) are satisfied; or

[18-e] a method for conducting identification or molecular design of the inhibitor according to aspects [18-a] to [18-d], wherein, in providing a cross-linking group connecting the group binding to the S1 pocket and the group binding to the S3 pocket (for example La and Lb in formula (I')), a ring having spiro union is provided in the cross-linking group as a means for suppressing alteration of the conformation of the cross-linking group itself; or

[18-f] a compound identified or designed by, or a compound adapted for (a compound identifiable or designable by) the method for conducting identification or molecular design of the inhibitor according to aspects [18-a] to [18-e], which has FXa inhibitory activity in terms of $IC_{50}$ determined by a bioassay of up to 1 $\mu$M, and which was unknown at the time of the filing of the present invention; or

[18-g] a pharmaceutical composition containing as an effective component at least one compound identified or designed by, or a compound adapted for the method for conducting identification or molecular design of the inhibitor according to aspects [18-a] to [18-e], which has FXa inhibitory activity in terms of $IC_{50}$ determined by a bioassay of up to 1 $\mu$M, and (1) which was unknown at the time of the filing of the present invention or (2) which was known but whose biological activity was unknown at the time of the filing of the present invention, or a pharmaceutically acceptable salt thereof; or

[18-h] a FXa inhibitor containing as an effective component at least one compound identified or designed by, or a compound adapted for the method for conducting identification or molecular design of the inhibitor according to aspects [18-a] to [18-e], which has FXa inhibitory activity in terms of $IC_{50}$ determined by a bioassay of up to 1 $\mu$M, and (1) which was unknown at the time of the filing of the present invention or (2) which was known but whose FXa inhibitory activity was unknown at the time of the filing of the present invention, or a pharmaceutically acceptable salt thereof.

It should be noted that, the compound used in the aspects [18-f] to [18-h] is preferably the one having the FXa inhibitory activity in terms of $IC_{50}$ of up to 0.5 $\mu$M, more preferably up to 0.1 $\mu$M, and most preferably up to 0.01 $\mu$M.

In all of the aspects as described above, the expression "compound" should be deemed to also include "the pharmaceutically acceptable salt thereof".

The compound of the present invention may include an asymmetric carbon, and the compound of the present invention may be a mixture or an isolation product of geometric isomer, tautomer, optical isomer or other stereoisomer. Isolation or purification of such stereoisomer may be accomplished by those skilled in the art using any of the techniques commonly used in the art, for example, by optical resolution using preferential crystallization or column chromatography, or by asymmetric synthesis.

The compound (I) of the present invention may be in the form of an acid addition salt, and depending on the type of the substituent, the compound (I) may also be in the form of a salt with a base. Such salt is not particularly limited as long as the salt is a pharmaceutically acceptable salt, and exemplary salts include acid addition salts with hydrochloric acid, hydrobromic acid, hydroiodic acid, sulfuric acid, nitric acid, phosphoric acid, or other mineral acid; acetic acid, propionic acid, oxalic acid, malonic acid, succinic acid, fumaric acid, maleic acid, lactic acid, formic acid, malic acid, tartaric acid, citric acid, mandelic acid, or other organic carboxylic acid; methanesulfonic acid, ethanesulfonic acid, p-toluenesulfonic acid, 2-hydroxy ethanesulfonic acid, or other organic sulfonic acid; or aspartic acid, glutamic acid, or other acidic amino acid; and salts with a base of sodium, potassium, magnesium, calcium, aluminum or other alkaline metal or alkaline earth metal; methylamine, ethylamine, ethanolamine, pyridine, lysine, arginine, ornithine, or other organic base; and ammonium salt.

Furthermore, the salts of the compound of the present invention also include mono-salts, di-salts, and tri-salts. Still further, the compound of the present invention may simultaneously form an acid addition salt and a salt with base depending on the type of the substituent on the side chain.

Still further, the present invention also includes hydrates of the compound (I) as well as pharmaceutically acceptable solvates and crystalline polymorphic forms of the compound (I). It should also be taken for granted that the present invention is by no means limited to the compounds mentioned in the Examples as described below, and all of the tricyclic compounds having the spiro union as represented by formula (I) and their pharmaceutically acceptable salts are within the scope of the present invention.

It would be understood that such situation also applies to the compounds of the formulae (I'), (Im), (V), (VI), (Ik), (I-a'), (I''), (I'''), and the like.

[Production Process]

The compounds of the present invention represented by formula (I) and the related compounds can be produced by the production processes as described below.

Unless otherwise noted, A, B, D, Q, T, X, Y, Z, l, m, n, and r in the compounds of formula (I), formula (I-a), formula (I-a'), formula (I-a-1), formula (I-a-2), formula (I-b), formula (Ik), formula (Ik'), formula (II), formula (II-a), formula (II-b), formula (II-c), formula (II-d), formula (II-e), formula (IIk), formula (II-1), formula (II-2), formula (II-3), formula (II-3a), formula (II-4), formula (II-5), formula (II-6), formula (II-7), formula (II-8), formula (II-9), formula (II-10), formula (II-11), formula (II-12), formula (II-13), formula (II-14), formula (III-15), formula (II-16), formula (III), formula (IIIk), formula (III-1), formula (III-2), formula (III-3), formula (III-4), formula (III-5), formula (IIIk-1), formula (IIIk-2), formula (IIIk-3), formula (IIIk-4), formula (IIIk-5), formula (IIIk-6), formula (IIIk-7), formula (IIIk-8), formula (IIIk-9), formula (IV), formula (V), and formula (VI) in the following <Production process 1>, <Production process 2>, <Production process 3>, and <Production process 4>, and their description, and their salts are as defined for formula (I). In the respective compounds described above, the side chains and the alkylene group in the rings are optionally substituted with the substituents defined for formula (I).

Unless otherwise noted, W in the production process represents the leaving group or the group convertible into the leaving group as described above. J represents a thiol protective group such as p-methoxybenzyl group. $P_1$ and $P_2$ in the intermediate compounds of formulae (Ik) to (IIIk-9)

marked with "k" independently represent hydrogen atom or a protective group of the imino group (—NH—). Exemplary protective groups of the imino group (—NH—) include aralkyl groups such as benzyl group; acyl groups such as acetyl group; and alkoxycarbonyl groups such as benzyloxycarbonyl group, and t-butoxycarbonyl group. When $P_1$ and $P_2$ are protective groups of the imino group (—NH—), deblocking may be accomplished by adequately selecting the type of the protective groups or the conditions of the deblocking to independently or simultaneously remove the protective groups, and if necessary, the protective groups and the like can also be reintroduced.

Unless otherwise noted, the reaction conditions employed in the production process are as described below. Reaction temperature is in the range of −78° C. to the solvent-reflux temperature, and reaction time is the time sufficient for required progress of the reaction. Solvent which is not involved in the reaction may be any of the aromatic hydrocarbon solvents such as toluene and benzene; polar solvents such as water, methanol, DMF, and DMSO; basic solvents such as triethylamine and pyridine; halogen solvents such as chloroform, methylene chloride, and 1,2-dichloroethane; ethereal solvent such as diethylether, tetrahydrofuran, and dioxane; and mixed solvents thereof; and the solvent used may be adequately selected depending on the reaction conditions. Base may be any of inorganic bases such as potassium carbonate, cesium carbonate, sodium hydroxide, potassium hydroxide, and sodium hydride; or organic bases such as triethylamine, pyridine, N,N-dialkylaniline, and lithium diisopropylamide; and acid may be any of mineral acids such as hydrochloric acid, and sulfuric acid; organic acids such as methanesulfonic acid and p-toluenesulfonic acid. The base and the acid are not necessarily limited to those mentioned above.

The compounds represented by formula (I) and formula (Ik) which are the compounds of the present invention or their salts may be synthesized from the compounds represented by formula (II), formula (IIk), formula (III), formula (IIIk), formula (III-3), formula (IIIk-4), formula (IIIk-6), formula (IV), formula (V), or formula (VI) or their salts which can be readily produced from known or commercially available compounds, by <Production process 1>, <Production process 2>, <Production process 3>, or <Production process 4>.

Next, the production process is described. The present invention, however, is by no means limited to the processes as described below.

<Production Process 1>

The compound represented by the formula:

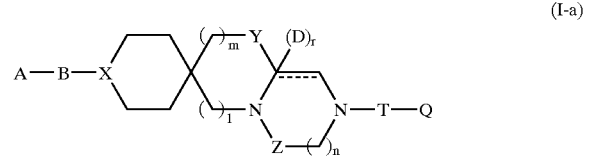

(I-a)

(wherein A, B, D, Q, T, X, Y, Z, l, m, and n, and substitution of each alkylene chain are as defined above; and r is 1) or its salt may be produced by the process as described below.

Compounds represented by formula (II) and formula (III):

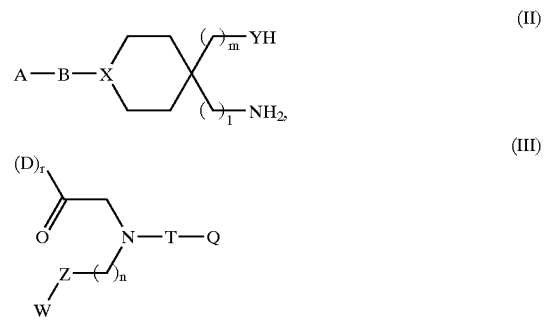

(wherein A, B, D, Q, T, X, Y, l, m, n, and W, and substitution of each alkylene chain are as defined above; r is 1; and Z represents carbonyl group or thiocarbonyl group) or their salts which are commercially available or readily derived from commercially available compounds may be reacted in accordance with the known process described in documents (for example, Journal of Medicinal Chemistry vol. 19, page 436, 1976; Journal of American Chemical Society vol. 107, page 7776, 1985; or Journal of Organic Chemistry vol. 63, page 1732, 1998) preferably by using toluene for the solvent in the presence or absence of an acid catalyst, and preferably, in the presence of p-toluenesulfonic acid. The reaction may be promoted at a temperature in the range of 0° C. to the solvent reflux temperature, and preferably at the solvent reflux temperature for a time sufficient for the progress of the required reaction, and preferably for 2 to 6 hours to produce the compound represented by formula (I-a) or its salt. With regard to the substituent z, interconversion between carbonyl group and thiocarbonyl group or conversion into methylene group may be accomplished, if necessary, by a known process, for example, by the process described in "Shin-jikkenkagakukouza 14 Synthesis and Reaction of Organic Compounds [III]", page 1817, 1978, Maruzen.

Next, typical processes for producing the compounds of formula (II) and formula (III) which are the starting compounds are described.

<1> Production Process of the Compound of Formula (II):

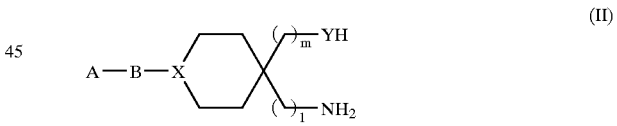

(In the formula, A, B, X, Y, l, and m, and substitution of each alkylene chain are as defined above.)

1-1) When l=1 and m=0

When Y is O (oxygen atom), the compound may be produced, for example, by the production process as described below.

<Step II-1-1>

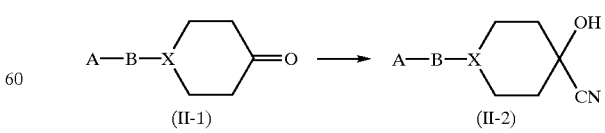

A compound represented by the formula (II-1) or its salt which is commercially available or readily derived from a commercially available compound may be reacted in accordance with the known process described in documents (for example, "Shinjikkenkagakukouza 14 Synthesis and Reaction of Organic Compounds [III]", page 1455, 1978, Maruzen) to produce the compound represented by formula (II-2) or its salt.

<Step II-1-2>

The compound represented by formula (II-2) or its salt obtained in <Step II-1-1> may be then reduced in accordance with the known process described in documents (for example, "Shinjikkenkagakukouza 14 Synthesis and Reaction of Organic Compounds [III]", page 1332, 1978, Maruzen) to produce the compound represented by formula (II-a) or its salt.

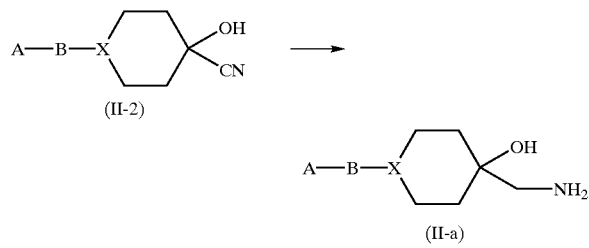

(II-2)

(II-a)

Next, another process for producing the compound represented by formula (II-a) or its salt is described.

<Step II-2-1>

A compound represented by formula (II-1) or its salt may be reacted in accordance with the known process described in documents (for example, "Shinjikkenkagakukouza 14 Synthesis and Reaction of Organic Compounds [I]", page 594, 1977, Maruzen) to produce the compound represented by formula (II-3) or its salt.

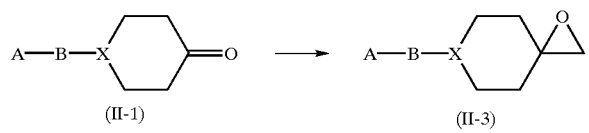

(II-1)    (II-3)

<Step II-2-2>

The compound represented by formula (II-3) or its salt obtained in <Step II-2-1> may be then reacted in accordance with the known process described in documents (for example, Synthesis, page 629, 1984) to produce the compound represented by formula (II-a) or its salt.

Furthermore, another process for producing the compound represented by formula (II-a) or its salt is described.

<Step II-2a-1>

A compound represented by formula (II-1) or its salt may be reacted in accordance with the known process described in documents (for example, "Shinjikkenkagakukouza 14 Synthesis and Reaction of Organic Compounds [III]", page 1294, 1978, Maruzen) to produce the compound represented by formula (II-3a) or its salt.

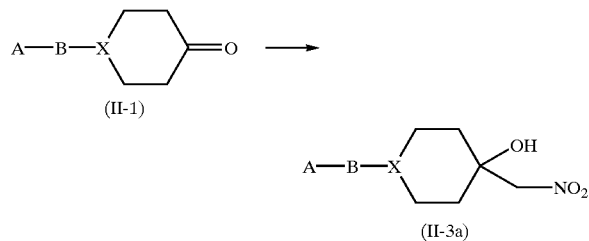

(II-1)

(II-3a)

<Step II-2a-2>

The compound represented by formula (II-3a) or its salt obtained in <Step II-2a-1> may be then reacted in accordance with the known process described in documents (for example, "Shinjikkenkagakukouza 14 Synthesis and Reaction of Organic Compounds [III]", page 1333, 1978, Maruzen) to produce the compound represented by formula (II-a) or its salt.

When Y is S (sulfur atom), the compound may be produced, for example, by the production process as described below.

<Step II-3-1>

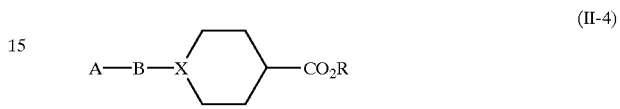

(II-4)

A compound represented by the formula (II-4) (wherein R is a hydrocarbon group as typically represented by $C_{1-6}$ alkyl groups such as methyl, ethyl, propyl, and t-butyl and aralkyl groups such as benzyl group) or its salt which is commercially available or readily derived from a commercially available compound may be reacted in accordance with the known process described in documents (for example, JP09510700) to produce the compound represented by formula (II-5):

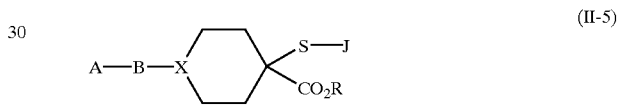

(II-5)

(wherein R is the same as R in (II-4); J is a protective group such as p-methoxybenzyl group) or its salt.

<Step II-3-2>

The compound represented by formula (II-5) or its salt obtained in <Step II-3-1> and ammonia or optionally protected amine are reacted for normal amidation to produce the compound represented by formula (II-6) or its salt.

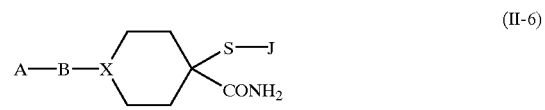

(II-6)

<Step II-3-3>

The compound represented by formula (II-6) or its salt obtained in <Step II-3-2> may be then reduced in accordance with the known process described in documents (for example, "Shinjikkenkagakukouza 14 Synthesis and Reaction of Organic Compounds [III]", page 1332, 1978, Maruzen) to produce the compound represented by formula (II-7) or its salt.

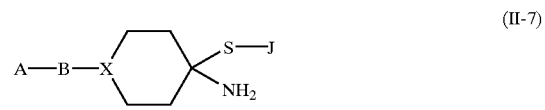

(II-7)

<Step II-3-4>

The compound represented by formula (II-7) or its salt obtained in <Step II-3-3> may be then reacted for normal deblocking of the thiol protective group to produce the compound represented by formula (II-b) or its salt.

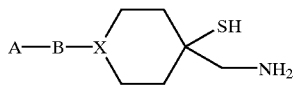

1-2) When l=0, 1, or 2, and m=1 or 2

When Y is O (oxygen atom), the compound may be produced, for example, by the production process as described below.

<Step II-4-1>

A compound represented by formula (II-8):

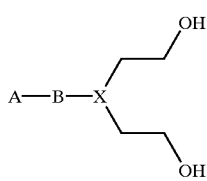

or its salt which is commercially available or readily derived from a commercially available compound may be reacted in accordance with the known process described in documents (for example, "Shinjikkenkagakukouza 14 Synthesis and Reaction of Organic Compounds [I]", page 331, 1977, Maruzen) to produce a reactive derivative represented by formula (II-9) or its salt.

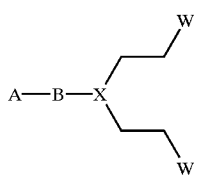

<Step II-4-2>

The compound represented by formula (II-9) or its salt obtained in <Step II-4-1> may be then reacted with an active methylene compound such as ethyl cyanoacetate, ethyl nitroacetate, ethyl malonate monoamide or ethyl cyanopropionate in a solvent which is not involved in the reaction in the presence of a base to produce the compound represented by formula (II-10) (wherein E represents nitro group, cyano group, or amide group; and R is the same as R defined in formula (II-4)) or its salt.

<Step II-4-3>

The compound represented by formula (II-10) or its salt obtained in <Step II-4-2> may be then reduced in accordance with the known process described in documents (for example, "Shinjikkenkagakukouza 14 Synthesis and Reaction of Organic Compounds [III]", page 1332, 1978, Maruzen) to produce the compound represented by formula (II-c) or its salt.

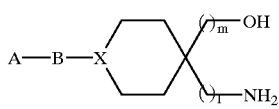

When Y is imino group (—NH—), the compound may be produced, for example, by the production process as described below.

<Step II-5-1>

The compound represented by formula (II-c) or its salt obtained in <Step II-4-3> may be reacted with a phosphorus compound such as triphenylphosphin or tributylphosphin and an azodicarboxylate as typically represented by diethyl azodicarboxylate (DEAD) in a solvent which is not involved in the reaction to activate the hydroxyl group, and the resulting product may be reacted with phthalimide to produce the compound represented by formula (II-11) or its salt.

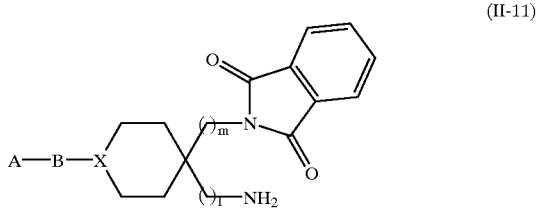

<Step II-5-2>

The compound represented by formula (II-11) or its salt obtained in <Step II-5-1> may be then reacted for deblocking to produce the compound represented by formula (II-d) or its salt.

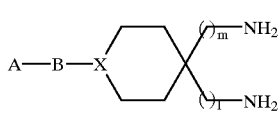

When Y is imino group (—NH—), the compound may be produced, for example, by the alternative production process as described below.

<Step II-6-1>

The compound represented by formula (II-2) or its salt may be reacted in accordance with the known process described in documents (for example, "Synthesis", page 832, Scheme 2, 1994) to produce the compound represented by formula (II-12) or its salt.

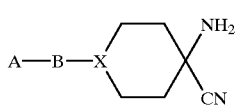

<Step II-6-2>

The compound represented by formula (II-12) or its salt obtained in <Step II-6-1> may be reduced in accordance with <Step II-1-2> to produce the compound represented by formula (II-e) or its salt.

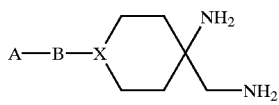

(II-e)

Next, another process for producing the compound represented by formula (II-12) or its salt is described.
<Step II-6-3>
The compound represented by formula (II-1) or its salt may be reacted in accordance with the known process described in documents (for example, DE4405140, Scheme 1 (Reaction i)) to produce the compound represented by formula (II-12) or its salt.

Next, another process for producing the compound represented by formula (II-e) or its salt is described.
<Step II-7-1>
A compound represented by formula (II-1) or its salt may be reacted in accordance with the known process described in documents (for example, "Shinjikkenkagakukouza 14 Synthesis and Reaction of Organic Compounds [III]", page 1399, 1978, Maruzen) to produce the compound represented by formula (II-13) or its salt.

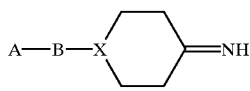

(II-13)

<Step II-7-2>
The compound represented by formula (II-13) or its salt obtained in <Step II-7-1> may be then reacted in accordance with the known process described in documents (for example, "Tetrahedron Letters", Vol. 24, page 4503, 1983) to produce the compound represented by formula (II-14) or its salt.

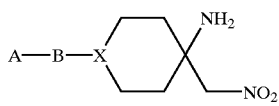

(II-14)

<Step II-7-3>
The compound represented by formula (II-14) or its salt obtained in <Step II-7-2> may be reduced in accordance with <Step II-2a-2> to produce the compound represented by formula (II-e) or its salt.

Furthermore, another process for producing the compound represented by formula (II-e) or its salt is described.
<Step II-8-1>
A compound represented by formula (II-1) or its salt may be reacted in accordance with the known process described in documents (for example, "Organic Reactions", Vol. 14, page 270, 1965, John Wiley & Sons, Inc.) to produce the compound represented by formula (II-15) or its salt.

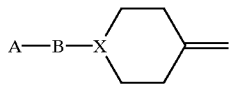

(II-15)

<Step II-8-2>
The compound represented by formula (II-15) or its salt obtained in <Step II-8-1> may be then reacted in accordance with the known process described in documents (for example, "Journal of American Chemical Society", Vol. 82, page 6068, 1960) to produce the compound represented by formula (II-16) or its salt.

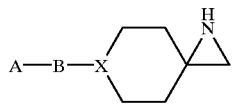

(II-16)

<Step II-8-3>
The compound represented by formula (II-16) or its salt obtained in <Step II-8-2> or its salt may be reacted in accordance with the known process described in documents (for example, "Shinjikkenkagakukouza 14 Synthesis and Reaction of Organic Compounds [III]", page 1362, 1978, Maruzen) to produce the compound represented by formula (II-e) or its salt.

In the foregoing steps, the substituent may be introduced into the alkylene chain, for example, by using a commercially available compound having the corresponding substituent for the starting material (II-1) or (II-8); by introducing the corresponding substituent in the starting material by the process commonly used in the synthesis; by converting the active methylene compound of <Step II-4-1> to an adequately substituted derivative before the reaction with the methylene compound; by reducing the cyano group in (II-2) or (II-4) to amide group, and converting and/or modifying the carbonyl group as desired; or if necessary, by directly introducing the substituent into the compound represented by formula (II).

With regard to the preferable substituent D, D may be introduced in accordance with the process employed for the synthesis of D as described below.

<2> Production Process of the Compound of Formula (III):

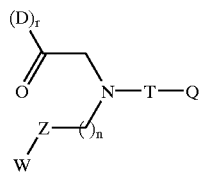

(III)

<Step III-1-1>
A compound represented by formula (III-1):

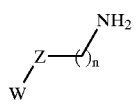

(III-1)

(wherein n is 1 or 2) or its salt which is commercially available or readily derived from a commercially available compound, and a compound represented by formula (III-2):

W-T-Q     (III-2)

(wherein W, Q, and T are as described above) or its salt which is commercially available or readily derived from a commercially available compound may be fused to produce the compound represented by formula (III-3) or its salt. When T is sulfonyl group and W is chlorine atom, for example, the reaction may be carried out in methylene chloride in the presence of triethylamine at a temperature in the range of 0° C. to room temperature, and preferably, at room temperature for 2 to 12 hours.

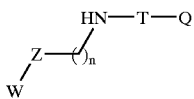
(III-3)

<Step III-1-2>

The compound represented by formula (III-3) or its salt obtained in <Step III-1-1> may be reacted with an alkylating agent represented by formula (III-4) in a solvent which is not involved in the reaction in the presence of a base to produce the compound represented by formula (III) or its salt.

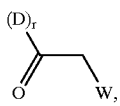
(III-4)

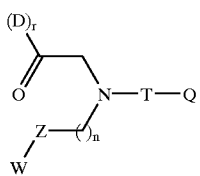
(III)

Next, another process for producing the compound represented by formula (III) or its salt is described.

<Step III-2-1>

A commercially available compound represented by formula (III-1):

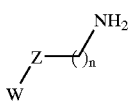
(III-1)

(wherein n is 1 or 2) or its salt is reacted in accordance with the procedure of <Step III-1-2> to produce the compound represented by formula (III-5) or its salt.

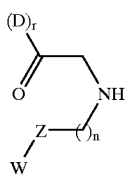
(III-5)

<Step III-2-2>

The compound represented by formula (III-5) or its salt obtained in <Step III-2-1> is condensed with the compound represented by formula (III-2) or its salt in accordance with the procedure of <Step III-1-1> to produce the compound represented by formula (III) or its salt.

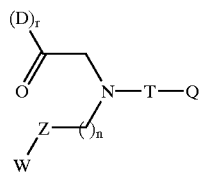
(III)

It should be noted that the carbonyl group in the formula (III) may be protected if necessary, and the protective group may be removed at an adequate stage.

In the steps of producing the compound of formula (III), substituent may be introduced at the alkylene chain, for example, by using a commercially available compound having the corresponding substituent for the starting material (III-1) or (III-4); or by introducing the corresponding substituent in the starting material by the known process described in the documents.

<Production Process 2>

The compound represented by:

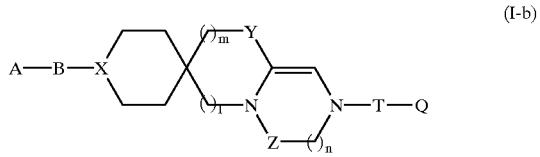
(I-b)

(wherein A, B, Q, T, X, Y, Z, l, m, and n are as defined above) or its salt may be produced by the process as described below.

<Step 1>

The compound represented by formula (II) produced by the process described in <Production process 1> or its salt and the compound represented by formula (IV) or its salt which is commercially available or readily derived from a commercially available compound

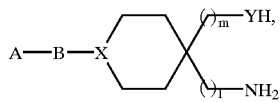
(II)

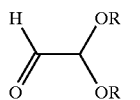
(IV)

(wherein A, B, X, Y, l, and m, and substitution of each alkylene chain are as defined above; and R is hydrogen atom, a $C_{1-6}$ alkyl, a $C_{1-6}$ alkoxy, or a $C_{1-6}$ alkyl group optionally substituted with hydroxyl or a halogen atom (and in particular, methyl group or ethyl group); or the two R may together represent a $C_{1-6}$ alkyl, a $C_{1-6}$ alkoxy, a $C_{2-4}$ alkylene group optionally substituted with hydroxyl or a halogen atom (in particular, 1,2-ethylene group or 1,3-propylene group)) may be reacted in accordance with the procedure of <Production process 1> to produce the compound represented by formula (V) or its salt.

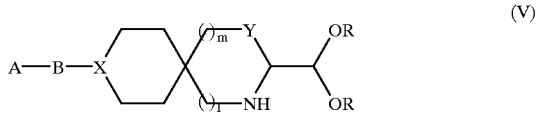

(V)

(In the formula, A, B, X, Y, l, and m, and substitution of each alkylene chain are as defined above; and R is the same as R defined in formula (IV).)

<Step 2>

The compound represented by formula (V) or its salt obtained in <Step 1> and the compound represented by formula (III-3):

(III-3)

(wherein Q, T, W, Z, and n, and substitution of each alkylene chain are as defined above) or its salt prepared by the procedure described in <Production process 1> may be reacted to produce the compound represented by formula (VI) or its salt.

When Z is carbonyl group or thiocarbonyl group, and W is a halogen atom, hydroxyl group, or an alkoxy group in the compound represented by formula (III-3) or its salt, amidation in normal peptide is carried out. For example, when W is hydroxyl group, a phenol such as 2,4,5-trichlorophenol, pentachlorophenol, 2-nitrophenol, or 4-nitrophenol, or a N-hydroxy compound such as N-hydroxysuccinimide, N-hydroxy-5-norbornene-endo-2,3-dicarboxyimide or N-hydroxypiperidine is condensed in the presence of a condensing agent such as N,N-dicyclohexylcarbodiimide for conversion into active ester form, and allowed for reaction.

Alternatively, the reaction may be conducted after producing a mixed acid anhydride by reacting with a halogenated acyl compound such as isobutylchloroformate. The reaction may be also promoted by using a peptide condensation reagent such as N,N-dicyclohexylcarbodiimide, diphenylphosphoric acid azide or diethyl cyanophosphate alone.

When Z is methylene group in the compound represented by formula (III-3) or its salt, normal N-alkylation may be promoted in a solvent which is not involved in the reaction to produce the compound represented by formula (VI) or its salt.

Furthermore, when W is hydroxyl group, the compound represented by formula (III-3) may be activated by using a phosphorus compound such as triphenylphosphin or tributylphosphin and an azodicarboxylate typically represented by diethyl azodicarboxylate, and then reacted in a solvent which is not involved in the reaction.

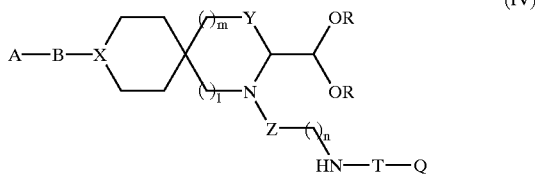

(IV)

(In the formula, A, B, Q, T, X, Y, Z, l, m, and n, and substitution of each alkylene chain are as defined above. R is the same as R defined in formula (IV).)

<Step 3>

The compound represented by formula (VI) (wherein A, B, Q, T, X, Y, Z, l, m, and n, and substitution of each alkylene chain are as defined above; and R is the same as R defined in the compound represented by formula (IV)) or its salt obtained in <Step 2> may be then reacted in accordance with the known process described in documents (for example, JP09316059) in a solvent which is not involved in the reaction, and preferably by using toluene for the solvent, in the presence of an acid catalyst, and preferably in the presence of p-toluenesulfonic acid to produce a compound represented by formula (I-b) or its salt. The reaction temperature is preferably in the range of 70° C. to 80° C., and the reaction time is preferably in the range of 1 to 2 hours. With regard to the substituent Z, interconversion between carbonyl group and thiocarbonyl group or conversion into methyelene group may be accomplished, if necessary, by a known process, for example, the process described in "Shin-jikkenkagakukouza 14 Synthesis and Reaction of organic Compounds [III]", page 1817, 1978, Maruzen.

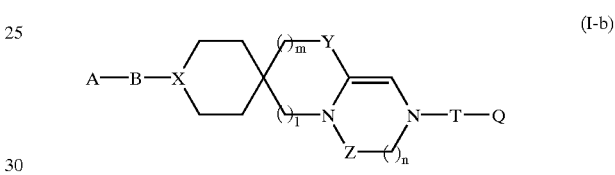

(I-b)

(In the formula, A, B, Q, T, X, Y, Z, l, m, and n are as defined above)

<Production Process 3>

Another process for producing a compound represented by formula (I-a) or its salt is as described below.

The compound represented by formula (I-b):

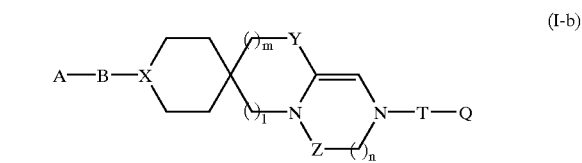

(I-b)

(wherein A, B, Q, T, X, Y, Z, l, m, and n are as defined above) or its salt produced in <Production process 2> may be reacted for reduction of the double bond in the formula to produce the compound represented by formula (I-a) or its salt. Exemplary reduction processes include reduction by a metal or a metal salt such as sodium, calcium and aluminum; reduction by a metal hydride such as diisopropyl aluminum hydride; and reduction by a metal hydride complex such as sodium borohydride; electrophilic reduction by diborane or substituted borane; and catalytic hydrogenation using a metal catalyst. The reaction solvents used is a solvent which is not involved in the reaction, for example, tetrahydrofuran, toluene, methylene chloride, or methanol, or a mixture thereof, and the reaction is conducted at a temperature of −78° C. to reflux temperature for a time sufficient for required progress of the reaction.

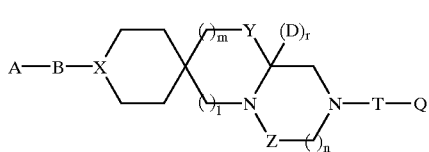
(I-a)

(In the formula, A, B, D, Q, T, X, Y, Z, l, m, n, and r are as defined above)

<Production Process 4>

The compound represented by formula:

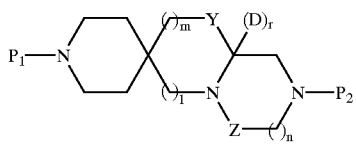
(Ik)

(wherein D, P₁, P₂, Y, Z, l, m, n, and r, and substitution of each alkylene chain are as defined above) or its salt may be produced by the process as described below.

<1> Production Process of the Compound of Formula (Ik) (Skeleton Forming Reaction)

<Step 1>

Compounds represented by formula (IIk) and formula (IIIk):

(II k)

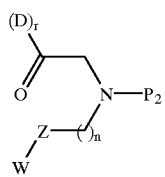
(III k)

(wherein D, P₁, P₂, W, Y, Z, l, m, and n, and substitution of each alkylene chain are as defined above; and r is 1) or their salts which are commercially available or readily derived from a commercially available compound may be reacted in accordance with <Production process 1> to produce a compound represented by formula (Ik) or its salt.

The compound represented by formula (Ik) or its salt may be produced also by another process as described below.

<Step 2>

The reaction may be promoted in accordance with <Step 1> by using a reaction solvent which is described in <Production process 1>, or alternatively, a halogen solvent such as methylene chloride, chloroform, or 1,2-dichloroethane, the preferred being chloroform, and there is produced a compound of formula (Ik') (wherein D, P₁, P₂, W, Y, Z, l, m, and n, and substitution of each alkylene chain are as defined above; and r is 1).

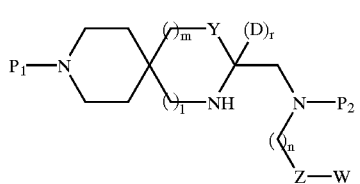
(I k')

<Step 3>

The compound represented by formula (Ik') or its salt produced in <Step 2> may be then condensed in accordance with <Production process 2> <Step 2> to produce the compound represented by formula (Ik) or its salt.

Next, typical production processes of the compounds of formula (IIk) and formula (IIIk) which are the starting compounds are described.

<2> Production Process of the Compound of Formula (IIk)

(II k)

(In the formula, P₁, Y, l, and m, and substitution of each alkylene chain are as defined above.)

The compound represented by formula (IIk) or its salt may be produced in accordance with the production process of <Production process 1> <formula (II)>.

<3> Production Process of the Compound of Formula (IIIk)

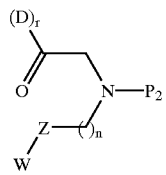
(III k)

(In the formula, D, P₂, W, Z, and n, and substitution of each alkylene chain are as defined above; and r is 1.) The compound represented by formula (IIIk) or its salt may be produced in accordance with the production process of <Production process 1> <formula (III)>.

The compound represented by formula (IIIk) may be produced also by different processes as described below.

<Step IIIk-1-1>

The compounds represented by formula (III-1) and formula (IIIk-1):

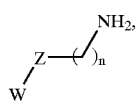
(III-1)

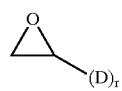
(III k-1)

(wherein n is 1 or 2) or their salts which are commercially available or readily derived from a commercially available compound may be reacted for nucleophilic addition associated with ring opening of the epoxide to produce the compound represented by formula (IIIk-2) or its salt.

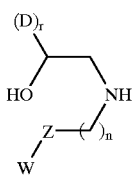
(III k-2)

<Step IIIk-1-2>

The compound represented by formula (IIIk-2) or its salt obtained in <Step IIIk-1-1> may be then reacted for normal introduction of the protective group $P_2$ into the imino group (—NH—) to produce the compound represented by formula (IIIk-3) or its salt.

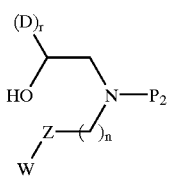
(III k-3)

<Step IIIk-1-3>

The compound represented by formula (IIIk-3) or its salt obtained in <Step IIIk-1-2> may be then reacted in a solvent which is not involved in the reaction for oxidation by manganese dioxide; chromic acid oxidation by chromium oxide (VI) or dichromate; oxidation by lead tetraacetate; oxidation by oxygen; oxidation by activated DMSO; oxidation by high valence iodine typically represented by Dess-Martin reagent; oxidation by halogen compound such as hypohalogenous acid or its salt to produce the compound represented by formula (IIIk) or its salt.

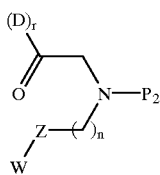
(III k)

<Step IIIk-2-1> and <Step IIIk-2-2>

Alternatively, the compound represented by formula (III-1) or its salt may be reacted by <Step IIIk-1-2> and <Step IIIk-1-1> through the compound represented by formula (IIIk-4) or its salt to produce the compound represented by formula (IIIk-3) or its salt.

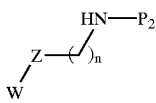
(III k-4)

<Step IIIk-3-1> and <Step IIIk-3-2>

Alternatively, the compound represented by formula (IIIk-2) or its salt may be reacted by <Step IIIk-1-3> and <Step IIIk-1-2> through the compound represented by formula (IIIk-5) or its salt to produce the compound represented by formula (IIIk) or its salt.

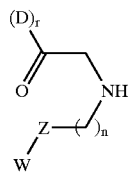
(III k-5)

<Step IIIk-4-1>

The compound represented by formula (IIIk-6) or its salt which is commercially available or readily derived from a commercially available compound may be reacted in accordance with <Production process 1> <Step III-1-2> to produce the compound represented by formula (IIIk-7) or its salt.

(III k-6)

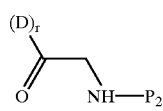
(III k-7)

<Step IIIk-4-2>

The compound represented by formula (IIIk-7) or its salt obtained in <Step IIIk-4-1> and the compound represented by formula (IIIk-8):

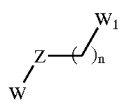
(III k-8)

(wherein W, Z, and n are as defined above; and $W_1$ is a group selected from the groups defined for W for selective substitution of $W_1$ in this reaction) or its salt which is commercially available or readily derived from a commercially available compound may be then condensed in accordance with the procedure of <Step IIIk-4-1> to produce the compound represented by formula (IIIk) or its salt.

<Step IIIk-5-1>, <Step IIIk-5-2> and <Step IIIk-5-3>

Alternatively, the compound represented by formula (IIIk-6) or its salt may be reacted in accordance with <Step IIIk-1-1> and <Step IIIk-1-2> through the compound represented by formula (IIIk-9) or its salt to produce the compound represented by formula (IIIk-3) or its salt. Alternatively, the compound of formula (IIIk-9) may be oxidized in accordance with <Step IIIk-1-3> to produce the compound represented by formula (IIIk-7) or its salt.

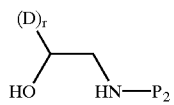
(III k-9)

Alternatively, a compound having -T-Q instead of the $-P_2$, for example, a compound of formula (IIIk-6) wherein $-P_2$ is -T-Q, or a compound of formula (IIIk-4) wherein $-P_2$ is -T-Q may be used in accordance with the alternative process as described above to produce the compound represented by formula (III) or its salt.

In the <Production process 4>, $P_1$ or $P_2$ may be independently deblocked at the most adequate stage for subsequent conversion into the A-B or the T-Q. Conversion into the A-B and the T-Q is described later.

Furthermore, when the <Production process 4> is adopted, the compound represented by formula (I-a) or its salt wherein $P_1$- is A-B-, and -$P_2$ is -T-Q can be produced by the production of the compound represented by formula (I-a'):

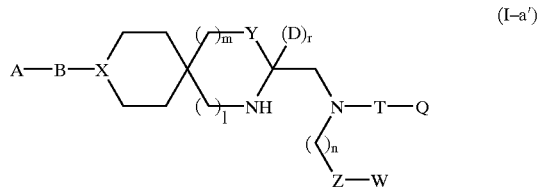

(I-a')

(wherein A, B, D, Q, T, X, Y, l, m, n, and W, and substitution of each alkylene chain are as defined above; r is 1; and Z represents carbonyl group or thiocarbonyl group) or its salt followed by condensation.

In the foregoing, production process of the skeleton of the compound of the present invention has been described in detail.

Next, conversion of the substituents D, A-B, and T-Q is described.

The conversion of the substituents D, A-B, and T-Q may be carried out at any stage in the <Production process 1>, <Production process 2>, <Production process 3>, and <Production process 4>, or in the stage of the starting compound, or in any reaction stage of producing such starting compound.

In the synthesis of the compound of the present invention (I), those skilled in the art can choose the best timing for the substituent conversion.

Typical conversion process of the substituents D, A-B, and T-Q are described in the following section which by no means limit the scope of the invention.

For example, the conversion of the substituent D is conducted as described below (for the case wherein m 1) when the compound represented by formula (I-a) or its salt is employed.

<Step D-1>

The compounds represented by formula (II-a) and formula (III-a-1):

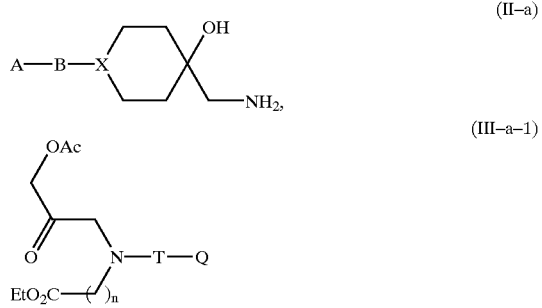

(II-a)

(III-a-1)

(wherein A, B, Q, T, X, and n, and substitution of each alkylene chain are as defined above; and Ac represents acetyl group) or their salts prepared by the procedure described in <Production process 1> were reacted in accordance with <Production process 1> to produce the compound represented by formula (I-a-1):

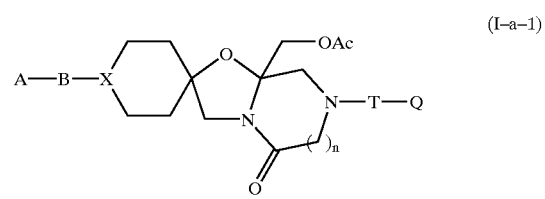

(I-a-1)

(wherein A, B, Q, T, X, n, and Ac, and substitution of each alkylene chain are as defined above) or its salt.

<Step D-2>

The compound represented by formula (I-a-1) or its salt obtained in <Step D-1> is reacted with aqueous solution of sodium hydroxide, for example, in methanol at room temperature to produce the compound represented by formula (I-a-2):

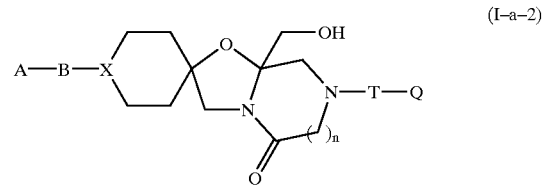

(I-a-2)

(wherein A, B, Q, T, X, and n, and substitution of each alkylene chain are as defined above) or its salt.

Next, typical production process for converting the side chain from an adequate precursor D', for example, the D' which is —$CH_2OH$ (as in the case of the compound of formula (I-a-2)) to the substituent D is described.

1) Substituent D Convertible from D' which is —$CH_2OH$ 1-1) Production of a Compound wherein D is —$CH_2$—OR' (wherein R' is an optionally substituted $C_{1-6}$ alkyl group) or its salt 1-1-1) Production Process Using R'—W The compound wherein D' is —$CH_2OH$ or its salt may be reacted with a compound represented by formula: R'—W in a solvent which is not involved in the reaction, and preferably, in the mixed solvent of methylene chloride and water in the presence of a base, and preferably, using sodium hydroxide in the presence or absence of a phase transfer catalyst such as quaternary ammonium salt or crown ether, and preferably, in the presence of benzyltriethylammonium chloride at a temperature of –78° C. to reflux temperature, and preferably, at 0° C. for a time sufficient for the required progress of the reaction, and preferably, for 2 hours for conversion into the compound wherein D is —$CH_2$—OR' or its salt.

1-1-2) Production Process Using R'—OH

The compound wherein D' is —$CH_2OH$ or its salt is reacted with a compound represented by formula: R'—OH activated by using a phosphorus compound such as triphenylphosphin or tributylphosphin and an azodicarboxylate as typically represented by diethyl azodicarboxylate(DEAD) in a solvent which is not involved in the reaction for conversion into the compound wherein D is —$CH_2$—OR' or its salt.

1-2) Production of a Compound wherein D is —$CH_2$—O—CO—R" (wherein R" is an optionally Substituted $C_{1-6}$ Alkyl Group) or its salt The compound wherein D' is —$CH_2OH$ or its salt may be reacted with R"—CO—W in a solvent which is not involved in the reaction in the presence or absence of a base or in the presence or absence of an acid for conversion into the compound wherein D is —$CH_2$—O—CO—R" or its salt.

1-3) Production of a compound wherein D is —$CH_2$—NR'R" (wherein —NR' and R" are an amino group represented, for example, by —$NR_6R_7$ (wherein $R_6$ and $R_7$ are independently hydrogen atom, a $C_{1-6}$ alkyl, a $C_{4-7}$ cycloalkyl, or a $C_{2-6}$ alkenyl; or $R_6$, $R_7$ and the nitrogen to which they are binding together represent a five- to seven-membered heterocyclic ring wherein the heterocyclic ring contains 1 to 2 heteroatoms selected from N, S, and O; said $R_6$ and $R_7$ being optionally further substituted with an adequate substituent)) or its salt The compound wherein D' is —$CH_2OH$ or its salt may be reacted with thionyl chloride, methanesulfonyl chloride, p-toluenesulfonyl chloride, or the like in a solvent which is not involved in the reaction in the presence or absence of a base or in the presence or absence of an acid for conversion into the compound wherein D' is —$CH_2$—W or its salt. The compound wherein D' is —$CH_2$—W or its salt may be further reacted with an amine represented by HNR'R" (for example, $HNR_6R_7$ and $NR_6R_7$ are as defined above) in a solvent which is not involved in the reaction in the presence or absence of copper powder, copper oxide powder, or iron powder in the presence or absence of a base or in the presence or absence of an acid for conversion into the compound wherein D is —$CH_2$—NR'R" or its salt. If necessary, a metal such as copper, palladium, chromium, or bismuth may be employed for formation of a complex with the compound wherein D' is represented by —$CH_2$—W in order to use the compound with a higher activity in the reaction.

Alternatively, the compound wherein D' is —$CH_2OH$ or its salt may be reacted with a phosphorus compound such as triphenylphosphin or tributylphosphin and an azodicarboxylate as typically represented by diethyl azodicarboxylate (DEAD) in a solvent which is not involved in the reaction to activate the hydroxyl group, and the resulting product may be reacted with the compound represented by formula: NHR'R" for conversion into the compound wherein D is —$CH_2$—NR'R" or its salt.

When R" is hydrogen in the resulting compound wherein D is —$CH_2$—NR'R" or its salt, the compound may be reacted with R'''—CO—W (wherein W is as defined above; and R''' is an optionally substituted $C_{1-6}$ alkyl group) in a solvent which is not involved in the reaction in the presence or absence of a base or in the presence or absence of an acid for conversion into the compound wherein D is —$CH_2$—NR'—CO—R''' or its salt. When the reaction is proceeded by using R'''—$S(O)_z$—W (wherein W, R''', and z are as defined above) instead of the R'''—CO—W, the compound can be converted into the compound wherein D is —$CH_2$—NR'—$S(O)_z$—R''' or its salt.

When R" is hydrogen in the resulting compound wherein D is —$CH_2$—NR'R" or its salt, the compound may be also alkylated with R'''—W (wherein R''' is an optionally substituted $C_{1-6}$ alkyl group) in a solvent which is not involved in the reaction in the presence or absence of a base or in the presence or absence of an acid for conversion into the compound wherein D is —$CH_2$—NR'R''' or its salt.

When R" is hydrogen in the resulting compound wherein D is —$CH_2$—NR'R" or its salt, the compound may be also reacted with a ketone or an aldehyde represented by formula: $R_{d1}$—CO—$R_{d2}$ (wherein $R_{d1}$ and $R_{d2}$ are independently hydrogen atom, an optionally substituted $C_{1-6}$ alkyl group, a $C_{3-6}$ cycloalkyl group, or a five- or six-membered heterocyclic group containing at least one heteroatom selected from N, O, and S, or d1, d2 and carbon atom of the ketone together form a five- or six-membered cyclic group which may contain at least one heteroatom selected from N, O, and S) in a solvent which is not involved in the reaction in the presence of a reducing agent such as sodium borohydride, lithium aluminum hydride, or diisobutylaluminum hydride for reductive amination of the compound to thereby convert the compound into the compound wherein D is —$CH_2$—NR'—$CHR_{d1}R_{d2}$ or its salt.

1-4) Production of a Compound wherein D is —CHO or its Salt

The compound wherein D' is —$CH_2OH$ or its salt may be reacted in a solvent which is not involved in the reaction for oxidation by manganese dioxide; chromic acid oxidation by chromium oxide (VI) or dichromate; oxidation by lead tetraacetate; oxidation by oxygen; oxidation by activated DMSO; oxidation by halogen compound such as hypohalogenous acid or its salt to thereby convert the compound into the compound wherein D is —CHO or its salt.

1-5) Production of a Compound wherein D is —$CO_2H$ or its Salt

The compound wherein D' is —$CH_2OH$ or its salt may be reacted in a solvent which is not involved in the reaction for oxidation by manganese dioxide; chromic acid oxidation by chromium oxide (VI) or dichromate; oxidation by lead tetraacetate; oxidation by oxygen; oxidation by activated DMSO; oxidation by halogen compound such as hypohalogenous acid or its salt to thereby convert the compound into the compound wherein D is —$CO_2H$ or its salt.

The compound wherein D is —$CO_2H$ or its salt can be also produced by reacting the compound wherein D is —CHO or its salt synthesized in 1-4) for oxidation by manganese dioxide; chromic acid oxidation by chromium oxide (VI) or dichromate; oxidation by lead tetraacetate; oxidation by oxygen; oxidation by activated DMSO; oxidation by halogen compound such as hypohalogenous acid or its salt.

2) Substituent D Convertible from D which is —CHO 2-1) Production of the Compound wherein D is —CH(OH)—$R_{d3}$ (wherein $R_{d3}$ is an Adequate Group Selected from the $R_{15}$ defined for D) or its Salt The compound wherein D is —CHO or its salt synthesized in 1-4) may be reacted with a nucleophilic reagent such as methyllithium or phenyllithium in a solvent which is not involved in the reaction for conversion into the compound wherein D is —CH(OH)$R_{d3}$ or its salt.

The resulting compound wherein D is —CH(OH)$R_{d3}$ or its salt may be converted into the compound wherein D is —CH(OR')$R_{d3}$ or its salt by the procedure similar to 1-1); into the compound wherein D is —CH(O—CO—R')$R_{d3}$ or its salt by the procedure similar to 1-2); and into the compound wherein D is —CH(NR'R")$R_{d3}$ (wherein NR'R" is as defined above) or its salt by the procedure similar to 1-3).

The compound wherein D is —CH(OH)$R_{d3}$ or its salt may be also converted into the compound wherein D is —CO—$R_{d4}$ (wherein $R_{d4}$ is an alkyl group adequately selected from for example $R_{15}$) by the procedure similar to 1-4). The resulting compound wherein D is —CO—$R_{d4}$ or its salt may be reacted with an alkylidene phosphorane represented by formula: $Ph_3P=CR_{d5}R_{d6}$ in a solvent which is not involved in the reaction for conversion into the compound wherein D is —$CR_{d4}=CR_{d5}R_{d6}$ or its salt. The compound wherein D is —$CR_{d4}=CR_{d5}R_{d6}$ or its salt may be hydrogenated by using a catalyst such as activated carbon-palladium to convert the compound into the compound wherein D is —$CHR_{d4}$—$CHR_{d5}R_{d6}$ (wherein $R_{d5}$ and $R_{d6}$ are, for example, a $C_{1-6}$ alkyl group) or its salt.

2-2) Production of the Compound wherein D is —$CH=CR_{d5}R_{d6}$ or its Salt

The compound wherein D is —CHO or its salt synthesized in 1-4) may be reacted with an alkylidene phosphorane represented by formula: $Ph_3P=CR_{d5}R_{d6}$ in a solvent which is not involved in the reaction for conversion into the compound wherein D is —CH=$CR_{d5}R_{d6}$ or its salt.

The resulting compound wherein D is —CH=$CR_{d5}R_{d6}$ or its salt may be hydrogenated by using a catalyst such as activated carbon-palladium in a solvent which is not involved in the reaction to convert the compound into the compound wherein D is —$CH_2$—$CHR_{d5}R_{d6}$ or its salt.

2-3) Production of the Compound wherein D is —CH—NR'R" or its Salt

The compound wherein D is —CHO or its salt synthesized in 1-4) may be reacted with the amine represented by the formula: HNR'R" as described above in a solvent which is not involved in the reaction in the presence of a reducing agent such as sodium borohydride, lithium aluminum hydride, or diisobutylaluminum hydride for reductive amination to thereby convert the compound into the compound wherein D is —CH—NR'R" or its salt.

3) Substituent D Convertible from D which is —$CO_2H$ 3-1) Production of the Compound wherein D is —$CO_2R'$ or its Salt The compound wherein D is —$CO_2H$ or its salt synthesized in 1-5) may be reacted with R'—OH (wherein R' is an optionally substituted $C_{1-6}$ alkyl group) in a solvent which is not involved in the reaction in the presence or absence of a condensing agent such as carbodiimidazole for conversion into the compound wherein D is —$CO_2R'$ or its salt. The compound wherein D is —$CO_2H$ or its salt may also be reacted with thionyl chloride or the like for conversion into a compound wherein D is —COCl, and the compound may be then reacted with R'—OH for conversion into the compound wherein D is —$CO_2R'$ or its salt.

3-2) Production of the Compound wherein D is —CO—NR'R" (wherein NR'R" is as Defined above) or its Salt The compound wherein D is —$CO_2H$ or its salt synthesized in 1-5) may be reacted with NHR'R" (as defined above) in a solvent which is not involved in the reaction in the presence or absence of a condensing agent such as carbodiimidazole for conversion into the compound wherein D is —CO—NR'R" or its salt. The resulting compound wherein D is —CO—NR'R" or its salt may be reacted with a reducing agent such as lithium aluminum hydride or diisobutylaluminum hydride to convert the compound into the compound wherein D is —CHO or its salt. The resulting compound wherein D is —CO—NR'R" or its salt may be also reacted with a reducing agent such as lithium aluminum hydride or diisobutylaluminum hydride to convert the compound into the compound wherein D is —$CH_2$—NR'R" or its salt.

3-3) Production of the Compound wherein D is —CO—R or its Salt

The compound wherein D is —$CO_2H$ or its salt synthesized in 1-5) may be reacted with a nucleophilic reagent such as methyllithium or phenyllithium in a solvent which is not involved in the reaction for conversion into the compound wherein D is —CO—R or its salt. The reaction with the nucleophilic reagent may be accomplished by using the compound wherein D is —$CO_2R'$ or its salt obtained in 3-1) or the compound wherein D is —CO—NR'R" or its salt obtained in 3-2).

Next, typical conversion process of the substituents A-B and T-Q are described.

It should be noted that most of the production processes are included in the production processes as described above for the conversion of the substituent D.

For example, when the substituent B or T is carbonyl group, the substituent may be derived by reaction with A—CO—W or Q—CO—W in accordance with the procedure described in 1-2) in a solvent which is not involved in the reaction in the presence or absence of a base or in the presence or absence of an acid. Alternatively, the substituent may be derived by condensation using A-$CO_2H$ or Q—$CO_2H$ as described in 3-2).

When the substituent B or T is —$S(O)_z$—, the substituent may be derived by reaction with A-$S(O)_z$—W or Q—$S(O)_z$—W in accordance with the procedure described in 1-2) in a solvent which is not involved in the reaction in the presence or absence of a base or in the presence or absence of an acid.

When the substituent B or T is an optionally substituted $C_{1-2}$ alkylene group, the substituent may be derived by converting the hydroxyl moiety of the corresponding alcohol form into a leaving group followed by nucleophilic substitution in accordance with the procedure described in 1-3); by using reductive amination of the corresponding aldehyde forms shown in 2-3); or by reducing the bond formed through the carbonyl as described above.

When the substituent B is single bond, the substituent may be derived by using A-W through coupling reaction using the metal as described in 1-3); or by reacting the compound with an organic base such as triethylamine or diisopropylethylamine or an inorganic base such as potassium carbonate or sodium hydroxide in a polar solvent such as DMF, 2-ethoxyethanol, ethanol, or water at solvent reflux temperature or by heating in a sealed tube.

It should be noted that, when the compound synthesized by <Production process 1>, <Production process 2>, <Production process 3> or <Production process 4> has a reactive group such as hydroxyl group, amino group, carboxyl group, or thiol group as its substituent, such group may be protected with a protective group as desired in each reaction step and the protective group may be removed at an adequate stage. The process of such introduction/removal of the protective group may be adequately determined depending on the group to be protected and the type of the protective group, for example, by the process described in review section of "Protective Groups in Organic Synthesis", Second edition, 1991, John Wiley & Sons, Inc.

Furthermore, geometric isomer, tautomer, optical isomer and other stereoisomers may be present for the compound of the present invention when X is methine carbon or when substituent D is present. These isomers and mixtures thereof are within the scope of the present invention. Isolation or purification of such stereoisomer may be accomplished by any of the techniques commonly used in the art, for example, recrystalization and various chromatographic processes. It is also possible to separately produce such isomer by asymmetric synthesis.

<Pharmacophore of the Present Invention and its Practical Use>

The pharmacophore of the present invention is the one which has been described in the seventeenth aspect of the present invention, and more specifically, the one described in detail in [17-a] to [17-e]. The use of such pharmacophore enables designing and/or screening of an inhibitor which selectively inhibits FXa by reversibly binding to the active site of the FXa to develop competitive inhibitory activity for the FXa. In particular, when the information of the pharmacophore of the present invention is provided to a computer system, a rapid evaluation of a large number of compounds will be enabled, and such evaluation will greatly increase the efficiency of the biological tests which require enormous expenditure and time. Such evaluation will also enable to limit the number of compounds actually synthesized and greatly increase the efficiency of the synthetic process.

Two factors should be considered in the designing and/or screening of the compound which binds to the active site of the FXa to inhibit the FXa. First, the compound should be capable of physically/structurally binding to the active site of the FXa. The noncovalent bond between a protein and an inhibitor generally takes the form of electrostatic interaction, hydrogen bond, van der Waals interaction, or hydrophobic interaction. Second, the compound should be capable of taking the conformation which enables the compound to bind to the active site of the FXa. An efficient designing and/or screening of the inhibitor is enabled by selecting the compound which meets such conditions and the pharmacophore of the present invention.

The discovery of the FXa inhibitory compound which fulfills the factors as described above may be accomplished by utilizing information on the three-dimensional structure of the FXa in combination with various computer programs and databases. A compound which exhibits FXa inhibitory activity can be detected by selecting the compounds which satisfy the pharmacophore of the present invention by the method as described below; purchasing or synthesizing the compound; and evaluating the compounds for their FXa inhibitory activity by a standard method.

Method 1)

Low molecular weight compounds are docked in the active site of the FXa. The three-dimensional structure of the FXa is disclosed by PDB, and the structure of the active site is available from PDB. The docking may be accomplished by various computer programs. Use of the computer database of the three-dimensional compounds enables a screening from several million to several ten millions of compounds as well as screening of the non-existing compounds. After selecting the compounds exhibiting the shape complementary to the active site of the FXa, the compounds exhibiting a binding mode which satisfy the pharmacophore of the present invention are extracted. The binding mode can be confirmed by using various molecular graphics software programs.

Method 2)

Compounds having both hydrophobic moiety and basic moiety are first selected from the database, and it is also possible to preliminarily include the non-existing compounds in the database. Three-dimensional structure of the selected compounds of low molecular weight are then docked in the active site of the FXa, and the compounds exhibiting a binding mode which satisfy the pharmacophore of the present invention are extracted. The docking may be accomplished by various computer programs, and the binding mode can be confirmed by using various molecular graphics software programs.

Method 3)

Low molecular weight compounds are docked to each of the S1 pocket and the S3 pocket of the FXa, respectively, so that the pharmacophore of the present invention is satisfied. The compounds used may be those of the computer database of three-dimensional compounds or any compounds or their fragments. The compound which was placed to the S1 pocket and the compound which was placed to the S3 pocket were connected by using an adequate skeleton which does not change relative spatial position. This process can also be accomplished by using various computer programs.

Method 4)

Complex structures between a chymotrypsin-like serine protease and its substrate or the inhibitor are prepared. The three-dimensional structure of the protease and the three-dimensional structure of the FXa are overlaid on each other at the structure-conserved area of the chymotrypsin-like serine protease family to thereby construct a virtual docking model between the substrate or the inhibitor and the FXa. The structure of the substrate or the inhibitor is then altered to satisfy the pharmacophore of the present invention. This process can also be accomplished by using various computer programs.

The designing and/or screening of the compounds as described above may be accomplished by using the so called molecular design-assisting integrated computer system such as Insight II, Cerius2, Sybyl, and their modules. Insight II and Cerius2 are available from Molecular Simulations Inc., San Diego, Calif., USA, and Sybyl is available from Tripos Inc., St. Louis, Mo., USA. In addition to these progeams, computer programs with specialized functions are also useful in the processes of detecting the low molecular weight compounds which fit with the structure of the active site; detecting the adequate compounds which satisfies the pharmacophore; or docking the low molecular weight compounds to the structure of the active site. Exemplary such programs include those as described below.

DOCK [I. D. Kuntz et al., "A Geometric Approach to Macromolecule-Ligand Interactions", J. Mol. Biol., 161: 269–288(1982)]. DOCK is commercially available from University of California, San Francisco, Calif., USA.

Catalyst [Green, J. et al., "Chemical Function Queries for 3D Database Search", J. Chem. Inf. Comput. Sci. 34, 1297–1308(1994)]. Catalyst is commercially available from Molecular Simulations Inc., San Diego, Calif., USA.

Ludi [Bohm, H. J. "LUDI: rule-based automatic design of new substituents for enzyme inhibitor or leads", J. Comput. Aided Mol. Des., 6: 593–606 (1992)]. Ludi is commercially available from Molecular Simulations Inc. San Diego, Calif., USA.

C2-LigandFit. C2-LigandFit is commercially available from Molecular Simulations Inc., San Diego, Calif., USA.

FlexX [Rarey, M. et al., "A fast flexible docking method using an incremental construction algorithm", J. Mol. Biol., 261: 470–489(1996)]. FlexX is commercially available from Tripos Inc., St. Louis, Mo., USA.

The compound having FXa inhibitory activity may also be designed or searched by a process other than the compound designing/screening process described in the present invention or the computer systems.

As shown in the tenth to eighteenth aspects of the present invention as typical use of the pharmacophore of the present invention, an inhibitor which competitively binds to the active site of the FXa or its fragment may be identified by:

providing three-dimensional structural information of the active site of the FXa (available by the method as described below) to a computer system;

identifying a compound which is assumed to bind to the FXa in a manner satisfying the pharmacophore of the present invention, namely, all of the conditions that:

(a) the compound associates with S1 pocket [the definition of the S1 pocket is the same as that defined in the tenth or seventeenth aspect] by its hydrophobic moiety, and the compound interacts with Tyr228, (b) the compounds associates with S3 pocket [the definition of the S3 pocket is the same as that defined in the tenth or seventeenth aspect] of the active site by its basic moiety, and (c) the compound does not form covalent bond with Ser195; and subjecting the compound to a biological assay which is capable of measuring FXa inhibitory activity to thereby determine whether the compound exhibits FXa inhibitory activity in the assay and identify the desired FXa inhibitor.

To be more specific, the inhibitor may be identified by providing a computer system with the three-dimensional structural information of the FXa molecule containing the active site defined by coordinates of Table A as described below; depicting the three-dimensional structure of the active site in the computer system; overlaying the three-dimensional structure of a test compound on the three-dimensional structure of the active site such that the three-dimensional structure of the test compound is arranged to meet all of the following conditions that:

(a) the hydrophobic moiety is arranged in the S1 pocket so that the hydrophobic moiety can interact with the Tyr228;

(b) the basic moiety is arranged in the S3 pocket; and (c) no covalent bond is formed with the Ser195; evaluating whether the three-dimensional structure of the test compound spatially fits with the active site; preparing the test compound which spatially fits with the active site; and subjecting the test compound to a biological assay which is capable of measuring FXa inhibitory activity to thereby determine whether the test compound exhibits FXa inhibitory activity in the assay and identify the desired FXa inhibitor.

Alternatively, drug design may be accomplished by conducting an evaluation on a computer by using the three-dimensional structural information of the FXa or its fragment for a compound which satisfies the following association conditions:

(a) the compound associates with the S1 pocket by its hydrophobic moiety, and the compound interacts with the Tyr228;

(b) the compound associates with the S3 pocket by its basic moiety; and (c) the compound does not form covalent bond with Ser195.

Furthermore, a more specific identification or molecular designing of the FXa inhibitor is enabled by adding the condition for the pharmacophore of the present invention that interaction with the Tyr228 is mediated by the halogen atom, methyl group, or ethyl group (preferably chlorine atom or bromine atom) constituting a part of the hydrophobic moiety.

Alternatively, the identification or molecular designing of the FXa inhibitor may be accomplished by adding the condition that, in the interaction with the Tyr228, the centroid of the hydrophobic moiety and the centroid of the Tyr228 side chain is within the range of 6.9 to 7.9 Å.

Alternatively, the identification or molecular designing of the FXa inhibitory compound may be accomplished by adding the condition that the pharmacophore also satisfies at least one of the following conditions 1) to 3):

1) when the compound binds to the FXa, the hydrophobic moiety does not either partly or entirely undergo an electrostatic interaction with the Asp189 of the S1 pocket;

2) when the compound binds to the FXa, centroid position of the hydrophobic moiety satisfies in the S1 pocket at least two of the following conditions that such position is:

i) at a distance of 3.6 to 4.6 Å from the Cys191 backbone $C_\alpha$ atom;

ii) at a distance of 6.2 to 7.2 Å from the Ser195 backbone $C_\alpha$ atom;

iii) at a distance of 5.5 to 6.5 Å from the Ser214 backbone $C_\alpha$ atom;

iv) at a distance of 3.6 to 4.6 Å from the Trp215 backbone $C_\alpha$ atom;

v) at a distance of 6.7 to 7.7 Å from the Glu217 backbone $C_\alpha$ atom; and vi) at a distance of 5.8 to 6.8 Å from the Cys220 backbone $C_\alpha$ atom; and 3) when the compound binds to the FXa, centroid position of the partial structure including the basic moiety of the La satisfies in the S3 pocket at least two of the following conditions that such position is:

i) at a distance of 4.1 to 5.5 Å from the Tyr99 side chain centroid;

ii) at a distance of 3.1 to 4.5 Å from the Phe174 side chain centroid;

iii) at a distance of 4.1 to 5.5 Å from the Trp215 side chain centroid;

iv) at a distance of 4.1 to 6.3 Å from the Lys96 backbone carbonyl oxygen atom; and v) at a distance of 3.5 to 5.1 Å from the Glu97 backbone carbonyl oxygen atom.

Alternatively, the identification or molecular designing of the FXa inhibitor may be accomplished by adding the condition that all of the conditions 1) to 3) are satisfied.

Furthermore, the molecular designing of the FXa inhibitor may be accomplished by adding the means for suppressing alteration of the conformation of the cross-linking group described in the aspect [18-e].

The thus identified or designed compound may be obtained by purchasing or synthesizing the compound, and the compound may be subjected to the bioassay, for example, the one described in the Examples of the present invention to determine its specific pharmacological activities, for example, in vitro $IC_{50}$.

With regard to the compound of the present invention, the compound is the one having a FXa inhibitory activity of up to 1 μM in terms of $IC_{50}$, and preferably, the one which was unknown at the time of the filing of the present invention.

The present invention is also directed to a pharmaceutical composition characterized by its inclusion as an effective component of at least one compound which has been identified or designed by the identification or drug designing method as described above, which has FXa inhibitory activity in terms of $IC_{50}$ determined by a bioassay of up to 1 μM, and which was (1) unknown at the time of the filing of the present invention or (2) known but whose biological activity was unknown at the time of the filing of the present invention. Usefulness of such pharmaceutical composition will be appreciated by referring to the second aspect of the invention or detailed description for the composition containing the compound of the present invention as described below.

The present invention is also directed to a FXa inhibitor characterized by its inclusion as an effective component of at least one compound which has FXa inhibitory activity in terms of $IC_{50}$ determined by a bioassay of up to 1 μM, and which was (1) unknown at the time of the filing of the present invention or (2) known but whose biological activity was unknown at the time of the filing of the present invention. Usefulness of such FXa inhibitor will be appreciated by referring to the third aspect of the invention or detailed description for the composition containing the compound of the present invention as described below.

It should be noted that, of the thus identified or designed compounds of the present invention, the preferred is the one having the FXa inhibitory activity in terms of $IC_{50}$ of up to 0.5 μM, more preferably up to 0.1 μM, and most preferably up to 0.01 μM.

It should be noted that the identification or designing of such compound may be accomplished by assuming that the compound has a partial structure comprising the spiro skeleton which is the structure wherein one or both of La and Lb have been removed from the general formula (I'), and then defining the residual Lb, the residual La, or the residual Lb and La.

In such procedure, Lb may be defined, for example, after assuming the group represented by A-B- of formula (I) as a particular La, and for example, after setting the condition of the aspect 10-d, 4), namely the condition that "La has an optionally substituted, five- to six-membered, aromatic monocyclic heterocyclic group" for the La, and in particular, after assuming that La comprises 4-pyridyl group. Alternatively, La may be defined by assuming the group represented by -T-Q of formula (I) as a particular Lb, and preferably, by assuming that Lb comprises a group wherein Q is the one described in the aspect [1-1-d] and T is the one described in the aspect [1-8-b], and most preferably, p-halogenostylylsulfonyl group, 6-halogenonaphthalen-2-ylsulfonyl group, or 7-halogeno-2H-benzopyran-3-ylsulfonyl group, as will be understood from the foregoing description.

Next, the therapeutic/prophylactic agent and the pharmaceutical composition of the present invention is described. The pharmaceutical composition of the present invention should contain at least one compound represented by formula (I) or formula (I'), formula (V), formula (VI), formula (Ik), formula (I-a'), formula (I'), or formula (I") (the definition which may be as defined above) as its effective component, and the composition may also contain a pharmacologically acceptable carrier. The preferable compounds for the compound represented by formula (I) are the same as those described above.

FXa Inhibitory Action of the Compounds of the Present Invention

The compounds of the present invention possess a potent FXa inhibitory activity. In other words, the compositions of the present invention are a potent FXa inhibitor, and more particularly, a specific FXa inhibitor, which does not inhibit other enzymes.

The compositions of the present invention are also an orally administrable FXa inhibitor, and more specifically, an orally administrable specific FXa inhibitor. The compounds of the present invention specifically inhibit activity of the FXa among the many serine proteases. To be more specific, it does not inhibit trypsin or chymotrypsin at all, nor do they inhibit thrombin, which is another serine protease in the blood coagulation cascade. Hence, the compounds of the present invention solve the aforementioned problems associated with the use of the conventional thrombin inhibitors, for example, the tendency to cause bleeding. As further advantage, the compounds of the present invention can be rapidly absorbed by the digestive tract after oral administration with no reduction in its activity by the absorption, and it also exhibit favorable absorption, distribution, metabolism, and excretion characteristics. Its value as an orally administrable agent is quite high.

The compositions containing the compounds of the present invention can be used as preventives and/or therapeutics of diseases wherein an FXa inhibitor is useful.

The compositions containing the compounds of the present invention cab also be used as an anticoagulant, and as preventives and/or therapeutics of diseases for which anticoagulant is useful.

To be more specific, such agents are effective in prevention and/or treatment of diseases caused by thrombus or embolism. To mention specific examples of such diseases, they include: diseases from ischemic cerebrovascular disorders such as cerebral thrombosis, brain infarction, cerebral embolism, transient cerebral ischemic attack (TIA) and cerebral vascular spasm after subarachnoid hemorrhage; Alzheimer's disease, cerebrovascular dementia, asymptomatic cerebrovascular disorder, disease associated with ischemic heart disease such as acute and chronic myocardial infarction, aftereffect after myocardial infarction, unstable angina pectoris, angina pectoris and coronary thrombolysis; thrombogenesis after artificial blood vessel or artificial valve replacement, reocclusion and restenosis after coronary artery bypass grafting, reocclusion and restenosis after PTCA or PTCA or stent placement, pulmonary infarction, lung thrombus/lung embolism, diseases associated with pulmonary vascular disorder (for example, drug-induced pneumonia), acute respiratory distress syndrome (ARDS), acute nephritis, acute progressive nephritis, chronic nephritis (for example, diabetic nephropathy, chronic glomerulonephritis, and IgA nephropathy), acute arterial occlusive disease, thromboangitis obliterans (Buerger disease), arteriosclerosis obliterans, peripheral arterial occlusive disease, peripheral venous occlussive disease, deep vein thrombosis, thrombophlebitis, disseminated intravascular coagulation (DIC), organ failures induced with the progress of the shock or DIC, thrombotic microangiopathy (TMA), systemic inflammatory response syndrome (SIRS), thrombotic thrombocytopenic purpura, hemolytic uremic syndrome (HUS), diseases associated with various vascular disorders such as thrombogenesis in extracorporeal circulation, thrombocytopenia in major operation, arterial sclerosis, cancer metastasis, rejection in transplantation, and organ protection or functional improvement in transplantation. Also included are prophilaxis of vascular endothelial cell injury associated with diabetes, hypercoagulation associated with transplantation or activated protein C (APC) resistance, blood hypercoagulation associated with vascular disease, injury after operation, obesity, pregnancy, use of oral contraceptive, sustained depression, heparin induced thrombocytopenia, collagen disease (for example, antiphospholipid syndrome, polyarteritis, and systemic lupus erythematosus), Bechet's disease, ischemic reperfusion injury, cancer or the like, and toxemia in pregnancy.

The agents of the present invention are particularly adapted for use in prevention of embolism associated with atrial fibrillation/artificial valve or valvular heart disease, and preferably for prevention of onset of cerebral embolism, prevention of transient cerebral ischemic attack and especially for prevention of recurrence of the transient cerebral ischemic attack, and prevention/treatment of deep vein thrombosis or DIC.

When the agents of the present invention are used as a drug for these diseases, preventive administration is recommended and such use is particularly important since the agents of the present invention are neither a direct thrombolytic agent nor a direct anti-platelet agents. In other words, the agents of the present invention are adapted for preventive use in patients suffering from thrombophilia or patients having the risk factor of thrombus/embolism for the purpose of preventing thrombus/embolism. In the case of the patients with atrial fibrillation/artificial valve or valvular heart disease, thrombosis is easily generated at the site of the lesion or the transplantation, and such thrombosis often triggers cerebral infarction, which is more than often a fatal attack. The agents of the present invention have a good potential to be a potent drug for preventing onset of the thrombus/embolism, and in particular, cerebral embolism induced in such patients.

Such therapy is continued for a long time. The agents of the present invention can be administered by oral administration with less side effects such as bleeding, and therefore, the agents of the present invention can be reliably used for a long time with no need of frequent monitoring.

In other words, the agents of the present invention are preventives and/or therapeutics for embolism associated with atrial fibrillation/artificial valve or valvular heart disease. Also, the agents of the present invention are preferably preventives of the onset of cerebral embolism associated with such disease. The agents of the present invention are also preventives and/or therapeutics, and in particular, a preventives of the onset of transient cerebral ischemic attack; and a preventives and/or therapeutics for deep vein thrombosis or DIC.

In addition, some compounds of the present invention are easily metabolized in the course of the absorption and secretion of the pharmaceutical substance by the substituent in D, and some of the thus produced metabolites are within the scope of the compound of the present invention as represented by formula (I), and exhibit a potent inhibitory activity for FXa. This is a finding quite interesting in pharmacological/pharmacokinetical point of view.

The compositions containing the compounds of the present invention as an active ingredient are also effective as veterinary drugs and have high value of use. The compositions are also useful as a reagent adapted for use in measuring various blood coagulative functions and as a laboratory reagents.

Owing to the FXa inhibitory action of the compounds of the present invention, such compositions are also useful as preventives/therapeutics for infection by influenza virus based on the inhibitory activity for the propagation of the influenza virus, and also, as preventives/therapeutics for periodontal disease.

Next, the present invention is further described by referring to Experimental Examples and Examples which by no means limit the scope of the present invention.

Excellent FXa inhibitory activity of the compounds of the present invention is confirmed by the test as described below.

1) Measurement of Enzyme Inhibitory Action a) Measurement of Human FXa Inhibitory Action In vitro FXa inhibitory activity is measured in accordance with the method of Kettner et al. (Journal of Biological Chemistry, vol. 265, pages 18289 to 18297, 1990). To be more specific, human FXa (product of Enzyme Research Laboratories, Inc., 0.019 U/ml) is mixed with a test compound diluted with dimethylsulfoxide (DMSO) at various concentrations and a synthetic substrate S-2222 (Chromogenix AB, 0.4 mM). The mixtures are incubated at 37° C. in Tris-hydrochloric acid buffer (pH 7.5) while the absorbance at 405 nm is measured continuously. To calculate the FXa inhibitory activity of the test compound, the initial reaction velocity is compared with the value for a control containing no test compound. It should be noted that the FXa inhibitory activity of the test compound is generally indicated as $IC_{50}$.

When the compounds of the present invention are evaluated for its FXa inhibitory activity by the procedure as describe above, the strength is in the range of 0.1 nM to 1 $\mu$M in terms of $IC_{50}$. Table 1 shows typical measurements.

TABLE 1

| Test compound (compounds of the Examples) | $IC_{50}$ ($\mu$M) |
| --- | --- |
| Example 1 | 0.0032 |
| Example 5 | 0.0029 |
| Example 10 | 0.0054 |
| Example 25 | 0.0015 |
| Example 50 | 0.0019 |
| Example 59 | 0.0034 |
| Example 61 | 0.0028 |
| Example 213 | 0.0006 |
| Example 628 | 0.0053 |
| Example 684 | 0.0018 |
| Example 712 | 0.0018 |
| Example 760 | 0.0059 |
| Example 765 | 0.0057 |
| Example 770 | 0.0018 |

2) Measurement of Anticoagulant Activity (In Vitro)

Measurement of Intrinsic Coagulation Time

Activated partial thromboplastin time (APTT) is measured in the presence of the test compounds diluted at various concentrations. A test compound diluted with DMSO at various concentrations is mixed with human plasma and APTT reagent. The mixture is incubated at 37° C. for 2 minutes; calcium chloride (25 mM) is added to the mixture; and the coagulation time is thereafter measured. It should be noted that the anticoagulant activity of the test compound is described in terms of the concentration required to double the coagulation time for the case where no test compound is added. In this test, the compounds of the present invention were found to be effective in extending the APTT. The effects of the compounds of the present invention are shown in Table 2.

TABLE 2

| Test compound (compounds of the Examples) | Concentration required to double coagulation time ($\mu$M) |
| --- | --- |
| Example 5 | 0.43 |
| Example 6 | 0.99 |
| Example 9 | 0.29 |
| Example 23 | 0.62 |
| Example 29 | 0.90 |
| Example 42 | 0.20 |
| Example 58 | 0.18 |
| Example 69 | 0.36 |
| Example 275 | 0.17 |
| Example 388 | 0.22 |
| Example 399 | 0.18 |
| Example 461 | 0.16 |
| Example 471 | 0.27 |
| Example 533 | 0.35 |
| Example 600 | 0.22 |
| Example 740 | 0.18 |

3) Characteristics of Anticoagulant Activity (Ex Vivo)

a) Ex Vivo Measurement of Coagulation Time in Rats (i.v.)

Male Wistar rats (200 g–300 g; Japan SLC Inc.) that have been starved for more than 12 hours are administered through a femoral vein with a single dose of a drug (3–30 mg/kg) dissolved in physiological saline (or 10% DMSO solution), and the blood is collected at a certain time interval (3.8% sodium citrate, 1/10 volume), and plasma is then separated by centrifugation at 3000 rpm for 10 minutes. Prothrombin time (PT) is measured by the procedure as described below by using the separated plasma. 50 $\mu$l of the plasma is incubated at 37° C. for 3 minutes and 100 $\mu$l of thromboplastin solution is added to start coagulation. The coagulation time is measured. In the actual test, the intravenously administered compounds of the present invention were found to be effective in extending the PT on account of enzyme inhibition.

b) Ex Vivo Measurement of Coagulation Time in Rats (p.o.)

The test compound is compulsorily administered by oral administration using an oral introducer instead of the administration from the femoral vein at a single dose in the test a), and a certain volume of the blood is collected at a certain time interval at 3.8% sodium citrate, $\frac{1}{10}$ volume. The blood is evaluated by the procedure as described in a) for extrinsic coagulation time and intrinsic coagulation time.

In this test b), the compounds of the present invention were found to be effective in extending the coagulation time upon oral administration of 10–100 mg.

It should be noted that no abnormality in the aspect of safety is observed in the ex vivo test of the rat.

The pharmaceutical compositions of the present invention may contain at least one compound represented by formula (I) (as already defined above) or salts thereof as an active ingredient. They may also contain any pharmaceutical acceptable carriers. The preferred examples of the compounds of the general formula (I) have already been mentioned.

As described above, the compounds of the present invention exhibit potent inhibitory action for FXa activity without exhibiting any inhibitory activity for trypsin, chymotrypsin, or thrombin, and the specificity of the compounds is high. Furthermore, the compounds of the present invention exhibit antithrombotic action when orally administered at a dose of 0.1 to 10 mg/kg, or intravenously administered at a dose of 0.01 to 1 mg/kg in rats.

On the other hand, the compounds of the present invention does not exhibit prolongation of bleeding time when orally administered at a dose of 10 mg/kg or intravenously administered at a dose of 1 mg/kg in rats. Accordingly, the compounds of the present invention exhibit the anticoagulation action with no risk of showing bleeding tendency, and this is a significant difference from heparin and warfarin, which are known anticoagulants. In addition, the compounds of the present invention exhibit excellent oral absorption, adequate long-lasting action, as well as high safety.

The compounds of the present invention may be administered to the disease as described above which is to be prevented and treated by the present invention either alone or in combined application with other pharmacologically active component. Exemplary such pharmacologically active components include known fibrinolytics (for example, tissue plasminogen activators (tPA) and their derivatives (including modified agents or the so called "second generation" agents), urokinase, and streptokinase); known anticoagulants (for example, warfarin, heparin, and thrombomodulin); known inhibitors of platelet aggregation (for example, aspirin, thromboxane antagonist, inhibitor of thromboxane synthesis, and GPIIb/IIIa antagonist); known therapeutic agents for hyperlipidemia (for example, clofibrate and related drugs, HMG-CoA reductase inhibitor, and EPA-E); and known hypotensive agents (for example, nifedipine and diltiazem).

The term "combined application" as used herein covers not only the administration of a combination drug containing both the compound of the present invention and another pharmacologically active ingredient but also the case where the two are in separate dosage forms and administered either at a time or at different times. The mode of administration is in no way limited as long as the compound of the present invention and another pharmacologically active ingredient exist simultaneously in the patient's blood.

The pharmaceutical composition containing one or more compounds of the present invention or its pharmaceutically acceptable salt as its effective component may be prepared into capsules, pills, tablets, granules, subtle granules, or powder; or alternatively, oral solution such as suspension, emulsion, limonades, elixir, or syrup; injectable solution; transnasal formation; suppository; ointment; epithem; and the like which are orally or perorally administered to human and other animals by using the commonly used pharmaceutical vehicle, excipient, or other additives.

Clinical dose of the compound of the present invention to human may be adequately determined in consideration of symptom, body weight, age, sex, and the like of the patient to which the compound is administered. The adult daily dose in oral administration is generally in the range of 0.1 mg to 1000 mg, and preferably 1 mg to 300 mg, and the dose in peroral administration is 0.01 to 300 mg, and preferably 0.1 mg to 100 mg. Such dose may be administered as a single dose or divided into several doses. The dose may vary depending on various conditions, and the dose below the above described range may be sufficient in some cases.

In order to accomplish oral administration according to the present invention, capsules, pills, tablets, powder, granules, and the like may be employed for the solid composition. Such solid composition is produced by combining at least one active substance with at least one inactive carrier. To be more specific, the composition may contain an excipient (for example, lactose, saccharose, mannitol, glucose, hydroxy propylcellulose, microcrystalline cellulose, or metasilicic acid), a binder (for example, crystalline cellulose, saccharide, dextrin, hydroxy propylcellulose, hydroxy propylmethylcellulose, polyvinyl pyrrolidone, or Macrogol), a lubricant (for example, magnesium stearate, calcium stearate, or talc), a disintegrant (for example, corn starch, carboxy methyl cellulose, or calcium cellulose glycorate), a stabilizer (for example, lactose and other sugar alcohols or sugar), a solubilizer or a solubilizing aid (for example, cholesterol, triethanolamine, glutamic acid, or aspartic acid), a colorant, a flavoring agent, an antiseptic, an isotonic agent, a dispersant, an antioxidant (for example, ascorbic acid, or butylhydroxyanisole), a buffer, or a preservative (for example, paraben or benzylalcohol).

It should be noted that the tablet, the pill and the granules may be coated with sugar, gelatin, hydroxy propylmethylcellulosse phthalate or other gastric or enteric film coating.

Exemplary injectable solution used for parenteral administration include aseptic aqueous or nonaqueous solution, suspension, and emulsion. Exemplary carriers for the aqueous solution and suspension include water for injection and physiological saline, and exemplary carriers for the non-aqueous solution and suspension include propylene glycol, polyethylene glycol, vegetable oils such as olive oil, and alcohols such as ethylalcohol, and polysorbate 80 (TM).

Such composition may further comprise an isotonic agent, antiseptic, emolient, emulsifier, dispersant, stabilizer, solubilizer, solubilizing aid, or other additives as described above, and these additives may be sterilized, for example, by filtration with a membrane filter, inclusion of an antimicrobial agent, or UV irradiation.

The composition may be also produced in the form of sterilized solid composition which can be dissolved, emulsified, or suspended before its use for use as an injectable solution. When the compound of the present invention has low solubility, the compound may be solubilized as desired.

Such solubilization may be accomplished by any of the processes known in the art to be applicable for the production of drugs, for example, addition of a surfactant (a polyoxyethylene hydrogenated castor oil, a polyoxyethylene sorbitan higher fatty acid ester, a sugar fatty acid ester, and the like); and formation of a solid dispersion of the drug and a solubilizer, for example, a polymer (a water-soluble polymer such as polyethylene glycol (PEG), hydroxy propyl methylcellulose (HPMC), or polyvinyl pyrrolidone (PVP); or an enteric polymer such as hydroxy propyl methylcellulose phthalate (HPMCP), or methyl methacrylate-methacrylic acid copolymer (Eudragid L,S (TM) manufactured by Rohm and Haas Company)). If desired, an inclusion compound may be formed by using α-, β-, or γ-cyclodextrin, hydroxy propyl cyclodextrin, or the like. The procedure employed for the solubilization may also be modified as desired depending on the drug desired by referring to Nagai, T., et al., "Monograph in Pharmacology No. 1, Biochemical Availability", Soft-Science Inc., 78–82(1988) or Utsumi, I., et al., "Current Pharmaceutical Technology and Its Application", Iyaku Journal, 157–159(1983). Among these, the preferred is formation of a solid dispersion comprising the drug and the solubilizer which exhibits an improved solubility (JP-A 56-49314, FR2460667).

<Formulation Examples>

Next, examples of the pharmaceutical composition of the present invention are described. The "Compound M" is the compound of the present invention represented by formula (I) or its pharmaceutically acceptable salt, and to be more specific, a compound selected from the compounds described in Examples.

| (a) Tablet (1 mg) | |
|---|---|
| Compound M | 1.0 g |
| Lactose | 90.0 g |
| Sodium carboxymethyl cellulose | 7.0 g |
| Corn starch paste (5% W/V paste) | 1.0 g |
| Magnesium stearate | 1.0 g |

The ingredients as described above were measured and made into 100 mg tablet by normal procedure.

| (b) Tablet (10 mg) | |
|---|---|
| Compound M | 10 g |
| Lactose | 150 g |
| Crosscarmellose sodium | 6.0 g |
| Corn starch | 28.5 g |
| Polyvinyl pyrrolidone | 2.5 g |
| Magnesium stearate | 3 g |

The ingredients as described above were measured and made into 200 mg tablet by normal procedure, and the tablet was coated with cellulose acetate phthalate to produce an enteric tablet.

| (c) Tablet (100 mg) | |
|---|---|
| Compound M | 100 g |
| Lactose | 180 g |
| Crosscarmellose sodium | 13 g |
| Corn starch (5% W/V paste) | 4 g |
| Magnesium stearate | 3 g |

The ingredients as described above were measured and made into 300 mg tablet by normal procedure.

| (d) Capsule (50 mg) | |
|---|---|
| Compound M | 100 g |
| Lactose | 395.5 g |
| Magnesium stearate | 4.5 g |

The ingredients as described above were measured and uniformly mixed. The uniform powder was sealed in a hard capsule (Pharmacopeia No. 1) at 250 mg/capsule.

| (e) Injectable solution (0.1 mg/ml) | |
|---|---|
| Compound M | 0.1% W/V |
| Sodium phosphate buffer | 2.3% W/V |
| Citric acid | 0.4% |
| Macrogol 400 | 3.5% |
| Water for injection | adequate amount to make up 100%. |

The ingredients as described above were mixed, and the resulting solution was sealed in an injection ample at 1 ml/ample to produce the injectable solution.

| (f) Injectable solution (1.0 mg/ml) | |
|---|---|
| Compound M | 1.0% W/V |
| Sodium phosphate buffer | 3.6% W/V |
| 1M Aqueous solution of sodium hydroxide | 15% W/V |
| Water for injection | adequate amount to make up 100%. |

The ingredients as described above were mixed, and the resulting solution was sealed in an injection ample at 1 ml/ample to produce the injectable solution.

SYNTHESIS EXAMPLES

Next, the present invention is described in further detail by referring to Synthesis Examples which by no means limit the scope of the present invention.

Nuclear magnetic resonance (NMR) spectrum was measured by using JEOL JNM-EX270 FT-NMR (manufactured by JEOL Ltd.) or JEOL JNM-LA300 FT-NMR (indicated by * in the data; manufactured by JEOL Ltd.). Infrared absorption spectrum (IR) was measured by using HORIBA FT-200 FT-IR (indicated by * in the data; manufactured by HORIBA Ltd.) or HORIBA FT-720 FT-IR (manufactured by HORIBA Ltd.). High resolution mass spectrometry (HRMS) spectrum was measured by JEOL JMS-GCMATE (manufactured by JEOL Ltd.). High performance liquid chromatography (HPLC) was conducted by using Shimadzu LC-10A (manufactured by Shimadzu Corporation).

Example 1

Synthesis of 1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one <Step A-1>

Synthesis of ethyl 2-[(6-chloronaphthalen-2-ylsulfonyl)amino]acetate

Glycine ethyl ester hydrochloride (9.88 g) was suspended in methylene chloride (500 ml), and triethylamine (20.2 ml) and then 6-chloronaphthalene-2-sulfonyl chloride (17.6 g) were added to the suspension under cooling with ice. After stirring at room temperature for 1 hour and adjusting the mixture to pH 2 by addition of 1N hydrochloric acid, the mixture was extracted with methylene chloride. The methylene chloride layer was washed with saturated sodium chloride solution and dried over anhydrous sodium sulfate, and the solvent was distilled off under reduced pressure. After washing the resulting crystals in n-hexane, the crystals were collected by filtration and air-dried to obtain the title compound (22.4 g).

NMR spectrum (*CDCl$_3$) δppm: 8.43–8.40(1H,m), 7.95–7.87(4H,m), 7.57(1H,dd,J=2,9 Hz), 5.22–5.15(1H,m), 4.01(2H,q,J=7 Hz), 3.82(2H,d,J=6 Hz), 1.11(3H,t,J=7 Hz)

<Step A-2>
Synthesis of Ethyl 2-[(3-acetoxy-2-oxopropan-1-yl)(6-chloronaphthalen-2-ylsulfonyl)amino]acetate To a solution of the compound obtained in Step A-1 (2.50 g) in N,N-dimethylformamide (25 ml) were added potassium carbonate (1.58 g) and sodium iodide (1.14 g), and a solution of 1-acetoxy-3-chloroacetone (1.72 g) in N,N-dimethylformamide (7 ml) was added dropwise at room temperature. The reaction mixture was stirred at room temperature for 1.5 hours, and the mixture was extracted with diethyl ether after adding water. The organic layer was washed with saturated sodium chloride solution and dried over anhydrous sodium sulfate, and the solvent was distilled off under reduced pressure. The resulting residue was crystallized in diethyl ether, and the crystals were collected by filtration and air-dried to obtain the title compound (2.72 g).

NMR spectrum (*CDCl$_3$) δppm: 8.42–8.37(1H,m), 7.98–7.85(3H,m), 7.80(1H,dd,J=2,9 Hz), 7.57(1H,dd,J=2,9 Hz), 4.84(2H,s), 4.31(2H,s), 4.15(2H,s), 4.06(2H,q,J=7 Hz), 2.16 (3H,s), 1.17(3H,t,J=7 Hz)

<Step A-3>
Synthesis of 6-(acetoxymethyl)-1,4-diaza-1'-benzyl-4-(6-chloronaphthalen-2-ylsulfonyl)-7-oxaspiro[bicyclo [4.3.0] nonane-8,4'-piperidin]-2-one To a solution of the compound obtained in Step A-2 (1.6 g) and 4-(aminomethyl)-1-benzyl-4-hydroxypiperidine (800 mg) in toluene (200 ml) was added p-toluenesulfonic acid monohydrate (34.0 mg), and the mixture was heated under reflux for 1 hour by using a Dean Stark. The reaction mixture was allowed to cool, and the solvent was distilled off under reduced pressure. The resulting residue was purified by silica gel column chromatography (eluent; ethyl acetate) to obtain the title compound (1.08 g).

NMR spectrum (*CDCl$_3$) δppm: 8.36(1H,s), 8.02–7.88 (3H,m), 7.78(1H,d,J=9 Hz), 7.60(1H,d,J=9 Hz), 7.36–7.19 (5H,m), 4.48–4.14(5H,m), 3.46 (2H,s), 3.34(1H,d,J=17 Hz), 3.08 (1H,d,J=12 Hz), 2.62–2.21(4H,m), 2.33(1H,d,J=12 Hz), 2.11(3H,s), 1.93–1.72(2H,m), 1.53–1.34(2H,m)

<Step A-4>
Synthesis of 1,4-diaza-1-benzyl-4-(6-chloronaphthalen-2-ylsulfonyl)-6-(hydroxymethyl)-7-oxa-spiro[bicyclo [4.3.0]nonane-8,4'-piperidin]-2-one To a solution of the compound obtained in Step A-3 (425 mg) in methanol (11 ml) was added 1N aqueous solution of sodium hydroxide (2.8 ml) under cooling with ice. The reaction mixture was stirred at room temperature for 1 hour, and the solvent was distilled off under reduced pressure. The residue was washed by adding water, collected by filtration, and dried under reduced pressure to obtain the title compound (365 mg).

NMR spectrum (*CDCl$_3$) δppm: 8.40–8.33(1H,m), 8.01–7.90(3H,m), 7.82–7.76(1H,m), 7.65–7.58(1H,m), 7.35–7.21 (5H,m), 4.50–4.31(2H,m), 4.24(1H,d,J=12 Hz), 3.89(1H,d, J=12 Hz), 3.62(1H,d,J=12 Hz), 3.47(2H,s), 3.35(1H,d, J=17 Hz), 3.07(1H,d,J=12 Hz), 2.66–2.07(4H,m), 2.26(1H,d,J=12 Hz) 1.97–1.75(2H,m),1.57–1.36(2H,m)

<Step A-5>
Synthesis of 1,4-diaza-1'-benzyl-4-(6-chloronaphthalen-2-ylsulfonyl)-6-(methoxymethyl)-7-oxa-spiro[bicyclo [4.3.0]nonane-8,4'-piperidin]-2-one To a solution of the compound obtained in Step A-4 (100 mg), benzyltriethylammonium chloride (4.0 mg), and dimethyl sulfate (0.018 ml) in methylene chloride (2 ml) was gradually added 50% aqueous solution of sodium hydroxide (0.6 ml) with vigorous stirring under cooling with ice. After stirring the reaction mixture at room temperature for 2 hours, water was added under cooling with ice, and the mixture was extracted with methylene chloride. The organic layer was washed with saturated sodium chloride solution and dried over anhydrous sodium sulfate, and the solvent was distilled off under reduced pressure. The resulting residue was purified by silica gel column chromatography (eluent; n-hexane:ethyl acetate=1:4–1:6) to obtain the title compound (48.0 mg). NMR spectrum (*CDCl$_3$) δppm: 8.36–8.33(1H,m), 7.97–7.92(3H,m), 7.80–7.75(1H,m), 7.63–7.57(1H,m), 7.33–7.20(5H,m), 4.40–4.30(2H,m), 4.18 (1H,d,J=12 Hz), 3.64(1H,d,J=10 Hz), 3.54(1H,d,J=10 Hz), 3.46(2H,s), 3.41(3H,s), 3.32(1H,d,J=17 Hz), 3.10(1H,d,J= 12 Hz), 2.67–2.18(4H,m), 2.24(1H,d,J=12 Hz), 1.99–1.75 (2H,m), 1.53–1.33(2H,m)

<Step A-6>
Synthesis of 1,4-diaza-4-(6-chloronaphthalen-2-ylsulfonyl)-6-(methoxymethyl)-7-oxa-spiro[bicyclo[4.3.0] nonane-8,4'-piperidin]-2-one hydrochloride To a solution of the compound obtained in Step A-5 (45.0 mg) in 1,2-dichloroethane (2 ml) was added 1-chloroethyl chloroformate (0.021 ml), and the mixture was heated under reflux for 30 minutes. The reaction mixture was allowed to cool, and the solvent was distilled off under reduced pressure. To the residue was added methanol (2 ml), and the mixture was heated under reflux for 30 minutes. The reaction mixture was allowed to cool, and the solvent was distilled off under reduced pressure. The resulting residue was crystallized by adding diethylether, and the supernatant was removed by decantation. The solvent was distilled off under reduced pressure to obtain the title compound (39.5 mg).

NMR spectrum (*DMSO-d$_6$) δppm: 8.89–8.75(1H,brs), 8.73–8.58(1H,brs), 8.61(1H,s), 8.33–8.13(3H,m), 7.93–7.84 (1H,m), 7.77–7.69(1H,m), 4.17–4.02(3H,m), 3.57–2.80(7H, m), 3.28(3H,s), 3.18(1H,d,J=12 Hz), 2.62(1H,d,J=11 Hz), 2.00–1.83(2H,m), 1.70–1.54(2H,m)

<Step A-7>
Synthesis of 1,4-diaza-4-(6-chloronaphthalen-2-ylsulfonyl)-6-(methoxymethyl)-7-oxa-1'-(4-pyridyl)spiro [bicyclo[4.3.0]nonane-8,4'-piperidin]-2-one To a suspension of the compound obtained in Step A-6 (35.0 mg) and 4-chloropyridine hydrochloride (10.2 mg) in 2-ethoxyethanol (2 ml) was added diisopropylethylamine (0.041 ml), and the mixture was heated under reflux for 2 hours. After allowing the mixture to cool, potassium carbonate (56 mg) was added to the reaction mixture, and the mixture was stirred for 30 minutes. The insoluble content was removed by filtration, and the filtrate was concentrated. The resulting residue was purified by silica gel column chromatography (eluent; methylene chloride:methanol= 10:1) to obtain the title compound (9.6 mg). HRMS: $C_{27}H_{29}ClN_4O_5S(M^+)$: Calculated: 556.1547. Found: 556.1540.

The resulting compound was optically resolved on HPLC [Waters DeltaPrep 4000 manufactured by Waters Inc.); Column used, Daicel Chiralcel OD manufactured by Daicel Chemical Industries, Ltd., 2 cm×25 cm; eluent;

n-hexane:ethanol diethylamine=60:40:1; flow rate, 10 ml/min, detection wavelength, 254 nm] to obtain (+)-1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one [retention time: 43.5 min, $[\alpha]^{25}_D$+48.8 (c1.247, chloroform), $[\alpha]^{33}_D$+91.3 (c1.000, methanol), >99% ee], and (−)-1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one [retention time: 63.0 min, $[\alpha]^{25}_D$−48.4 (c1.175, chloroform), $[\alpha]^{33}_D$−90.7 (c1.000, methanol), >99% ee], respectively.

In addition, racemic body of the title compound (50.9 mg) was mixed with (+)-O,O'-dibenzoyl-D-tartaric acid (32.7 mg), and methanol (6.6 ml) was added to the mixture. After stirring the mixture, the insoluble content was collected by filtration and dried in vacuum. The thus obtained crystals (20 mg) were desalted by using saturated aqueous solution of sodium hydrogencarbonate to obtain the (+) form of the title compound at an optical purity of 94.6% ee. The (−) form of the title compound was also obtained by the similar manner using (−)-O,O'-dibenzoyl-L-tartaric acid.

<Step B-1>

Synthesis of 1,4-diaza-1'-(benzyloxycarbonyl)-4-(6-chloronaphthalen-2-ylsulfonyl)-6-(hydroxymethyl)-7-oxa-spiro[bicyclo[4.3.0]nonane-8,4'-piperidin]-2-one The compound obtained in <Step A-3> (70.0 g) and 1,8-bis(N,N-dimethylamino)naphthalene (5.00 g) were dissolved in 1,2-dichloroethane (700 ml), and with the solution temperature maintained at 0° C., benzyl chloroformate (33.4 ml) was added dropwise to the solution. The reaction mixture was stirred at room temperature for 2 hours, and saturated aqueous solution of sodium hydrogencarbonate was added under cooling with ice. The mixture was extracted with methylene chloride, and the organic layer was washed with saturated sodium chloride solution and dried over anhydrous sodium sulfate, and the solvent was distilled off under reduced pressure. The resulting residue was dissolved in a mixed solution of methanol (1.33 l) and methylene chloride (1.33 l), and 1N aqueous solution of sodium hydroxide (140 ml) was added dropwise to this solution under cooling with ice. After stirring at room temperature for 30 minutes, the solvent was distilled off under reduced pressure. To the residue was added saturated aqueous solution of ammonium chloride, and the mixture was extracted with methylene chloride. The organic layer was washed with saturated sodium chloride solution and dried over anhydrous sodium sulfate, and the solvent was distilled off under reduced pressure. The resulting residue was purified by silica gel column chromatography (eluent; methylene chloride:methanol 40:1–30:1) to obtain the title compound (64.6 g). NMR spectrum (*CDCl$_3$) δppm: 8.37–8.33(1H,m), 7.97–7.91(3H,m), 7.80–7.74(1H,m), 7.63–7.58(1H,m), 7.39–7.25(5H,m), 5.10(2H,s), 4.46–4.32(2H,m), 4.22(1H,d,J=12 Hz), 3.96–3.85(1H,m), 3.76–3.53(3H,m), 3.52–3.40(1H,m), 3.36(1H,d,J=17 Hz), 3.37–3.24(1H,m), 3.15(1H,d,J=12 Hz), 2.41(1H,brs), 2.28(1H,d,J=12 Hz), 1.89–1.68(2H,m), 1.48–1.34(2H,m)

<Step B-2>

Synthesis of 1,4-diaza-1'-(benzyloxycarbonyl)-4-(6-chloronaphthalen-2-ylsulfonyl)-6-(methoxymethyl)-7-oxa-spiro[bicyclo[4.3.0]nonane-8,4'-piperidin]-2-one The procedure of <Step A-5> was repeated by using the compound obtained in Step B-1 (30.0 g) and a large excess of dimethyl sulfate (62.4 ml) to obtain the title compound (26.4 g).

NMR spectrum (*CDCl$_3$) δppm: 8.34(1H,s), 7.99–7.91(3H,m), 7.80–7.74(1H,m), 7.64–7.58(1H,m), 7.38–7.25(5H, m), 5.09(2H,s), 4.42–4.29(2H,m), 4.16(1H,d,J=11 Hz), 3.41(3H,s), 3.65(1H,d,J=10 Hz), 3.59(1H,d,J=10 Hz), 3.74–3.13(6H,m), 2.25(1H,d,J=12 Hz), 1.94–1.66(2H,m), 1.46–1.31(2H,m)

<Step B-3>

Synthesis of 1,4-diaza-4-(6-chloronaphthalen-2-ylsulfonyl)-6-(methoxymethyl)-7-oxaspiro[bicyclo[4.3.0]nonane-8,4'-piperidin]-2-one To a solution of the compound obtained in Step B-2 (76.5 g) in acetonitrile (1.53 l) was added trimethylsilyl iodide (32 ml) under cooling with ice. After stirring the mixture for 45 minutes under cooling with ice, the reaction mixture was poured into 1N hydrochloric acid under cooling with ice, and n-hexane was added to this mixture. The mixture was stirred for separation, and the aqueous layer was washed with n-hexane followed by addition of methylene chloride. 2N aqueous solution of sodium hydroxide was added with stirring under cooling with ice and the mixture was adjusted to pH 11. The mixture was extracted with methylene chloride, and the organic layer was washed with saturated sodium chloride solution and dried over anhydrous sodium sulfate, and the solvent was distilled off under reduced pressure to thereby obtain the title compound (55.9 g).

NMR spectrum (*CDCl$_3$) δppm: 8.38–8.32(1H,m), 7.99–7.91(3H,m), 7.82–7.74(1H,m), 7.61(1H,dd,J=2,9 Hz), 4.41–4.29(2H,m), 4.21(1H,d,J=12 Hz), 3.65(1H,d,J=10 Hz), 3.58(1H,d,J=10 Hz), 3.41(3H,s), 3.32(1H,d,J=17 Hz), 3.20–3.04(2H,m), 3.01–2.74(3H,m), 2.25(1H,d,J=12 Hz), 1.98–1.82(2H,m), 1.58–1.38(2H,m)

<Step B-4>

Synthesis of 1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one To a solution of the compound obtained in Step B-3 (7.50 g) and 4-chloropyridine hydrochloride (2.34 g) in ethanol (150 ml) was added diisopropylethylamine (13.6 ml), and the mixture was stirred in a sealed tube at 150° C. for 15 hours. The reaction mixture was allowed to cool and concentrated. The resulting residue was purified by silica gel column chromatography (eluent; methylene chloride:methanol=100:1—methanol) to obtain the title compound (1.85 g).

<Step C-1>

Synthesis of ethyl 2-[[[2-(acetoxymethyl)-3,8-diaza-1-oxa-8-benzylspiro[4.5]decan-2-yl]methyl](6-chloronaphthalen-2-ylsulfonyl)amino]acetate To a solution of the compound obtained in Step A-2 (200 mg) and 4-(aminomethyl)-1-benzyl-4-hydroxypiperidine (140 mg) in methylene chloride (7.5 ml) was added 3A molecular sieves (400 mg), and the mixture was stirred at room temperature. 0.09N acetic acid-methylene chloride solution (0.50 ml) was added to this mixture. The mixture was heated under reflux for 3.5 hours, allowed to cool and concentrated, and the resulting residue was purified by silica gel column chromatography (eluent; methylene chloride:methanol=19:1) to obtain the title compound (142 mg).

NMR spectrum (*CDCl$_3$) δppm: 8.37–8.32(1H,m), 7.94–7.76(4H,m), 7.55(1H,dd,J=2,9 Hz), 7.33–7.22(5H,m), 4.44(2H,s), 4.14(1H,d,J=12 Hz), 4.02(1H,d,J=12 Hz), 3.95–3.77(2H,m), 3.60(1H,d,J=15 Hz), 3.50(1H,d,J=15 Hz), 3.49(2H,s), 3.38–3.23(1H,m), 3.11–2.85(2H,m), 2.62–2.20(4H,m), 2.04(3H,s), 1.82–1.54(4H,m), 1.06(3H,t,J=7 Hz)

<Step C-2>

Synthesis of 6-(acetoxymethyl)-1,4-diaza-1'-benzyl-4-(6-chloronaphthalen-2-ylsulfonyl)-7-oxa-spiro[bicyclo[4.3.0]nonane-8,4'-piperidin]-2-one A solution of the compound obtained in Step C-1 (125 mg) in toluene was heated under reflux for 2.5 hours. The solution was allowed to cool and concentrated, and the resulting residue was purified by silica gel column chromatography (eluent; n-hexane:ethyl acetate=1:8) to obtain the title compound (97.3 mg).

<Step D-1>

Synthesis of ethyl 2-(2-hydroxy-3-methoxypropylamino) acetate

A solution of glycidyl methyl ether (1.00 g) and glycine ethyl ester (5.91 g) in ethanol was stirred overnight, and concentrated under reduced pressure to obtain the title compound (2.17 g).

NMR spectrum (*CDCl$_3$) δppm: 4.19(2H,q,J=7 Hz), 3.87–3.78(1H,m), 3.39(3H,s), 3.50–3.35(4H,m), 2.81–2.62 (2H,m), 1.29 (3H, t, J=7 Hz)

<Step D-2>

Synthesis of ethyl 2-[(6-chloronaphthalen-2-ylsulfonyl) (2-hydroxy-3-methoxypropyl)amino]acetate To a solution of the compound obtained in Step D-1 (1.60 g) and 6-chloronaphthalene-2-sulfonyl chloride (2.20 g) in methylene chloride (30 ml) was added dropwise triethylamine (1.17 ml) at 0° C. After stirring overnight at room temperature, the reaction mixture was acidified with hydrochloric acid. The mixture was then extracted with ethyl acetate and dried over anhydrous sodium sulfate, and the solvent was distilled off under reduced pressure. The resulting residue was purified by silica gel column chromatography (eluent; n-hexane:ethyl acetate=1:1) to obtain the title compound (800 mg).

NMR spectrum (*CDCl$_3$) δppm: 8.38(1H,s), 7.88(1H,d, J=9 Hz), 7.87–7.81(3H,m), 7.50(1H,dd,J=2,9 Hz), 4.22(2H, s), 4.05(2H,q,J=7 Hz), 4.06–3.97(1H,m), 3.33(3H,s), 3.56–3.31(4H,m), 1.14(3H,t,J=7 Hz)

<Step D-3>

Synthesis of ethyl 2-[(6-chloronaphthalen-2-ylsulfonyl) (3-methoxy-2-oxopropyl)amino]acetate To a solution of the compound obtained in Step D-2 (220 mg) in methylene chloride (5 ml) was added Dess-Martin reagent (336 mg) at room temperature, and the mixture was stirred overnight. To the reaction mixture was added a 1:1 mixed solution of saturated aqueous solution of sodium hydrogencarbonate and saturated aqueous solution of sodium hydrogensulfate, and after stirring, the mixture was extracted with methylene chloride, and the organic layer was dried over anhydrous sodium sulfate. After distilling off the solvent under reduced pressure, the resulting residue was purified by silica gel column chromatography (eluent; n-hexane:ethyl acetate=1:1) to obtain the title compound (190 mg).

NMR spectrum (*CDCl$_3$) δppm: 8.38(1H,s), 7.93–7.77 (4H,m), 7.54–7.48(1H,m), 4.44(2H,s), 4.20(2H,s), 4.13(2H, s), 4.02(2H,q,J=7 Hz), 3.39(3H,s), 1.13(3H,t,J=7 Hz)

<Step D-4>

Ethyl 2-[[[3,8-diaza-2-(methoxymethyl)-1-oxa-8-benzylspiro[4.5]decan-2-yl] methyl](6-chloro-2-naphthalen-2-ylsulfonyl)amino]acetate The procedure of Step C-1 was repeated by using the compound obtained in Step D-3 (100 mg) to obtain the title compound (145 mg).

NMR spectrum (*CDCl$_3$) δppm: 8.37–8.32(1H,m), 7.96–7.77(4H,m), 7.56–7.50(1H,m), 7.35–7.22(5H,m), 4.53–4.37(2H,m), 3.93–3.81(2H,m), 3.59–3.54(2H,m), 3.50–3.44(4H,m), 3.34(3H,s), 2.94(1H,d,J=12 Hz), 2.86 (1H,d,J=12 Hz), 2.68–2.34(4H,m), 1.88–1.53(4H,m), 1.05 (3H,t,J=7 Hz)

<Step D-5>

Synthesis of 1,4-diaza-1'-benzyl-4-(6-chloronaphthalen-2-ylsulfonyl)-6-(methoxymethyl)-7-oxa-spiro[bicyclo [4.3.0]nonane-8,4'-piperidin]-2-one The procedure of Step C-2 was repeated by using the compound obtained in Step D-4 (72.5 mg) to obtain the title compound (67.0 mg).

<Step E>

Synthesis of 1,4-diaza-4-(6-chloronaphthalen-2-ylsulfonyl)-6-(methoxymethyl)-7-oxa-1'-(4-pyridyl)spiro [bicyclo[4.3.0]nonane-8,4'-piperidin]-2-one The procedure of <Step A-5> was repeated by using the compound obtained in Example 3 <Step A-2> (70 mg) to obtain the title compound (38.7 mg).

<Step F-1>

Synthesis of 1,4-diaza-4-(6-chloronaphthalen-2-ylsulfonyl)-6-(hydroxymethyl)-7-oxa-spiro[bicyclo[4.3.0] nonane-8,4'-piperidin]-2-one The procedure of Example 1 <Step A-4> was repeated by using the compound obtained in Example 7 <Step B-1> (938 mg) to obtain the title compound (626 mg).

NMR spectrum (*CD$_3$OD) δppm: 8.52–8.47(1H,m), 8.16–8.04 (3H,m), 7.87(1H,dd,J=2,9 Hz), 7.65(1H,dd,J=2,9 Hz), 4.32–4.19(2H,m), 4.16(1H,d, J=12 Hz), 3.78–3.68(2H, m), 3.48(1H,d,J=17 Hz), 3.35–3.25(1H,m), 3.23–3.11(1H, m), 3.08–2.83(3H,m), 2.58(1H,d,J=12 Hz), 2.06–1.79(2H, m), 1.66–1.35(2H,m)

<Step F-2>

Synthesis of 1,4-diaza-1'-(benzyloxycarbonyl)-4-(6-chloronaphthalen-2-ylsulfonyl)-6-(hydroxymethyl)-7-oxa-spiro[bicyclo[4.3.0]nonane-8,4'-piperidin]-2-one The compound obtained in Step F-1 (3.29 g) was suspended in water (132 ml), and after adding sodium carbonate (1.80 g) to the suspension, benzyl chloroformate (1.21 ml) was added dropwise to the suspension with stirring under cooling with ice. The mixture was stirred for 1 hour under cooling with ice and water was added. The mixture was then extracted with methylene chloride and the organic layer was washed with saturated sodium chloride solution and dried over anhydrous sodium sulfate. The solvent was distilled off under reduced pressure, and the resulting residue was purified by silica gel column chromatography (eluent; methylene chloride:methanol=40:1) to obtain the title compound (3.82 g).

Example 2

Synthesis of 1,4-diaza-4-(6-chloronaphthalen-2-ylsulfonyl)-6-(methoxymethyl)-7-oxa-1-(4-pyrimidinyl) spiro[bicyclo[4.3.0]nonane-8,4'-piperidin]-2-one <Step 1>

Synthesis of 1,4-diaza-4-(6-chloronaphthalen-2-ylsulfonyl)-6-(methoxymethyl)-7-oxa-1'-[2-(methylthio) pyrimidin-4-yl]spiro[bicyclo[4.3.0]nonane-8,4'-piperidin]-2-one To a suspension of the compound obtained in Example 1 <Step A-6> (200 mg) and 4-chloro-2-(methylthio) pyrimidine (0.049 ml) in isoamyl alcohol(2 ml) was added sodium hydrogencarbonate (87.5 mg), and the mixture was heated under reflux for 1.5 hours. The reaction mixture was allowed to cool and concentrated, and the resulting residue was purified by silica gel column chromatography (eluent; methylene chloride:methanol=50:1) to obtain an oily product. This product was solidified in n-hexane, and the solid content was collected by filtration to obtain the title compound (63.2 mg).

NMR spectrum (*CDCl$_3$) δppm: 8.36(1H,s), 8.07–7.90 (4H,m), 7.84–7.74(1H,m), 7.67–7.58(1H,m), 6.16(1H,d,J=6 Hz), 4.44–4.29(2H,m), 4.24–4.14(1H,m), 3.95–3.28(6H,m), 3.43(3H,s), 3.35(1H,d,J=17 Hz), 3.28–3.17 (1H,m), 2.46 (3H,s), 2.29(1H,d,J=12 Hz), 2.01–1.73(2H,m), 1.53–1.40 (2H,m)

<Step 2>

Synthesis of 1,4-diaza-4-(6-chloronaphthalen-2-ylsulfonyl)-6-(methoxymethyl)-7-oxa-1'-(4-pyrimidinyl)spiro[bicyclo[4.3.0]nonane-8,4'-piperidin]-2-one Raney nickel (manufactured by Aldrich Company, 50% aqueous solution, 0.2 m 2001) which had been washed with ethanol was added to a solution of the compound obtained in Step 1 (58.0 mg) in ethanol (1 ml), and the mixture was heated under reflux for 1 hour. After allowing the reaction mixture to cool, the catalyst was removed by filtration, and the filtrate was concentrated. The residue was purified by silica gel column chromatography (eluent; methylene chloride:methanol=50:1) to obtain the title compound (23.0 mg). HRMS: $C_{26}H_{28}ClN_5O_5S(M^+)$: Calculated: 557.1499. Found: 557.1520.

Example 3

Synthesis of 1,4-diaza-4-(6-chloronaphthalen-2-ylsulfonyl)-6-(hydroxymethyl)-7-oxa-1'-(4-pyridyl)spiro[bicyclo [4.3.0]nonane-8,4'-piperidin]-2-one <Step A-1>

Synthesis of 1,4-diaza-4-(6-chloronaphthalen-2-ylsulfonyl)-6-(hydroxymethyl)-7-oxa-spiro[bicyclo[4.3.0]nonane-8,4'-piperidin]-2-one hydrochloride The procedure of Example 1 <Step A-6> was repeated by using the compound obtained in Example 1 <Step A-3> (584 mg) to obtain the title compound (430 mg).

NMR spectrum (*DMSO-$d_6$) δppm: 8.77(1H,brs), 8.68–8.52(2H,m), 8.34–8.14(3H,m), 7.93–7.86(1H,m), 7.74 (1H,dd,J=2,9 Hz), 5.32–5.22(1H,m), 4.17–3.97(3H,m), 3.63–2.80(7H,m), 3.21(1H,d,J=12 Hz), 2.63(1H,d,J=12 Hz), 2.04–1.84(2H,m), 1.69–1.53(2H,m)

<Step A-2>

Synthesis of 1,4-diaza-4-(6-chloronaphthalen-2-ylsulfonyl)-6-(hydroxymethyl)-7-oxa-1'-(4-pyridyl)spiro[bicyclo[4.3.0]nonane-8,4'-piperidin]-2-one The compound obtained in Step A-1 (370 mg) was used to synthesize according to the procedure of Example 1 <Step A-7> to thereby obtain the title compound (30.0 mg). HRMS: $C_{26}H_{27}ClN_4O_5S(M^+)$: Calculated: 542.1390. Found: 542.1421.

<Step B>

Synthesis of 1,4-diaza-4-(6-chloronaphthalen-2-ylsulfonyl)-6-(hydroxymethyl)-7-oxa-1'-(4-pyridyl)spiro[bicyclo[4.3.0]nonane-8,4'-piperidin]-2-one To a solution of the compound obtained in Example 7 <Step A-4> (30.0 mg) in ethanol (1 ml) was added hydrazine monohydrate (0.04 ml), and the mixture was heated under reflux for 30 minutes. The reaction mixture was allowed to cool and concentrated under reduced pressure. The resulting residue was purified by silica gel column chromatography (eluent; methylene chloride:methanol=8:1) to obtain the title compound (20.7 mg).

Example 4

Synthesis of 1,4-diaza-4-(6-chloronaphthalen-2-ylsulfonyl)-6-(ethoxycarbonylmethoxymethyl)-7-oxa-1'-(4-pyridyl)spiro[bicyclo[4.3.0]nonane-8,4'-piperidin]-2-one <Step A-1>

Synthesis of 1,4-diaza-1'-benzyl-4-(6-chloronaphthalen-2-ylsulfonyl)-6-(ethoxycarbonylmethoxymethyl)-7-oxaspiro[bicyclo-[4.3.0]nonane-8,4'-piperidin]-2-one To a solution in methylene chloride (20 ml) of the compound obtained in Example 1 <Step A-4> (1.0 g), benzyltriethylammonium chloride (41 mg) and ethyl bromoacetate (259 ml), was gradually added 50% aqueous solution of sodium hydroxide (6 ml) with vigorous stirring under cooling with ice.

After stirring the reaction mixture for 1.5 hours under cooling with ice, ethyl bromoacetate (120 ml) was added and the mixture was stirred for further 30 minutes. After adding water to the reaction mixture and extracting with methylene chloride, the organic layer was washed with saturated sodium chloride solution and dried over anhydrous sodium sulfate. The solvent was distilled off under reduced pressure and the resulting residue was purified by silica gel column chromatography (eluent; methylene chloride:methanol=50:1) to obtain the title compound (413 mg)

NMR spectrum (CDCl$_3$) δppm: 8.37–8.32(1H,m), 7.97–7.90 (3H,m), 7.80–7.73(1H,m), 7.60(1H,dd,J=2,9 Hz), 7.34–7.18(5H,m), 4.42–4.08(7H,m),3.90–3.73(2H,m),3.47 (2H,s), 3.31(1H,d,J=17 Hz),3.18(1H,d,J=12 Hz),2.68–2.19 (4H,m), 2.27(1H,d,J=12 Hz),2.07–1.79(2H,m),1.66–1.33 (2H,m),1.33–1.22(3H,m)

<Step A-2>

Synthesis of 1,4-diaza-4-(6-chloronaphthalen-2-ylsulfonyl)-6-(ethoxycarbonylmethoxymethyl)-7-oxaspiro[bicyclo[4.3.0]nonane-8,4'-piperidin]-2-one hydrochloride The compound obtained in Step A-1 (300 mg) was used to synthesize according to the procedure of Example 1 <Step A-6> to thereby obtain the title compound (276 mg). NMR spectrum (*CDCl$_3$) δppm: 9.65–9.45(2H,brs),8.33(1H,s), 8.00–7.90(3H,m),7.80–7.73(1H,m),7.65–7.58(1H,m), 4.40–4.05(7H,m),3.90 (1H,d,J=10 Hz),3.77(1H,d,J=10 Hz), 3.42–3.01(6H,m),2.37–2.09(2H,m),2.26(1H,d,J=12 Hz), 2.05–1.91(1H,m),1.58–1.45(1H,m),1.29(3H,t,J=7 Hz)

<Step A-3>

Synthesis of 1,4-diaza-4-(6-chloronaphthalen-2-ylsulfonyl)-6-(ethoxycarbonylmethoxymethyl)-7-oxa-1'-(4-pyridyl)spiro[bicyclo[4.3.0]nonane-8,4'-piperidin]-2-one The compound obtained in Step A-2 (200 mg) was used to synthesize according to the procedure of Example 1 <Step A-7> to thereby obtain the title compound (11.4 mg).

HRMS:$C_{30}H_{33}ClN_4O_7S(M^+)$: Calculated: 628.1758. Found: 628.1802.

<Step B>

Synthesis of 1,4-diaza-4-(6-chloronaphthalen-2-ylsulfonyl)-6-(ethoxycarbonylmethoxymethyl)-7-oxa-1'-(4-pyridyl)spiro[bicyclo[4.3.0]nonane-8,4'-piperidin]-2-one The compound obtained in Example 3 <Step A-2> (300 mg) was used to synthesize according to the procedure of Example 4 <Step A-1> to thereby obtain the title compound (168 mg).

Example 5

Synthesis of 1,4-diaza-4-(6-chloronaphthalen-2-ylsulfonyl)-6-(carboxymethoxymethyl)-7-oxa-1'-(4-pyridyl)spiro[bicyclo[4.3.0]nonane-8,4'-piperidin]-2-one <Step A>

Synthesis of 1,4-diaza-4-(6-chloronaphthalen-2-ylsulfonyl)-6-(carboxymethoxymethyl)-7-oxa-1'-(4-pyridyl)spiro[bicyclo[4.3.0]nonane-8,4'-piperidin]-2-one To a solution of the compound obtained in Example 4 <Step A-3> (10.0 mg) in ethanol (320 ml) was added 2N aqueous solution of potassium hydroxide (32.0 ml) and the mixture was stirred at room temperature for 20 minutes. The reaction mixture was adjusted to pH 5 by adding saturated aqueous solution of ammonium chloride and the solvent was distilled off under reduced pressure. The resulting residue was purified by silica gel column chromatography (eluent; methylene chloride:methanol=4:1) to obtain the title compound (3.3 mg).

IR (*KBr)cm$^{-1}$: 3412, 3149, 1998, 1744, 1647, 1402
<Step B-1>
Synthesis of 1,4-diaza-6-(t-butoxycarbonylmethoxymethyl)-4-(6-chloronaphthalen-2-ylsulfonyl)-7-oxa-1'-(4-pyridyl)spiro[bicyclo[4.3.0]nonane-8,4'-piperidin]-2-one To a solution in methylene chloride (1.4 ml) of the compound obtained in Example 3 <Step A-2> (85.0 mg), benzyltriethylammonium chloride (3.57 mg) and t-butyl bromoacetate (0.03 ml), was gradually added 50% aqueous solution of sodium hydroxide (0.43 ml) with vigorous stirring under cooling with ice. After stirring the reaction mixture for 40 minutes under cooling with ice, water was added and the reaction mixture was extracted with chloroform. The organic layer was washed with saturated sodium chloride solution and dried over anhydrous sodium sulfate. The solvent was distilled off under reduced pressure and the resulting residue was purified by silica gel column chromatography (eluent; methylene chloride:methanol=20:1–15:1) to obtain the title compound (53.5 mg).

NMR spectrum (*CDCl$_3$) δppm: 8.38–8.32(1H,m), 8.28–8.17(2H,m),8.00–7.89(3H,m),7.83–7.74(1H,m), 7.66–7.58(1H,m),6.66–6.56(2H,m),4.42–4.28(2H,m),4.19 (1H,d,J=11 Hz),4.12(1H,d,J=17 Hz),4.02(1H,d,J=17 Hz), 3.96–3.88(1H,m),3.81–3.72(1H,m),3.53–3.17(4H,m),3.35 (1H,d,J=17 Hz),3.30(1H,d,J=11 Hz),2.32(1H,d,J=12 Hz), 2.16–2.04(1H,m),1.96–1.82(1H,m),1.78–1.41(2H,m),1.50 (9H,s)
<Step B-2>
Synthesis of 1,4-diaza-4-(6-chloronaphthalen-2-ylsulfonyl)-6-(carboxymethoxymethyl)-7-oxa-1'-(4-pyridyl)spiro[bicyclo[4.3.0]nonane-8,4'-piperidin]-2-one The compound obtained in Step B-1 (48 mg) was dissolved in formic acid (1.0 ml) and the solution was stirred overnight at room temperature. The mixture was solidified by addition of diethyl ether and the supernatant was removed by decantation and dried in vacuum to obtain the title compound (35.3 mg).

Example 6

Synthesis of 1,4-diaza-6-(methoxymethyl)-4-(2-naphthalenesulfonyl)-7-oxa-1'-(4-pyridyl)spiro[bicyclo [4.3.0]nonane-8,4'-piperidin]-2-one To a solution of the compound obtained in Example 1 <Step A-7> (12.0 mg) in methanol (1 ml) was added 10% palladium-active carbon (6.0 mg). The mixture was stirred at room temperature for 3 days under a hydrogen atmosphere. The reaction mixture was filtered and the filtrate was concentrated under reduced pressure. The resulting residue was purified by silica gel column chromatography [ChromatorexNH™] (eluent; n-hexane:ethyl acetate=1:1) to obtain the title compound (8.6 mg).

HRMS:C$_{27}$H$_{30}$N$_4$ O$_5$ S(M$^+$): Calculated: 522.1937. Found: 522.1949.

Example 7

Synthesis of 6-(acetoxymethyl)-1,4-diaza-4-(6-chloronaphthalen-2-ylsulfonyl)-7-oxa-1'-(4-pyridyl)spiro [bicyclo[4.3.0]nonane-8,4'-piperidin]-2-one
<Step A-1>
Synthesis of 4-[4-(t-butoxycarbonylamino)methyl-4-hydroxypiperidin-1-yl]pyridine 1-oxide To a suspension in isoamyl alcohol (35 ml) of conventionally known compounds: 4-[(t-butoxycarbonylamino) methyl]-4-hydroxypiperidine (2.00 g) and 4-chloropyridine 1-oxide (1.12 g), was added sodium hydrogencarbonate (1.75 g) and the mixture was heated under reflux for 4 hours. The reaction mixture was allowed to cool and water was added thereto. The reaction mixture was extracted with methylene chloride and the organic layer was washed with saturated sodium chloride solution and dried over anhydrous sodium sulfate. The solvent was distilled off under reduced pressure and the resulting residue was purified by silica gel column chromatography (eluent:methylene chloride:methanol=9:1–4:1) to obtain the title compound (1.03 g).

NMR spectrum (*DMSO-d$_6$) δppm: 7.90–7.83(2H,m), 6.92–6.84(2H,m),6.78–6.70(1H,m),4.58(1H,brs),3.64–3.50 (2H,m),3.17–3.04(2H,m),2.92(2H,d,J=6 Hz),1.60–1.30(4H, m),1.35(9H,s)
<Step A-2>
Synthesis of 4-[(t-butoxycarbonylamino)methyl]-4-hydroxy-1-(4-pyridyl)piperidine Raney nickel (catalytic amount) prepared by the procedure described in the literature: "Aromatic Amine Oxide" (Eiji Ochiai, Elsevier, page 189, 1967) was added to a solution of the compound obtained in Step A-1 (300 mg) in methanol (3 ml). The mixture was stirred at room temperature for 3.5 hours under a hydrogen atmosphere. The catalyst was filtered off and the filtrate was concentrated. The residue was purified by silica gel column chromatography (eluent; methylene chloride:methanol=4:1) to obtain the title compound (214 mg).

NMR spectrum (*DMSO-d$_6$) δppm: 8.10(2H,d,J=7 Hz), 6.87 (2H,d,J=7 Hz),6.76–6.68(1H,m),4.55(1H,brs), 3.78–3.65(2H,m),3.24–3.11(2H,m),2.92(2H,d,J=6 Hz), 1.58–1.30(4H,m),1.35(9H,s)
<Step A-3>
Synthesis of 4-(aminomethyl)-4-hydroxy-1-(4-pyridyl) piperidine hydrochloride The compound obtained in Step A-2 (175 mg) was dissolved in 10% hydrogen chloride-methanol solution (2 ml) and the solution was stirred at room temperature for 2 hours. The reaction mixture was concentrated under reduced pressure and the resulting residue was solidified by addition of diethyl ether, and thereafter fully triturated. The solvent was distilled off under reduced pressure to obtain the title compound (160 mg).

NMR spectrum (*DMSO-d$_6$) δppm: 13.68(1H,brs),8.20 (2H,d,J=8 Hz),8.13(2H,brs),7.22(2H,d,J=8 Hz),5.43(1H,s), 4.08–3.96(2H,m),3.52–3.32(2H,m),2.80(2H,brs),1.77–1.46 (4H,m)
<Step A-4>
Synthesis of 6-(acetoxymethyl)-1,4-diaza-4-(6-chloronaphthalen-2-ylsulfonyl)-7-oxa-1'-(4-pyridyl)spiro [bicyclo[4.3.0]nonane-8,4'-piperidin]-2-one The procedure of Example 1 <Step A-3> was repeated by using the compound obtained in Step A-3 instead of 4-(aminomethyl)-1-benzyl-4-hydroxypiperidine and chloroform-ethanol instead of toluene to obtain the title compound.

HRMS:C$_{28}$H$_{29}$ClN$_4$O$_6$S(M$^+$): Calculated: 584.1496. Found: 584.1459.
<Step B-1>
Synthesis of 6-(acetoxymethyl)-1,4-diaza-4-(6-chloronaphthalen-2-ylsulfonyl)-7-oxaspiro[bicyclo[4.3.0] nonane-8,4'-piperidin]-2-one To a solution of the compound obtained in Example 1 <Step A-3> (4.00 g) in 1,2-dichloroethane (42 ml) were added 1,8-bis(N,N-dimethylamino)naphthalene (287 mg) and 1-chloroethyl chloroformate (1.82 ml) and the mixture was heated under reflux for 1 hour. The reaction mixture was allowed to cool and purified by silica gel column chromatography (eluent; methylene chloride:methanol=8:1) to obtain a solid. The solid (4.29 g) was dissolved in methanol (43 ml) and the solution was heated under reflux for 30 minutes. The reaction mixture was concentrated and to the resulting residue was added 1N aqueous solution of sodium hydroxide. The mixture was extracted with methylene chloride. The organic layer was washed with saturated sodium chloride solution and dried over anhydrous sodium sulfate. The solvent was distilled off under reduced pressure to obtain the title compound (3.47 g).

NMR spectrum (*CDCl$_3$) δppm: 8.38–8.34(1H,m), 7.99–7.92(3H,m),7.82–7.76(1H,m),7.65–7.58(1H,m),4.43 (1H,d,J=12 Hz),4.45–4.30(2H,m),4.27(1H,d,J=12 Hz), 4.19 (1H,d,J=12 Hz),3.34(1H,d,J=17 Hz),3.08(1H,d,J=12 Hz), 3.04–2.82(2H,m),2.77–2.61(2H,m),2.33(1H,d,J=12 Hz), 2.12(3H,s),1.86–1.67(2H,m),1.47–1.29(2H,m)

<Step B-2>

Synthesis of 6-(acetoxymethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one The procedure of Example 1 <Step A-7> was repeated by using the compound obtained in Step B-1 (2.60 g) to obtain the title compound (240 mg).

Example 8

Synthesis of 1,4-diaza-4-[6-chloronaphthalen-2-ylsulfonyl)-6-(methoxymethyl)-7-oxa-1'-(4-pyridyl)spiro[bicyclo[4.4.0]decane-9,4'-piperidin]-2-one <Step 1>

Synthesis of 6-(acetoxymethyl)-1,4-diaza-1'-benzyl-4-(6-chloronaphthalen-2-ylsulfonyl)-7-oxaspiro[bicyclo[4.4.0]decane-9,4'-piperidin]-2-one To a solution in toluene (1 L) of the compound obtained in Example 1 <Step A-2> (3.77 g) and the conventionally known compound: 4-(aminomethyl)-1-benzyl-4-(hydroxymethyl)piperidine (2.00 g) was added p-toluenesulfonic acid monohydrate (162 mg) and the mixture was heated under reflux for 1 hour using a Dean Stark. After allowing the reaction mixture to cool, saturated aqueous solution of sodium hydrogencarbonate was added and the mixture was extracted with ethyl acetate. The organic layer was washed with saturated sodium chloride solution and dried over anhydrous sodium sulfate. The solvent was distilled off under reduced pressure and the resulting residue was purified by silica gel column chromatography (eluent; methylene chloride:methanol=40:1) to obtain the title compound (1.53 g).

NMR spectrum (*CDCl$_3$) δppm: 8.35(1H,s),7.97–7.90 (3H,m),7.82–7.76(1H,m),7.63–7.56(1H,m),7.33–7.18(5H, m),5.03(1H,d,J=13 Hz),4.68 (1H,d,J=14 Hz),4.32–4.20(2H, m),4.06(1H,d,J=13 Hz),3.67(1H,d,J=12 Hz),3.54–3.43(1H, m),3.46(2H,s),3.32(1H,d,J=16 Hz),2.54(1H,d,J=14 Hz), 2.46(1H,d,J=12 Hz),2.45–2.35(2H,m),2.32–2.19(2H,m), 2.13(3H,s),1.54–1.24(4H,m)

<Step 2>

Synthesis of 1,4-diaza-1'-benzyl-4-(6-chloronaphthalen-2-ylsulfonyl)-6-(hydroxymethyl)-7-oxaspiro[bicyclo[4.4.0]decane-9,4'-piperidin]-2-one To a solution of the compound obtained in Step 1 (76.6 mg) in methanol (2 ml) was added 1N aqueous solution of sodium hydroxide (2.84 ml) at room temperature. The reaction mixture was stirred at room temperature for 20 minutes and the solvent was distilled off under reduced pressure. Water was added to the residue and the mixture was extracted with methylene chloride. The organic layer was washed with saturated sodium chloride solution and dried over anhydrous sodium sulfate. The solvent was distilled off under reduced pressure to obtain the title compound (63.1 mg).

NMR spectrum (*CDCl$_3$) δppm: 8.36–8.32(1H,m), 7.96–7.90(3H,m),7.81–7.75(1H,m),7.63–7.57(1H,m), 7.32–7.18(5H,m),4.73–4.62(1H,m),4.34–4.15(3H,m), 3.90–3.80(1H,m),3.68–3.44(2H,m),3.46(2H,s),3.34(1H,d, J=17 Hz),2.51(1H,d,J=14 Hz),2.47–2.36(3H,m),2.32–2.20 (2H,m),2.14–2.07(1H,m),1.58–1.28(4H,m)

<Step 3>

Synthesis of 1,4-diaza-1'-benzyl-4-(6-chloronaphthalen-2-ylsulfonyl)-6-(methoxymethyl)-7-oxaspiro[bicyclo[4.4.0]decane-9,4'-piperidin]-2-one To a solution in methylene chloride (30 ml) of the compound obtained in Step 2 (1.20 g), benzyltriethylammonium chloride (39.0 mg) and dimethyl sulfate (260 ml), was gradually added 50% aqueous solution of sodium hydroxide (7.5 ml) with vigorous stirring under cooling with ice. The reaction mixture was stirred at room temperature for 45 minutes, adjusted to pH 9 with saturated aqueous solution of ammonium chloride under cooling with ice and extracted with methylene chloride. The organic layer was washed with saturated sodium chloride solution and dried over anhydrous sodium sulfate. The solvent was distilled off under reduced pressure and the resulting residue was purified by silica gel column chromatography (eluent; methylene chloride:methanol=30:1) to obtain the title compound (541 mg).

NMR spectrum (*CDCl$_3$) δppm: 8.34(1H,s),7.96–7.89 (3H,m), 7.81–7.75(1H,m),7.62–7.56(1H,m),7.35–7.17(5H, m), 4.67(1H,d,J=14 Hz),4.35–4.23(2H,m),4.04(1H,d,J=11 Hz),3.69–3.42(5H,m),3.47(3H,s),3.29(1H,d,J=17 Hz),2.55 (1H,d,J=14 Hz), 2.49–2.19(5H,m),1.58–1.23(4H,m)

<Step 4>

Synthesis of 1,4-diaza-4-(6-chloronaphthalen-2-ylsulfonyl)-6-(methoxymethyl)-7-oxaspiro[bicyclo[4.4.0]decane-9,4'-piperidin]-2-one hydrochloride To a suspension in 1,2-dichloroethane (10 ml) of the compound obtained in Step 3 (200 mg) and 1,8-bis (dimethylamino)naphthalene (15.0 mg) was added 1-chloroethyl chloroformate (92.0 ml) and the mixture was heated under reflux for 30 minutes. The mixture was allowed to cool and thereafter purified by silica gel column chromatography (eluent; methylene chloride methanol=20:1). The solvent was distilled off under reduced pressure. To the residue was added methanol (10 ml) and the mixture was heated under reflux for 30 minutes. After allowing the reaction mixture to cool, the solvent was distilled off under reduced pressure and the resulting residue was crystallized by addition of diethyl ether. The supernatant was removed by decantation. The solvent was distilled off under reduced pressure to obtain the title compound (167 mg).

NMR spectrum (*DMSO-d$_6$) δppm: 8.71(2H,brs),8.60 (1H,s), 8.35–8.14(3H,m),7.94–7.83(1H,m),7.80–7.68(1H, m),4.36(1H,d,J=14 Hz),4.21–4.09(2H,m),3.98–3.88(2H,m), 3.77–2.72(7H,m),3.32(3H,s),2.79(1H,d,J=14 Hz), 2.67(1H, d,J=12 Hz), 1.62–1.42(4H,m)

<Step 5>

Synthesis of 1,4-diaza-4-(6-chloronaphthalen-2-ylsulfonyl)-6-(methoxymethyl)-7-oxa-1'-(4-pyridyl)spiro [bicyclo[4.4.0]decane-9,4'-piperidin]-2-one To a suspension in 2-ethoxyethanol (3 ml) of the compound obtained in Step 4 (50.0 mg) and 4-chloropyridine hydrochloride (14 mg), was added diisopropylethylamine (57.0 ml) and the mixture was heated under reflux for 4 hours. After allowing the reaction mixture to cool, potassium carbonate (78.0 mg) was added and the mixture was stirred for 1 hour. The insoluble content was removed by filtration and the filtrate was concentrated. The resulting residue was purified by silica gel column chromatography (eluent; methylene chloride:methanol=10:1–5:1). Then, the residue was purified by silica gel column chromatography [ChromatorexNH™] (eluent; ethyl acetate) to obtain the title compound (7.4 mg).

HRMS:$C_{28}H_{31}ClN_4O_5S(M^+)$: Calculated: 570.1703. Found: 570.1658.

Example 9

Synthesis of 1,4-diaza-4-(6-chloronaphthalen-2-ylsulfonyl)-7-oxa-1'-(4-pyridyl)spiro[bicyclo[4.3.0]nonane-8,4'-piperidin]-2-one <Step 1>

Synthesis of ethyl 2-[(2,2-diethoxyethyl)amino]acetate

To a suspension of the glycine ethyl ester hydrochloride (1.00 g) and bromoacetaldehyde diethyl acetal (1.08 ml) in N,N-dimethylformamide (30 ml), were added cesium carbonate (4.67 g) and sodium iodide (107 mg) and the mixture was stirred at 100° C. for 4 hours. The reaction mixture was adjusted to pH 2 with 1N hydrochloric acid and washed with ethyl acetate. The aqueous layer was adjusted to pH 11 with 1N aqueous solution of sodium hydroxide and extracted with methylene chloride. The organic layer was dried over anhydrous sodium sulfate and thereafter the solvent was distilled off under reduced pressure to obtain the title compound (860 mg).

NMR spectrum (CDCl$_3$) δppm: 4.63–4.57(1H,m), 4.24–4.14 (2H,m),3.78–3.64(2H,m), 3.61–3.48(2H,m), 3.44 (2H,s), 2.76(2H,d,J=6 Hz),1.32–1.15(9H,m)

<Step 2>

Synthesis of Ethyl 2-[(6-chloronaphthalen-2-ylsulfonyl)(2,2-diethoxyethyl)amino]acetate The compound obtained in Step 1 (504 mg) was suspended in methylene chloride (20 ml) and to the suspension were added triethylamine (336 ml) and then 6-chloronaphthalene-2-sulfonyl chloride (600 mg) under cooling with ice. After stirring the mixture overnight at room temperature, saturated sodium chloride solution was added and the mixture was extracted with methylene chloride. The organic layer was dried over anhydrous sodium sulfate and thereafter the solvent was distilled off under reduced pressure. The resulting residue was purified by silica gel column chromatography (eluent; n-hexane:ethyl acetate=20:1–4:1) to obtain the title compound (750 mg).

NMR spectrum (*CDCl$_3$) δppm:8.40(1H,s),7.93–7.82 (4H,m), 7.55(1H,dd,J=2,9 Hz),4.68–4.63(1H,m),4.33(2H,s), 3.96(2H,q,J=7 Hz),3.77–3.64(2H,m),3.60–3.47(2H,m),3.37 (2H,d,J=6 Hz),1.23–1.13(6H,m),1.12–1.04(3H,m)

<Step 3>

Synthesis of ethyl 2-[(6-chloronaphthalen-2-ylsulfonyl)(formylmethyl)amino]acetate To a mixed solution of trifluoroacetic acid (5 ml), chloroform (1.5 ml) and water (2.5 ml) was added a solution of the compound obtained in Step 2 (560 mg) in chloroform (1 ml) under cooling with ice water. After stirring for 1.5 hours under cooling with ice water, the reaction mixture was adjusted to pH 8 with saturated aqueous solution of sodium hydrogencarbonate and extracted with diethyl ether. The organic layer was dried over anhydrous sodium sulfate and thereafter the solvent was distilled off under reduced pressure. The resulting residue was purified by silica gel column chromatography (eluent; n-hexane:ethyl acetate=5:1–2:1) to obtain the title compound (240 mg).

NMR spectrum (*CDCl$_3$) δppm: 9.74–9.70(1H,m),8.39 (1H,s), 7.98–7.85(3H,m),7.85–7.78(1H,m)7.62–7.53(1H, m),4.24–4.03(6H,m),1.21–1.13(3H,m)

<Step 4>

Synthesis of 1,4-diaza-1'-benzyl-4-(6-chloronaphthalen-2-ylsulfonyl)-7-oxaspiro[bicyclo[4.3.0]nonane-8,4'-piperidin]-2-one To a solution in toluene (25 ml) of the compound obtained in Step 3 (200 mg) and 4-(aminomethyl)-1-benzyl-4-hydroxypiperidine (119 mg) was added p-toluenesulfonic acid monohydrate (5.0 mg) and the mixture was heated under reflux for 1 hour using a Dean Stark. After allowing the reaction mixture to cool, the solvent was distilled off under reduced pressure and the resulting residue was purified by silica gel column chromatography (eluent; methylene chloride:methanol=50:1) to obtain the title compound (200 mg).

NMR spectrum (CDCl$_3$) δppm: 8.36–8.32(1H,m), 7.97–7.88(3H,m),7.81–7.74(1H,m),7.60 (1H,dd,J=2,9 Hz), 7.37–7.21(5H,m),5.17–5.10 (1H,m),4.41–4.24(2H,m), 3.65 (1H,d,J=12 Hz),3.49(2H,s),3.28(1H,d,J=17 Hz),3.16(1H,d, J=12 Hz),2.60–2.32(5H,m),1.92–1.58(4H,m)

<Step 5>

Synthesis of 1,4-diaza-4-(6-chloronaphthalen-2-ylsulfonyl)-7-oxaspiro[bicyclo[4.3.0]nonane-8,4'-piperidin]-2-one hydrochloride The procedure of Example 1 <Step A-6> was repeated by using the compound obtained in Step 4 (180 mg) to obtain the title compound (162 mg).

NMR spectrum (DMSO-d$_6$) δppm: 9.00–8.57(3H,m), 8.33–8.13(3H,m),7.98–7.87(1H,m),7.75(1H,dd,J=2,9 Hz), 5.16(1H,dd,J=4,8 Hz), 4.22–4.08(1H,m),4.05(1H,d,J=16 Hz), 3.81–3.69(1H,m),3.62–2.78(6H,m), 2.78–2.64(1H,m), 2.05–1.58(4H,m)

<Step 6>

Synthesis of 1,4-diaza-4-(6-chloronaphthalen-2-ylsulfonyl)-7-oxa-1'-(4-pyridyl)spiro[bicyclo[4.3.0]nonane-8,4'-piperidin]-2-one The procedure of Example 1 <Step A-7> was repeated by using the compound obtained in Step 5 (100 mg) to obtain the title compound (3.8 mg).

HRMS:$C_{25}H_{25}ClN_4O_4$ S(M$^+$): Calculated: 512.1285. Found: 512.1310.

Example 10

Synthesis of 1,4-diaza-4-(6-chloronaphthalen-2-ylsulfonyl)-7-oxa-1'-(4-pyrimidinyl)spiro[bicyclo[4.3.0]nonane-8,4'-piperidin]-2-one <Step 1>

Synthesis of 1,4-diaza-4-(6-chloronaphthalen-2-ylsulfonyl)-7-oxa-1'-[2-(methylthio)pyrimidin-4-yl]spiro[bicyclo[4.3.0]nonane-8,4'-piperidin]-2-one The procedure of Example 2 <Step 1> was repeated by using the compound obtained in Example 9 <Step 5> to obtain the title compound (293 mg).

NMR spectrum (CDCl$_3$) δppm: 8.42–8.35(1H,m), 8.07–7.92(3H,m),8.02(1H,d,J=6 Hz),7.84–7.76(1H,m), 7.68–7.58(1H,m),6.21(1H,d,J=6 Hz),5.21(1H,dd,J=4,9 Hz), 4.45–4.34(1H,m),4.33(1H,d,J=17 Hz),4.12–3.93(2H,m), 3.80–3.71(1H,m),3.52–3.27(2H,m),3.32(1H,d,J=17 Hz), 3.23–3.15(1H,m),2.48(3H,s),2.57–2.39(1H,m),2.23–1.80 (1H,m),1.80–1.57(3H,m)

<Step 2>

Synthesis of 1,4-diaza-4-(6-chloronaphthalen-2-ylsulfonyl)-7-oxa-1'-(4-pyrimidinyl)spiro[bicyclo[4.3.0]nonane-8,4'-piperidin]-2-one The procedure of Example 2 <Step 2> was repeated by using the compound obtained in Step 1 (290 mg) to obtain the title compound (15.0 mg).

HRMS:$C_{24}H_{24}ClN_5O_4$ S(M$^+$): Calculated: 513.1237. Found: 513.1276.

Example 11

Synthesis of 1,4-diaza-4-((E)-4-chlorostyrylsulfonyl)-7-oxa-1'-(4-pyridyl)spiro[bicyclo[4.3.0]nonane-8,4'-piperidin]-2-one <Step 1>

Synthesis of ethyl 2-[((E)-4-chlorostyrylsulfonyl)(2,2-diethoxyethyl)amino]acetate The compound obtained in Example 9 <Step 1> (2.46 g) was suspended in methylene chloride (90 ml) and to the suspension were added triethylamine (1.56 ml) and then (E)-4-chlorostyrylsulfonyl chloride (2.26 g) under cooling with ice. The mixture was stirred at room temperature for 4 hours and water was added thereto. The mixture was extracted with methylene chloride. The organic layer was dried over anhydrous sodium sulfate and thereafter the solvent was distilled off under reduced pressure. The resulting residue was purified by silica gel column chromatography (eluent; n-hexane:ethyl acetate=5:1) to obtain the title compound (2.03 g).

NMR spectrum (*CDCl$_3$) δppm: 7.48–7.35(5H,m), 6.96–6.88(1H,m),4.64(1H,t,J=5 Hz),4.29(2H,s),4.17(2H,q,J=7 Hz), 3.78–3.47(4H,m), 3.24(2H,d,J=5 Hz),1.32–1.14(9H,m)

<Step 2>

Synthesis of ethyl 2-[((E)-4-chlorostyrylsulfonyl)(formylmethyl)amino]acetate

To a mixed solution of the compound obtained in Step 1 (2.00 g), chloroform (9.5 ml) and water (9.5 ml) was added trifluoroacetic acid (13.5 ml) under cooling with ice water. The reaction mixture was stirred at room temperature for 4 hours, adjusted to pH 8 with saturated aqueous solution of sodium hydrogencarbonate and extracted with methylene chloride. The organic layer was dried over anhydrous sodium sulfate and thereafter the solvent was distilled off under reduced pressure. The resulting residue was purified by silica gel column chromatography (eluent; n-hexane ethyl acetate=2:1) to obtain the title compound (1.27 g).

NMR spectrum (CDCl$_3$) δppm: 9.68(1H,s),7.50–7.35(5H,m), 6.82(1H,d,J=15 Hz),4.25–4.10(6H,m),1.32–1.21(3H,m)

<Step 3>

Synthesis of 1,4-diaza-1'-benzyl-4-((E)-4-chlorostyrylsulfonyl)-7-oxaspiro[bicyclo[4.3.0]nonane-8,4'-piperidin]-2-one To a solution in toluene (175 ml) of the compound obtained in Step 2 (1.27 g) and 4-(aminomethyl)-1-benzyl-4-hydroxypiperidine (810 mg) was added p-toluenesulfonic acid monohydrate (35.0 mg) and the mixture was heated under reflux for 1 hour using a Dean Stark. The reaction mixture was allowed to cool and the solvent was distilled off under reduced pressure. The resulting residue was purified by silica gel column chromatography (eluent; methylene chloride:methanol=50:1) to obtain the title compound (1.08 g).

NMR spectrum (CDCl$_3$) δppm: 7.48(1H,d,J=15 Hz), 7.49–7.37(4H,m),7.37–7.22(5H,m),6.63(1H,d,J=15 Hz), 5.13(1H,dd,J=4,9 Hz),4.32–4.18(2H,m),3.74(1H,d,J=12 Hz),3.56 (1H,d,J=17 Hz),3.51(2H,s),3.20(1H,d,J=12 Hz), 2.75–2.64(1H,m),2.61–2.36(4H,m),1.94–1.66(4H,m)

<Step 4>

Synthesis of 1,4-diaza-4-((E)-4-chlorostyrylsulfonyl)-7-oxaspiro[bicyclo[4.3.0]nonane-8,4'-piperidin]-2-one hydrochloride The procedure of Example 1 <Step A-6> was repeated by using the compound obtained in Step 3 (1.00 g) to obtain the title compound (914 mg).

NMR spectrum (*CDCl$_3$) δppm: 9.68(2H,brs),7.49 (1H, d,J=15 Hz),7.58–7.31(4H,m),6.66(1H,d,J=15 Hz),5.21–5.12 (1H,m),4.33–4.14(2H,m),3.93(1H,d,J=12 Hz), 3.59(1H,d,J=17 Hz),3.54–3.10(4H,m),3.23(1H,d,J=12 Hz),2.80–2.68 (1H,m),2.35–2.00(2H,m),1.92–1.65(2H,m)

<Step 5>

Synthesis of 1,4-diaza-4-((E)-4-chlorostyrylsulfonyl)-7-oxa-1'-(4-pyridyl)spiro[bicyclo[4.3.0]nonane-8,4'-piperidin]-2-one The procedure of Example 1 <Step A-7> was repeated by using the compound obtained in Step 4 (350 mg) to obtain the title compound (46.0 mg).

HRMS:C$_{23}$H$_{25}$ClN$_4$O$_4$ S(M$^+$): Calculated: 488.1285. Found: 488.1306.

Example 12

Synthesis of 1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one methanesulfonate To a solution of the compound obtained in Example 1 (111 mg) in methanol (0.4 ml) was added methanesulfonic acid (0.01313.6 ml) and the mixture was stirred for 30 minutes. The reaction mixture was concentrated under reduced pressure and the residue was crystallized by addition of diethyl ether. The supernatant was removed by decantation and the solvent was distilled off under reduced pressure to obtain the title compound (119 mg).

Example 13

Synthesis of (−)-1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one methanesulfonate The procedure of Example 12 was repeated by using the (−)-1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one (111 mg) produced by the optical resolution method described in Example 1 <Step A-7> to obtain the title compound (119 mg).

Example 14

Synthesis of 1,4-diaza-4-(6-chloronaphthalen-2-ylsulfonyl)-6-(hydroxymethyl)-7-oxa-1'-(4-pyridyl)spiro[bicyclo[4.3.0]nonane-8,4'-piperidin]-2-one methanesulfonate The procedure of Example 12 was repeated by using the compound obtained in Example 3 <Step A-2> (33.0 mg) to obtain the title compound (38.0 mg).

Example 15

Synthesis of 1,4-diaza-4-(6-chloronaphthalen-2-ylsulfonyl)-6-(ethoxycarbonylmethoxymethyl)-7-oxa-1'-(4-pyridyl)spiro[bicyclo[4.3.0]nonane-8,4'-piperidin]-2-one methanesulfonate The procedure of Example 12 was repeated by using the compound obtained in Example 4 <Step A-3> (40.0 mg) to obtain the title compound (43.0 mg).

Example 16

Synthesis of 6-(acetoxymethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 7 <Step A-4> (33.0 mg) to obtain the title compound (34.2 mg).

Example 17

Synthesis of 1,4-diaza-4-(6-chloronaphthalen-2-ylsulfonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 9 <Step 6> (27.8 mg) to obtain the title compound (30.0 mg).

Example 18

Synthesis of 1,4-diaza-4-(6-chloronaphthalen-2-ylsulfonyl)-7-oxa-1'-(4-pyrimidinyl)spiro[bicyclo[4.3.0]nonane-8,4'-piperidin]-2-one methanesulfonate The procedure of Example 12 was repeated by using the compound obtained in Example 10 <Step 2> (31.2 mg) to obtain the title compound (34.0 mg).

Example 19

Synthesis of 1,4-diaza-4-((E)-4-chlorostyrylsulfonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 11 <Step 5> (30.6 mg) to obtain the title compound (31.5 mg).

Example 20

Synthesis of 1,4-diaza-4-(6-chloronaphthalen-2-ylsulfonyl)-6-(2-methoxyethoxymethyl)-7-oxa-1'-(4-pyridyl)spiro[bicyclo[4.3.0]nonane-8,4'-piperidin]-2-one <Step 1>

Synthesis of 1,4-diaza-1'-(benzyloxycarbonyl)-4-(6-chloronaphthalen-2-ylsulfonyl)-6-(ethoxycarbonylmethoxymethyl)-7-oxaspiro[bicyclo[4.3.0]nonane-8,4'-piperidin]-2-one The procedure of Example 4 <Step A-1> was repeated by using the compound obtained in Example 1 <Step B-1> (4.00 g) to obtain the title compound (3.90 g).

NMR spectrum (*CDCl$_3$) δppm: 8.36–8.31(1H,m), 7.98–7.90(3H,m),7.81–7.74(1H,m),7.65–7.57(1H,m), 7.40–7.24(5H,m), 5.10(2H,s),4.40–4.06(7H,m),3.89(1H,d, J=10 Hz), 3.78 (1H,d,J=10 Hz),3.82–3.20(6H,m),2.29(1H, d,J=12 Hz),2.03–1.91(1H,m),1.84–1.70(1H,m),1.46–1.24 (5H,m)

<Step 2>

Synthesis of 1,4-diaza-1'-(benzyloxycarbonyl)-4-(6-chloronaphthalen-2-ylsulfonyl)-6-(2-hydroxyethoxymethyl)-7-oxaspiro[bicyclo[4.3.0]nonane-8,4'-piperidin]-2-one The compound obtained in Step 1 (100 mg) was dissolved in a mixed solution of tetrahydrofuran (1 ml) and ethanol (1 ml) and to the solution were added lithium chloride (18.6 mg) and sodium borohydride (16.5 mg). After stirring at room temperature for 3 hours, saturated aqueous solution of ammonium chloride was added to the reaction mixture under cooling with ice, followed by extraction with methylene chloride. The organic layer was washed with saturated sodium chloride solution and dried over anhydrous sodium sulfate. Thereafter, the solvent was distilled off under reduced pressure and the resulting residue was purified by silica gel column chromatography (eluent;methylene chloride: methanol=40:1–20:1) to obtain the title compound (86.4 mg).

NMR spectrum (*CDCl$_3$) δppm: 8.37–8.33(1H,m), 7.98–7.92(3H,m),7.78(1H,dd,J=2,9 Hz),7.64–7.58(1H,m), 7.39–7.24(5H,m),5.10(2H,s),4.50(1H,d,J=12 Hz),4.38(1H, d,J=17 Hz), 4.21(1H,d,J=12 Hz),3.86(1H,d,J=10 Hz), 3.83–3.26(9H,m), 3.60(1H,d,J=10 Hz),3.13(1H,d,J=12 Hz), 2.40–2.33(1H,m), 2.24(1H,d,J=12 Hz),1.90–1.70(2H,m), 1.46–1.33(2H,m)

<Step 3>

Synthesis of 1,4-diaza-1'-(benzyloxycarbonyl)-4-(6-chloronaphthalen-2-ylsulfonyl)-6-(2-methoxyethoxymethyl)-7-oxaspiro[bicyclo[4.3.0]nonane-8,4'-piperidin]-2-one The procedure of Example 1 <Step B-2> was repeated by using the compound obtained in Step 2 (50 mg) to obtain the title compound (35 mg).

NMR spectrum (*CDCl$_3$) δppm: 8.36–8.32(1H,m), 7.98–7.90(3H,m),7.80–7.74(1H,m),7.61(1H,dd,J=2,9 Hz), 7.40–7.26(5H,m),5.10(2H,s),4.40–4.26(2H,m),4.13(1H,d, J=11 Hz), 3.36(3H,s), 3.82–3.20(12H,m), 2.27(1H,d,J=12 Hz),1.98–1.66(2H,m),1.46–1.30(2H,m)

<Step 4>

Synthesis of 1,4-diaza-4-(6-chloronaphthalen-2-ylsulfonyl)-6-(2-methoxyethoxymethyl)-7-oxaspiro[bicyclo[4.3.0]nonane-8,4'-piperidin]-2-one The procedure of Example 1 <Step B-3> was repeated by using the compound obtained in Step 3 (2.00 g) to obtain the title compound (1.54 g).

NMR spectrum (*CDCl$_3$) δppm: 8.38–8.32(1H,m), 7.99–7.91(3H,m),7.81–7.75(1H,m),7.64–7.58(1H,m), 4.39–4.16(3H,m),3.80–3.66(4H,m),3.60–3.51(2H,m),3.37 (3H,s), 3.31(1H,d,J=17 Hz),3.17(1H,d,J=11 Hz), 3.10–2.99 (1H,m),2.96–2.84(1H,m),2.76–2.60(2H,m),2.27(1H,d,J=12 Hz),1.96–1.62(2H,m),1.48–1.27(2H,m)

<Step 5>

Synthesis of 1,4-diaza-4-(6-chloronaphthalen-2-ylsulfonyl)-6-(2-methoxyethoxymethyl)-7-oxa-1'-(4-pyridyl)spiro[bicyclo[4.3.0]nonane-8,4'-piperidin]-2-one To a solution in ethanol (14 ml) of the compound obtained in Step 4 (700 mg) and 4-chloropyridine hydrochloride (201 mg) was added diisopropylethylamine (1.17 ml) and the mixture was stirred in a sealed tube at 150° C. for 15 hours. The reaction mixture was allowed to cool and concentrated. The resulting residue was purified by silica gel column chromatography (eluent; methylene chloride:methanol=20:1–10:1) to obtain the title compound (140 mg).

HRMS:$C_{29}H_{33}ClN_4$ $O_6$ S(M$^+$): Calculated: 600.1809. Found: 600.1785.

Example 21

Synthesis of 1,4-diaza-4-(6-chloronaphthalen-2-ylsulfonyl)-6-(2-methoxyethoxymethyl)-7-oxa-1'-(4-pyridyl)spiro[bicyclo[4.3.0]nonane-8,4'-piperidin]-2-one methanesulfonate The procedure of Example 12 was repeated by using the compound obtained in Example 20 <Step 5> (50.0 mg) to obtain the title compound (59.3 mg).

Example 22

Synthesis of 1,4-diaza-4-(6-chloronaphthalen-2-ylsulfonyl)-6-(2-hydroxyethoxymethyl)-7-oxa-1'-(4-pyridyl)spiro[bicyclo[4.3.0]nonane-8,4'-piperidin]-2-one The procedure of Example 20 <Step 2> was repeated by using the compound obtained in Example 4 <Step A-3> (50.0 mg) to obtain the title compound (39.2 mg).

HRMS:$C_{28}H_{31}ClN_4$ $O_6$ S(M$^+$): Calculated: 586.1652. Found: 586.1685.

Example 23

Synthesis of 4-[1,4-diaza-4-(6-chloronaphthalen-2-ylsulfonyl)-6-(methoxymethyl)-7-oxa-2-oxospiro[bicyclo

[4.3.0]nonane-8,4'-piperidin-1'-yl]]-1-methylpyridinium p-toluenesulfonate

The compound obtained in Example 1 <Step A-7> was dissolved in a mixed solution of methanol (2 ml)-chloroform (1 ml) and to the solution were added silica gel (50 mg) and methyl p-toluenesulfonate (36.8 mg). Thereafter, the mixture was heated under reflux all day long. The reaction mixture was concentrated under reduced pressure and the resulting residue was purified by silica gel column chromatography (eluent; methylene chloride: methanol=10:1–5:1) to obtain the title compound (65.3 mg).

IR(KBr)cm$^{-1}$: 3435, 3066, 1657, 1554, 1205, 1122

Example 24

Synthesis of 1,4-diaza-4-(6-chloronaphthalen-2-ylsulfonyl)-6-(methoxymethyl)-7-oxa-1-(4-pyridyl)spiro[bicyclo[4.3.0]nonane-8,4'-piperidine]

To a suspension of the compound obtained in Example 1 <Step A-7> (100 mg) in tetrahydrofuran (2 ml) was added a borane-tetrahydrofuran complex (1.0 N tetrahydrofuran solution, 0.54 ml) under cooling with ice. After stirring the mixture for 1 hour under cooling with ice, 10% hydrochloric acid-methanol solution was added and the mixture was stirred for 15 minutes under cooling with ice. The solvent was distilled off under reduced pressure. The resulting residue was adjusted to pH 9 with saturated aqueous solution of sodium hydrogencarbonate and extracted with methylene chloride. The organic layer was washed with saturated sodium chloride solution and dried over anhydrous sodium sulfate. Thereafter, the solvent was distilled off under reduced pressure. The resulting residue was purified by thin-layer chromatography (developer; methylene chloride:methanol=10:1) to obtain the title compound (14.6 mg).

Example 25

Synthesis of 1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one
<Step 1>
Synthesis of 1,4-diaza-1'-(benzyloxycarbonyl)-6-carboxy-4-(6-chloronaphthalen-2-ylsulfonyl)-7-oxaspiro[bicyclo[4.3.0]nonane-8,4'-piperidin]-2-one To a solution of the compound obtained in Example 1 <Step B-1> (6834.0 g) in methylene chloride (68340 ml) were added 4-hydroxy-2,2,6,6-tetramethylpiperidine 1-oxylbenzoate and a free radical (314 mg). 5% Aqueous solution of sodium hydrogencarbonate (1.36 ml) was added dropwise with stirring under cooling with ice and bleaching powder (54.0 g) was added. The mixture was vigorously stirred for 1.5 hours under cooling with ice, adjusted to pH 1 with 1N hydrochloric acid and extracted with methylene chloride. The organic layer was washed with water and saturated sodium chloride solution and dried over anhydrous sodium sulfate. The solvent was distilled off under reduced pressure to obtain the title compound (62.7 g).

NMR spectrum (*CD$_3$ OD) δppm: 8.52–8.44(1H,m), 8.15–7.97 (3H,m),7.83(1H,dd,J=2,9 Hz),7.63(1H,dd,J=2,9 Hz),7.41–7.25(5H,m),5.08(2H,s),4.69–4.61(1H,m),4.18 (1H,d,J=17 Hz), 4.03(1H,d,J=12 Hz),3.82–3.64(2H,m), 3.57–3.17(3H,m), 3.44(1H,d,J=17 Hz),2.79–2.66(1H,m), 1.87–1.39(4H,m),
<Step 2>
Synthesis of 1,4-diaza-1'-(benzyloxycarbonyl)-4-(6-chloronaphthalen-2-ylsulfonyl)-6-(ethoxycarbonyl)-7-oxaspiro[bicyclo[4.3.0]nonane-8,4'-piperidin]-2-one To a solution of the compound obtained in Step 1 (62.7 g) in pyridine (640 ml) was added ethanol (58.4 ml). After gradually adding p-toluenesulfonyl chloride (97.3 g) with stirring under cooling with ice, the mixture was stirred at room temperature for 4 hours. After addition of ice water, the reaction mixture was extracted with ethyl acetate. The organic layer was washed with water, dilute hydrochloric acid and saturated sodium chloride solution, and thereafter dried over anhydrous sodium sulfate. The solvent was distilled off under reduced pressure and the resulting residue was purified by silica gel column chromatography (eluent; n-hexane:ethyl acetate=3:1–2:1) to obtain the title compound (40.1 g).

NMR spectrum (*CDCl$_3$) δppm: 8.35(1H,s),7.99–7.87 (3H,m),7.80–7.72(1H,m),7.65–7.56(1H,m), 7.40–7.28(5H, m), 5.10(2H,s), 4.75(1H,d,J =12 Hz),4.38–4.18(3H,m),4.07 (1H,d,J=12 Hz),3.81–3.58(2H,m),3.48–3.22(4H,m),2.45 (1H,d,J=12 Hz),1.75–1.60(2H,m),1.56–1.42(2H,m), 1.39–1.30(3H,m)
<Step 3>
Synthesis of 1,4-diaza-4-(6-chloronaphthalen-2-ylsulfonyl)-6-(ethoxycarbonyl)-7-oxaspiro[bicyclo[4.3.0]nonane-8,4'-piperidin]-2-one The procedure of Example 1 <Step B-3> was repeated by using the compound obtained in Step 2 (40.0 g) to obtain the title compound (29.7 g).

NMR spectrum (CDCl$_3$) δppm: 8.38–8.31(1H,m), 8.01–7.85 (3H,m),7.77(1H,dd,J=2,9 Hz),7.61(1H,dd,J=2,9 Hz),4.74(1H,d, J11=Hz),4.38–4.17(3H,m),4.11(1H,d,J=12 Hz),3.41–3.26(2H,m), 3.16–2.77(4H,m),2.45(1H,d,J=11 Hz),1.90–1.45(4H,m), 1.34 (3H,t, J=7 Hz)
<Step 4>
Synthesis of 1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one The procedure of Example 20 <Step 5> was repeated by using the compound obtained in Step 3 (30.0 g) to obtain the title compound (14.2 g).

HRMS:C$_{28}$H$_{29}$ClN$_4$ O$_6$ S(M$^+$): Calculated: 584.1496. Found: 584.1532.

Example 26

Synthesis of 1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 25 <Step 4> (56.0 mg) to obtain the title compound (58.9 mg).

Example 27

Synthesis of 1,4-diaza-6-carboxy-4-(6-chloronaphthalen-2-ylsulfonyl)-7-oxa-1'-(4-pyridyl)spiro[bicyclo[4.3.0]nonane-8,4'-piperidin]-2-one To a solution of the compound obtained in Example 25 <Step 4> (400 mg) in methanol (9.6 ml) was added 1N aqueous solution of sodium hydroxide (2.74 ml) under cooling with ice and the mixture was stirred at room temperature for 1 hour. After adjusting the mixture to pH 4 with 1N hydrochloric acid, the precipitated solid was collected by filtration, washed with water and dried in vacuum to obtain the title compound (335 mg).

IR(KBr)cm$^{-1}$: 1666, 1647, 1537, 1460, 1350, 1169, 698

Example 28

Synthesis of 1,4-diaza-4-(6-chloronaphthalen-2-ylsulfonyl)-6-(methoxycarbonyl)-7-oxa-1'-(4-pyridyl)spiro[bicyclo[4.3.0]nonane-8,4'-piperidin]-2-one To a solution of the compound obtained in Example 27 (20.0 mg) in pyridine (0.20 ml) was added methanol (0.015 ml). After gradually adding p-toluenesulfonyl chloride (34.2 mg), the mixture was stirred at room temperature for 0.5 hour. After addition of saturated aqueous solution of sodium hydrogencarbonate, the reaction mixture was extracted with methylene chloride and the organic layer was dried over anhydrous sodium sulfate. The solvent was distilled off under reduced pressure and the resulting residue was purified by silica gel column chromatography (eluent; methylene chloride:methanol=15:1–10:1) to obtain the title compound (17.1 mg).

IR(KBr)cm$^{-1}$: 1751, 1678, 1597, 1350, 1165, 1080

Example 29

Synthesis of 1,4-diaza-4-(6-chloronaphthalen-2-ylsulfonyl)-6-(isopropoxycarbonyl)-7-oxa-1'-(4-pyridyl)spiro[bicyclo[4.3.0]nonane-8,4'-piperidin]-2-one The procedure of Example 28 was repeated by using the compound obtained in Example 27 (20 mg) and using isopropyl alcohol (0.028 ml) instead of methanol to obtain the title compound (18.1 mg).

HRMS:$C_{29}H_{31}ClN_4 O_6$ S(M$^+$): Calculated: 598.1652. Found: 598.1668.

Example 30

Synthesis of 1,4-diaza-4-(6-chloronaphthalen-2-ylsulfonyl)-7-oxa-6-(propoxycarbonyl)-1'-(4-pyridyl)spiro[bicyclo[4.3.0]nonane-8, 4'-piperidin]-2-one The procedure of Example 28 was repeated by using the compound obtained in Example 27 (20 mg) and using n-propyl alcohol (0.026 ml) instead of methanol to obtain the title compound (15.3 mg).

HRMS:$C_{29}H_{31}ClN_4O_6$ S(M$^+$): Calculated: 598.1652. Found: 598.1625.

Example 31

Synthesis of 6-(allyloxycarbonyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one The procedure of Example 28 was repeated by using the compound obtained in Example 27 (20 mg) and using allyl alcohol (0.025 ml) instead of methanol to obtain the title compound.

IR(KBr)cm$^{-1}$: 1747, 1678, 1597, 1350, 1167, 972

Example 32

Synthesis of 1,4-diaza-4-(6-chloronaphthalen-2-ylsulfonyl)-6-(2-methoxyethoxycarbonyl)-7-oxa-1'-(4-pyridyl)spiro[bicyclo[4.3.0]nonane-8,4'-piperidin]-2-one The procedure of Example 28 was repeated by using the compound obtained in Example 27 (20 mg) and using 2-methoxyethanol (0.028 ml) instead of methanol to obtain the title compound (13.1 mg).

HRMS:$C_{29}H_{31}ClN_4 O_7$ S(M$^+$): Calculated: 614.1602. Found: 614.1597.

Example 33

Synthesis of 1,4-diaza-6-(t-butoxycarbonyl)-4-(6-chloronaphthalen-2-ylsulfonyl)-7-oxa-1'-(4-pyridyl)spiro[bicyclo[4.3.0]nonane-8,4'-piperidin]-2-one Dioxane (1.0 ml) solidified in a bath cooled to −20° C. was added concentrated sulfuric acid (0.1 ml). The mixture was warmed to room temperature to obtain a homogenous solution. The solution was solidified again in the bath cooled to −20° C. and the compound obtained in Example 27 (18.0 mg) was added. The mixture was warmed to room temperature to obtain a homogenous solution, which was solidified in the bath cooled to −20° C. After adding liquid isobutylene (0.7 ml), the mixture was stirred in a sealed tube at room temperature for 5 hours. Saturated aqueous solution of sodium hydrogencarbonate was added to the reaction mixture, followed by extraction with methylene chloride. The organic layer was washed with saturated sodium chloride solution and dried over anhydrous sodium sulfate. The solvent was distilled off under reduced pressure and the resulting residue was purified by silica gel column chromatography (eluent; methylene chloride:methanol=15:1) to obtain the title compound (17.1 mg).

HRMS:$C_{30}H_{33}ClN_4 O_6$ S(M$^+$): Calculated: 612.1809. Found: 612.1786.

Example 34

Synthesis of 1,4-diaza-4-(6-chloronaphthalen-2-ylsulfonyl)-6-[1-(ethoxycarbonyloxy)ethoxycarbonyl]-7-oxa-1'-(4-pyridyl)spiro[bicyclo[4.3.0]nonane-8,4'-piperidin]-2-one To a solution of the compound obtained in Example 27 (42.0 mg) in N,N-dimethylformamide (2.1 ml) were added triethylamine (0.063 ml) and 1-iodochloroethylethyl carbonate (0.0164 ml) and the mixture was stirred at room temperature for 2 days. After adding water to the reaction mixture and extracting with methylene chloride, the organic layer was washed with saturated sodium chloride solution and dried over anhydrous sodium sulfate. The solvent was distilled off under reduced pressure and the resulting residue was purified by silica gel column chromatography (eluent; methylene chloride:methanol=15:1) to obtain the title compound (11.6 mg).

IR(KBr)cm$^{-1}$: 1765, 1670, 1645, 1599, 1543, 1167

Example 35

Syntheses of (+)-1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one and (−)-1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one The compound obtained in Example 25 <Step 4> was optically resolved on HPLC [column used, Daicel Chiralcel OD manufactured by Daicel Chemical Industries, Ltd., 0.46 cm×25 cm; eluent; n-hexane:ethanol=1:1; flow rate, 1.0 ml/min, detection wavelength, 254 nm] to obtain the (+) form of the title compound [retention time: 12.7 min, $[\alpha]^{33}_D$+b 99.7 (c1.000, ethanol] and the (−) form of the title compound [retention time: 14.9 min, $[\alpha]^{33}_D$−99.3 (c1.000, ethanol], respectively.

In addition, to a solution of the compound obtained in Example 25 <Step 4> (845 mg) in methanol (20 ml) was added (−)-O,O'-dibenzoyl-LD-tartaric acid (543 mg) and the mixture was stirred at room temperature for 1 hour. The precipitate was collected by filtration and air-dried. The thus obtained crystals (598 mg) were suspended in methanol (15 ml) and heated under reflux for 10 minutes. After allowing the suspension to cool, the precipitate was collected by filtration and air-dried. The thus obtained crystals (386 mg) were dissolved in saturated aqueous solution of sodium hydrogencarbonate and extracted with methylene chloride.

The organic layer was dried over anhydrous sodium sulfate and the solvent was distilled off under reduced pressure to thereby obtain the (−) form of the title compound (230 mg, 97.2% ee). The same procedure was repeated by using (+)-O,O'-dibenzoyl-D-tartaric acid to obtain the (+) form of the title compound.

(+) form: HRMS:$C_{28}H_{29}ClN_4$ $O_6$ S(M$^+$): Calculated: 584.1496. Found: 584.1462. (−) form: HRMS:$C_{28}H_{29}ClN_4$ $O_6$ S(M$^+$): Calculated: 584.1496. Found: 584.1540.

Example 36

Synthesis of (−)-1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one methanesulfonate The procedure of Example 12 was repeated by using the (−) form of the compound obtained in Example 35 (100 mg) to obtain the title compound (104 mg).

Example 37

Synthesis of (−)-1,4-diaza-6-carboxy-4-(6-chloronaphthalen-2-ylsulfonyl)-7-oxa-1'-(4-pyridyl)spiro[bicyclo[4.3.0]nonane-8,4'-piperidin]-2-one The procedure of Example 27 was repeated by using the compound obtained in Example 35 (1.80 g) to obtain the title compound (1.63 g).

IR(KBr)cm$^{-1}$: 1664, 1647, 1543, 1460, 1350, 1169

Example 38

Synthesis of (−)-1,4-diaza-4-(6-chloronaphthalen-2-ylsulfonyl)-6-(methoxycarbonyl)-7-oxa-1'-(4-pyridyl)spiro[bicyclo[4.3.0]nonane-8,4'-piperidin]-2-one The procedure of Example 28 was repeated by using the compound obtained in Example 37 (160 mg) to obtain the title compound (153 mg).

IR(KBr)cm 1:1749, 1678, 1599, 1349

Example 39

Synthesis of (−)-1,4-diaza-4-(6-chloronaphthalen-2-ylsulfonyl)-6-(isopropoxycarbonyl)-7-oxa-1'-(4-pyridyl)spiro[bicyclo[4.3.0]nonane-8,4'-piperidin]-2-one The procedure of Example 28 was repeated by using the compound obtained in Example 37 (150 mg) and using isopropyl alcohol (0.206 ml) instead of methanol to obtain the title compound (147.7 mg).

HRMS:$C_{29}H_{31}ClN_4$ $O_6$ S(M$^+$): Calculated: 598.1652. Found: 598.1667.

Example 40

Synthesis of (−)-1,4-diaza-4-(6-chloronaphthalen-2-ylsulfonyl)-7-oxa-6-(propoxycarbonyl)-1'-(4-pyridyl)spiro[bicyclo[4.3.0]nonane-8,4'-piperidin]-2-one The procedure of Example 28 was repeated by using the compound obtained in Example 37 (170 mg) and using n-propyl alcohol (0.023 ml) instead of methanol to obtain the title compound (158 mg).

HRMS:$C_{29}H_{31}ClN_4$ $O_6$ S(M$^+$): Calculated: 598.1652. Found: 598.1666.

Example 41

Synthesis of (−)-6-(allyloxycarbonyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one The procedure of Example 28 was repeated by using the compound obtained in Example 37 (160 mg) and using allyl alcohol (0.196 ml) instead of methanol to obtain the title compound (158 mg).

IR(KBr)cm$^{-1}$: 1747, 1678, 1597, 1419, 1352

Example 42

Synthesis of (−)-1,4-diaza-4-(6-chloronaphthalen-2-ylsulfonyl)-6-(2-methoxyethoxycarbonyl)-7-oxa-1'-(4-pyridyl)spiro[bicyclo[4.3.0]nonane-8,4'-piperidin]-2-one The procedure of Example 28 was repeated by using the compound obtained in Example 37 (180 mg) and using 2-methoxyethanol (0.255 ml) instead of methanol to obtain the title compound (178.6 mg).

HRMS:$C_{29}H_{31}ClN_4$ $O_7$ S(M$^+$): Calculated: 614.1602. Found: 614.1572.

Example 43

Synthesis of (−)-1,4-diaza-6-(t-butoxycarbonyl)-4-(6-chloronaphthalen-2-ylsulfonyl)-7-oxa-1'-(4-pyridyl)spiro[bicyclo[4.3.0]nonane-8,4'-piperidin]-2-one The procedure of Example 33 was repeated by using the compound obtained in Example 37 (160 mg) to obtain the title compound (146 mg).

IR(KBr)cm$^{-1}$: 1738, 1678, 1597, 1352, 1157, 1132

Example 44

Synthesis of (−)-1,4-diaza-4-(6-chloronaphthalen-2-ylsulfonyl)-6-(methoxycarbonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 38 (110 mg) to obtain the title compound (12 mg).

Example 45

Synthesis of (−)-1,4-diaza-4-(6-chloronaphthalen-2-ylsulfonyl)-6-(isopropoxycarbonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 39 (110 mg) to obtain the title compound (125 mg).

Example 46

Synthesis of (−)-1,4-diaza-4-(6-chloronaphthalen-2-ylsulfonyl)-7-oxa-6-(propoxycarbonyl)-1'-(4-pyridyl)spiro[bicyclo[4.3.0]nonane-8,4'-piperidin]-2-one methanesulfonate The procedure of Example 12 was repeated by using the compound obtained in Example 40 (110 mg) to obtain the title compound (126 mg).

Example 47

Synthesis of (−)-6-(allyloxycarbonyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 41 (110 mg) to obtain the title compound (129 mg).

Example 48

Synthesis of (−)-1,4-diaza-4-(6-chloronaphthalen-2-ylsulfonyl)-6-(2-methoxyethoxycarbonyl)-7-oxa-1'-(4- pyridyl)spiro[bicyclo[4.3.0]nonane-8,4'-piperidin]-2-one methanesulfonate

The procedure of Example 12 was repeated by using the compound obtained in Example 42 (110 mg) to obtain the title compound (127 mg).

Example 49

Synthesis of (−)-1,4-diaza-6-(t-butoxycarbonyl)-4-(6-chloronaphthalen-2-ylsulfonyl)-7-oxa-1'-(4-pyridyl)spiro[bicyclo[4.3.0]nonane-8,4'-piperidin]-2-one methanesulfonate The procedure of Example 12 was repeated by using the compound obtained in Example 43 (119 mg) to obtain the title compound (137 mg).

Example 50

Synthesis of ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine]-6-carboxylate To a solution of the compound obtained in Example 25 <Step 4> (100 mg) in methanol (2.4 ml) was added 1N aqueous solution of sodium hydroxide (0.684 ml) at room temperature. The mixture was stirred for 1 hour and adjusted to pH 2–3 with 1N hydrochloric acid. Thereafter, the solvent was distilled off under reduced pressure and the resulting residue was dissolved in methanol (5 ml) and ion-exchange resin MSC-1 (100–200 mesh, H-form, manufactured by Muromachi Chemicals Inc., 2.0 g) was added and the mixture was stirred for 30 minutes. The resin was collected by filtration, washed with methanol and added to 2N ammonia–methanol solution (5 ml). The mixture was stirred for 30 minutes. The solution obtained by filtering off the resin was concentrated under reduced pressure to obtain the title compound (54.8 mg).

IR(KBr)cm$^{-1}$: 1657, 1628, 1601, 1396, 1348, 1169

Example 51

Syntheses of (+)-ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine]-6-carboxylate and (−)-ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine]-6-carboxylate The procedure of Example 50 was repeated by using the (+) form of the compound obtained in Example 35 (40.0 mg) to obtain the (+) form of the title compound (20.5 mg).

IR(KBr)cm$^{-1}$: 1626, 1603, 1398, 1348, 1169

Further, the procedure of Example 50 was repeated by using the (−) form of the compound obtained in Example 35 (55.0 mg) to obtain the (−) form of the title compound (28.3 mg). IR(KBr)cm$^{-1}$: 1657, 1626, 1603, 1396, 1348, 1169

Example 52

Synthesis of 4-[1,4-diaza-4-(6-chloronaphthalen-2-ylsulfonyl)-6-(ethoxycarbonyl)-7-oxa-2-oxospiro[bicyclo[4.3.0]nonane-8,4'-piperidin]-1'-yl]-1-ethylpyridinium p-toluenesulfonate The procedure of Example 23 was repeated by using the (−) form of the compound obtained in Example 35 and using ethyl p-toluenesulfonate instead of methyl p-toluenesulfonate to obtain the title compound.

IR(KBr)cm$^{-1}$: 3064, 1676, 1649, 1349, 1221, 1192, 1169, 1124, 1012.

The procedures of Examples 36 and 52 can be repeated by using the (+) form obtained in Example 35 to thereby obtain the respective (+) bodies. Further, the procedures of Examples 37 and 38–49 can be repeated to obtain the respective (+) bodies.

Example 53

Synthesis of 1'-(4-amidinophenyl)-1,4-diaza-4-(6-chloronaphthalen-2-ylsulfonyl)-6-(methoxymethyl)-7-oxaspiro[bicyclo[4.3.0]nonane-8,4'-piperidin]-2-one
<Step 1>
Synthesis of 1,4-diaza-4-(6-chloronaphthalen-2-ylsulfonyl)-1'-(4-cyanophenyl)-6-(methoxymethyl)-7-oxaspiro[bicyclo[4.3.0]nonane-8,4'-piperidin]-2-one To a solution of the compound obtained in Example 1 <Step B-3> (50.0 mg) in 1,3-dimethyl-2-imidazolidone (1 ml) were added 4-fluorobenzonitrile (18.9 mg) and diisopropylethylamine (20.2 mg). The mixture was heated under reflux at 150° C. to 160° C. for 4 hours. After allowing the reaction mixture to cool, water was added thereto and the reaction mixture was extracted with ethyl acetate. The organic layer was washed with water and saturated sodium chloride solution and dried over anhydrous sodium sulfate. The solvent was distilled off under reduced pressure and the resulting residue was purified by silica gel column chromatography (eluent; methylene chloride:methanol=25:1) to obtain the title compound (25.0 mg).

NMR spectrum (CDCl$_3$) δppm: 8.36(1H,s),7.99–7.90 (3H,m), 7.82–7.74(1H,m),7.65–7.56(1H,m),7.45(2H,d,J=9 Hz), 6.81(2H,d,J=9 Hz),4.42–4.29(2H,m),4.21(1H,d,J=12 Hz), 3.67(1H,d,J=10 Hz), 3.61(1H,d,J=10 Hz),3.43(3H,s), 3.50–3.16(5H,m),3.21(1H,d,J=12 Hz),2.31(1H,d,J=12 Hz), 2.08–1.80(2H,m),1.58–1.46(2H,m)
<Step 2>
Synthesis of 1,4-diaza-4-(6-chloronaphthalen-2-ylsulfonyl)-1'-(4-ethoxyimidoylphenyl)-6-(methoxymethyl)-7-oxaspiro[bicyclo[4.3.0]nonane-8,4'-piperidin]-2-one The compound obtained in Step 1 (24.0 mg) was dissolved in 20% hydrochloric acid—ethanol solution (2 ml) and the solution was stirred at room temperature for 3 hours. Thereafter, the reaction mixture was concentrated under reduced pressure. To the resulting residue was added saturated aqueous solution of sodium hydrogencarbonate and the mixture was extracted with methylene chloride and the organic layer was washed with saturated sodium chloride solution and dried over anhydrous sodium sulfate. The solvent was distilled off under reduced pressure and the resulting residue was purified by silica gel column chromatography (eluent; methylene chloride:methanol 25:1) to obtain the title compound (16.8 mg).

NMR spectrum (*CDCl$_3$) δppm: 8.38–8.33(1H,m), 7.99–7.91(3H,m),7.82–7.76(1H,m),7.66–7.58(3H,m), 6.87–6.80(2H,m),4.42–4.18(5H,m),3.67(1H,d,J=10 Hz), 3.61(1H,d,J=10 Hz), 3.43(3H,s), 3.48–3.16(6H,m), 2.29 (1H,d,J=12 Hz),2.08–1.84(2H,m),1.58–1.50(2H,m), 1.44–1.36(3H,m)
<Step 3>
Synthesis of 1-(4-amidinophenyl)-1,4-diaza-4-(6-chloronaphthalen-2-ylsulfonyl)-6-(methoxymethyl)-7-oxaspiro[bicyclo[4.3.0]nonane-8,4'-piperidin]-2-one To a solution of the compound obtained in Step 2 (16.8 mg) in ethanol (2 ml) was added an excess of ammonium acetate and the mixture was heated under reflux at room temperature for 13 hours. After stirring, the reaction mixture was concentrated under reduced pressure. To the resulting residue was added saturated aqueous solution of sodium hydrogencarbonate and the mixture was extracted with methylene chloride. Thereafter, the organic layer was washed with saturated sodium chloride solution and dried over anhydrous sodium sulfate. The solvent was distilled off under reduced pressure and the resulting residue was suspended in methylene chloride and subjected to suction filtration. Thereafter, the filtrate was concentrated under reduced pressure to obtain the title compound (4.7 mg).

Example 54

Synthesis of 1,4-diaza-4-(6-chloronaphthalen-2-ylsulfonyl)-6-(methoxymethyl)-7-oxa-1'-(4-pyridylmethyl)spiro[bicyclo[4.3.0]nonane-8,4'-piperidin]-2-one To a solution of the compound obtained in Example 1 <Step B-3> (50.0 mg) in methylene chloride (1.0 ml) were added 3A molecular sieves (15 mg), 4-pyridinecarboxyaldehyde (12.2 mg) and acetic acid (18.1 mg) and the mixture was stirred at room temperature for 30 minutes. Thereafter, sodium triacetoxy borohydride (55.1 mg) was added under cooling with ice. The mixture was stirred at room temperature for 8 hours. After adding 10% hydrochloric acid—methanol to the reaction mixture and stirring for 10 minutes, the reaction mixture was adjusted to pH 9 with saturated aqueous solution of sodium hydrogencarbonate. The insoluble content was removed by filtration, followed by extraction with methylene chloride. The organic layer was washed with saturated sodium chloride solution and dried over anhydrous sodium sulfate. The solvent was distilled off under reduced pressure and the resulting residue was purified by silica gel column chromatography [ChromatorexNH ](eluent; methylene chloride:methanol= 400:1) to obtain the title compound (51.2 mg).

HRMS:$C_{28}H_{31}ClN_4$ $O_5$ S(M$^+$): Calculated: 570.1703. Found: 570.1716.

Example 55

Synthesis of 4-[1,4-diaza-4-(6-chloronaphthalen-2-ylsulfonyl)-6-(methoxymethyl)-7-oxa-2-oxospiro[bicyclo[4.3.0]nonane-8,4'-piperidin]-1'-yl]pyridine 1-oxide To a solution of the compound obtained in Example 1 <Step B-3> (50.0 mg) in ethanol (1 ml) were added 4-chloropyridine-N-oxide (16.2 mg) and diisopropylethylamine (26.9 mg) and the mixture was heated with stirring in a sealed tube at 150° C. to 160° C. for 18 hours. The reaction mixture was concentrated under reduced pressure and the resulting residue was purified by silica gel column chromatography (eluent; methylene chloride:methanol= 10:1) to obtain the title compound (8.7 mg).

IR(KBr)cm$^{-1}$: 2925, 1658, 1506, 1346, 1165

Example 56

Synthesis of 1'-acetimidoyl-1,4-diaza-4-(6-chloronaphthalen-2-ylsulfonyl)-7-oxaspiro[bicyclo[4.3.0]nonane-8,4'-piperidin]-2-one To a solution of the compound obtained in Example 1 <Step B-3> (100 mg) in ethanol (4 ml) were added ethyl acetimidate hydrochloride (60.9 mg) and triethylamine (0.093 ml) and the mixture was stirred overnight at room temperature. The reaction mixture was concentrated under reduced pressure and the resulting residue was purified by silica gel column chromatography (eluent; methylene chloride:methanol 10:1) to obtain the title compound (97 mg).

IR(KBr)cm$^{-1}$: 3422, 2817, 1670, 1454, 1419, 1350, 1169

Example 57

Synthesis of 1'-acetimidoyl-1,4-diaza-4-(6-chloronaphthalen-2-ylsulfonyl)-7-oxaspiro[bicyclo[4.3.0]nonane-8,4'-piperidin]-2-one methanesulfonate The procedure of Example 12 was repeated by using the compound obtained in Example 56 (40.0 mg) to obtain the title compound (43.7 mg).

Example 58

Synthesis of 6-(aminomethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one <Step 1>

Synthesis of 1,4-diaza-4-(6-chloronaphthalen-2-ylsulfonyl)-7-oxa-6-(phthalimidoylmethyl)-1'-(4-pyridyl)spiro[bicyclo[4.3.0]nonane-8,4'-piperidin]-2-one To a solution of phthalimide (4.88 g) and triphenylphosphine (8.69 g) in methylene chloride (150 ml) was added dropwise diethyl azodicarboxylate (40% toluene solution, 10.0 ml) under cooling with ice. Thereafter, the compound obtained in Example 3 <Step A-2> (3.0 g) was added and the mixture was stirred overnight at room temperature. After adding saturated aqueous solution of sodium hydrogencarbonate to the reaction mixture and extracting with methylene chloride, the organic layer was washed with water and saturated sodium chloride solution, and dried over anhydrous sodium sulfate. The solvent was distilled off under reduced pressure and the resulting residue was purified by silica gel column chromatography (eluent; methylene chloride:methanol=19:1) to obtain the title compound (2.5 g).

NMR spectrum (*CDCl$_3$) δppm: 8.44–8.41(1H,m), 8.25–8.18(2H,m),8.00–7.75(8H,m), 7.62(1H,dd,J=2,9 Hz), 6.65–6.51(2H,m),4.58–4.51(1H,m),4.39–4.24(2H,m), 4.19 (1H,d,J=15 Hz), 4.09(1H,d,J=15 Hz),3.44(1H,d,J=17 Hz), 3.44–3.16(4H,m),3.04(1H,d,J=12 Hz),2.45–2.38(1H,m), 1.89–1.62(2H,m),1.47–1.40(2H,m)

<Step 2>

Synthesis of 6-(aminomethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one To a suspension of the compound obtained in Step 1 (2.45 g) in ethanol (50 ml) was added hydrazine monohydrate (0.37 ml) and the mixture was heated under reflux for 16 hours. The reaction mixture was concentrated under reduced pressure and the resulting residue was purified by silica gel column chromatography (eluent; methylene chloride methanol=4:1) to obtain the title compound (1.432.5 g).

IR(KBr)cm$^{-1}$: 3395, 2920, 2360, 1666, 1597, 1348, 1167

Example 59

Synthesis of 1,4-diaza-4-(6-chloronaphthalen-2-ylsulfonyl)-6-(ethoxycarbonylaminomethyl)-7-oxa-1'-(4-pyridyl)spiro[bicyclo[4.3.0]nonane-8,4'-piperidin]-2-one To a solution of the compound obtained in Example 58 <Step 2> (50.0 mg) and triethylamine (0.02 ml) in methylene chloride (1 ml) was added ethyl chloroformate (12 mg) under cooling with ice and the mixture was stirred at room temperature for 2 days. After adding saturated aqueous solution of sodium hydrogencarbonate to the reaction mixture and extracting with methylene chloride, the organic layer was washed with saturated sodium chloride solution and dried over anhydrous sodium sulfate. The solvent was distilled off under reduced pressure and the resulting residue was purified by silica gel column chromatography (eluent;

Example 60

Synthesis of 1,4-diaza-4-(6-chloronaphthalen-2-ylsulfonyl)-6-(ethoxycarbonylmethylaminomethyl)-7-oxa-1'-(4-pyridyl)spiro[bicyclo[4.3.0]nonane-8,4'-piperidin]-2-one To a solution of oxalyl dichloride (0.16 ml) in methylene chloride (7 ml) was gradually added dropwise a solution of dimethyl sulfoxide (0.29 ml) in methylene chloride (7 ml) at −75° C. to −70° C. Thereafter, a solution of the compound obtained in Example 3 <Step A-2> (500 mg) in methylene chloride (7 ml) was gradually added thereto at the same temperature. After stirring the reaction mixture at −60° C. to −50° C. for 4 hours, triethylamine (0.77 ml) was added dropwise. The reaction mixture was warmed to room temperature and water was added. The mixture was extracted with methylene chloride. The organic layer was washed with water and saturated sodium chloride solution, and dried over anhydrous sodium sulfate. The amorphous content (450 mg) obtained by distilling off the solvent under reduced pressure was dissolved in methylene chloride (1.3 ml) and to the solution were added glycine ethyl ester hydrochloride (50.4 mg) and acetic acid (0.03 ml). Thereafter, sodium triacetoxy borohydride (127 mg) was added under cooling with ice and the mixture was stirred at room temperature for 8 hours. After adding saturated aqueous solution of sodium hydrogencarbonate to the reaction mixture and extracting with methylene chloride, the organic layer was wished with water and saturated sodium chloride solution, and dried over anhydrous sodium sulfate. The solvent was distilled off under reduced pressure and the resulting residue was purified by silica gel column chromatography (eluent; methylene chloride:methanol=19:1) to obtain the title compound (17.8 mg).

IR(KBr)cm$^{-1}$: 3360, 2854, 1736, 1670, 1597, 1348, 1169

Example 61

Synthesis of 1,4-diaza-4-(6-chloronaphthalen-2-ylsulfonyl)-6-(morpholinomethyl)-7-oxa-1'-(4-pyridyl)spiro[bicyclo[4.3.0]nonane-8,4'-piperidin]-2-one <Step 1>

Synthesis of 1,4-diaza-4-(6-chloronaphthalen-2-ylsulfonyl)-7-oxa-1'-(4-pyridyl)-6-(p-toluenesulfonyloxymethyl)spiro[bicyclo[4.3.0]nonane-8,4'-piperidin]-2-one To a solution of the compound obtained in Example 3 <Step A-2> (200 mg) in methylene chloride (4 ml) were added triethylamine (0.146 ml) and p-toluenesulfonyl chloride (120 mg) under cooling with ice and the mixture was stirred overnight at room temperature. After adding saturated aqueous solution of sodium hydrogencarbonate to the reaction mixture and extracting with methylene chloride, the organic layer was washed with water and saturated sodium chloride solution, and dried over anhydrous sodium sulfate. The solvent was distilled off under reduced pressure and the resulting residue was purified by silica gel column chromatography (eluent; methylene chloride:methanol=19:1) to obtain the title compound (234 mg).

NMR spectrum (*CDCl$_3$) δppm: 8.36–8.31(1H,m), 8.28–8.20(2H,m),8.00–7.92(3H,m), 7.85–7.72(3H,m), 7.63 (1H,dd,J=2,9 Hz), 7.44–7.37(2H,m),6.68–6.63(2H,m), 4.31–4.17(5H,m),3.64–3.37(3H,m),3.34–3.17(3H,m),2.49 (3H,s), 2.32(1H,d,J=12 Hz),2.10–1.98(1H,m),1.94–1.81 (1H,m),1.58–1.43(2H,m)

<Step 2>

Synthesis of 1,4-diaza-4-(6-chloronaphthalen-2-ylsulfonyl)-6-(morpholinomethyl)-7-oxa-1'-(4-pyridyl)spiro[bicyclo[4.3.0]nonane-8,4'-piperidin]-2-one A solution of the compound obtained in Step 1 (171 mg) in morpholine (1.7 ml) was heated under reflux for 18 hours. After allowing the reaction mixture to cool, water was added thereto and the reaction mixture was extracted with methylene chloride. The organic layer was washed with water and saturated sodium chloride solution, and dried over anhydrous sodium sulfate. The solvent was distilled off under reduced pressure and the resulting residue was purified by silica gel column chromatography [ChromatorexNH™] (eluent; n-hexane:ethyl acetate=1:1–1:2) to obtain the title compound (88.8 mg).

IR(KBr)cm$^{-1}$: 2951, 2852, 1670, 1597, 1350, 1167

Example 62

Synthesis of 1,4-diaza-4-(6-chloronaphthalen-2-ylsulfonyl)-6-(morpholinomethyl)-7-oxa-1'-(4-pyridyl)spiro[bicyclo[4.3.0]nonane-8,4'-piperidin]-2-one dimethanesulfonate The procedure of Example 12 was repeated by using the compound obtained in Example 61 <Step 2> (50.9 mg) to obtain the title compound (50.8 mg).

Example 63

Synthesis of 6-(acetoxymethyl)-1,4-diaza-4-(6-chloronaphthalen-2-ylsulfonyl)-1'-(2-chloropyrimidin-4-yl)-7-oxaspiro[bicyclo[4.3.0]nonane-8,4'-piperidin]-2-one To a suspension of the compound obtained in Example 7 <Step B-1> (300 mg) and 2,4-dichloropyrimidine (88 mg) in isoamyl alcohol (4 ml) was added sodium hydrogencarbonate (174 mg) and the mixture was stirred at 70° C. for 1.5 hours. After allowing the reaction mixture to cool, water was added and the reaction mixture was extracted with methylene chloride. The organic layer was washed with saturated sodium chloride solution and dried over anhydrous sodium sulfate. The solvent was distilled off under reduced pressure and the resulting residue was purified by silica gel column chromatography (eluent; methylene chloride:methanol= 125:1–100:1) to obtain the title compound (237 mg).

Example 64

Synthesis of 6-(acetoxymethyl)-1,4-diaza-4-(2-naphthalenesulfonyl)-7-oxa-1'-(4-pyrimidinyl)spiro[bicyclo[4.3.0]nonane-8,4'-piperidin]-2-one The compound obtained in Example 63 (110 mg) was dissolved in ethanol (6 ml) and to the solution was added 5% palladium—barium carbonate (1.65 g). The mixture was stirred at room temperature for 15 hours under a hydrogen atmosphere. The reaction mixture was filtered through Celite. The solvent was distilled off under reduced pressure and the resulting residue was purified by thin-layer chromatography (developer; n-hexane:acetone=1:1) to obtain the title compound (5.5 mg).

HRMS:$C_{27}H_{29}N_5 O_6 S(M^+)$: Calculated: 551.1838. Found: 551.1804.

Example 65

Synthesis of 6-(acetoxymethyl)-1,4-diaza-4-(6-chloronaphthalen-2-ylsulfonyl)-7-oxa-1'-(4-pyrimidinyl)spiro[bicyclo[4.3.0]nonane-8,4'-piperidin]-2-one To a suspension of the compound obtained in Example 7 <Step B-1> (100 mg) and sodium hydrogencarbonate (49.6 mg) in isoamyl alcohol (5 ml) was added 4-chloropyrimidine hydrochloride (29.7 mg) synthesized by the procedure described in WO98/21188. The mixture was stirred at 80° C. for 4 hours. The reaction mixture was allowed to cool and concentrated under reduced pressure. The resulting residue was purified by silica gel column chromatography (eluent; methylene chloride:methanol= 19:1) to obtain the title compound (37.0 mg).

HRMS:$C_{27}H_{28}ClN_5O_6$ $S(M^+)$: Calculated: 585.1448. Found: 585.1497.

Example 66

Synthesis of 1,4-diaza-4-(6-chloronaphthalen-2-ylsulfonyl)-6-(hydroxymethyl)-7-oxa-1'-(4-pyrimidinyl)spiro[bicyclo[4.3.0]nonane-8,4'-piperidin]-2-one <Step 1>

Synthesis of 1,4-diaza-4-(6-chloronaphthalen-2-ylsulfonyl)-6-(hydroxymethyl)-1'-[2-(methylthio)pyrimidin-4-yl]-7-oxaspiro[bicyclo[4.3.0]nonane-8,4'-piperidin]-2-one The procedure of Example 2 <Step 1> was repeated by using the compound obtained in Example 7 <Step B-1> (930 mg) to obtain the title compound (480 mg).

NMR spectrum (*CDCl$_3$) δppm: 8.41–8.34(1H,m), 8.04–7.89(4H,m),7.79(1H,dd,J=2,9 Hz), 7.62(1H,dd,J=2,9 Hz), 6.17(1H,d,J=6 Hz),4.50–4.32(2H,m),4.25(1H,d,J=12 Hz), 4.01–3.30(6H,m), 3.38(1H,d,J=17 Hz), 3.20(1H,d,J=12 Hz), 2.76–2.60(1H,m),2.45(3H,s),2.33(1H,d,J=12 Hz), 2.00–1.67(2H,m),1.56–1.36(2H,m)

At that time, 6-(acetoxymethyl)-1,4-diaza-4-(6-chloronaphthalen-2-ylsulfonyl)-1'-[2-(methylthio)pyrimidin-4-yl]-7-oxaspiro[bicyclo[4.3.0]nonane-8,4'-piperidin]-2-one (228 mg) was also obtained.

NMR spectrum (*CDCl$_3$) δppm: 8.38(1H,s),8.01(1H,d,J=6 Hz), 8.01–7.90(3H,m),7.84–7.78(1H,m),7.66–7.60(1H, m), 6.16(1H,d,J=6 Hz),4.51 (1H,d,J=12 Hz),4.48–4.32(2H, m), 4.26(1H,d,J=12 Hz),4.18(1H,d,J=12 Hz),4.00–3.80(2H, m),3.51–3.30(2H,m),3.37(1H,d,J=17 Hz),3.18(1H,d,J=12 Hz),2.46(3H,s), 2.36(1H,d,J=12 Hz),2.14(3H,s),1.97–1.40 (4H,m)

<Step 2>

Synthesis of 1,4-diaza-4-(6-chloronaphthalen-2-ylsulfonyl)-6-(hydroxymethyl)-7-oxa-1'-(4-pyrimidinyl)spiro[bicyclo[4.3.0]nonane-8,4'-piperidin]-2-one The procedure of Example 2 <Step 2> was repeated by using the compound obtained in <Step 1> (300 mg) to obtain the title compound (197 mg).

IR(KBr)cm$^{-1}$: 3400, 1666, 1595, 1348, 1169

Example 67

Synthesis of 1,4-diaza-4-(6-chloronaphthalen-2-ylsulfonyl)-6-(ethoxycarbonyl)-7-oxa-1'-(4-pyrimidinyl)spiro[bicyclo[4.3.0]nonane-8,4'-piperidin]-2-one <Step 1>

Synthesis of 1,4-diaza-4-(6-chloronaphthalen-2-ylsulfonyl)-6-(ethoxycarbonyl)-1'-[2-(methylthio)pyrimidinyl-4-yl]-7-oxaspiro[bicyclo[4.3.0]nonane-8,4'-piperidin]-2-one The procedure of Example 2 <Step 1> was repeated by using the compound obtained in Example 25 <Step 3> (390 mg) to obtain the title compound (363 mg).

NMR spectrum (*CDCl$_3$) δppm: 8.36(1H,s),8.02(1H,d, J=6 Hz), 7.99–7.92(3H,m),7.81–7.75(1H,m),7.65–7.59(1H, m), 6.18(1H,d,J=6 Hz),4.77 (1H,d,J=11 Hz),4.38–4.22(3H, m), 4.10(1H,d,J=12 Hz),4.00–3.80(2H,m),3.58–3.34 (3H, m), 3.35(1H,d,J=17 Hz),2.53–2.43(1H,m),2.47(3H,s), 1.83–1.51(4H,m),1.36(3H,t,J=7 Hz)

<Step 2>

Synthesis of 1,4-diaza-4-(6-chloronaphthalen-2-ylsulfonyl)-6-(ethoxycarbonyl)-7-oxa-1'-(4-pyrimidinyl)spiro[bicyclo[4.3.0]nonane-8,4'-piperidin]-2-one The procedure of Example 2 <Step 2> was repeated by using the compound obtained in Step 1 (360 mg) to obtain the title compound (41 mg).

HRMS:$C_{27}H_{28}ClN_5O_6$ $S(M^+)$: Calculated: 585.1448. Found: 585.1456.

Example 68

Synthesis of 1,4-diaza-6-carboxy-4-(6-chloronaphthalen-2-ylsulfonyl)-7-oxa-1'-(4-pyrimidinyl)spiro[bicyclo[4.3.0]nonane-8,4'-piperidin]-2-one The procedure of Example 27 was repeated by using the compound obtained in Example 67 <Step 2> (10 mg) to obtain the title compound (1.9 mg).

IR(KBr)cm$^{-1}$: 3400, 1657, 1599, 1346, 1169

Example 69

Synthesis of 1,4-diaza-4-(6-chloronaphthalen-2-ylsulfonyl)-6-methyl-7-oxa-1'-(4-pyridyl)spiro[bicyclo [4.3.0]nonane-8,4'-piperidin]-2-one <Step 1>

Synthesis of ethyl 2-[(6-chloronaphthalen-2-ylsulfonyl)(2-oxopropan-1-yl)amino]acetate The procedure of Example 1 <Step A-2> was repeated by using the compound obtained in Example 1 <Step A-1> (1.0 g) and using chloroacetone (0.368 ml) instead of 1-acetoxy-3-chloroacetone to obtain the title compound (1.08 g).

NMR spectrum (*CDCl$_3$) δppm: 8.40–8.38(1H,m), 7.93–7.86(3H,m),7.83–7.78(1H,m),7.56(1H,dd,J=2,9 Hz), 4.29(2H,s), 4.17(2H,s),4.04(2H,q,J=7 Hz),2.19(3H,s),1.16 (3H,t,J=7 Hz)

<Step 2>

Synthesis of 1,4-diaza-1'-benzyl-4-(6-chloronaphthalen-2-ylsulfonyl)-6-methyl-7-oxaspiro[bicyclo[4.3.0]nonane-8, 4'-piperidin]-2-one The procedure of Example 1 <Step A-3> was repeated by using the compound obtained in Step 1 (870 mg) to obtain the title compound (150 mg).

NMR spectrum (CDCl$_3$) δppm: 8.33(1H,s),7.97–7.88 (3H,m),7.80–7.73(1H,m),7.60(1H,dd,J=2,9 Hz),7.34–7.18 (5H,m),4.37–4.26(1H,m),4.25–4.08(2H,m),3.46(2H,s), 3.32–3.22(1H,m),3.04(1H,d,J=12 Hz),2.65–2.20(4H,m), 2.33(1H,d,J=11 Hz),1.90–1.73(2H,m),1.59(3H,s),1.47–1.37 (2H,m)

<Step 3>

Synthesis of 1,4-diaza-4-(6-chloronaphthalen-2-ylsulfonyl)-6-methyl-7-oxaspiro[bicyclo[4.3.0]nonane-8,4'-piperidin]-2-one The procedure of Example 7 <Step B-1> was repeated by using the compound obtained in Step 2 (195 mg) to obtain the title compound (142 mg).

NMR spectrum (*CDCl$_3$) δppm: 8.36–8.33(1H,m), 7.97–7.92(3H,m),7.80–7.76(1H,m),7.61(1H,dd,J=2,9 Hz), 4.38–4.29(1H,m),4.24(1H,d,J=12 Hz),4.14(1H,d,J=11 Hz), 3.32–3.23(1H,m),3.08–2.98(1H,m),3.04(1H,d,J=12 Hz), 2.92–2.82(1H,m),2.78–2.61(2H,m),2.34(1H,d,J=11 Hz), 1.85–1.69(2H,m),1.61(3H,s),1.44–1.27(2H,m)

<Step 4>

Synthesis of 1,4-diaza-4-(6-chloronaphthalen-2-ylsulfonyl)-6-methyl-7-oxa-1'-(4-pyridyl)spiro[bicyclo[4.3.0]nonane-8,4'-piperidin]-2-one The procedure of Example 20 <Step 5> was repeated by using the compound obtained in Step 3 (130 mg) to obtain the title compound (95 mg).

HRMS:$C_{26}H_{27}ClN_4$ $O_4$ S(M$^+$): Calculated: 526.1441. Found: 526.1408.

Example 70

Synthesis of 1,4-diaza-4-(6-chloronaphthalen-2-ylsulfonyl)-6-methyl-7-oxa-1'-(4-pyridyl)spiro[bicyclo[4.3.0]nonane-8,4'-piperidin]-2-one methanesulfonate The procedure of Example 12 was repeated by using the compound obtained in Example 69 <Step 4> (35.0 mg) to obtain the title compound (37.9 mg).

Example 71

Synthesis of 1,4-diaza-4-(6-chloronaphthalen-2-ylsulfonyl)-6-(3-methoxycarbonylpropyl)-7-oxa-1'-(4-pyridyl)spiro[bicyclo[4.3.0]nonane-8,4'-piperidin]-2-one <Step 1>

Synthesis of ethyl 2-[(5-methoxycarbonyl-2-oxopentan-1-yl)(6-chloronaphthalen-2-ylsulfonyl)amino]acetate The procedure of Example 1 <Step A-2> was repeated by using methyl 6-bromo-5-oxohexanoate (10.8 g) to obtain the title compound (11.4 g).

NMR spectrum (*CDCl$_3$) δppm: 8.39(1H,s) 7.95–7.84(3H,m),7.84–7.77(1H,m),7.60–7.52(1H,m),4.27(2H,s), 4.17(2H,s),4.04(2H,q,J=7 Hz),3.66(3H,s),2.55(2H,t,J=7 Hz), 2.31(2H,t,J=7 Hz),1.96–1.83(2H,m),1.15(3H,t,J=7 Hz)

<Step 2>

Synthesis of 1,4-diaza-1'-benzyl-4-(6-chloronaphthalen-2-ylsulfonyl)-6-(3-methoxycarbonylpropyl)-7-oxaspiro[bicyclo[4.3.0]nonane-8,4'-piperidin]-2-one The procedure of Example 1 <Step C-1> was repeated by using the compound obtained in Step 1 (5.56 g). The thus obtained compound was used as the starting material to synthesize according to the procedure of Example 1 <Step C-2> to thereby obtain the title compound (1.50 g).

NMR spectrum (*CDCl$_3$) δppm: 8.39–8.31(1H,m), 8.00–7.87(3H,m),7.78(1H,dd,J=2,9 Hz),7.60(1H,dd,J=2,9 Hz),7.36–7.17(5H,m),4.39–4.13(3H,m),3.69(3H,s),3.47(2H,s), 3.30(1H,d,J=17 Hz),3.04(1H,d,J=12 Hz),2.67–2.12(6H,m), 2.22(1H,d,J=12 Hz),2.12–1.53(6H,m),1.53–1.30(2H,m)

<Step 3>

Synthesis of 1,4-diaza-4-(6-chloronaphthalen-2-ylsulfonyl)-6-(3-methoxycarbonylpropyl)-7-oxaspiro[bicyclo[4.3.0]nonane-8,4'-piperidin]-2-one The procedure of Example 7 <Step B-1> was repeated by using the compound obtained in Step 2 (0.53 g) to obtain the title compound (0.30 g).

NMR spectrum (*CDCl$_3$) δppm: 8.35(1H,s),8.02–7.92(3H,m), 7.83–7.74(1H,m),7.61(1H,dd,J=2,9 Hz),4.40–4.17(3H,m), 3.70(3H,s),3.31(1H,d,J=17 Hz),3.11–2.97(1H,m), 3.04(1H,d,J=12 Hz), 2.97–2.79(1H,m), 2.79–2.68 (2H,m), 2.48–2.30(2H,m),2.24(1H,d,J=12 Hz),2.12–1.67(6H,m), 1.45–1.30(2H,m)

<Step 4>

Synthesis of 1,4-diaza-4-(6-chloronaphthalen-2-ylsulfonyl)-6-(3-methoxycarbonylpropyl)-7-oxa-1'-(4-pyridyl)spiro[bicyclo[4.3.0]nonane-8,4'-piperidin]-2-one The procedure of Example 20 <Step 5> was repeated by using the compound obtained in Step 3 (420 mg) to obtain the title compound (90 mg).

IR(KBr)cm$^{-1}$: 3442, 2949, 1732, 1666, 1597, 1348, 1167

Example 72

Synthesis of ammonium 4-[1,4-diaza-4-(6-chloronaphthalen-2-ylsulfonyl)-7-oxa-2-oxo-1'-(4-pyridyl)spiro[bicyclo[4.3.0]nonane-8,4'-piperidin]-6-yl]butylate The procedure of Example 50 was repeated by using the compound obtained in Example 71 <Step 4> (90 mg) to obtain the title compound (70 mg).

IR(KBr)cm$^{-1}$: 3445, 2949, 1666, 1599, 1348, 1167

Example 73

Synthesis of 1,4,7-triaza-4-(6-chloronaphthalen-2-ylsulfonyl)-6-(hydroxymethyl)-1'-(4-pyridyl)spiro[bicyclo[4.3.0]nonane-8,4'-piperidin]-2-one <Step 1>

Synthesis of 6-(acetoxymethyl)-1,4,7-triaza-1'-benzyl-4-(6-chloronaphthalen-2-ylsulfonyl)spiro[bicyclo[4.3.0]-nonane-8,4'-piperidin]-2-one The procedure of Example 1 <Step A-3> was repeated by using the compound obtained in Example 1 <Step A-2> (10.3 g) and 4-amino-4-(aminomethyl)-1-benzylpiperidine (5.26 g) to obtain the title compound (7.76 g).

NMR spectrum (*CDCl$_3$) δppm: 8.37–8.32(1H,m), 7.97–7.89(3H,m),7.80–7.74(1H,m),7.59(1H,dd,J=2,9 Hz), 7.35–7.17(5H,m),4.36–4.12(5H,m),3.45(2H,s),3.33(1H,d, J=17 Hz), 2.88(1H,d,J=12 Hz),2.63–2.40(2H,m),2.31(1H,d, J=12 Hz),2.37–1.93(2H,m),2.11(3H,s),1.80–1.65(2H,m), 1.40–1.25(2H,m)

<Step 2>

Synthesis of 1,4,7-triaza-4-(6-chloronaphthalen-2-ylsulfonyl)-6-(hydroxymethyl)spiro[bicyclo[4.3.0]nonane-8,4'-piperidin]-2-one To a solution of the compound obtained in Step 1 (5.00 g) and 1,8-bis(N,N-dimethylamino)naphthalene (2.15 g) in 1,2-dichloroethane (50 ml) was added 1-chloroethyl chloroformate (2.28 ml) under cooling with ice. The mixture was stirred at room temperature for 30 minutes and then heated under reflux for 2 hours. After allowing the reaction mixture to cool, the solvent was distilled off under reduced pressure. To the residue was added methanol (50 ml) and the mixture was heated under reflux for 1 hour. After allowing the reaction mixture to cool, the solvent was distilled off under reduced pressure. The resulting residue was crystallized by addition of diethyl ether. The supernatant was removed by decantation and the solvent was distilled off under reduced pressure. The resulting residue was dissolved in methanol (50 ml) and to the solution was added 1N aqueous solution of sodium hydroxide (33.5 ml) at room temperature. The mixture was stirred at room temperature for 1 hour. The precipitated crystals were collected by filtration and washed with methylene chloride to obtain the title compound (3.30 g).

NMR spectrum (*DMSO-d$_6$) δppm: 8.60–8.55(1H,m), 8.30(1H,d,J=9 Hz),8.27–8.24(1H,m),8.17(1H,d,J=9 Hz), 7.87(1H,dd,J=2,9 Hz),7.73(1H,dd,J=2,9 Hz),5.26–5.18(1H, m),4.01(1H,d,J=17 Hz),4.00–3.89(2H,m),3.58–3.30(3H,m), 2.78(1H,d,J=11 Hz),2.85–2.25(4H,m), 2.36(1H,d,J=12 Hz), 1.99(1H,brs),1.60–1.44(2H,m),1.20–1.04(2H,m)

<Step 3>

Synthesis of 1,4,7-triaza-4-(6-chloronaphthalen-2-ylsulfonyl)-6-(hydroxymethyl)-1'-(4-pyridyl)spiro[bicyclo[4.3.0]nonane-8,4'-piperidin]-2-one The procedure of Example 20 <Step 5> was repeated by using the compound obtained in Step 2 (3.30 g) to obtain the title compound (2.50 g).

IR(KBr)cm$^{-1}$: 3336, 2939, 1657, 1601, 1454, 1421, 1346, 1167

Example 74

Synthesis of 1,4,7-triaza-4-(6-chloronaphthalen-2-ylsulfonyl)-6-(hydroxymethyl)-7-methyl-1'-(4-pyridyl)spiro[bicyclo[4.3.0]nonane-8,4'-piperidin]-2-one To a solution of the compound obtained in Example 73 <Step 3> (1.00 g) in methylene chloride (10 ml) were added acetic acid (0.42 ml) and paraformaldehyde (0.12 g) at room temperature. After stirring the mixture for 30 minutes, sodium triacetoxy borohydride (1.56 g) was added thereto. The mixture was stirred at room temperature for 6 days and thereafter heated under reflux for 8 hours. After addition of water, the reaction mixture was extracted with methylene chloride. The organic layer was washed with saturated sodium chloride solution and dried over anhydrous sodium sulfate. The solvent was distilled off under reduced pressure and the resulting residue was purified by silica gel column chromatography [ChromatorexNH™ (eluent; methylene chloride–1% methanol/methylene chloride) to obtain the title compound (0.45 g).

IR(KBr)cm$^{-1}$: 3444, 2943, 1657, 1599, 1456, 1348, 1167

Example 75

Synthesis of 1,4,7-triaza-4-(6-chloronaphthalen-2-ylsulfonyl)-6-(methoxymethyl)-7-methyl-1'-(4-pyridyl)spiro[bicyclo[4.3.0]nonane-8,4'-piperidin]-2-one The procedure of Example 1 <Step A-5> was repeated by using the compound obtained in Example 7466 (0.34 g) to obtain the title compound (0.14 g).

IR(KBr)cm$^{-1}$: 3446, 2930, 1662, 1597, 1454, 1348, 1167

Example 76

Synthesis of 1,4,7-triaza-4-(6-chloronaphthalen-2-ylsulfonyl)-6-(methoxymethyl)-7-methyl-1'-(4-pyridyl)spiro[bicyclo[4.3.0]nonane-8,4'-piperidin]-2-one Dimethanesulfonate The procedure of Example 12 was repeated by using the compound obtained in Example 75 (0.13 g) to obtain the title compound (0.17 g).

Example 77

Synthesis of 1,4,7-triaza-4-(6-chloronaphthalen-2-ylsulfonyl)-6-(methoxymethyl)-1'-(4-pyridyl)-spiro[bicyclo[4.3.0]nonane-8,4'-piperidin]-2-one The procedure of Example 1 <Step A-5> was repeated by using the compound obtained in Example 73 <Step 3> (1.50 g) to obtain the title compound (0.75 g).

IR(KBr)cm$^{-1}$: 3435, 2939, 1662, 1597, 1454, 1421, 1350, 1167

The resulting compound (30 mg) was optically resolved on HPLC [Shimadzu LC-10A (manufactured by Shimadzu Corporation); Column used, Daicel Chiralpak AS manufactured by Daicel Chemical Industries, Ltd.; eluent, methanol:diethylamine=100:0.1; flow rate, 1 ml/min; detection wavelength, 254 nm] to obtain (+)-1,4,7-triaza-4-(6-chloronaphthalen-2-ylsulfonyl)-6-(methoxymethyl)-1'-(4-pyridyl)-spiro[bicyclo[4.3.0]nonane-8,4'-piperidin]-2-one (9.9 mg) [retention time: 11 min, $[\alpha]^{26}_D$+113 (c 0.330, methanol), >99% ee], and (−)-1,4,7-triaza-4-(6-chloronaphthalen-2-ylsulfonyl)-6-(methoxymethyl)-1'-(4-pyridyl)-spiro[bicyclo[4.3.0]nonane-8,4'-piperidin]-2-one (8.7 mg) [retention time: 14 min, $[\alpha]^{26}_D$−111 (c 0.320, methanol), 98.6% ee], respectively. Both enantiomers represent the same NMR spectrum as the title racemic compound.

Example 78

Synthesis of 7-acetyl-1,4,7-triaza-4-(6-chloronaphthalen-2-ylsulfonyl)-6-(methoxymethyl)-1'-(4-pyridyl)spiro[bicyclo[4.3.0]nonane-8,4'-piperidin]-2-one <Step 1>

Synthesis of 1,4,7-triaza-1'-benzyl-4-(6-chloronaphthalen-2-ylsulfonyl)-6-(hydroxymethyl)spiro[bicyclo[4.3.0]nonane-8,4'-piperidin]-2-one The procedure of Example 1 <Step A-4> was repeated by using the compound obtained in Example 73 <Step 1> (2.00 g) to obtain the title compound (1.75 g).

NMR spectrum (*CDCl$_3$) δppm: 8.35–8.32(1H,m), 7.96–7.88(3H,m),7.80–7.73(1H,m), 7.60(1H,dd,J=2,9 Hz), 7.34–7.19(5H,m),4.37–4.20(2H,m),4.17–4.08(1H,m), 4.00–3.93(1H,m), 3.55–3.47(1H,m),3,46(2H,s),3.32(1H,d,J=17 Hz), 2.93(1H,d,J=12 Hz),2.64–2.40(2H,m), 2.35–2.15(2H,m), 2.25(1H,d,J=12 Hz),1.80–1.71(2H,m),1.44–1.35(2H,m)

<Step 2>

Synthesis of 1,4,7-triaza-1'-benzyl-4-(6-chloronaphthalen-2-ylsulfonyl)-6-(methoxymethyl)spiro[bicyclo[4.3.0]nonane-8,4'-piperidin]-2-one The procedure of Example 1 <Step A-5> was repeated by using the compound obtained in Step 1 (1.72 g) to obtain the title compound (1.43 g).

NMR spectrum (*CDCl$_3$) δppm: 8.35–8.31(1H,m), 7.97–7.88(3H,m),7.80–7.74(1H,m),7.59(1H,dd,J=2,9 Hz), 7.34–7.19(5H,m),4.31(1H,d,J=17 Hz),4.22–4.08(2H,m), 3.70(1H,d,J=10 Hz),3.49–3.38(1H,m),3.45(2H,s),3.42(3H,s), 3.27(1H,d,J=17 Hz),2.88(1H,d,J=12 Hz),2.60–2.40(2H,m),2.31–2.10(2H,m),2.21(1H,d,J=12 Hz),1.80–1.65(2H,m), 1.40–1.21(2H,m)

<Step 3>

Synthesis of 7-acetyl-1,4,7-triaza-1'-benzyl-4-(6-chloronaphthalen-2-ylsulfonyl)-6-(methoxymethyl)spiro[bicyclo[4.3.0]nonane-8,4'-piperidin]-2-one To a solution of the compound obtained in Step 2 (0.30 g) and triethylamine (0.11 ml) in methylene chloride (3 ml) was added acetyl chloride (56 µl) under cooling with ice and the mixture was stirred at room temperature for 2 hours. After addition of saturated aqueous solution of sodium hydrogencarbonate, the reaction mixture was extracted with methylene chloride and the organic layer was washed with saturated sodium chloride solution and dried over anhydrous sodium sulfate. The solvent was distilled off under reduced pressure and the resulting residue was purified by silica gel column chromatography (eluent; ethyl acetate:methanol=19:1) to obtain the title compound (0.31 g).

NMR spectrum (*CDCl$_3$) δppm: 8.35–8.31(1H,m), 7.98–7.88(3H,m),7.77(1H,dd,J=2,9 Hz), 7.59(1H,dd,J=2,9 Hz), 7.35–7.20(5H,m),5.16(1H,d,J=13 Hz),4.54(1H,d,J=11 Hz),4.42(1H,d,J=17 Hz),4.37–4.29(1H,m),3.90–3.83(1H,m),3.47(2H,s),3.37–3.25(2H,m),3.32(3H,s),2.94–2.75(2H,m),2.55–2.25(2H,m), 2.29(1H,d,J=13 Hz),2.28(3H,s), 2.18–2.00(2H,m),1.95–1.80(1H,m),1.28–1.13(1H,m)

<Step 4>

Synthesis of 7-acetyl-1,4,7-triaza-4-(6-chloronaphthalen-2-ylsulfonyl)-6-(methoxymethyl)spiro[bicyclo[4.3.0]nonane-8,4'-piperidin]-2-one To a solution of the compound obtained in Step 3 (0.28 g) and 1,8-bis(N,N-dimethylamino)naphthalene (20 mg) in 1,2-dichloroethane (3 ml) was added 1-chloroethyl chloroformate (0.13 ml) under cooling with ice and the mixture was stirred at room temperature for 1 hour. After allowing the reaction mixture to cool, the solvent was distilled off under reduced pressure. To the residue was added methanol (3 ml) and the mixture was heated under reflux for 1 hour. After allowing the reaction mixture to cool, the solvent was distilled off under reduced pressure. To the resulting residue was added water and the mixture was washed with diethyl ether. The aqueous layer was adjusted to pH 10 with potassium carbonate and extracted with methylene chloride. The organic layer was washed with saturated sodium chloride solution and dried over anhydrous sodium sulfate. The solvent was distilled off under reduced pressure and the resulting residue was purified by silica gel column chromatography [ChromatorexNH™] (eluent; methylene chloride—2% methanol/methylene chloride) to obtain the title compound (0.15 g).

NMR spectrum (*CDCl$_3$) δppm: 8.34(1H,s),8.00–7.88 (3H,m),7.81–7.74(1H,m),7.60(1H,dd,J=2,9 Hz), 5.16(1H,d, J=12 Hz),4.61(1H,d,J=11 Hz),4.42(1H,d,J=17 Hz), 4.34(1H, d,J=10 Hz),3.87(1H,d,J=10 Hz),3.40–3.27(2H,m), 3.34(3H, s),3.15–2.97(2H,m),2.80–2.65(1H,m),2.55–2.44(1H,m), 2.43–2.23(2H,m),2.28(3H,s),2.03–1.85(2H,m),1.30–1.17 (1H,m)

<Step 5>

Synthesis of 7-acetyl-1,4,7-triaza-4-(6-chloronaphthalen-2-ylsulfonyl)-6-(methoxymethyl)-1'-(4-pyridyl)spiro[bicyclo[4.3.0]nonane-8,4'-piperidin]-2-one The procedure of Example 20 <Step 5> was repeated by using the compound obtained in Step 4 (110 mg) to obtain the title compound (78 mg).

IR(KBr)cm$^{-1}$: 3435, 2920, 1666, 1639, 1597, 1383, 1346, 1167

Example 79

Synthesis of 1,4,7-triaza-4-(2-naphthalenesulfonyl)-6-(methoxymethyl)-1'-(4-pyridyl)spiro[bicyclo[4.3.0]nonane-8,4'-piperidin]-2-one To a solution of the compound obtained in Example 77 (200 mg) in methanol (4 ml) were added 1N hydrochloric acid (1.8 ml), then 10% palladium-active carbon (40 mg). The mixture was stirred at room temperature for 4 days under a hydrogen atmosphere. The reaction mixture was filtered through Celite and thereafter concentrated under reduced pressure. The resulting residue was adjusted to pH 10 with aqueous solution of sodium hydrogencarbonate and extracted with methylene chloride. The organic layer was washed with saturated sodium chloride solution and dried over anhydrous sodium sulfate. The solvent was distilled off under reduced pressure. The resulting residue was purified by silica gel column chromatography [ChromatorexNH™] (eluent; methylene chloride—methylene chloride:methanol=199:1) to obtain the title compound (140 mg).

Example 80

Synthesis of 1,4,7-triaza-4-(2-naphthalenesulfonyl)-6-(methoxymethyl)-7-methyl-1'-(4-pyridyl)spiro[bicyclo[4.3.0]nonane-8,4'-piperidin]-2-one The procedure of Example 79 was repeated by using the compound obtained in Example 75 (130 mg) to obtain the title compound (69.0 mg).

Example 81

Synthesis of (+)-1,4-diaza-6-(methoxymethyl)-4-(2-naphthalenesulfonyl)-7-oxa-1'-(4-pyridyl)spiro[bicyclo[4.3.0]nonane-8,4'-piperidin]-2-one The procedure of Example 79 was repeated by using (+)-1,4-diaza-4-(6-chloronaphthalen-2-ylsulfonyl)-6-(methoxymethyl)-7-oxa-1'-(4-pyridyl)spiro[bicyclo[4.3.0]nonane-8,4$^1$-piperidin]-2-one (100 mg) to obtain the title compound (90.7 mg).

Example 82

Synthesis of (−)-1,4-diaza-6-(methoxymethyl)-4-(2-naphthalenesulfonyl)-7-oxa-1'-(4-pyridyl)spiro[bicyclo[4.3.0]nonane-8,4'-piperidin]-2-one The procedure of Example 79 was repeated by using (−)-1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one (100 mg) to obtain the title compound (84.1 mg).

Synthesis examples of the intermediate compounds of the present invention are described below as Reference Examples.

Reference Example 1

<Step 1>

Synthesis of ethyl 2-[(2-nitrobenzenesulfonyl)amino] acetate

To a suspension of glycine ethyl ester hydrochloride (9.45 g) in methylene chloride (100 ml) were added triethylamine (18.9 ml) and 2-nitrobenzenesulfonyl chloride (10.0 g) in succession under cooling with ice and the mixture was stirred at room temperature for 2 days. To the reaction mixture was added 1N hydrochloric acid under cooling with ice, followed by extraction with methylene chloride. The organic layer was washed with saturated aqueous solution of sodium hydrogencarbonate, then saturated sodium chloride solution, and dried over anhydrous sodium sulfate. The solvent was distilled off under reduced pressure and the precipitated crystals were washed with a mixed solvent of n-hexane and diethyl ether, collected by filtration and air-dried to obtain the title compound (10.8 g).

NMR spectrum (*CDCl$_3$) δppm: 8.14–8.06(1H,m), 7.98–7.91(1H,m),7.80–7.71(2H,m),6.06(1H,brs),4.06(2H,q, J=7 Hz), 4.01(2H,s),1.20–1.13(3H,m)

<Step 2>

Synthesis of ethyl 2-[(3-acetoxy-2-oxopropan-1-yl)(2-nitrobenzenesulfonyl)amino]acetate To a suspension of the compound obtained in Step 1 (10.0 g), potassium carbonate (7.20 g) and sodium iodide (5.2 g) in N,N-dimethylformamide (100 ml) was added a solution (20 ml) of 1-acetoxy-3-chloroacetone (7.84 g) in N,N-dimethylformamide under cooling with ice and the mixture was stirred at room temperature for 2 hours. Water was added to the reaction mixture under cooling with ice, followed by extraction with ethyl acetate. The organic layer was washed with saturated sodium chloride solution and dried over anhydrous sodium sulfate. The solvent was distilled off under reduced pressure. To the resulting residue was added hexane and the mixture was stirred. The supernatant was removed by decantation and crystallized by addition of diethyl ether. The crystals were collected by filtration and air-dried to thereby obtain the title compound (9.36 g). NMR spectrum (*CDCl$_3$) δppm: 8.10–8.02(1H, m),7.76–7.62(3H,m),4.73(2H,s),4.53(2H,s), 4.24(2H,s), 4.15(2H,q,J=7 Hz),2.16(3H,s),1.24(3H,t,J=7 Hz)

<Step 3>

Synthesis of ethyl 2-[(3-acetoxy-2-oxopropan-1-yl) (benzyloxycarbonyl)amino]acetate To a solution of the compound obtained in Step 21 (5.0 g) in acetonitrile (75 ml) were added thiophenol (1.40 ml) and cesium carbonate (12.1 g) under cooling with ice. The mixture was stirred at room temperature for 1 hour. After further adding thiophenol (1.0 ml) and stirring at room temperature, the reaction mixture was filtered through Celite. After washing the Celite with methylene chloride (500 ml), to the filtrate were added triethylamine (5.20 ml), then benzyl chloroformate (4.68 ml) under cooling with ice. The mixture was stirred overnight at room temperature. After addition of water, the reaction mixture was extracted with methylene chloride. The organic layer was washed with saturated sodium chloride solution and dried over anhydrous sodium sulfate. The solvent was distilled off under reduced pressure and the resulting residue was purified by silica gel column chromatography (eluent; n-hexane:ethyl acetate= 20:1–2:1) to obtain the title compound (1.41 g).

NMR spectrum (*DMSO-$d_6$,100° C.) δppm: 7.38–7.24 (5H,m), 5.08(2H,s),4.75(2H,s),4.25(2H,s),4.10(2H,q,J=7 Hz),4.03 (2H,s),2.07(3H,s),1.17(3H,t,J=7 Hz)

<Step 4>

Synthesis of ethyl 2-[[2-(acetoxymethyl)-3,8-diaza-8benzyl-1-oxaspiro[bicyclo[4.5]decan-2-yl]methyl](benzyloxycarbonyl)amino]acetate To a solution of the compound obtained in Step 3 (1.0 g) and 4-(aminomethyl)-1-benzyl-4-hydroxypiperidine (879 mg) in methylene chloride (50 ml) were added acetic acid (0.1 ml) and 3A molecular sieves (2.0 g). The mixture was heated under reflux for 2 hours. The reaction mixture was allowed to cool and purified by silica gel column chromatography (eluent; methylene chloride:methanol= 100:0–50:1–20:1) to obtain the title compound quantitatively.

NMR spectrum (*DMSO-$d_6$,100° C.) δppm: 7.37–7.16 (10H,m), 5.07(2H,s),4.21–3.88(6H,m),3.54–3.34(2H,m), 3.44(2H,s),3.30–3.20(1H,m),2.90–2.76(2H,m),2.52–2.38 (2H,m),2.34–2.22(2H,m),1.94(3H,s),1.65–1.45(4H,m),1.16 (3H,t,J=7 Hz)

<Step 5>

Synthesis of 6-(acetoxymethyl)-1,4-diaza-1'-benzyl-4-benzyloxycarbonyl-7-oxaspiro[bicyclo[4.3.0]nonane-8,4'-piperidin]-2-one The solution of the compound obtained in Step 43 (1.60 g) in toluene (32 ml) was stirred in a sealed tube at 180° C. for 2 hours. The reaction mixture was concentrated under reduced pressure and the resulting residue was purified by silica gel column chromatography (eluent; methylene chloride:methanol=50:1–20:1) to obtain the title compound (890 mg).

NMR spectrum (*DMSO-$d_6$,100° C.) δppm: 7.38–7.16 (10H,m), 5.11(2H,s),4.38(1H,d,J=13 Hz),4.30–3.99(4H,m), 3.82(1H,d,J=18 Hz),3.47(2H,s),3.09(1H,d,J=11 Hz),3.00 (1H,d,J=13 Hz),2.58–2.22(4H,m),1.94(3H,s),1.80–1.72(2H, m),1.56–1.50(2H,m)

<Step 6>

Synthesis of 1,4-diaza-1'-benzyl-4-(benzyloxycarbonyl)-6-(hydroxymethyl)-7-oxaspiro[bicyclo[4.3.0]nonane-8,4'-piperidin]-2-one To a solution of the compound obtained in Step 5 (400 mg) in ethanol (8 ml) was added hydrazine monohydrate (0.38 ml) under cooling with ice. The mixture was stirred overnight at room temperature. The reaction mixture was concentrated and the resulting residue was purified by silica gel chromatography (eluent; methylene chloride methanol= 50:1–25:1) to obtain the title compound (329 mg).

NMR spectrum (*DMSO-$d_6$,100° C.) δppm: 7.38–7.16 (10H,m), 5.10(2H,s),4.76–4.67(1H,m),4.29(1H,d,J=13 Hz), 4.17(1H,d,J=18 Hz),4.10(1H,d, J=11 Hz),3.81(1H,d,J=18 Hz), 3.47(2H,s),3.44–3.35(2H,m),3.09(1H,d,J=11 Hz), 2.99–2.91(1H,m),2.59–2.42(2H,m),2.37–2.24(2H,m), 1.86–1.72(2H,m),1.58–1.42(2H,m)

<Step 7>

Synthesis of 1,4-diaza-4-(benzyloxycarbonyl)-6-(hydroxymethyl)-7-oxaspiro[bicyclo[4.3.0]nonane-8,4'-piperidin]-2-one To a solution of the compound obtained in Step 6 (100 mg) and 1,8-bis(N,N-dimethylamino)naphthalene (9.2 mg) in 1,2-dichloroethane (3 ml) was added 1-chloroethyl chloroformate (58 μl) under cooling with ice and the mixture was stirred at room temperature for 1 hour. Then, methanol (3 ml) was added to the reaction mixture and the mixture was heated with stirring at an ambient temperature of 70° C. The reaction mixture was allowed to cool and concentrated. To the residue was added 1N hydrochloric acid and benzyl chloride was extracted with diethyl ether. The diethyl ether layer was further extracted with 1N hydrochloric acid and combined with the above aqueous layer. The aqueous layer was adjusted to pH 9 with sodium carbonate under cooling with ice and extracted with methylene chloride. The organic layer was washed with saturated sodium chloride solution and dried over anhydrous sodium sulfate. The solvent was distilled off under reduced pressure and the resulting residue was purified by silica gel column chromatography [Chromatorex NH™](eluent; methylene chloride:methanol=50:1–25:1) to obtain the title compound quantitatively.

NMR spectrum (*DMSO-$d_{6,100}$° C.) δppm: 7.38–7.26 (5H,m), 5.11(2H,s),4.69(1H,brs),4.30(1H,d,J=13 Hz),4.18 (1H,d, J=18 Hz),4.12(1H,d,J=11 Hz),3.81(1H,d,J=18 Hz), 3.40(2H,s), 3.06(1H,d,J=11 Hz),2.94(1H,d,J=13 Hz), 3.02–2.74(2H,m),2.62–2.50(2H,m),1.72–1.66(2H,m), 1.44–1.36(2H,m)

<Step 8>

Synthesis of 1,4-diaza-6-(hydroxymethyl)-7-oxaspiro [bicyclo[4.3.0]nonane-8,4'-piperidin]-2-one To a solution of the compound obtained in Step 7 (4.5 mg) in methanol (1 ml) was added 10% palladium-active carbon (2 mg) and the mixture was stirred at room temperature for 2 hours under a hydrogen atmosphere. The reaction mixture was filtered through Celite and washed with methanol. The filtrate was concentrated to obtain the title compound quantitatively.

NMR spectrum (*CDCl$_3$) δppm: 4.42(1H,d,J=12 Hz), 3.77–3.58(4H,m),3.50(1H,d,J=18 Hz),3.05(1H,d,J=12 Hz), 3.10–2.94(2H,m),2.82–2.70(2H,m),2.67(1H,d,J=12 Hz), 1.90–1.46(4H,m)

Reference Example 2

<Step 1>

Synthesis of 1,4-diaza-1'-benzyl-6-(hydroxymethyl)-7-oxaspiro[bicyclo[4.3.0]nonane-8,4'-piperidin]-2-one To a solution of the compound obtained in Reference Example 1 <Step 6> (25.0 mg) in acetonitrile (1 ml) was added trimethylsilane iodide (20 μl) under cooling with ice. The mixture was stirred under cooling with ice for 30 minutes, then at room temperature for 3 days. Trimethylsilane iodide (0.2 ml) was further added and the mixture was stirred overnight at room temperature. To the reaction mixture was added 1N hydrochloric acid under cooling with ice and benzyl iodide was extracted with diethyl ether. The organic layer was extracted with 1N hydrochloric acid and combined with the previous aqueous layer. After adjusting to pH 9 with sodium carbonate, the aqueous layer was concentrated. To the resulting residue was added methylene chloride and the insoluble content was removed by filtration and the filtrate was washed with methylene chloride and concentrated to obtain the title compound (18.3 mg).

NMR spectrum (*CDCl$_3$) δppm: 7.36–7.22(5H,m),4.37 (1H,d, J=12 Hz),3.76–3.42(5H,m),3.51(2H,s),3.05(1H,d,J=

12 Hz),2.70–2.48(3H,m),2.46–2.29(2H,m),1.94–1.73(2H, m),1.70–1.50(2H,m)

<Step 2>
Synthesis of 1,4-diaza-1'-benzyl-4-(6-chloronaphthalen-2-ylsulfonyl)-6-(hydroxymethyl)-7-oxaspiro[bicyclo[4.3.0] nonane-8,4'-piperidin]-2-one To a solution of the compound obtained in Step 1 (13.5 mg) and triethylamine (9 μl) in methylene chloride (0.5 ml) was added 6-chloronaphthalene-2-sulfonyl chloride (12 mg) under cooling with ice and the mixture was stirred at room temperature for 5 days. After addition of water under cooling with ice, the reaction mixture was extracted with methylene chloride. The organic layer was washed with saturated sodium chloride solution and dried over anhydrous sodium sulfate. The solvent was distilled off under reduced pressure and the resulting residue was purified by preparative thin-layer chromatography (developer; methylene chloride:methanol=20:1) to obtain the title compound (2.8 mg).

Reference Example 3

<Step 1>
Synthesis of ethyl 2-[(benzyloxycarbonyl)(2,2-diethoxyethyl)amino]acetate To aminoacetaldehyde diethyl acetal (43.6 ml) was added dropwise ethyl bromoacetate (34.5 ml) under cooling with ice and N,N-dimethylformamide (150 ml), cesium carbonate (97.7 g) and sodium iodide (4.5 g) were added. The mixture was stirred overnight at room temperature. The reaction mixture was poured into ice water, adjusted to pH 1 with hydrochloric acid and extracted with ethyl acetate. The aqueous layer was adjusted to pH 10 with sodium carbonate and extracted with methylene chloride. Thereafter, the organic layer was dried over anhydrous sodium sulfate. The solvent was distilled off under reduced pressure and the resulting residue was dissolved in methylene chloride (200 ml) and triethylamine (16.1 ml) was added. Thereafter, a solution of benzyl chloroformate (16.5 ml) in methylene chloride (20 ml) was added dropwise over 30 minutes under cooling with ice. The reaction mixture was stirred under cooling with ice for 30 minutes, then at room temperature for 1 hour, and thereafter extracted with 1N hydrochloric acid. The organic layer was washed with saturated sodium chloride solution and dried over anhydrous sodium sulfate and the solvent was distilled off under reduced pressure. The resulting residue was purified by silica gel column chromatography (eluent; n-hexane:diethyl ether=2:1–1:1) to obtain the title compound (28.9 g).

NMR spectrum (*CDCl$_3$) δppm: 7.42–7.25(5H,m), 5.24–5.08(2H,m),4.62–4.44(1H,m),4.23–4.07(4H,m), 3.78–3.36(6H,m),1.30–1.11(9H,m)

<Step 2>
Synthesis of ethyl 2-[(benzyloxycarbonyl)(formylmethyl)amino]acetate

After adding water (60 ml) to a solution of the compound obtained in Step 1 (14.1 g) in chloroform (120 ml), trifluoroacetic acid (153 ml) was added dropwise over 2 hours under cooling with ice. The mixture was stirred under cooling with ice for 1 hour and at room temperature for 1.5 hours. After adding water to the reaction mixture and extracting with methylene chloride, the organic layer was washed with aqueous solution of 10% potassium carbonate, water and saturated sodium chloride solution, and dried over anhydrous sodium sulfate. Thereafter, the solvent was distilled off under reduced pressure to obtain the title compound (10.3 g).

NMR spectrum (*CDCl$_3$) δppm: 9.70–9.56(1H,m), 7.40–7.26(5H,m),5.23–5.11(2H,m),4.25–4.01(6H,m), 1.32–1.18(3H,m)

<Step 3>
Synthesis of 2-[[(3,8-diaza-8-benzyl-1-oxaspiro[4.3.0] decan-2-yl)methyl](benzyloxycarbonyl)amino]acetic acid To a solution of the compound obtained in Step 2 (1.35 g) in methanol (25 ml), was added a solution of lithium hydroxide monohydrate (0.24 g) in water (10 ml) under cooling with ice. The mixture was stirred under cooling with ice for 10 minutes and at room temperature for 40 minutes. The reaction mixture was concentrated under reduced pressure and to the resulting residue was added water, followed by extraction with ethyl acetate. The aqueous layer was adjusted to pH 2 with 6N hydrochloric acid and extracted with ethyl acetate. The organic layer was washed with water and saturated sodium chloride solution and dried over anhydrous sodium sulfate. Thereafter, the solvent was distilled off under reduced pressure to obtain a compound. To a solution of this compound (1.21 g) in methylene chloride (40 ml) were added toluene (40 ml), 4-(aminomethyl)-1-benzyl-4-hydroxypiperidine (1.06 g) and magnesium sulfate (2.90 g) and the mixture was stirred overnight at room temperature. The reaction mixture was filtered and the filtrate was concentrated under reduced pressure. The resulting residue was solidified by addition of diethyl ether and thereafter the solid content was collected by filtration and dried in vacuum to thereby obtain the title compound (2.05 g).

NMR spectrum (*DMSO-d$_6$,100° C.) δppm: 7.39–7.15 (10H,m), 5.15–4.98(2H,m),4.62–4.57(1H,m),4.13–3.91(2H, m),3.67–3.25(4H,m),2.88–2.60 (2H,m),2.56–2.26(4H,m), 1.65–1.33(4H,m)

<Step 4>
Synthesis of 1,4-diaza-1'-benzyl-4-(benzyloxycarbonyl)-7-oxaspiro[bicyclo[4.3.0]nonane-8,4'-piperidin]-2-one To a solution of the compound obtained in Step 3 (1.61 g) in methylene chloride (30 ml) was added dicyclohexylcarbodiimide (0.81 g) under cooling with ice. The mixture was stirred for 30 minutes under cooling with ice and overnight at room temperature. Thereafter, the insoluble content was removed by filtration. The reaction mixture was concentrated under reduced pressure and the resulting residue was purified by silica gel column chromatography (eluent; ethyl acetate:methanol=9:1) to obtain the title compound (0.63 g).

NMR spectrum (*DMSO-d$_6$,100° C.) δppm: 7.40–7.15 (10H,m), 5.12(2H,s),5.00(1H,dd,J=4,9 Hz),4.35–4.27(1H, m), 4,21(1H,d,J=18 Hz),3.76(1H,d,J=18 Hz),3.70(1H,d,J= 11 Hz), 3.48(2H,s),3.10(1H,d,J=11 Hz),3.00–2.88(1H,m), 2.57–2.32(4H,m),1.84–1.55(4H,m)

<Step 5>
Synthesis of 1,4-diaza-4-(benzyloxycarbonyl)-7-oxaspiro [bicyclo[4.3.0]nonane-8,4'-piperidin]-2-one The procedure of Reference Example 1 <Step 7> was repeated by using the compound obtained in Step 4 (1.00 g) to obtain the title compound (0.57 g).

NMR spectrum (*DMSO-d$_6$,100° C.) δppm: 7.38–7.27 (5H,m), 5.12(2H,s),5.01(1H,dd,J=4,9 Hz),4.36–4.27(1H,m), 4.26–4.17(1H,m),3.81–3.65(2H,m),3.12–3.06(1H,m), 2.98–2.74(3H,m), 2.64–2.54(2H,m),1.67–1.60(2H,m), 1.55–1.47(2H,m)

<Step 6>
Synthesis of 1,4-diaza-4-(benzyloxycarbonyl)-7-oxa-1'-(4-pyridyl)spiro[bicyclo[4.3.0]nonane-8,4'-piperidin]-2-one To a solution of the compound obtained in Step 5 (0.1 g) and 4-chloropyridine (0.33 g) in ethanol (2.9 ml) was added N-ethyldiisopropylamine (56 μl). The mixture was heated with stirring in a sealed tube at 150–160° C. The reaction mixture was concentrated under reduced pressure and the residue was purified by silica gel column chromatography [ChromatorexNH™](eluent; ethyl acetate methanol=

98:2–95:5). The fraction containing the compound of interest was concentrated under reduced pressure and crystallized from n-hexane-diethyl ether. The crystals were collected by filtration and air-dried to obtain the title compound (60 mg).

NMR spectrum (DMSO-d$_6$,100° C.) δppm: 8.13(2H,dd, J=2,5 Hz), 7.40–7.25(5H,m),6.76(2H,dd,J=2,5 Hz),5.13(2H, s), 5.07(1H,dd,J=4,9 Hz),4.38–4.28(1H,m),4.23(1H,d,J=18 Hz),3.84–3.73(2H,m),3.52–3.23(4H,m),3.17(1H,d,J=11 Hz),3.04–2.92(1H,m),1.90–1.60(4H,m)

<Step 7>

Synthesis of 1,4-diaza-7-oxa-1'-(4-pyridyl)spiro[bicyclo [4.3.0]nonane-8,4'-piperidin]-2-one The procedure of Reference Example 1 <Step 8> was repeated by using the compound obtained in Step 6. To a solution of this compound (100 mg) in methanol (2.4 ml) was added 10% palladium-carbon (20 mg). After stirring at room temperature for 1 hour under a hydrogen atmosphere, the reaction mixture was filtered. The filtrate was concentrated under reduced pressure and the resulting residue was purified by silica gel column chromatography [ChromatorexNH™](eluent; ethyl acetate:methanol=9:1) to obtain the title compound (60 mg).

NMR spectrum (*CDCl$_3$) δppm: 8.31–8.22(2H,m), 6.72–6.63(2H,m),5.00(1H,dd,J=4,8 Hz),3.96–3.88(1H,m), 3.65–3.28(7H,m),3.19–3.10(1H,m),2.66(1H,dd,J=8,13 Hz), 2.00–1.55(4H,m)

Reference Example 4

<Step 1>

Synthesis of 1,4-diaza-1'-benzyl-7-oxaspiro[bicyclo [4.3.0]nonane-8,4'-piperidin]-2-one The procedure of Reference Example 2 <Step 1> was repeated by using the compound obtained in Reference Example 3 <Step 4> (50 mg) to obtain the title compound (15 mg).

NMR spectrum (*CDCl$_3$) δppm: 7.40–7.25(5H,m),4.94 (1H,dd, J=4,8 Hz),3.83(1H,d,J=11 Hz),3.62–3.37(5H,m), 3.14(1H,d,J=11 Hz),2.62(1H,dd,J=8,13 Hz),2.65–2.35(4H, m), 1.95–1.53 (4H,m)

<Step 2>

Synthesis of 1,4-diaza-1'-benzyl-4-(6-chloronaphthalen-2-ylsulfonyl)-7-oxaspiro[bicyclo[4.3.0]nonane-8,4'-piperidin]-2-one The procedure of Reference Example 2 <Step 2> was repeated by using the compound obtained in Step 1 (10.0 mg) to obtain the title compound quantitatively.

<Step 3>

The procedure of Example 1 <Step A-1> was repeated by using the compound obtained in Step 1 (10 mg) to obtain the title compound (22 mg).

Reference Example 5

Synthesis of 1,4-diaza-7-oxaspiro[bicyclo[4.3.0]nonane-8,4'-piperidin]-2-one

The procedure of Reference Example 1 <Step 8> was repeated by using the compound obtained in Reference Example 3 <Step 5> (10.0 mg) to obtain the title compound (6.0 mg).

NMR spectrum (*CDCl$_3$) δppm: 4.97(1H,dd,J=4,8 Hz), 3.87(1H,d,J=12 Hz),3.59(1H,d,J=18 Hz),3.51–3.38(2H,m), 3.15(1H,d,J=12 Hz),3.15–2.97(2H,m),2.94–2.77(2H,m), 2.63(1H,dd,J=8,13 Hz),1.88–1.63(4H,m)

Reference Example 6

Synthesis of 4-aminomethyl-4-hydroxy-1-(4-pyridyl) piperidine diacetate

<Step 1>

Synthesis of 4-hydroxy-4-nitromethyl-1-(4-pyridyl) piperidine

To a solution of nitromethane (2.31 ml) in methanol (5.4 ml) was added sodium (70 mg) at ice-cooled temperature. The resulting mixture was added dropwise to a solution of 1-(4-pyridyl)-4-piperidone (5.36 g) in methanol (10.7 ml) at ice-cooled temperature for 10 minutes, and stirred for 15 hours at room temperature. The precipitate was filtered, and washed with methanol to obtain the title compound (5.31 g).

NMR spectrum (*DMSO-d$_6$) δppm: 8.13(2H,dd,J=1,5 Hz), 6.82(2H,dd,J=1,5 Hz),5.38(1H,s),4.57(2H,s),3.77–3.63 (2H,m), 3.25–3.08(2H,m),1.74–1.59(4H,m)

<Step 2>

Synthesis of 4-aminomethyl-4-hydroxy-1-(4-pyridyl) piperidine Diacetate

Acetic acid (20 ml) was added to a mixture of the compound obtained in <step 1> (2.00 g) and 10% palladium-active carbon (200 mg). The reaction mixture was vigorously stirred for 3days under a hydrogen atmosphere at room temperature. The catalyst was filtered off, and washed with methanol. The filtrate was concentrated under reduced pressure to obtain the title compound (3.39 g).

NMR spectrum (*DMSO-d$_6$) δppm: 8.12(2H,d,J=6 Hz), 6.82(2H,d, J=6 Hz),3.72–3.58(2H,m),3.26–3.10(2H,m),2.66 (2H,s), 1.84(6H,s),1.64–1.40(4H,m)

Reference Example 7

Synthesis of ethyl 2-[(benzyloxycarbonyl)(2-hydroxy-3-methoxypropan-1-yl) amino]acetate <Step 1>

Synthesis of ethyl 2-[(2-hydroxy-3-methoxypropyl) benzylamino]acetate and 6-(methoxymethyl)-4-benzylmorpholin-2-one A mixture of ethyl benzylaminoacetate (30.0 g) and glycidyl methyl ether (18.1 ml) was stirred at 120° C. for 2 hours. Excess glycidyl methyl ether and generated ethanol were removed under reduced pressure to obtain a mixture of the title compounds (41.8 g).

<Step 2>

Synthesis of ethyl 2-[(benzyloxycarbonyl)(2-hydroxy-3-methoxypropan-1-yl)amino]acetate A mixture of the compounds obtained in <step 1> (41.8 g) was dissolved in 5% hydrogen chloride in ethanol (w/w) (400 ml). To the above solution, 10% palladium-active carbon (4.2 g) was added and the reducing reaction was carried out under hydrogen atmosphere at room temperature for 5 hours. The catalyst was filtered off with Celite™ pad and then the filtrate was concentrated under reduced pressure. The residue was dissolved in tetrahydrofuran (350 ml) and water (350 ml). To the above solution, sodium hydrogencarbonate (31.2 g) was added carefully at 0° C. Successively, benzyl chloroformate (26.6 ml) was added dropwise to the reaction mixture at 0° C. After stirring for 1.5 hour at room temperature, then the reaction mixture was extracted with ethyl acetate. The organic layer was washed with saturated aqueous sodium hydrogencarbonate and brine, and then dried over anhydrous sodium sulfate. The solvent was removed under reduced pressure to obtain the title compound (52.8 g).

NMR spectrum (*DMSO-d$_{6, 100}$° C.) δppm: 7.40–7.25 (5H,m), 5.07(2H,s),4.50–4.45(1H,m),4.14–4.04(4H,m), 3.85–3.75(1H,m), 3.50–3.42(1H,m),3.30–3.13(3H,m),3.24 (3H,s),1.16(3H,t,J=7 Hz)

Reference Example 8

Synthesis of ethyl 2-[(6-chloronaphthalen-2-ylsulfonyl)(2-hydroxy-3-methoxypropyl)amino]acetate <Step 1>

Synthesis of (6-chloronaphthalen-2-ylsulfonyl)(2-hydroxy-3-methoxypropyl)amine

Using 1-amino-3-methoxypropan-2-ol (0.30 g), the method of synthesis in Example 9 <step 2> was repeated to yield the title compound (0.57 g).

NMR spectrum (*CDCl$_3$) δppm: 8.41(1H,s),7.95–7.82(4H,m), 7.57(1H,dd,J=2,9 Hz),5.15–5.00(1H,m),3.92–3.83(1H,m),3.45–3.31(2H,m),3.33(3H,s),3.23–3.13(1H,m), 3.05–2.94(1H,m), 2.55–2.40(1H,m)

<Step 2>

Synthesis of ethyl 2-[(6-chloronaphthalen-2-ylsulfonyl)(2-hydroxy-3-methoxypropyl)amino]acetate Using the compound obtained in <step 1> (0.10 g) and ethyl bromoacetate (40 μl), the method of synthesis in Example 1 <step A-2> was repeated to yield the title compound (64 mg).

NMR spectrum (*CDCl$_3$) δppm: 8.38(1H,s), 7.88(1H,d, J=9 Hz), 7.87–7.81(3H,m), 7.50(1H,dd,J=2,9 Hz), 4.22(2H, s), 4.05(2H,q,J=7 Hz), 4.06–3.97(1H,m), 3.33(3H,s), 3.56–3.31(4H,m), 1.14(3H,t,J=7 Hz)

Reference Example 9

Synthesis of ethyl 2-[(6-chloronaphthalen-2-ylsulfonyl)(3-methoxy-2-oxopropyl)amino]acetate Using the compound obtained in Example 1 <step A-1> (0.10 g) and (3-methoxy-2-oxopropyl)amine (75 mg), the method of synthesis in Example 1 <step A-2> was repeated to yield the title compound (54 mg).

NMR spectrum (*CDCl$_3$) δppm: 8.38(1H,s), 7.93–7.77(4H,m), 7.54–7.48(1H,m), 4.44(2H,s), 4.20(2H,s), 4.13(2H, s), 4.02(2H,q,J=7 Hz), 3.39(3H,s), 1.13(3H,t,J=7 Hz)

The structures of the compounds of the present invention obtained in Examples mentioned above are shown in FIGS. 1–9. The synthesis routes of the compounds of the present invention are shown in FIGS. 11–20.

Further, the NMR spectrum data of these Examples are shown in FIGS. 21–38.

In addition, the compounds mentioned below are also synthesized in the same manner as in Examples.

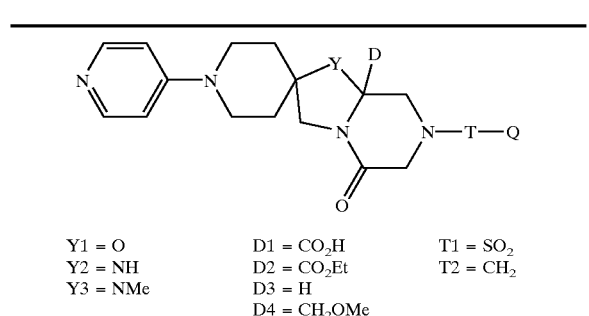

Y1 = O    D1 = CO$_2$H    T1 = SO$_2$
Y2 = NH    D2 = CO$_2$Et    T2 = CH$_2$
Y3 = NMe    D3 = H
    D4 = CH$_2$OMe

Q:

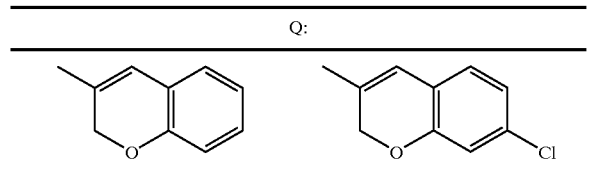

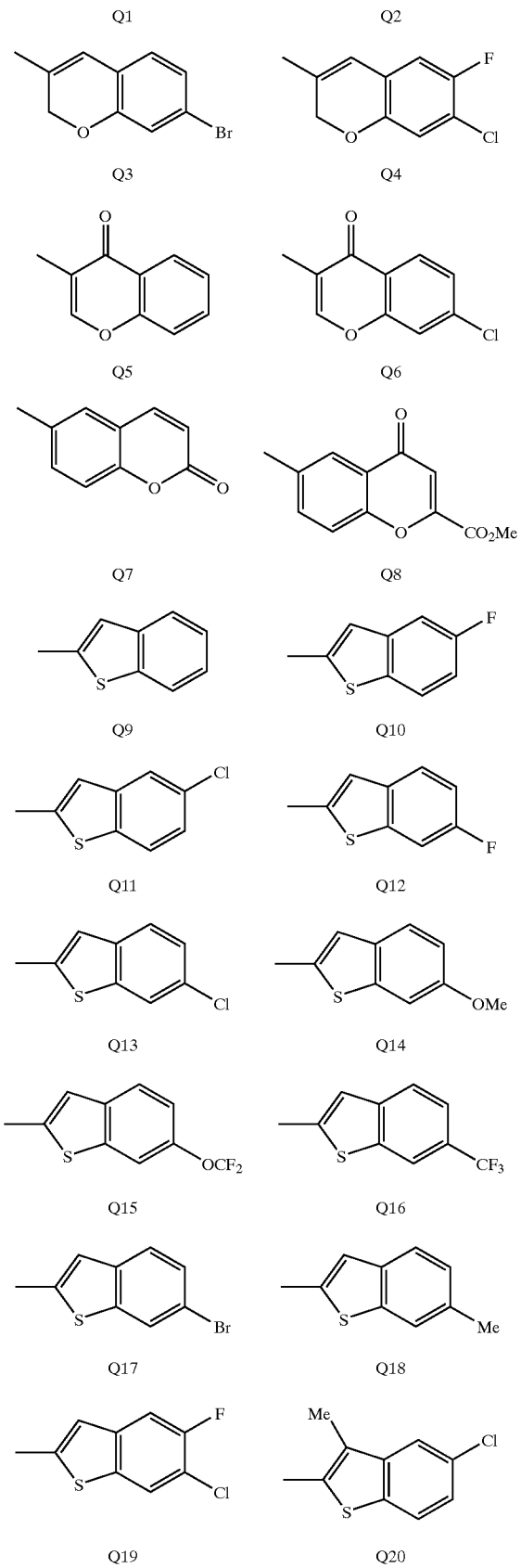

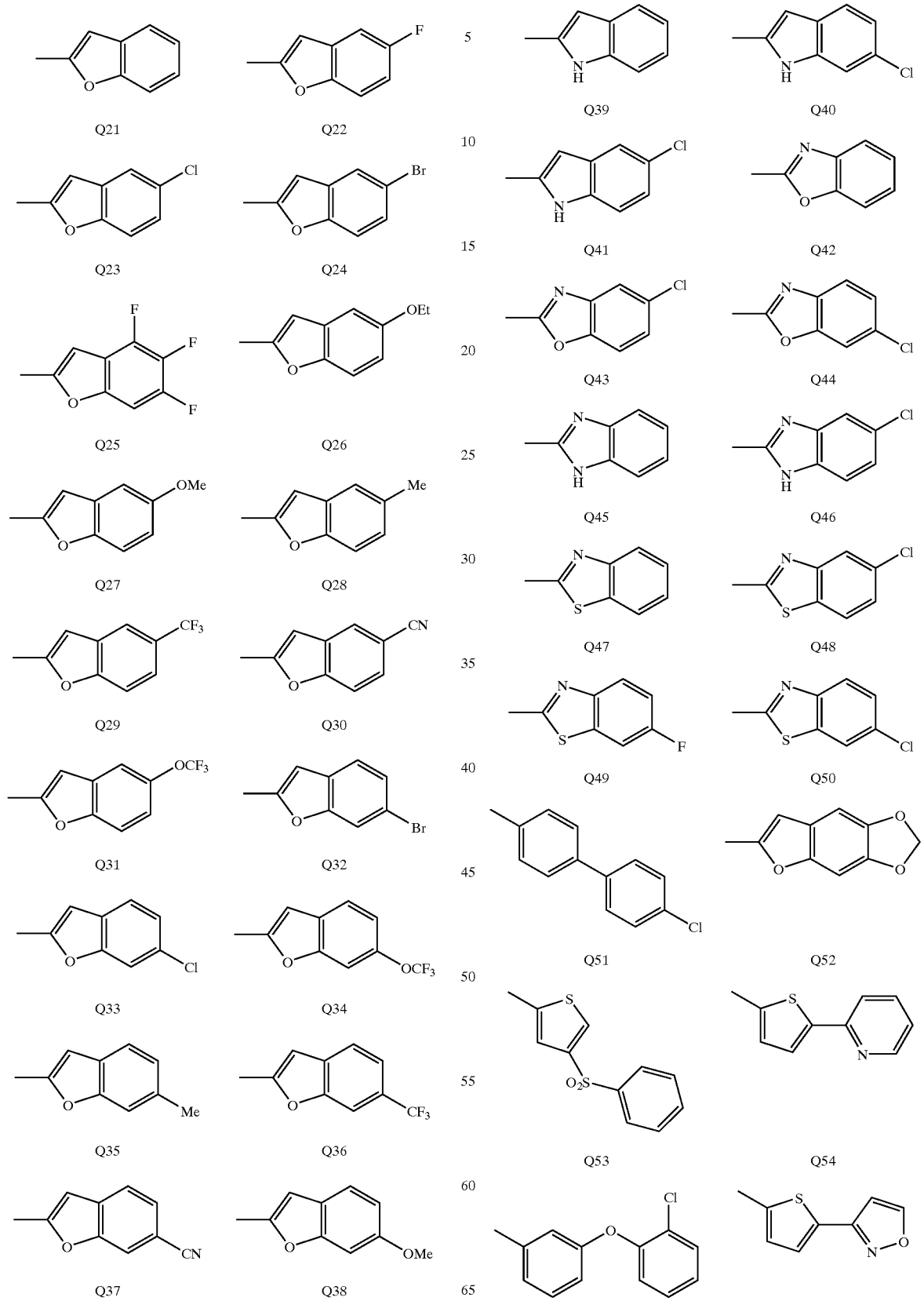

-continued

Q55, Q56, Q57, Q58, Q59, Q60, Q61, Q62, Q63

| Ex No. | Y | D | T | Q |
|---|---|---|---|---|
| 83 | Y1 | D1 | T1 | Q1 |
| 84 | Y1 | D1 | T1 | Q2 |
| 85 | Y1 | D1 | T1 | Q3 |
| 86 | Y1 | D1 | T1 | Q4 |
| 87 | Y1 | D1 | T1 | Q5 |
| 88 | Y1 | D1 | T1 | Q6 |
| 89 | Y1 | D1 | T1 | Q7 |
| 90 | Y1 | D1 | T1 | Q8 |
| 91 | Y1 | D1 | T1 | Q9 |
| 92 | Y1 | D1 | T1 | Q10 |
| 93 | Y1 | D1 | T1 | Q11 |
| 94 | Y1 | D1 | T1 | Q12 |
| 95 | Y1 | D1 | T1 | Q13 |
| 96 | Y1 | D1 | T1 | Q14 |
| 97 | Y1 | D1 | T1 | Q15 |
| 98 | Y1 | D1 | T1 | Q16 |
| 99 | Y1 | D1 | T1 | Q17 |
| 100 | Y1 | D1 | T1 | Q18 |
| 101 | Y1 | D1 | T1 | Q19 |
| 102 | Y1 | D1 | T1 | Q20 |
| 103 | Y1 | D1 | T1 | Q21 |
| 104 | Y1 | D1 | T1 | Q22 |
| 105 | Y1 | D1 | T1 | Q23 |
| 106 | Y1 | D1 | T1 | Q24 |
| 107 | Y1 | D1 | T1 | Q25 |
| 108 | Y1 | D1 | T1 | Q26 |
| 109 | Y1 | D1 | T1 | Q27 |
| 110 | Y1 | D1 | T1 | Q28 |
| 111 | Y1 | D1 | T1 | Q29 |
| 112 | Y1 | D1 | T1 | Q30 |
| 113 | Y1 | D1 | T1 | Q31 |
| 114 | Y1 | D1 | T1 | Q32 |
| 115 | Y1 | D1 | T1 | Q33 |
| 116 | Y1 | D1 | T1 | Q34 |
| 117 | Y1 | D1 | T1 | Q35 |
| 118 | Y1 | D1 | T1 | Q36 |
| 119 | Y1 | D1 | T1 | Q37 |
| 120 | Y1 | D1 | T1 | Q38 |
| 121 | Y1 | D1 | T1 | Q39 |
| 122 | Y1 | D1 | T1 | Q40 |
| 123 | Y1 | D1 | T1 | Q41 |
| 124 | Y1 | D1 | T1 | Q42 |
| 125 | Y1 | D1 | T1 | Q43 |
| 126 | Y1 | D1 | T1 | Q44 |
| 127 | Y1 | D1 | T1 | Q45 |
| 128 | Y1 | D1 | T1 | Q46 |
| 129 | Y1 | D1 | T1 | Q47 |
| 130 | Y1 | D1 | T1 | Q48 |
| 131 | Y1 | D1 | T1 | Q49 |
| 132 | Y1 | D1 | T1 | Q50 |
| 133 | Y1 | D1 | T1 | Q51 |
| 134 | Y1 | D1 | T1 | Q52 |
| 135 | Y1 | D1 | T1 | Q53 |
| 136 | Y1 | D1 | T1 | Q54 |
| 137 | Y1 | D1 | T1 | Q55 |
| 138 | Y1 | D1 | T1 | Q56 |
| 139 | Y1 | D1 | T1 | Q57 |
| 140 | Y1 | D1 | T1 | Q58 |
| 141 | Y1 | D1 | T1 | Q59 |
| 142 | Y1 | D2 | T1 | Q1 |
| 143 | Y1 | D2 | T1 | Q2 |
| 144 | Y1 | D2 | T1 | Q3 |
| 145 | Y1 | D2 | T1 | Q4 |
| 146 | Y1 | D2 | T1 | Q5 |
| 147 | Y1 | D2 | T1 | Q6 |
| 148 | Y1 | D2 | T1 | Q7 |
| 149 | Y1 | D2 | T1 | Q8 |
| 150 | Y1 | D2 | T1 | Q9 |
| 151 | Y1 | D2 | T1 | Q10 |
| 152 | Y1 | D2 | T1 | Q11 |
| 153 | Y1 | D2 | T1 | Q12 |
| 154 | Y1 | D2 | T1 | Q13 |
| 155 | Y1 | D2 | T1 | Q14 |
| 156 | Y1 | D2 | T1 | Q15 |
| 157 | Y1 | D2 | T1 | Q16 |
| 158 | Y1 | D2 | T1 | Q17 |
| 159 | Y1 | D2 | T1 | Q18 |
| 160 | Y1 | D2 | T1 | Q19 |
| 161 | Y1 | D2 | T1 | Q20 |
| 162 | Y1 | D2 | T1 | Q21 |
| 163 | Y1 | D2 | T1 | Q22 |
| 164 | Y1 | D2 | T1 | Q23 |
| 165 | Y1 | D2 | T1 | Q24 |
| 166 | Y1 | D2 | T1 | Q25 |
| 167 | Y1 | D2 | T1 | Q26 |
| 168 | Y1 | D2 | T1 | Q27 |
| 169 | Y1 | D2 | T1 | Q28 |
| 170 | Y1 | D2 | T1 | Q29 |
| 171 | Y1 | D2 | T1 | Q30 |
| 172 | Y1 | D2 | T1 | Q31 |
| 173 | Y1 | D2 | T1 | Q32 |
| 174 | Y1 | D2 | T1 | Q33 |
| 175 | Y1 | D2 | T1 | Q34 |
| 176 | Y1 | D2 | T1 | Q35 |
| 177 | Y1 | D2 | T1 | Q36 |
| 178 | Y1 | D2 | T1 | Q37 |
| 179 | Y1 | D2 | T1 | Q38 |
| 180 | Y1 | D2 | T1 | Q39 |
| 181 | Y1 | D2 | T1 | Q40 |
| 182 | Y1 | D2 | T1 | Q41 |
| 183 | Y1 | D2 | T1 | Q42 |
| 184 | Y1 | D2 | T1 | Q43 |
| 185 | Y1 | D2 | T1 | Q44 |
| 186 | Y1 | D2 | T1 | Q45 |
| 187 | Y1 | D2 | T1 | Q46 |
| 188 | Y1 | D2 | T1 | Q47 |
| 189 | Y1 | D2 | T1 | Q48 |
| 190 | Y1 | D2 | T1 | Q49 |
| 191 | Y1 | D2 | T1 | Q50 |
| 192 | Y1 | D2 | T1 | Q51 |
| 193 | Y1 | D2 | T1 | Q52 |
| 194 | Y1 | D2 | T1 | Q53 |
| 195 | Y1 | D2 | T1 | Q54 |
| 196 | Y1 | D2 | T1 | Q55 |
| 197 | Y1 | D2 | T1 | Q56 |
| 198 | Y1 | D2 | T1 | Q57 |
| 199 | Y1 | D2 | T1 | Q58 |
| 200 | Y1 | D2 | T1 | Q59 |
| 201 | Y1 | D3 | T1 | Q1 |
| 202 | Y1 | D3 | T1 | Q2 |
| 203 | Y1 | D3 | T1 | Q3 |
| 204 | Y1 | D3 | T1 | Q4 |
| 205 | Y1 | D3 | T1 | Q5 |

| | | | | |
|---|---|---|---|---|
| 206 | Y1 | D3 | T1 | Q6 |
| 207 | Y1 | D3 | T1 | Q7 |
| 208 | Y1 | D3 | T1 | Q8 |
| 209 | Y1 | D3 | T1 | Q9 |
| 210 | Y1 | D3 | T1 | Q10 |
| 211 | Y1 | D3 | T1 | Q11 |
| 212 | Y1 | D3 | T1 | Q12 |
| 213 | Y1 | D3 | T1 | Q13 |
| 214 | Y1 | D3 | T1 | Q14 |
| 215 | Y1 | D3 | T1 | Q15 |
| 216 | Y1 | D3 | T1 | Q16 |
| 217 | Y1 | D3 | T1 | Q17 |
| 218 | Y1 | D3 | T1 | Q18 |
| 219 | Y1 | D3 | T1 | Q19 |
| 220 | Y1 | D3 | T1 | Q20 |
| 221 | Y1 | D3 | T1 | Q21 |
| 222 | Y1 | D3 | T1 | Q22 |
| 223 | Y1 | D3 | T1 | Q23 |
| 224 | Y1 | D3 | T1 | Q24 |
| 225 | Y1 | D3 | T1 | Q25 |
| 226 | Y1 | D3 | T1 | Q26 |
| 227 | Y1 | D3 | T1 | Q27 |
| 228 | Y1 | D3 | T1 | Q28 |
| 229 | Y1 | D3 | T1 | Q29 |
| 230 | Y1 | D3 | T1 | Q30 |
| 231 | Y1 | D3 | T1 | Q31 |
| 232 | Y1 | D3 | T2 | Q1 |
| 233 | Y1 | D3 | T2 | Q2 |
| 234 | Y1 | D3 | T2 | Q3 |
| 235 | Y1 | D3 | T2 | Q4 |
| 236 | Y1 | D3 | T2 | Q5 |
| 237 | Y1 | D3 | T2 | Q6 |
| 238 | Y1 | D3 | T2 | Q7 |
| 239 | Y1 | D3 | T2 | Q8 |
| 240 | Y1 | D3 | T2 | Q9 |
| 241 | Y1 | D3 | T2 | Q10 |
| 242 | Y1 | D3 | T2 | Q11 |
| 243 | Y1 | D3 | T2 | Q12 |
| 244 | Y1 | D3 | T2 | Q13 |
| 245 | Y1 | D3 | T2 | Q14 |
| 246 | Y1 | D3 | T2 | Q15 |
| 247 | Y1 | D3 | T2 | Q16 |
| 248 | Y1 | D3 | T2 | Q17 |
| 249 | Y1 | D3 | T2 | Q18 |
| 250 | Y1 | D3 | T2 | Q19 |
| 251 | Y1 | D3 | T2 | Q20 |
| 252 | Y1 | D3 | T2 | Q21 |
| 253 | Y1 | D3 | T2 | Q22 |
| 254 | Y1 | D3 | T2 | Q23 |
| 255 | Y1 | D3 | T2 | Q24 |
| 256 | Y1 | D3 | T2 | Q25 |
| 257 | Y1 | D3 | T2 | Q26 |
| 258 | Y1 | D3 | T2 | Q27 |
| 259 | Y1 | D3 | T2 | Q28 |
| 260 | Y1 | D3 | T2 | Q29 |
| 261 | Y1 | D3 | T2 | Q30 |
| 262 | Y1 | D3 | T2 | Q31 |
| 263 | Y2 | D3 | T1 | Q1 |
| 264 | Y2 | D3 | T1 | Q2 |
| 265 | Y2 | D3 | T1 | Q3 |
| 266 | Y2 | D3 | T1 | Q4 |
| 267 | Y2 | D3 | T1 | Q5 |
| 268 | Y2 | D3 | T1 | Q6 |
| 269 | Y2 | D3 | T1 | Q7 |
| 270 | Y2 | D3 | T1 | Q8 |
| 271 | Y2 | D3 | T1 | Q9 |
| 272 | Y2 | D3 | T1 | Q10 |
| 273 | Y2 | D3 | T1 | Q11 |
| 274 | Y2 | D3 | T1 | Q12 |
| 275 | Y2 | D3 | T1 | Q13 |
| 276 | Y2 | D3 | T1 | Q14 |
| 277 | Y2 | D3 | T1 | Q15 |
| 278 | Y2 | D3 | T1 | Q16 |
| 279 | Y2 | D3 | T1 | Q17 |
| 280 | Y2 | D3 | T1 | Q18 |
| 281 | Y2 | D3 | T1 | Q19 |
| 282 | Y2 | D3 | T1 | Q20 |
| 283 | Y2 | D3 | T1 | Q21 |
| 284 | Y2 | D3 | T1 | Q22 |
| 285 | Y2 | D3 | T1 | Q23 |
| 286 | Y2 | D3 | T1 | Q24 |
| 287 | Y2 | D3 | T1 | Q25 |
| 288 | Y2 | D3 | T1 | Q26 |
| 289 | Y2 | D3 | T1 | Q27 |
| 290 | Y2 | D3 | T1 | Q28 |
| 291 | Y2 | D3 | T1 | Q29 |
| 292 | Y2 | D3 | T1 | Q30 |
| 293 | Y2 | D3 | T1 | Q31 |
| 294 | Y2 | D3 | T2 | Q1 |
| 295 | Y2 | D3 | T2 | Q2 |
| 296 | Y2 | D3 | T2 | Q3 |
| 297 | Y2 | D3 | T2 | Q4 |
| 298 | Y2 | D3 | T2 | Q5 |
| 299 | Y2 | D3 | T2 | Q6 |
| 300 | Y2 | D3 | T2 | Q7 |
| 301 | Y2 | D3 | T2 | Q8 |
| 302 | Y2 | D3 | T2 | Q9 |
| 303 | Y2 | D3 | T2 | Q10 |
| 304 | Y2 | D3 | T2 | Q11 |
| 305 | Y2 | D3 | T2 | Q12 |
| 306 | Y2 | D3 | T2 | Q13 |
| 307 | Y2 | D3 | T2 | Q14 |
| 308 | Y2 | D3 | T2 | Q15 |
| 309 | Y2 | D3 | T2 | Q16 |
| 310 | Y2 | D3 | T2 | Q17 |
| 311 | Y2 | D3 | T2 | Q18 |
| 312 | Y2 | D3 | T2 | Q19 |
| 313 | Y2 | D3 | T2 | Q20 |
| 314 | Y2 | D3 | T2 | Q21 |
| 315 | Y2 | D3 | T2 | Q22 |
| 316 | Y2 | D3 | T2 | Q23 |
| 317 | Y2 | D3 | T2 | Q24 |
| 318 | Y2 | D3 | T2 | Q25 |
| 319 | Y2 | D3 | T2 | Q26 |
| 320 | Y2 | D3 | T2 | Q27 |
| 321 | Y2 | D3 | T2 | Q28 |
| 322 | Y2 | D3 | T2 | Q29 |
| 323 | Y2 | D3 | T2 | Q30 |
| 324 | Y2 | D3 | T2 | Q31 |
| 325 | Y3 | D3 | T1 | Q1 |
| 326 | Y3 | D3 | T1 | Q2 |
| 327 | Y3 | D3 | T1 | Q3 |
| 328 | Y3 | D3 | T1 | Q4 |
| 329 | Y3 | D3 | T1 | Q5 |
| 330 | Y3 | D3 | T1 | Q6 |
| 331 | Y3 | D3 | T1 | Q7 |
| 332 | Y3 | D3 | T1 | Q8 |
| 333 | Y3 | D3 | T1 | Q9 |
| 334 | Y3 | D3 | T1 | Q10 |
| 335 | Y3 | D3 | T1 | Q11 |
| 336 | Y3 | D3 | T1 | Q12 |
| 337 | Y3 | D3 | T1 | Q13 |
| 338 | Y3 | D3 | T1 | Q14 |
| 339 | Y3 | D3 | T1 | Q15 |
| 340 | Y3 | D3 | T1 | Q16 |
| 341 | Y3 | D3 | T1 | Q17 |
| 342 | Y3 | D3 | T1 | Q18 |
| 343 | Y3 | D3 | T1 | Q19 |
| 344 | Y3 | D3 | T1 | Q20 |
| 345 | Y3 | D3 | T1 | Q21 |
| 346 | Y3 | D3 | T1 | Q22 |
| 347 | Y3 | D3 | T1 | Q23 |
| 348 | Y3 | D3 | T1 | Q24 |
| 349 | Y3 | D3 | T1 | Q25 |
| 350 | Y3 | D3 | T1 | Q26 |
| 351 | Y3 | D3 | T1 | Q27 |
| 352 | Y3 | D3 | T1 | Q28 |
| 353 | Y3 | D3 | T1 | Q29 |
| 354 | Y3 | D3 | T1 | Q30 |
| 355 | Y3 | D3 | T1 | Q31 |
| 356 | Y3 | D3 | T2 | Q1 |
| 357 | Y3 | D3 | T2 | Q2 |
| 358 | Y3 | D3 | T2 | Q3 |
| 359 | Y3 | D3 | T2 | Q4 |
| 360 | Y3 | D3 | T2 | Q5 |
| 361 | Y3 | D3 | T2 | Q6 |
| 362 | Y3 | D3 | T2 | Q7 |
| 363 | Y3 | D3 | T2 | Q8 |

| | | | | |
|---|---|---|---|---|
| 364 | Y3 | D3 | T2 | Q9 |
| 365 | Y3 | D3 | T2 | Q10 |
| 366 | Y3 | D3 | T2 | Q11 |
| 367 | Y3 | D3 | T2 | Q12 |
| 368 | Y3 | D3 | T2 | Q13 |
| 369 | Y3 | D3 | T2 | Q14 |
| 370 | Y3 | D3 | T2 | Q15 |
| 371 | Y3 | D3 | T2 | Q16 |
| 372 | Y3 | D3 | T2 | Q17 |
| 373 | Y3 | D3 | T2 | Q18 |
| 374 | Y3 | D3 | T2 | Q19 |
| 375 | Y3 | D3 | T2 | Q20 |
| 376 | Y3 | D3 | T2 | Q21 |
| 377 | Y3 | D3 | T2 | Q22 |
| 378 | Y3 | D3 | T2 | Q23 |
| 379 | Y3 | D3 | T2 | Q24 |
| 380 | Y3 | D3 | T2 | Q25 |
| 381 | Y3 | D3 | T2 | Q26 |
| 382 | Y3 | D3 | T2 | Q27 |
| 383 | Y3 | D3 | T2 | Q28 |
| 384 | Y3 | D3 | T2 | Q29 |
| 385 | Y3 | D3 | T2 | Q30 |
| 386 | Y3 | D3 | T2 | Q31 |
| 387 | Y1 | D4 | T1 | Q1 |
| 388 | Y1 | D4 | T1 | Q2 |
| 389 | Y1 | D4 | T1 | Q3 |
| 390 | Y1 | D4 | T1 | Q4 |
| 391 | Y1 | D4 | T1 | Q5 |
| 392 | Y1 | D4 | T1 | Q6 |
| 393 | Y1 | D4 | T1 | Q7 |
| 394 | Y1 | D4 | T1 | Q8 |
| 395 | Y1 | D4 | T1 | Q9 |
| 396 | Y1 | D4 | T1 | Q10 |
| 397 | Y1 | D4 | T1 | Q11 |
| 398 | Y1 | D4 | T1 | Q12 |
| 399 | Y1 | D4 | T1 | Q13 |
| 400 | Y1 | D4 | T1 | Q14 |
| 401 | Y1 | D4 | T1 | Q15 |
| 402 | Y1 | D4 | T1 | Q16 |
| 403 | Y1 | D4 | T1 | Q17 |
| 404 | Y1 | D4 | T1 | Q18 |
| 405 | Y1 | D4 | T1 | Q19 |
| 406 | Y1 | D4 | T1 | Q20 |
| 407 | Y1 | D4 | T1 | Q21 |
| 408 | Y1 | D4 | T1 | Q22 |
| 409 | Y1 | D4 | T1 | Q23 |
| 410 | Y1 | D4 | T1 | Q24 |
| 411 | Y1 | D4 | T1 | Q25 |
| 412 | Y1 | D4 | T1 | Q26 |
| 413 | Y1 | D4 | T1 | Q27 |
| 414 | Y1 | D4 | T1 | Q28 |
| 415 | Y1 | D4 | T1 | Q29 |
| 416 | Y1 | D4 | T1 | Q30 |
| 417 | Y1 | D4 | T1 | Q31 |
| 418 | Y1 | D4 | T2 | Q1 |
| 419 | Y1 | D4 | T2 | Q2 |
| 420 | Y1 | D4 | T2 | Q3 |
| 421 | Y1 | D4 | T2 | Q4 |
| 422 | Y1 | D4 | T2 | Q5 |
| 423 | Y1 | D4 | T2 | Q6 |
| 424 | Y1 | D4 | T2 | Q7 |
| 425 | Y1 | D4 | T2 | Q8 |
| 426 | Y1 | D4 | T2 | Q9 |
| 427 | Y1 | D4 | T2 | Q10 |
| 428 | Y1 | D4 | T2 | Q11 |
| 429 | Y1 | D4 | T2 | Q12 |
| 430 | Y1 | D4 | T2 | Q13 |
| 431 | Y1 | D4 | T2 | Q14 |
| 432 | Y1 | D4 | T2 | Q15 |
| 433 | Y1 | D4 | T2 | Q16 |
| 434 | Y1 | D4 | T2 | Q17 |
| 435 | Y1 | D4 | T2 | Q18 |
| 436 | Y1 | D4 | T2 | Q19 |
| 437 | Y1 | D4 | T2 | Q20 |
| 438 | Y1 | D4 | T2 | Q21 |
| 439 | Y1 | D4 | T2 | Q22 |
| 440 | Y1 | D4 | T2 | Q23 |
| 441 | Y1 | D4 | T2 | Q24 |
| 442 | Y1 | D4 | T2 | Q25 |
| 443 | Y1 | D4 | T2 | Q26 |
| 444 | Y1 | D4 | T2 | Q27 |
| 445 | Y1 | D4 | T2 | Q28 |
| 446 | Y1 | D4 | T2 | Q29 |
| 447 | Y1 | D4 | T2 | Q30 |
| 448 | Y1 | D4 | T2 | Q31 |
| 449 | Y2 | D4 | T1 | Q1 |
| 450 | Y2 | D4 | T1 | Q2 |
| 451 | Y2 | D4 | T1 | Q3 |
| 452 | Y2 | D4 | T1 | Q4 |
| 453 | Y2 | D4 | T1 | Q5 |
| 454 | Y2 | D4 | T1 | Q6 |
| 455 | Y2 | D4 | T1 | Q7 |
| 456 | Y2 | D4 | T1 | Q8 |
| 457 | Y2 | D4 | T1 | Q9 |
| 458 | Y2 | D4 | T1 | Q10 |
| 459 | Y2 | D4 | T1 | Q11 |
| 460 | Y2 | D4 | T1 | Q12 |
| 461 | Y2 | D4 | T1 | Q13 |
| 462 | Y2 | D4 | T1 | Q14 |
| 463 | Y2 | D4 | T1 | Q15 |
| 464 | Y2 | D4 | T1 | Q16 |
| 465 | Y2 | D4 | T1 | Q17 |
| 466 | Y2 | D4 | T1 | Q18 |
| 467 | Y2 | D4 | T1 | Q19 |
| 468 | Y2 | D4 | T1 | Q20 |
| 469 | Y2 | D4 | T1 | Q21 |
| 470 | Y2 | D4 | T1 | Q22 |
| 471 | Y2 | D4 | T1 | Q23 |
| 472 | Y2 | D4 | T1 | Q24 |
| 473 | Y2 | D4 | T1 | Q25 |
| 474 | Y2 | D4 | T1 | Q26 |
| 475 | Y2 | D4 | T1 | Q27 |
| 476 | Y2 | D4 | T1 | Q28 |
| 477 | Y2 | D4 | T1 | Q29 |
| 478 | Y2 | D4 | T1 | Q30 |
| 479 | Y2 | D4 | T1 | Q31 |
| 480 | Y2 | D4 | T2 | Q1 |
| 481 | Y2 | D4 | T2 | Q2 |
| 482 | Y2 | D4 | T2 | Q3 |
| 483 | Y2 | D4 | T2 | Q4 |
| 484 | Y2 | D4 | T2 | Q5 |
| 485 | Y2 | D4 | T2 | Q6 |
| 486 | Y2 | D4 | T2 | Q7 |
| 487 | Y2 | D4 | T2 | Q8 |
| 488 | Y2 | D4 | T2 | Q9 |
| 489 | Y2 | D4 | T2 | Q10 |
| 490 | Y2 | D4 | T2 | Q11 |
| 491 | Y2 | D4 | T2 | Q12 |
| 492 | Y2 | D4 | T2 | Q13 |
| 493 | Y2 | D4 | T2 | Q14 |
| 494 | Y2 | D4 | T2 | Q15 |
| 495 | Y2 | D4 | T2 | Q16 |
| 496 | Y2 | D4 | T2 | Q17 |
| 497 | Y2 | D4 | T2 | Q18 |
| 498 | Y2 | D4 | T2 | Q19 |
| 499 | Y2 | D4 | T2 | Q20 |
| 500 | Y2 | D4 | T2 | Q21 |
| 501 | Y2 | D4 | T2 | Q22 |
| 502 | Y2 | D4 | T2 | Q23 |
| 503 | Y2 | D4 | T2 | Q24 |
| 504 | Y2 | D4 | T2 | Q25 |
| 505 | Y2 | D4 | T2 | Q26 |
| 506 | Y2 | D4 | T2 | Q27 |
| 507 | Y2 | D4 | T2 | Q28 |
| 508 | Y2 | D4 | T2 | Q29 |
| 509 | Y2 | D4 | T2 | Q30 |
| 510 | Y2 | D4 | T2 | Q31 |
| 511 | Y3 | D4 | T1 | Q1 |
| 512 | Y3 | D4 | T1 | Q2 |
| 513 | Y3 | D4 | T1 | Q3 |
| 514 | Y3 | D4 | T1 | Q4 |
| 515 | Y3 | D4 | T1 | Q5 |
| 516 | Y3 | D4 | T1 | Q6 |
| 517 | Y3 | D4 | T1 | Q7 |
| 518 | Y3 | D4 | T1 | Q8 |
| 519 | Y3 | D4 | T1 | Q9 |
| 520 | Y3 | D4 | T1 | Q10 |
| 521 | Y3 | D4 | T1 | Q11 |

| | | | | | | | | |
|---|---|---|---|---|---|---|---|---|
| 522 | Y3 | D4 | T1 | Q12 | | 601 | Y2 | D3 | T1 | Q32 |
| 523 | Y3 | D4 | T1 | Q13 | | 602 | Y2 | D3 | T1 | Q33 |
| 524 | Y3 | D4 | T1 | Q14 | | 603 | Y2 | D3 | T1 | Q34 |
| 525 | Y3 | D4 | T1 | Q15 | | 604 | Y2 | D3 | T1 | Q35 |
| 526 | Y3 | D4 | T1 | Q16 | | 605 | Y2 | D3 | T1 | Q36 |
| 527 | Y3 | D4 | T1 | Q17 | | 606 | Y2 | D3 | T1 | Q37 |
| 528 | Y3 | D4 | T1 | Q18 | | 607 | Y2 | D3 | T1 | Q38 |
| 529 | Y3 | D4 | T1 | Q19 | | 608 | Y2 | D3 | T1 | Q39 |
| 530 | Y3 | D4 | T1 | Q20 | | 609 | Y2 | D3 | T1 | Q40 |
| 531 | Y3 | D4 | T1 | Q21 | | 610 | Y2 | D3 | T1 | Q41 |
| 532 | Y3 | D4 | T1 | Q22 | | 611 | Y2 | D3 | T1 | Q42 |
| 533 | Y3 | D4 | T1 | Q23 | | 612 | Y2 | D3 | T1 | Q43 |
| 534 | Y3 | D4 | T1 | Q24 | | 613 | Y2 | D3 | T1 | Q44 |
| 535 | Y3 | D4 | T1 | Q25 | | 614 | Y2 | D3 | T1 | Q45 |
| 536 | Y3 | D4 | T1 | Q26 | | 615 | Y2 | D3 | T1 | Q46 |
| 537 | Y3 | D4 | T1 | Q27 | | 616 | Y2 | D3 | T1 | Q47 |
| 538 | Y3 | D4 | T1 | Q28 | | 617 | Y2 | D3 | T1 | Q48 |
| 539 | Y3 | D4 | T1 | Q29 | | 618 | Y2 | D3 | T1 | Q49 |
| 540 | Y3 | D4 | T1 | Q30 | | 619 | Y2 | D3 | T1 | Q50 |
| 541 | Y3 | D4 | T1 | Q31 | | 620 | Y2 | D3 | T1 | Q51 |
| 542 | Y3 | D4 | T2 | Q1 | | 621 | Y2 | D3 | T1 | Q52 |
| 543 | Y3 | D4 | T2 | Q2 | | 622 | Y2 | D3 | T1 | Q53 |
| 544 | Y3 | D4 | T2 | Q3 | | 623 | Y2 | D3 | T1 | Q54 |
| 545 | Y3 | D4 | T2 | Q4 | | 624 | Y2 | D3 | T1 | Q55 |
| 546 | Y3 | D4 | T2 | Q5 | | 625 | Y2 | D3 | T1 | Q56 |
| 547 | Y3 | D4 | T2 | Q6 | | 626 | Y2 | D3 | T1 | Q57 |
| 548 | Y3 | D4 | T2 | Q7 | | 627 | Y2 | D3 | T1 | Q58 |
| 549 | Y3 | D4 | T2 | Q8 | | 628 | Y2 | D3 | T1 | Q59 |
| 550 | Y3 | D4 | T2 | Q9 | | 629 | Y3 | D3 | T1 | Q32 |
| 551 | Y3 | D4 | T2 | Q10 | | 630 | Y3 | D3 | T1 | Q33 |
| 552 | Y3 | D4 | T2 | Q11 | | 631 | Y3 | D3 | T1 | Q34 |
| 553 | Y3 | D4 | T2 | Q12 | | 632 | Y3 | D3 | T1 | Q35 |
| 554 | Y3 | D4 | T2 | Q13 | | 633 | Y3 | D3 | T1 | Q36 |
| 555 | Y3 | D4 | T2 | Q14 | | 634 | Y3 | D3 | T1 | Q37 |
| 556 | Y3 | D4 | T2 | Q15 | | 635 | Y3 | D3 | T1 | Q38 |
| 557 | Y3 | D4 | T2 | Q16 | | 636 | Y3 | D3 | T1 | Q39 |
| 558 | Y3 | D4 | T2 | Q17 | | 637 | Y3 | D3 | T1 | Q40 |
| 559 | Y3 | D4 | T2 | Q18 | | 638 | Y3 | D3 | T1 | Q41 |
| 560 | Y3 | D4 | T2 | Q19 | | 639 | Y3 | D3 | T1 | Q42 |
| 561 | Y3 | D4 | T2 | Q20 | | 640 | Y3 | D3 | T1 | Q43 |
| 562 | Y3 | D4 | T2 | Q21 | | 641 | Y3 | D3 | T1 | Q44 |
| 563 | Y3 | D4 | T2 | Q22 | | 642 | Y3 | D3 | T1 | Q45 |
| 564 | Y3 | D4 | T2 | Q23 | | 643 | Y3 | D3 | T1 | Q46 |
| 565 | Y3 | D4 | T2 | Q24 | | 644 | Y3 | D3 | T1 | Q47 |
| 566 | Y3 | D4 | T2 | Q25 | | 645 | Y3 | D3 | T1 | Q48 |
| 567 | Y3 | D4 | T2 | Q26 | | 646 | Y3 | D3 | T1 | Q49 |
| 568 | Y3 | D4 | T2 | Q27 | | 647 | Y3 | D3 | T1 | Q50 |
| 569 | Y3 | D4 | T2 | Q28 | | 648 | Y3 | D3 | T1 | Q51 |
| 570 | Y3 | D4 | T2 | Q29 | | 649 | Y3 | D3 | T1 | Q52 |
| 571 | Y3 | D4 | T2 | Q30 | | 650 | Y3 | D3 | T1 | Q53 |
| 572 | Y3 | D4 | T2 | Q31 | | 651 | Y3 | D3 | T1 | Q54 |
| 573 | Y1 | D3 | T1 | Q32 | | 652 | Y3 | D3 | T1 | Q55 |
| 574 | Y1 | D3 | T1 | Q33 | | 653 | Y3 | D3 | T1 | Q56 |
| 575 | Y1 | D3 | T1 | Q34 | | 654 | Y3 | D3 | T1 | Q57 |
| 576 | Y1 | D3 | T1 | Q35 | | 655 | Y3 | D3 | T1 | Q58 |
| 577 | Y1 | D3 | T1 | Q36 | | 656 | Y3 | D3 | T1 | Q59 |
| 578 | Y1 | D3 | T1 | Q37 | | 657 | Y1 | D4 | T1 | Q32 |
| 579 | Y1 | D3 | T1 | Q38 | | 658 | Y1 | D4 | T1 | Q33 |
| 580 | Y1 | D3 | T1 | Q39 | | 659 | Y1 | D4 | T1 | Q34 |
| 581 | Y1 | D3 | T1 | Q40 | | 660 | Y1 | D4 | T1 | Q35 |
| 582 | Y1 | D3 | T1 | Q41 | | 661 | Y1 | D4 | T1 | Q36 |
| 583 | Y1 | D3 | T1 | Q42 | | 662 | Y1 | D4 | T1 | Q37 |
| 584 | Y1 | D3 | T1 | Q43 | | 663 | Y1 | D4 | T1 | Q38 |
| 585 | Y1 | D3 | T1 | Q44 | | 664 | Y1 | D4 | T1 | Q39 |
| 586 | Y1 | D3 | T1 | Q45 | | 665 | Y1 | D4 | T1 | Q40 |
| 587 | Y1 | D3 | T1 | Q46 | | 666 | Y1 | D4 | T1 | Q41 |
| 588 | Y1 | D3 | T1 | Q47 | | 667 | Y1 | D4 | T1 | Q42 |
| 589 | Y1 | D3 | T1 | Q48 | | 668 | Y1 | D4 | T1 | Q43 |
| 590 | Y1 | D3 | T1 | Q49 | | 669 | Y1 | D4 | T1 | Q44 |
| 591 | Y1 | D3 | T1 | Q50 | | 670 | Y1 | D4 | T1 | Q45 |
| 592 | Y1 | D3 | T1 | Q51 | | 671 | Y1 | D4 | T1 | Q46 |
| 593 | Y1 | D3 | T1 | Q52 | | 672 | Y1 | D4 | T1 | Q47 |
| 594 | Y1 | D3 | T1 | Q53 | | 673 | Y1 | D4 | T1 | Q48 |
| 595 | Y1 | D3 | T1 | Q54 | | 674 | Y1 | D4 | T1 | Q49 |
| 596 | Y1 | D3 | T1 | Q55 | | 675 | Y1 | D4 | T1 | Q50 |
| 597 | Y1 | D3 | T1 | Q56 | | 676 | Y1 | D4 | T1 | Q51 |
| 598 | Y1 | D3 | T1 | Q57 | | 677 | Y1 | D4 | T1 | Q52 |
| 599 | Y1 | D3 | T1 | Q58 | | 678 | Y1 | D4 | T1 | Q53 |
| 600 | Y1 | D3 | T1 | Q59 | | 679 | Y1 | D4 | T1 | Q54 |

| | | | |
|---|---|---|---|
| 680 | Y1 | D4 | T1 | Q55 |
| 681 | Y1 | D4 | T1 | Q56 |
| 682 | Y1 | D4 | T1 | Q57 |
| 683 | Y1 | D4 | T1 | Q58 |
| 684 | Y1 | D4 | T1 | Q59 |
| 685 | Y2 | D4 | T1 | Q32 |
| 686 | Y2 | D4 | T1 | Q33 |
| 687 | Y2 | D4 | T1 | Q34 |
| 688 | Y2 | D4 | T1 | Q35 |
| 689 | Y2 | D4 | T1 | Q36 |
| 690 | Y2 | D4 | T1 | Q37 |
| 691 | Y2 | D4 | T1 | Q38 |
| 692 | Y2 | D4 | T1 | Q39 |
| 693 | Y2 | D4 | T1 | Q40 |
| 694 | Y2 | D4 | T1 | Q41 |
| 695 | Y2 | D4 | T1 | Q42 |
| 696 | Y2 | D4 | T1 | Q43 |
| 697 | Y2 | D4 | T1 | Q44 |
| 698 | Y2 | D4 | T1 | Q45 |
| 699 | Y2 | D4 | T1 | Q46 |
| 700 | Y2 | D4 | T1 | Q47 |
| 701 | Y2 | D4 | T1 | Q48 |
| 702 | Y2 | D4 | T1 | Q49 |
| 703 | Y2 | D4 | T1 | Q50 |
| 704 | Y2 | D4 | T1 | Q51 |
| 705 | Y2 | D4 | T1 | Q52 |
| 706 | Y2 | D4 | T1 | Q53 |
| 707 | Y2 | D4 | T1 | Q54 |
| 708 | Y2 | D4 | T1 | Q55 |
| 709 | Y2 | D4 | T1 | Q56 |
| 710 | Y2 | D4 | T1 | Q57 |
| 711 | Y2 | D4 | T1 | Q58 |
| 712 | Y2 | D4 | T1 | Q59 |
| 713 | Y3 | D4 | T1 | Q32 |
| 714 | Y3 | D4 | T1 | Q33 |
| 715 | Y3 | D4 | T1 | Q34 |
| 716 | Y3 | D4 | T1 | Q35 |
| 717 | Y3 | D4 | T1 | Q36 |
| 718 | Y3 | D4 | T1 | Q37 |
| 719 | Y3 | D4 | T1 | Q38 |
| 720 | Y3 | D4 | T1 | Q39 |
| 721 | Y3 | D4 | T1 | Q40 |
| 722 | Y3 | D4 | T1 | Q41 |
| 723 | Y3 | D4 | T1 | Q42 |
| 724 | Y3 | D4 | T1 | Q43 |
| 725 | Y3 | D4 | T1 | Q44 |
| 726 | Y3 | D4 | T1 | Q45 |
| 727 | Y3 | D4 | T1 | Q46 |
| 728 | Y3 | D4 | T1 | Q47 |
| 729 | Y3 | D4 | T1 | Q48 |
| 730 | Y3 | D4 | T1 | Q49 |
| 731 | Y3 | D4 | T1 | Q50 |
| 732 | Y3 | D4 | T1 | Q51 |
| 733 | Y3 | D4 | T1 | Q52 |
| 734 | Y3 | D4 | T1 | Q53 |
| 735 | Y3 | D4 | T1 | Q54 |
| 736 | Y3 | D4 | T1 | Q55 |
| 737 | Y3 | D4 | T1 | Q56 |
| 738 | Y3 | D4 | T1 | Q57 |
| 739 | Y3 | D4 | T1 | Q58 |
| 740 | Y3 | D4 | T1 | Q59 |
| 741 | Y1 | D1 | T1 | Q60 |
| 742 | Y1 | D1 | T1 | Q61 |
| 743 | Y1 | D1 | T1 | Q62 |
| 744 | Y2 | D1 | T1 | Q60 |
| 745 | Y2 | D1 | T1 | Q61 |
| 746 | Y2 | D1 | T1 | Q62 |
| 747 | Y3 | D1 | T1 | Q60 |
| 748 | Y3 | D1 | T1 | Q61 |
| 749 | Y3 | D1 | T1 | Q62 |
| 750 | Y1 | D2 | T1 | Q60 |
| 751 | Y1 | D2 | T1 | Q61 |
| 752 | Y1 | D2 | T1 | Q62 |
| 753 | Y2 | D2 | T1 | Q60 |
| 754 | Y2 | D2 | T1 | Q61 |
| 755 | Y2 | D2 | T1 | Q62 |
| 756 | Y3 | D2 | T1 | Q60 |
| 757 | Y3 | D2 | T1 | Q61 |
| 758 | Y3 | D2 | T1 | Q62 |
| 759 | Y1 | D3 | T1 | Q60 |
| 760 | Y1 | D3 | T1 | Q61 |
| 761 | Y1 | D3 | T1 | Q62 |
| 762 | Y2 | D3 | T1 | Q60 |
| 763 | Y2 | D3 | T1 | Q61 |
| 764 | Y2 | D3 | T1 | Q62 |
| 765 | Y2 | D3 | T1 | Q63 |
| 766 | Y3 | D3 | T1 | Q60 |
| 767 | Y3 | D3 | T1 | Q61 |
| 768 | Y3 | D3 | T1 | Q62 |
| 769 | Y3 | D3 | T1 | Q63 |
| 770 | Y1 | D4 | T1 | Q61 |
| 771 | Y1 | D4 | T1 | Q62 |
| 772 | Y2 | D4 | T1 | Q61 |
| 773 | Y2 | D4 | T1 | Q62 |
| 774 | Y3 | D4 | T1 | Q61 |
| 775 | Y3 | D4 | T1 | Q62 |

Example 201

Synthesis of 1,4-diaza-4-(2H-benzopyran-3-sulfonyl)-7-oxa-1'-(4-pyridyl)spiro[bicyclo[4.3.0]nonane-8,4'-piperidin]-2-one <Step 1>

Synthesis of 1,4-diaza-1'-benzyl-4-vinylsulfonyl-7-oxaspiro[bicyclo[4.3.0]nonane-8,4'-piperidin]-2-one Using the compound (270 mg) obtained in Reference Example 4 <step 1>, the method of synthesis in Example 9 <step 2> was repeated to yield the title compound (300 mg).

NMR spectrum (*CDCl$_3$) δppm: 7.34–7.25(5H,m),6.46 (1H,dd, J=10, 17 Hz),6.31(1H,d,J=17 Hz),6.11(1H,d,J=10 Hz),5.13–5.06(1H,m), 4.24–4.12(2H,m),3.75(1H,d,J=11 Hz),3.53(1H,d,J=17 Hz),3.51(2H, s),3.20(1H,d,J=11 Hz), 2.73–2.62(1H,m),2.59–2.38(4H,m),1.94–1.67(4H,m)

<Step 2>

Synthesis of 1,4-diaza-4-(2H-benzopyran-3-sulfonyl)-1'-benzyl-7-oxaspiro[bicyclo[4.3.0]nonane-8,4'-piperidin]-2-one To a stirred solution of the compound (300 mg) obtained in <step 1> and salicylaldehyde (112 mg) in t-butanol (25 ml), potassium t-butoxide (25 mg) was added at room temperature. The resulting mixture was heated under reflux for 10 hours. After cooling, the reaction mixture was concentrated under reduced pressure. The residue was purified by silica gel column chromatography (eluent; ethyl acetate:methanol=10:0–9:1) to yield the title compound (130 mg).

NMR spectrum (*CDCl$_3$) δppm: 7.36–7.18(8H,m), 7.04–6.96(1H,m), 6.92–6.87(1H,m),5.11(1H,dd,J=4,9 Hz), 4.92–4.80(2H,m),4.28–4.17(2H,m),3.78–3.71(1H,m),3.61 (1H,d,J=17 Hz),3.51(2H,s), 3.22–3.16(1H,m),2.78(1H,dd, J=9,12 Hz),2.60–2.35(4H,m),1.90–1.70 (4H,m)

<Step 3>

Synthesis of 1,4-diaza-4-(2H-benzopyran-3-sulfonyl)-7-oxaspiro[bicyclo[4.3.0]nonane-8,4'-piperidin]-2-one Using the compound (130 mg) obtained in <step 2>, the method of synthesis in Example 7 <step B-1> was repeated to yield the title compound (70 mg).

NMR spectrum (*CDCl$_3$) δppm: 7.36–7.18(3H,m), 7.05–6.98(1H,m), 6.93–6.88(1H,m),5.15(1H,dd,J=4,9 Hz), 4.94–4.81(2H,m),4.30–4.18(2H,m),3.81–3.75(1H,m),3.63 (1H,d,J=17 Hz),3.25–3.19(1H, m),3.08–2.93(2H,m), 2.85–2.72(3H,m),1.85–1.80(1H,m),1.75–1.60(4H,m)

<Step 4>

Synthesis of 1,4-diaza-4-(2H-benzopyran-3-sulfonyl)-7-oxa-1'-(4-pyridyl)spiro[bicyclo[4.3.0]nonane-8,4'-piperidin]-2-one Using the compound (100 mg) obtained in <step 3>, the method of synthesis in Example 1 <step A-7> was repeated to yield the title compound (40 mg).

IR spectrum (KBr) cm$^{-1}$: 1670, 1597, 1460, 1348, 1232, 1161, 968, 544

Example 202

Synthesis of 1,4-diaza-4-(7-chloro-2H-benzopyran-3-sulfonyl)-7-oxa-1'-(4-pyridyl)spiro[bicyclo[4.3.0]nonane-8,4'-piperidin]-2-one <Step 1>

Synthesis of 1,4-diaza-1'-benzyl-4-(7-chloro-4-oxo-4H-benzopyran-3-sulfonyl)-7-oxaspiro[bicyclo[4.3.0]nonane-8,4'-piperidin]-2-one Using the compound (0.50 g) obtained in Reference Example 4 <step 1>, the method of synthesis in Example 9 <step 2> was repeated to yield the title compound (0.49 g).

NMR spectrum (*CDCl$_3$) δppm: 8.65(1H,s),8.19–8.14 (1H,m), 7.59(1H,d,J=2 Hz),7.52–7.47(1H,m),7.36–7.23 (5H,m),5.14–5.08(1H,m),4.60–4.52(1H,m),4.34(1H,d,J=17 Hz),3.78–3.69(2H,m),3.51(2H,s),3.18(1H,d,J=11 Hz), 2.97–2.88(1H,m), 2.60–2.35(4H,m),1.95–1.60(4H,m)

<Step 2>

Synthesis of 1,4-diaza-1'-benzyl-4-(7-chloro-2H-benzopyran-3-sulfonyl)-7-oxaspiro[bicyclo[4.3.0]nonane-8,4'-piperidin]-2-one To a stirred solution of the compound (420 mg) obtained in <step 1> in methanol (10 ml), sodium borohydride (44 mg) was added under cooling with ice. The resulting mixture was stirred at room temperature for 1 hour. The reaction mixture was concentrated under reduced pressure. Saturated aqueous sodium hydrogencarbonate was added to the residue, and then the mixture was extracted with methylene chloride. The organic layer was washed with saturated aqueous sodium chloride, dried with anhydrous sodium sulfate and the solvent was distilled off under reduced pressure. The residue was dissolved with methylene chloride (10 ml). To the solution, triethylamine (0.65 ml) and methanesulfonyl chloride (0.12 ml) were added successively under cooling with ice. The resulting mixture was stirred at room temperature for 1 hour. Saturated aqueous sodium hydrogencarbonate was added to the reaction mixture, stirred at room temperature for 30 minutes, and then the mixture was extracted with methylene chloride. The organic layer was washed with saturated aqueous sodium chloride, dried with anhydrous sodium sulfate and the solvent was distilled off under reduced pressure. The residue was purified by silica gel column chromatography (eluent; ethyl acetate) to yield the title compound (334 mg).

NMR spectrum (*CDCl$_3$) δppm: 7.36–7.22(6H,m), 7.15–7.10(1H,m), 7.02–6.97(1H,m),6.93–6.90(1H,m),5.11 (1H,dd,J=4,9 Hz),4.93–4.81(2H,m),4.28–4.17(2H,m), 3.79–3.72(1H,m),3.62(1H,d, J=17 Hz),3.51(2H,s), 3.24–3.17(1H,m),2.79(1H,dd,J=9,12 Hz), 2.60–2.35(4H,m), 1.93–1.83(1H,m),1.82–1.67(3H,m)

<Step 3>

Synthesis of 1,4-diaza-4-(7-chloro-2H-benzopyran-3-sulfonyl)-7-oxaspiro[bicyclo[4.3.0]nonane-8,4'-piperidin]-2-one Using the compound (330 mg) obtained in <step 2>, the method of synthesis in Example 7 <step B-1> was repeated to yield the title compound (217 mg).

NMR spectrum (*CDCl$_3$) δppm: 7.29(1H,s),7.16–7.11 (1H,m), 7.02–6.97(1H,m),6.94–6.91(1H,m),5.18–5.10(1H, m),4.95–4.82(2H,m),4.30–4.17(2H,m),3.82–3.75(1H,m), 3.63(1H,d, J=17 Hz),3.27–3.18(1H,m),3.09–2.93(2H,m), 2.87–2.73(3H,m), 1.87–1.77(1H,m),1.75–1.55(4H,m)

<Step 4>

Synthesis of 1,4-diaza-4-(7-chloro-2H-benzopyran-3-sulfonyl)-7-oxa-1'-(4-pyridyl)spiro[bicyclo[4.3.0]nonane-8,4'-piperidin]-2-one Using the compound (50 mg) obtained in <step 3>, the method of synthesis in Example 1 <step A-7> was repeated to yield the title compound (35 mg).

IR spectrum (KBr) cm$^{-1}$: 1672, 1599, 1462, 1348, 1228, 1159, 1076, 968

Example 209

Synthesis of 1,4-diaza-4-(benzo[b]thiophen-2-ylsulfonyl)-7-oxa-1'-(4-pyridyl)spiro[bicyclo[4.3.0]nonane-8,4'-piperidin]-2-one Using the compound (50 mg) obtained in Reference Example 3 <step 7>, the method of synthesis in Example 9 <step 2> was repeated to yield the title compound (70 mg).

IR spectrum (KBr) cm$^{-1}$: 1672, 1595, 1460, 1360, 1165, 970, 631, 550

Example 210

Synthesis of 1,4-diaza-4-(5-fluorobenzo[b]thiophen-2-ylsulfonyl)-7-oxa-1'-(4-pyridyl)spiro[bicyclo[4.3.0]nonane-8,4'-piperidin]-2-one Using the compound (50 mg) obtained in Reference Example 3 <step 7>, the method of synthesis in Example 9 <step 2> was repeated to yield the title compound (89 mg).

IR spectrum (KBr) cm$^{-1}$: 1672, 1595, 1508, 1427, 1362, 1167, 1128, 627

Example 211

Synthesis of 1,4-diaza-4-(5-chlorobenzo[b]thiophen-2-ylsulfonyl)-7-oxa-1'-(4-pyridyl)spiro[bicyclo[4.3.0]nonane-8,4'-piperidin]-2-one Using the compound (50 mg) obtained in Reference Example 3 <step 7>, the method of synthesis in Example 9 <step 2> was repeated to yield the title compound (85 mg).

IR spectrum (KBr) cm$^{-1}$: 1672, 1595, 1460, 1362, 1165, 970, 642, 552

Example 213

Synthesis of 1,4-diaza-4-(6-chlorobenzo[b]thiophen-2-ylsulfonyl)-7-oxa-1'-(4-pyridyl)spiro[bicyclo[4.3.0]nonane-8,4'-piperidin]-2-one Using the compound (100 mg) obtained in Reference Example 3 <step 7>, the method of synthesis in Example 9 <step 2> was repeated to yield the title compound (135 mg).

IR spectrum (KBr) cm$^{-1}$: 1672, 1595, 1462, 1362, 1165, 1103, 999, 970

Example 219

Synthesis of 1,4-diaza-4-(6-chloro-5-fluorobenzo[b]thiophen-2-ylsulfonyl)-7-oxa-1'-(4-pyridyl)spiro[bicyclo[4.3.0]nonane-8,4'-piperidin]-2-one Using the compound (20 mg) obtained in Reference Example 3 <step 7>, the method of synthesis in Example 9 <step 2> was repeated to yield the title compound (23 mg).

IR spectrum (KBr) cm$^{-1}$: 1674, 1597, 1496, 1462, 1363, 1230, 1167, 970

Example 220

Synthesis of 1,4-diaza-4-(5-chloro-3-methylbenzo[b]thiophen-2-ylsulfonyl)-7-oxa-1'-(4-pyridyl)spiro[bicyclo[4.3.0]nonane-8,4'-piperidin]-2-one Using the compound (50 mg) obtained in Reference Example 3 <step 7>, the method of synthesis in Example 9 <step 2> was repeated to yield the title compound (83 mg).

IR spectrum (KBr) cm$^{-1}$: 1672, 1595, 1510, 1460, 1356, 1167, 970, 555

Example 223

Synthesis of 1,4-diaza-4-(5-chlorobenzo[b]furan-2-ylsulfonyl)-7-oxa-1'-(4-pyridyl)spiro[bicyclo[4.3.0]nonane-8,4'-piperidin]-2-one Using the compound (130 mg) obtained in Reference Example 3 <step 7>, the method of synthesis in Example 9 <step 2> was repeated to yield the title compound (185 mg).

IR spectrum (KBr) cm$^{-1}$: 1672, 1595, 1462, 1373, 1232, 1165, 970, 808

Example 224

Synthesis of 1,4-diaza-4-(5-bromobenzo[b]furan-2-ylsulfonyl)-7-oxa-1'-(4-pyridyl)spiro[bicyclo[4.3.0]nonane-8,4'-piperidin]-2-one Using the compound (464 mg) obtained in Reference Example 3 <step 7>, the method of synthesis in Example 9 <step 2> was repeated to yield the title compound (820 mg).

IR spectrum (KBr) cm$^{-1}$: 1672, 1595, 1462, 1373, 1165, 970, 806, 631

Example 275

Synthesis of 1,4,7-triaza-4-(6-chlorobenzo[b]thiophen-2-ylsulfonyl)-1'-(4-pyridyl)spiro[bicyclo[4.3.0]nonane-8,4'-piperidin]-2-one
<Step 1>
Synthesis of 1,4,7-triaza-1'-benzyl-4-(benzyloxycarbonyl)spiro[bicyclo[4.3.0]nonane-8,4'-piperidin]-2-one Using the compound (7.43 g) obtained in Reference Example 3 <step 2> and 4-amino-4-(aminomethyl)-1-benzylpiperidine (7.00 g), the method of synthesis in Example 1 <step A-3> was repeated to yield the title compound (8.99 g).

NMR spectrum (*DMSO-d$_6$, 100° C.) δppm: 7.40–7.20 (10H,m), 5.11(2H,s),4.51–4.40(1H,m),4.28–4.14(2H,m), 3.67(1H,d, J=18 Hz),3.48(2H,s),3.35(1H,d,J=11 Hz),3.04 (1H,d,J=11 Hz), 2.89–2.72(2H,m),2.60–2.45(2H,m), 2.37–2.23(2H,m),1.70–1.50(4H,m)
<Step 2>
Synthesis of 1,4,7-triaza-4-(benzyloxycarbonyl)spiro [bicyclo[4.3.0]nonane-8,4'-piperidin]-2-one Using the compound (6.00 g) obtained in <step 1>, the method of synthesis in Example 7 <step B-1> was repeated to yield the title compound (3.66 g).

NMR spectrum (*DMSO-d$_6$, 100° C.) δppm: 7.40–7.30 (5H,m), 5.12(2H,s),4.52–4.42(1H,m),4.28–4.20(1H,m),4.19 (1H,d, J=18 Hz),3.67(1H,d,J=18 Hz),3.34(1H,d,J=11 Hz), 3.07–2.69(5H,m), 2.63–2.45(2H,m),1.57–1.38(4H,m)
<Step 3>
Synthesis of 1,4,7-triaza-4-(benzyloxycarbonyl)-1'-(4-pyridyl)spiro[bicyclo[4.3.0]nonane-8,4'-piperidin]-2-one Using the compound (3.66 g) obtained in <step 2>, the method of synthesis in Example 1 <step A-7> was repeated to yield the title compound (2.85 g).

NMR spectrum (*DMSO-d$_{6, 100}$° C.) δppm: 8.12(2H,dd, J=2,5 Hz), 7.39–7.27(5H,m),6.75(2H,dd,J=2,5 Hz),5.12(2H, s),4.58–4.47(1H, m),4.30–4.17(2H,m),3.70(1H,d,J=18 Hz), 3.48–3.30(5H,m), 3.11(1H,d,J=11 Hz),2.94–2.82(1H,m), 1.79–1.55(4H,m)

<Step 4>
Synthesis of 1,4,7-triaza-1'-(4-pyridyl)spiro[bicyclo [4.3.0]nonane-8,4'-piperidin]-2-one Using the compound (1.20 g) obtained in <step 3>, the method of synthesis in Example 20 <step 4> was repeated to yield the title compound (0.77 g).

NMR spectrum (*CDCl$_3$) δppm: 8.30–8.23(2H,m), 6.72–6.65(2H,m), 4.55–4.46(1H,m),3.67–3.36(8H,m),3.25 (1H,d,J=12 Hz),2.58–2.46(1H,m),2.00–1.65(6H,m)
<Step 5>
Synthesis of 1,4,7-triaza-4-(6-chlorobenzo[b]thiophen-2-ylsulfonyl)-1'-(4-pyridyl)spiro[bicyclo[4.3.0]nonane-8,4'-piperidin]-2-one Using the compound (120 mg) obtained in <step 4>, the method of synthesis in Example 9 <step 2> was repeated to yield the title compound (143 mg).

IR spectrum (KBr) cm$^{-1}$: 1666, 1601, 1473, 1429, 1340, 1161, 968, 596

Example 285

Synthesis of 1,4,7-triaza-4-(5-chlorobenzo[b]furan-2-ylsulfonyl)-1'-(4-pyridyl)spiro[bicyclo[4.3.0]nonane-8,4'-piperidin]-2-one Using the compound (120 mg) obtained in Example 275 <step 4>, the method of synthesis in Example 9 <step 2> was repeated to yield the title compound (135 mg).

IR spectrum (KBr) cm$^{-1}$: 1657, 1597, 1460, 1441, 1369, 1165, 808

Example 337

Synthesis of 1,4,7-triaza-4-(6-chlorobenzo[b]thiophen-2-ylsulfonyl)-7-methyl-1'-(4-pyridyl)spiro[bicyclo[4.3.0] nonane-8,4'-piperidin]-2-one
<Step 1>
Synthesis of 1,4,7-triaza-4-(benzyloxycarbonyl)-7-methyl-1'-(4-pyridyl)spiro[bicyclo[4.3.0]nonane-8,4'-piperidin]-2-one Using the compound (1.65 g) obtained in Example 275 <step 3>, the method of synthesis in Example 74 was repeated to yield the title compound (1.33 g).

NMR spectrum (*DMSO-d$_{6, 100}$° C.) δppm: 8.17–8.10 (2H,m),7.40–7.25(5H,m),6.79–6.73(2H,m),5.14(2H,s), 4.38–4.28(1H,m), 4.24(1H,d,J=18 Hz),4.13–4.05(1H,m), 3.98–3.84(2H,m),3.76(1H, d,J=18 Hz),3.61(1H,d,J=11 Hz), 3.37(1H,d,J=11 Hz),3.00–2.66(3H, m),2.21(3H,s), 1.93–1.78(1H,m),1.76–1.50(2H,m),1.48–1.34(1H,m)
<Step 2>
Synthesis of 1,4,7-triaza-7-methyl-1'-(4-pyridyl)spiro [bicyclo[4.3.0]nonane-8,4'-piperidin]-2-one Using the compound (1.20 g) obtained in <step 1>, the method of synthesis in Example 20 <step 4> was repeated to yield the title compound (0.82 g).

NMR spectrum (*CDCl$_3$) δppm: 8.31–8.24(2H,m), 6.72–6.50(2H,m), 4.08–3.90(3H,m),3.75–3.30(5H,m), 3.00–2.78(2H,m),2.51(1H,dd, J=9,12 Hz),2.25(3H,s),2.03 (1H,brs),2.01–1.88(1H,m),1.85–1.70(1H,m),1.63–1.44(2H, m)
<Step 3>
Synthesis of 1,4,7-triaza-4-(6-chlorobenzo[b]thiophen-2-ylsulfonyl)-7-methyl-1'-(4-pyridyl)spiro[bicyclo[4.3.0] nonane-8,4'-piperidin]-2-one Using the compound (120 mg) obtained in <step 2>, the method of synthesis in Example 9 <step 2> was repeated to yield the title compound (121 mg).

IR spectrum (KBr) cm$^{-1}$: 1666, 1595, 1460, 1358, 1161, 1001, 604

Example 347

Synthesis of 1,4,7-triaza-4-(5-chlorobenzo[b]furan-2-ylsulfonyl)-7-methyl-1'-(4-pyridyl)spiro[bicyclo[4.3.0]nonane-8,4'-piperidin]-2-one Using the compound (120 mg) obtained in Example 337 <step 2>, the method of synthesis in Example 9 <step 2> was repeated to yield the title compound (140 mg).

IR spectrum (KBr) cm$^{-1}$: 1664, 1595, 1460, 1379, 1169, 808, 631

Example 388

Synthesis of 1,4-diaza-4-(7-chloro-2H-benzopyran-3-sulfonyl)-6-(methoxymethyl)-7-oxa-1'-(4-pyridyl)spiro[bicyclo[4.3.0]nonane-8,4'-piperidin]-2-one <Step 1>

Synthesis of ethyl 2-[(benzyloxycarbonyl) (2-hydroxy-3-methoxypropan-1-yl)amino]acetate A solution of glycine ethyl ester (19.3 g) and glycidyl methyl ether (16.5 g) in ethanol (60 ml) was stirred at room temperature for 6 hours. The reaction mixture was concentrated under reduced pressure. The residue was dissolved with tetrahydrofuran (100 ml), and then to the solution water (100 ml) and sodium carbonate (16.0 g) were added successively To the resulting mixture, benzyl chloroformate (21.6 ml) was added under cooling with ice and the mixture was stirred at room temperature overnight. Water was added to the reaction mixture and extracted with diethyl ether. The organic layers were washed with saturated aqueous sodium chloride, dried with anhydrous sodium sulfate and the solvent was distilled off under reduced pressure. The residue was purified by silica gel column chromatography (eluent; n-hexane:ethyl acetate=1:1) to yield the title compound (13.5 g).

NMR spectrum (*DMSO-d$_6$, 100° C.) δppm: 7.40–7.25 (5H,m), 5.07(2H,s),4.50–4.45(1H,m),4.14–4.04(4H,m), 3.85–3.75(1H,m), 3.50–3.42(1H,m),3.30–3.13(3H,m),3.24 (3H,s),1.16(3H,t,J=7 Hz)

<Step 2>

Synthesis of ethyl 2-[(benzyloxycarbonyl)(3-methoxy-2-oxopropan-1-yl)amino]acetate Using the compound (20.0 g) obtained in <step 1>, the method of synthesis in Example 1 <step D-3> was repeated to yield the title compound (19.6 g).

NMR spectrum (*DMSO-d$_6$, 100° C.) δppm: 7.40–7.20 (5H,m), 5.07(2H,s),4.23(2H,s),4.14–4.05(2H,m),4.05(2H, s),4.03(2H,s), 3.29(3H,s),1.25–1.15(3H,m)

<Step 3>

Synthesis of 1,4-diaza-1'-benzyl-4-(benzyloxycarbonyl)-6-(methoxymethyl)-7-oxaspiro[bicyclo[4.3.0]nonane-8,4'-piperidin]-2-one Using the compound (5.10 g) obtained in <step 2>, the method of synthesis in Example 1 <step A-3> was repeated to yield the title compound (6.30 g).

NMR spectrum (*DMSO-d$_6$, 100° C.) δppm: 7.40–7.20 (10H,m),5.17–5.06(2H,m),4.35(1H,d,J=13 Hz),4.22(1H,d, J=18 Hz),4.12(1H,d, J=12 Hz),3.80(1H,d,J=18 Hz),3.47 (2H,s),3.37(1H,d,J=11 Hz), 3.31(1H,d,J=11 Hz),3.23(3H,s), 3.10–2.89(2H,m),2.58–2.43(2H, m),2.38–2.26(2H,m), 1.83–1.72(2H,m),1.58–1.43(2H,m)

<Step 4>

Synthesis of 1,4-diaza-1'-benzyl-6-(methoxymethyl)-7-oxaspiro[bicyclo[4.3.0]nonane-8,4'-piperidin]-2-one Using the compound (6.30 g) obtained in <step 3>, the method of synthesis inof Example 1 <step B-3> was repeated to yield the title compound (3.01 g).

NMR spectrum (*CDCl$_3$) δppm: 7.40–7.20(5H,m),4.38 (1H,d, J=12 Hz),3.60–3.30(7H,m),3.38(3H,s),3.03(1H,d,J= 12 Hz),2.73–2.50(2H,m),2.62(1H,d,J=13 Hz),2.45–2.25 (2H,m),1.90–1.70(2H, m) 11.67–1.45 (2H,m)

<Step 5>

Synthesis of 1,4-diaza-1'-benzyl-4-(7-chloro-4-oxo-4H-benzopyran-3-sulfonyl)-6-(methoxymethyl)-7-oxaspiro[bicyclo[4.3.0]nonane-8,4'-piperidin]-2-one Using the compound (2.85 g) obtained in <step 4>, the method of synthesis in Example 9 <step 2> was repeated to yield the title compound (0.86 g).

NMR spectrum (*CDCl$_3$) δppm: 8.65(1H,s),8.17(1H,d, J=9 Hz), 7.59(1H,d,J=2 Hz),7.49(1H,dd,J=2,9 Hz), 7.35–7.20(5H,m),4.47–4.37(2H,m),4.28–4.20(1H,m),3.85 (1H,d,J=17 Hz),3.59(1H,d, J=10 Hz),3.55–3.43(3H,m),3.35 (3H,s),3.18–3.10(1H,m),2.83(1H, d,J=13 Hz),2.68–2.48 (2H,m),2.42–2.25(2H,m),2.00–1.77(2H,m), 1.73–1.45 (2H, m)

<Step 6>

Synthesis of 1,4-diaza-1'-benzyl-4-(7-chloro-2H-benzopyran-3-sulfonyl)-6-(methoxymethyl)-7-oxaspiro[bicyclo[4.3.0]nonane-8,4'-piperidin]-2-one Using the compound (700 mg) obtained in <step 5>, the method of synthesis in Example 202 <step 2> was repeated to yield the title compound (482 mg).

NMR spectrum (*CDCl$_3$) δppm: 7.35–7.21(6H,m), 7.15–7.10(1H,m), 7.01–6.97(1H,m),6.92(1H,d,J=2 Hz), 4.95–4.81(2H,m),4.30–4.17(3H,m),3.65(1H,d,J=17 Hz), 3.63–3.56(1H,m),3.50(2H,s), 3.50–3.43(1H,m),3.39(3H,s), 3.12(1H,d,J=11 Hz),2.68(1H,d, J=12 Hz),2.68–2.48(2H,m), 2.42–2.29(2H,m),2.00–1.77(2H,m), 1.70–1.46(2H,m)

<Step 7>

Synthesis of 1,4-diaza-4-(7-chloro-2H-benzopyran-3-sulfonyl)-6-(methoxymethyl)-7-oxaspiro[bicyclo[4.3.0]nonane-8,4'-piperidin]-2-one Using the compound (480 mg) obtained in <step 6>, the method of synthesis in Example 7 <step B-1> was repeated to yield the title compound (345 mg)

NMR spectrum (*CDCl$_3$) δppm: 7.27(1H,s),7.13(1H,d, J=8 Hz), 7.02–6.97(1H,m),6.94–6.90(1H,m),4.96–4.82(2H, m),4.35–4.17(3H,m),3.66(1H,d,J=17 Hz),3.61(1H,d,J=10 Hz),3.47(1H,d, J=10 Hz),3.40(3H,s),3.13(1H,d,12 Hz), 3.17–2.93(2H,m),2.79–2.65(2H,m),2.69(1H,d,J=12 Hz), 1.93–1.73(2H,m),1.65–1.42(3H,m)

<Step 8>

Synthesis of 1,4-diaza-4-(7-chloro-2H-benzopyran-3-sulfonyl)-6-(methoxymethyl)-7-oxa-1'-(4-pyridyl)spiro [bicyclo[4.3.0]nonane-8,4'-piperidin]-2-one Using the compound (330 mg) obtained in <step 7>, the method of synthesis in Example 1 <step A-7> was repeated to yield the title compound (160 mg).

IR spectrum (KBr) cm$^{-1}$: 1672, 1597, 1450, 1419, 1350, 1151, 1105, 1076

Example 399

Synthesis of 1,4-diaza-4-(6-chlorobenzo[b]thiophen-2-ylsulfonyl)-6-(methoxymethyl)-7-oxa-1'-(4-pyridyl)spiro [bicyclo[4.3.0]nonane-8,4'-piperidin]-2-one <Step 1>

Synthesis of 1,4-diaza-4-(benzyloxycarbonyl)-6-(methoxymethyl)-7-oxaspiro[bicyclo[4.3.0]nonane-8,4'-piperidin]-2-one Using the compound (3.50 g) obtained in Example 388 <step 3>, the method of synthesis in Example 7 <step B-1> was repeated to yield the title compound (2.23 g).

NMR spectrum (DMSO-d$_6$, 100° C.) δppm: 7.39–7.26 (5H,m),5.18–5.05(2H,m),4.36(1H,d,J=13 Hz),4.23(1H,d,J= 18 Hz),4.13(1H,d, J=12 Hz),3.80(1H,d,J=18 Hz),3.38(1H, d,J=11 Hz),3.30(1H,d, J=11 Hz),3.24(3H,s),3.08–2.50(7H, m),1.76–1.60(2H,m),1.48–1.32(2H,m)

<Step 2>
Synthesis of 1,4-diaza-4-(benzyloxycarbonyl)-6-(methoxymethyl)-7-oxa-1'-(4-pyridly)spiro[bicyclo[4.3.0]nonane-8,4'-piperidin]-2-one Using the compound (2.10 g) obtained in <step 1>, the method of synthesis in Example 1 <step A-7> was repeated to yield the title compound (1.25 g).

NMR spectrum (DMSO-d$_6$, 100° C.) δppm: 8.15–8.09 (2H,m),7.40–7.25(5H,m),6.78–6.72(2H,m),5.20–5.05(2H,m),4.40–4.12(3H,m), 3.83(1H,d,J=17 Hz),3.47–3.21(9H,m),3.16(1H,d,J=12 Hz),2.99(1H, d,J=13 Hz),1.93–1.72(2H,m),1.63–1.53(2H,m)

<Step 3>
Synthesis of 1,4-diaza-6-(methoxymethyl)-7-oxa-1'-(4-pyridly)spiro[bicyclo[4.3.0]nonane-8,4'-piperidin]-2-one Using the compound (1.24 g) obtained in <step 2>, the method of synthesis in Example 20 <step 4> was repeated to yield the title compound (0.84 g).

NMR spectrum (*CDCl$_3$) δppm: 8.28–8.21(2H,m), 6.73–6.65(2H,m), 4.40(1H,d,J=12 Hz),3.65–3.35(9H,m), 3.40(3H,s),3.15(1H,d, J=12 Hz),2.64(1H,d,J=13 Hz), 2.75–2.50(1H,m),1.94–1.83(2H,m), 1.73–1.57(2H,m)

<Step 4>
Synthesis of 1,4-diaza-4-(6-chlorobenzo[b]thiophen-2-ylsulfonyl)-6-(methoxymethyl)-7-oxa-1'-(4-pyridyl)spiro[bicyclo[4.3.0]nonane-8,4'-piperidin]-2-one Using the compound (90 mg) obtained in <step 3>, the method of synthesis in Example 9 <step 2> was repeated to yield the title compound (115 mg).

IR spectrum (KBr) cm$^{-1}$: 1680, 1597, 1415, 1360, 1163, 1105, 1005, 972

Example 409

Synthesis of 1,4-diaza-4-(5-chlorobenzo[b]furan-2-ylsulfonyl)-6-(methoxymethyl)-7-oxa-1'-(4-pyridyl)spiro[bicyclo[4.3.0]nonane-8,4'-piperidin]-2-one Using the compound (100 mg) obtained in Example 399 <step 3>, the method of synthesis in Example 9 <step 2> was repeated to yield the title compound (137 mg).

IR spectrum (KBr) cm$^{-1}$: 1674, 1595, 1441, 1419, 1373, 1151, 1119, 808

Example 461

Synthesis of 1,4,7-triaza-4-(6-chlorobenzo[b]thiophen-2-ylsulfonyl)-6-(methoxymethyl)-1'-(4-pyridyl)spiro[bicyclo[4.3.0]nonane-8,4'-piperidin]-2-one <Step 1>
Synthesis of 1,4,7-triaza-1'-benzyl-4-(benzyloxycarbonyl)-6-(methoxymethyl)spiro[bicyclo[4.3.0]nonane-8,4'-piperidin]-2-one Using the compound (19.0 g) obtained in Example 388 <step 2> and 4-amino-4-(aminomethyl)-1-benzylpiperidine (15.4 g), the method of synthesis in Example 1 <step A-3> was repeated to yield the title compound (23.9 g).

NMR spectrum (*DMSO-d$_6$, 100° C.) δppm: 7.37–7.17 (10H,m), 5.14(1H,d,J=13 Hz),5.08(1H,d,J=13 Hz), 4.23–4.14(1H,m),4.22(1H, d,J=13 Hz),4.02–3.96(1H,m), 3.77–3.68(1H,m),3.46(2H,s), 3.32(1H,d,J=10 Hz),3.25(1H,d,J=10 Hz),3.22(3H,s),2.88–2.82(1H, m),2.80(1H,d,J=13 Hz),2.58–2.45(2H,m),2.29–2.17(2H,m),1.75–1.59(2H,m), 1.44–1.38(2H,m)

<Step 2>
Synthesis of 1,4,7-triaza-4-(benzyloxycarbonyl)-6-(methoxymethyl)spiro[bicyclo[4.3.0]nonane-8,4'-piperidin]-2-one Using the compound (18.9 g) obtained in <step 1>, the method of synthesis in Example 7 <step B-1> was repeated to yield the title compound (13.5 g).

NMR spectrum (*DMSO-d$_6$, 100° C.) δppm: 7.39–7.26 (5H,m), 5.14(1H,d,J=13 Hz),5.09(1H,d,J=13 Hz),4.23–4.14 (1H,m),4.22(1H, d,J=13 Hz),4.01(1H,d,J=11 Hz),3.77–3.68 (1H,m),3.35–3.22(2H,m), 3.23(3H,s),2.96–2.75(4H,m), 2.63–2.46(2H,m),1.66–1.48(2H,m), 1.35–1.27 (2H,m)

<Step 3>
Synthesis of 1,4,7-triaza-4-(benzyloxycarbonyl)-6-(methoxymethyl)-1'-(4-pyridyl)spiro[bicyclo[4.3.0]nonane-8,4'-piperidin]-2-one Using the compound (12.0 g) obtained in <step 2>, the method of synthesis in Example 1 <step A-7> was repeated to yield the title compound (7.27 g).

NMR spectrum (*DMSO-d$_6$, 100° C.) δppm: 8.16–8.08 (2H,m),7.42–7.26(5H,m),6.80–6.73(2H,m),5.15(1H,d,J=13 Hz),5.10(1H,d, J=13 Hz),4.24(1H,d,J=12 Hz),4.21(1H,d,J= 18 Hz),4.05(1H,d, J=11 Hz),3.76(1H,d,J=18 Hz),3.50–3.22 (6H,m),3.24(3H,s),3.06–2.76(2H,m),1.85–1.65(2H,m), 1.56–1.46(2H,m)

<Step 4>
Synthesis of 1,4,7-triaza-6-(methoxymethyl)-1'-(4-pyridyl)spiro[bicyclo[4.3.0]nonane-8,4'-piperidin]-2-one Using the compound (1.00 g) obtained in <step 3>, the method of synthesis in Example 20 <step 4> was repeated to yield the title compound (0.70 g).

NMR spectrum (*CDCl$_3$) δppm: 8.25(2H,dd,J=1, 5 Hz), 6.67(2H,dd, J=1,5 Hz),4.36–4.28(1H,m),3.71–3.64(1H,m), 3.62(1H,d,J=18 Hz), 3.55–3.27(5H,m),3.48(1H,d,J=18 Hz), 3.41(3H,s),3.36(1H,d, J=13 Hz),3.04–2.96(1H,m),2.57(1H, d,J=13 Hz),1.93–1.73(2H,m), 1.66–1.53 (2H,m)

<Step 5>
Synthesis of 1,4,7-triaza-4-(6-chlorobenzo[b]thiophen-2-ylsulfonyl)-6-(methoxymethyl)-1'-(4-pyridyl)spiro[bicyclo[4.3.0]nonane-8,4'-piperidin]-2-one Using the compound (110 mg) obtained in <step 4>, the method of synthesis in Example 9 <step 2> was repeated to yield the title compound (128 mg).

IR spectrum (KBr) cm$^{-1}$: 1662, 1595, 1452, 1421, 1360, 1167, 1105

Example 471

Synthesis of 1,4,7-triaza-4-(5-chlorobenzo[b]furan-2-ylsulfonyl)-6-(methoxymethyl)-1'-(4-pyridyl)spiro[bicyclo[4.3.0]nonane-8,4'-piperidin]-2-one Using the compound (160 mg) obtained in Example 461 <step 4>, the method of synthesis in Example 9 <step 2> was repeated to yield the title compound (193 mg).

IR spectrum (KBr) cm$^{-1}$: 1664, 1595, 1441, 1421, 1369, 1167, 1107, 806

Example 523

Synthesis of 1,4,7-triaza-4-(6-chlorobenzo[b]thiophen-2-ylsulfonyl)-6-(methoxymethyl)-7-methyl-1'-(4-pyridyl)spiro[bicyclo[4.3.0]nonane-8,4'-piperidin]-2-one <Step 1>
Synthesis of 1,4,7-triaza-4-(benzyloxycarbonyl)-6-(methoxymethyl)-7-methyl-1'-(4-pyridyl)spiro[bicyclo[4.3.0]nonane-8,4'-piperidin]-2-one Using the compound (3.00 g) obtained in Example 461 <step 3>, the method of synthesis in Example 74 was repeated to yield the title compound (2.85 g).

NMR spectrum (*DMSO-d$_6$, 100° C.) δppm: 8.16–8.10 (2H,m),7.42–7.27(5H,m),6.80–6.73(2H,m),5.13(2H,s),4.37 (1H,d,J=13 Hz), 4.28–4.18(2H,m),3.97–3.75(3H,m), 3.48–3.42(1H,m),3.37–3.30(1H,m),3.21(3H,s),3.14–2.77 (4H,m),2.34(3H,s),1.97–1.85(1H,m),1.80–1.57(2H,m), 1.28–1.17(1H,m)

<Step 2>

Synthesis of 1,4,7-triaza-6-(methoxymethyl)-7-methyl-1'-(4-pyridyl)spiro[bicyclo[4.3.0]nonane-8,4'-piperidin]-2-one Using the compound (1.00 g) obtained in <step 1>, the method of synthesis in Example 20 <step 4> was repeated to yield the title compound (0.72 g).

NMR spectrum (*CDCl$_3$) δppm: 8.28–8.23(2H,m), 6.67–6.62(2H,m), 4.53(1H,d,J=12 Hz),3.98–3.82(2H,m), 3.63–3.50(3H,m),3.47–3.33(2H,m),3.36(3H,s),3.05(1H,d, J=12 Hz),3.02–2.76(2H,m), 2.65(1H,d,J=13 Hz),2.34(3H,s), 2.03–1.92(1H,m),1.86–1.73(1H, m),1.67–1.57(1H,m), 1.32–1.22(1H,m)

<Step 3>

Synthesis of 1,4,7-triaza-4-(6-chlorobenzo[b]thiophen-2-ylsulfonyl)-6-(methoxymethyl)-7-methyl-1'-(4-pyridyl)spiro[bicyclo[4.3.0]nonane-8,4'-piperidin]-2-one Using the compound (120 mg) obtained in <step 2>, the method of synthesis in Example 9 <step 2> was repeated to yield the title compound (113 mg).

IR spectrum (KBr) cm$^{-1}$: 1662, 1595, 1452, 1421, 1360, 1167, 602

Example 533

Synthesis of 1,4,7-triaza-4-(5-chlorobenzo[b]furan-2-ylsulfonyl)-6-(methoxymethyl)-7-methyl-1'-(4-pyridyl)spiro[bicyclo[4.3.0]nonane-8,4'-piperidin]-2-one Using the compound (170 mg) obtained in Example 523 <step 2>, the method of synthesis in Example 9 <step 2> was repeated to yield the title compound (205 mg).

IR spectrum (KBr) cm$^{-1}$: 1664, 1595, 1441, 1371, 1171, 1120, 806, 633

Example 574

Synthesis of 1,4-diaza-4-(6-chlorobenzo[b]furan-2-ylsulfonyl)-7-oxa-1'-(4-pyridyl)spiro[bicyclo[4.3.0]nonane-8,4'-piperidin]-2-one Using the compound (50 mg) obtained in Reference Example 3 <step 7>, the method of synthesis in Example 9 <step 2> was repeated to yield the title compound (76 mg).

IR spectrum (KBr) cm$^{-1}$: 1674, 1595, 1464, 1371, 1169, 970, 933, 646

Example 580

Synthesis of 1,4-diaza-4-(indol-2-ylsulfonyl)-7-oxa-1'-(4-pyridyl)spiro[bicyclo[4.3.0]nonane-8,4'-piperidin]-2-one <Step 1>

Synthesis of 1,4-diaza-4-[1-(benzenesulfonyl)indol-2-ylsulfonyl]-7-oxa-1'-(4-pyridyl)spiro[bicyclo[4.3.0]nonane-8,4'-piperidin]-2-one Using the compound (100 mg) obtained in Reference Example 3 <step 7>, the method of synthesis in Example 9 <step 2> was repeated to yield the title compound (96 mg).

NMR spectrum (CDCl$_3$) δppm: 8.30–8.23(2H,m), 8.17–8.03(1H,m), 7.86–7.75(2H,m),7.65–7.25(7H,m), 6.70–6.63(2H,m),5.26–5.06(1H,m),4.18–3.50(5H,m), 3.44–3.12(4H,m),3.08–2.90(1H,m), 2.00–1.70(4H,m)

<Step 2>

Synthesis of 1,4-diaza-4-(indol-2-ylsulfonyl)-7-oxa-1'-(4-pyridyl)spiro[bicyclo[4.3.0]nonane-8,4'-piperidin]-2-one To a stirred solution of the compound (38 mg) obtained in <step 1> in tetrahydrofuran (0.35 ml), potassium hydroxide (3.54 mg) in methanol (0.39 ml) was added under cooling with ice. The resulting mixture was stirred at room temperature for 4 hours. Saturated aqueous ammonium chloride and saturated aqueous sodium hydrogencarbonate were added successively to the mixture under cooling with ice, then the mixture was extracted with methylene chloride. The organic layers were washed with saturated aqueous sodium chloride, dried with anhydrous sodium sulfate and the solvent was distilled off under reduced pressure. The residue was purified by silica gel column chromatography [ChromatorexNH™] (eluent; methylene chloride:methanol=100:0–99:1) to yield the title compound (7 mg).

IR spectrum (KBr) cm$^{-1}$: 2924, 1672, 1601, 1360, 1230, 1165, 1099, 970

Example 600

Synthesis of 1,4-diaza-4-[2-(5-chlorothiophen-2-yl)ethenesulfonyl]-7-oxa-1'-(4-pyridyl)spiro[bicyclo[4.3.0]nonane-8,4'-piperidin]-2-one Using the compound (90 mg) obtained in Reference Example 3 <step 7>, the method of synthesis in Example 9 <step 2> was repeated to yield the title compound (110 mg).

IR spectrum (KBr) cm$^{-1}$: 1670, 1597, 1510, 1462, 1427, 1348, 1155, 968

Example 628

Synthesis of 1,4,7-triaza-4-[2-(5-chlorothiophen-2-yl)ethenesulfonyl]-1'-(4-pyridyl)spiro[bicyclo[4.3.0]nonane-8,4'-piperidin]-2-one Using the compound (120 mg) obtained in Example 275 <step 4>, the method of synthesis in Example 9 <step 2> was repeated to yield the title compound (123 mg).

IR spectrum (KBr) cm$^{-1}$: 1658, 1599, 1510, 1462, 1427, 1348, 1155, 966, 849

Example 656

Synthesis of 1,4,7-triaza-4-[2-(5-chlorothiophen-2-yl)ethenesulfonyl]-7-methyl-1'-(4-pyridyl)spiro[bicyclo[4.3.0]nonane-8,4'-piperidin]-2-one Using the compound (120 mg) obtained in Example 337 <step 2>, the method of synthesis in Example 9 <step 2> was repeated to yield the title compound (146 mg).

IR spectrum (KBr) cm$^{-1}$: 1657, 1595, 1427, 1356, 1153, 995, 847, 594

Example 684

Synthesis of 1,4-diaza-4-[2-(5-chlorothiophen-2-yl)ethenesulfonyl]-6-(methoxymethyl)-7-oxa-1'-(4-pyridyl)spiro[bicyclo[4.3.0]nonane-8,4'-piperidin]-2-one Using the compound (100 mg) obtained in Example 399 <step 3>, the method of synthesis in Example 9 <step 2> was repeated to yield the title compound (137 mg).

IR spectrum (KBr) cm$^{-1}$: 1670, 1597, 1421, 1352, 1144, 1105, 972, 850

Example 712

Synthesis of 1,4,7-triaza-4-[2-(5-chlorothiophen-2-yl)ethenesulfonyl]-6-(methoxymethyl)-1'-(4-pyridyl)spiro[bicyclo[4.3.0]nonane-8,4'-piperidin]-2-one Using the compound (120 mg) obtained in Example 461 <step 4>, the method of synthesis in Example 9 <step 2> was repeated to yield the title compound (132 mg).

IR spectrum (KBr) cm$^{-1}$: 1658, 1597, 1510, 1452, 1425, 1348, 1146, 1107, 852

Example 740

Synthesis of 1,4,7-triaza-4-[2-(5-chlorothiophen-2-yl)ethenesulfonyl]-6-(methoxymethyl)-7-methyl-1'-(4-pyridyl)spiro[bicyclo[4.3.0]nonane-8,4'-piperidin]-2-one Using the compound (130 mg) obtained in Example 523 <step 2>, the method of synthesis in Example 9 <step 2> was repeated to yield the title compound (144 mg).

IR spectrum (KBr) cm$^{-1}$: 1657, 1597, 1510, 1456, 1427, 1350, 1144, 850

Example 759

Synthesis of 1,4-diaza-4-(naphthalen-2-ylsulfonyl)-7-oxa-1'-(4-pyridyl)spiro[bicyclo[4.3.0]nonane-8,4'-piperidin]-2-one Using the compound (0.28 g) obtained in Reference Example 3 <step 7>, the method of synthesis in Example 9 <step 2> was repeated to yield the title compound (0.36 g).

IR spectrum (KBr) cm$^{-1}$: IR spectrum (KBr) cm$^{-1}$: 1672, 1595, 1462, 1348, 1169, 1072, 970

Example 760

Synthesis of 1,4-diaza-4-(2-chloroquinolin-6-ylsulfonyl)-7-oxa-1'-(4-pyridyl)spiro[bicyclo[4.3.0]nonane-8,4'-piperidin]-2-one Using the compound (50 mg) obtained in Reference Example 3 <step 7>, the method of synthesis in Example 9 <step 2> was repeated to yield the title compound (90 mg).

IR spectrum (KBr) cm$^{-1}$: 1672, 1597, 1462, 1352, 1167, 1099, 970, 698

Example 761

Synthesis of 1,4-diaza-4-(5-ethynylbenzo[b]furan-2-ylsulfonyl)-7-oxa-1'-(4-pyridyl)spiro[bicyclo[4.3.0]nonane-8,4'-piperidin]-2-one <Step 1>

Synthesis of 1,4-diaza-7-oxa-1'-(4-pyridyl)-4-[5-[(trimethylsilyl)ethynyl]benzo[b]furan-2-ylsulfonyl]spiro[bicyclo[4.3.0]nonane-8,4'-piperidin]-2-one To a stirred solution of the compound (200 mg) obtained in Example 224 in N,N-dimethylformamide (2.5 ml) were added palladium(II) acetate (1 mg), triphenylphosphine (2 mg), triethylamine (0.5 ml) and (trimethylsilyl)acetylene (77 µl), and the mixture was stirred at 120° C. for 1 hour. After cooling, water was added to the reaction mixture, which was extracted with methylene chloride. The organic layers were washed with saturated aqueous sodium chloride, dried with anhydrous sodium sulfate and the solvent was distilled off under reduced pressure. The residue was purified by silica gel column chromatography [ChromatorexNH™] (eluent; n-hexane:ethyl acetate=3:1–1:9) to yield the title compound (110 mg).

NMR spectrum (*CDCl$_3$) δppm: 8.31–8.23(2H,m),7.84 (1H,s), 7.63–7.57(1H,m),7.53–7.46(1H,m),7.41(1H,s), 6.70–6.63(2H,m), 5.22–5.12(1H,m),4.50–4.35(2H,m),3.80 (1H,d,J=11 Hz),3.75–3.50(3H,m),3.45–3.15(3H,m), 2.85–2.70(1H,m),2.00–1.65(4H,m), 0.27(9H,s)

<Step 2>

Synthesis of 1,4-diaza-4-(5-ethynylbenzo[b]furan-2-ylsulfonyl)-7-oxa-1'-(4-pyridyl)spiro[bicyclo[4.3.0]nonane-8,4'-piperidin]-2-one To a stirred solution of the compound (100 mg) obtained in <step 1> in methanol (8 ml), potassium carbonate (122 mg) was added and the mixture was stirred at room temperature for 2 hours. Insoluble materials were filtered off and washed with methylene chloride. Filtrate and washings were concentrated under reduced pressure. Water was added to the residue, which was extracted with methylene chloride. The organic layer was washed with saturated aqueous sodium chloride, dried with anhydrous sodium sulfate and the solvent was distilled off under reduced pressure. The residue was purified by silica gel column chromatography [ChromatorexNH™] (eluent; n-hexane ethyl acetate=1:9) to yield the title compound (48 mg).

IR spectrum (KBr) cm$^{-1}$: 1672, 1595, 1458, 1371, 1171, 970, 648

Example 765

Synthesis of 1,4,7-triaza-4-(6-chloronaphthalen-2-ylsulfonyl)-1'-(4-pyridyl)spiro[bicyclo[4.3.0]nonane-8,4'-piperidin]-2-one Using the compound (20 mg) obtained in Example 275 <step 4>, the method of synthesis in Example 9 <step 2> was repeated to yield the title compound (28 mg).

IR spectrum (KBr) cm$^{-1}$: 1666, 1593, 1462, 1429, 1331, 1161, 968, 700

Example 769

Synthesis of 1,4,7-triaza-4-(6-chloronaphthalen-2-ylsulfonyl)-7-methyl-1'-(4-pyridyl)spiro[bicyclo[4.3.0]nonane-8,4'-piperidin]-2-one Using the compound (120 mg) obtained in Example 337 <step 2>, the method of synthesis in Example 9 <step 2> was repeated to yield the title compound (154 mg).

IR spectrum (KBr) cm$^{-1}$: 1657, 1595, 1456, 1350, 1165, 698, 600

Example 770

Synthesis of 1,4-diaza-4-(2-chloroquinolin-6-ylsulfonyl)-6-(methoxymethyl)-7-oxa-1'-(4-pyridyl)spiro[bicyclo[4.3.0]nonane-8,4'-piperidin]-2-one Using the compound (50 mg) obtained in Example 399 <step 3>, the method of synthesis in Example 9 <step 2> was repeated to yield the title compound (68 mg).

IR spectrum (KBr) cm$^{-1}$: 1672, 1595, 1446, 1419, 1356, 1171, 1099, 698

Example 776

Synthesis of 1,4-diaza-4-(naphthalen-2-ylsulfonyl)-7-oxa-1'-(4-pyridyl)spiro[bicyclo[4.3.0]nonane-8,4'-piperidin]-2-one methanesulfonate (methanesulfonate of the compound of Example 759)

Using the compound (200 mg) obtained in Example 759, the method of synthesis in Example 12 was repeated to yield the title compound (230 mg).

IR spectrum (KBr) cm$^{-1}$: 1670, 1645, 1547, 1348, 1211, 1169, 1039, 968, 548

Example 777

Synthesis of 1,4-diaza-4-(6-chlorobenzo[b]thiophen-2-ylsulfonyl)-6-(methoxymethyl)-7-oxa-1'-(4-pyridyl)spiro[bicyclo[4.3.0]nonane-8,4'-piperidin]-2-one methanesulfonate (methanesulfonate of the compound of Example 399)

Using the compound (30 mg) obtained in Example 399 <step 4>, the method of synthesis in Example 12 was repeated to yield the title compound (34 mg).

IR spectrum (KBr) cm$^{-1}$: 1676, 1643, 1543, 1419, 1358, 1209, 1165, 1103

Example 778

Synthesis of 1,4-diaza-4-[2-(5-chlorothiophen-2-yl)ethenesulfonyl]-6-(methoxymethyl)-7-oxa-1'-(4-pyridyl)

spiro[bicyclo[4.3.0]nonane-8,4'-piperidin]-2-one methanesulfonate (methanesulfonate of the compound of Example 684)

Using the compound (30 mg) obtained in Example 684, the method of synthesis in Example 12 was repeated to yield the title compound (34 mg).

IR spectrum (KBr) cm$^{-1}$: 1666, 1645, 1547, 1421, 1346, 1209, 1144, 1103

Example 779

Synthesis of 1,4-diaza-4-(5-chlorobenzo[b]furan-2-ylsulfonyl)-6-(methoxymethyl)-7-oxa-1'-(4-pyridyl)spiro[bicyclo[4.3.0]nonane-8,4'-piperidin]-2-one methanesulfonate Using the compound (30 mg) obtained in Example 409, the method of synthesis in Example 12 was repeated to yield the title compound (35 mg).

IR spectrum (KBr) cm$^{-1}$: 1670, 1645, 1545, 1419, 1369, 1209, 1153, 1119

Example 780

Synthesis of 1,4-diaza-4-(7-chloro-2H-benzopyran-3-sulfonyl)-6-(methoxymethyl)-7-oxa-1'-(4-pyridyl)spiro[bicyclo[4.3.0]nonane-8,4'-piperidin]-2-one methanesulfonate (Methanesulfonate of the Compound of Example 388)

Using the compound (35 mg) obtained in Example 388 <step 8>, the method of synthesis in Example 12 was repeated to yield the title compound (40 mg).

IR spectrum (KBr) cm$^{-1}$: 1658, 1547, 1417, 1333, 1207, 1149, 1101, 1045, 1022

The NMR spectrum data of these Examples are shown in FIGS. 33–38.

<Examples of X Ray Crystallography>

A. X ray crystallography of FXa and (−) Optical Isomer of Example 1 of the Present Invention (Hereinafter Referred to as Compound A)

(A-1) Purification and Crystallization of Human FXa from which Gla Domain has been Removed (Hereinafter Referred to as Des-Gla-FXa)

A purified sample of human FXa was purchased from Enzyme Research Laboratories, Inc. and the sample was digested with a protease in accordance with J. Biol. Chem., 271, 16614–16620(1996) to remove Gla domain (1–44). The Des-Gla-FXa was purified by using Mono-P (Amersham Pharmacia Biotech Inc.), and the crystallization was accomplished by hanging drop vapor diffusion method.

Good crystals were obtained when vapor diffusion of drops produced by mixing an equivalent amount of the concentrated sample and 26% (w/v) PEG1500 were conducted against 26% (w/v) PEG1500 solution.

The complex crystal was subjected to X-ray diffraction experiment at a low temperature of −180° C. using diffractometer R-AXIS IV (Rigaku K.K.) and data set was collected at 2.8 Å resolution. The complex crystal was orthorhombic, and the space group was P2$_1$2$_1$2$_1$, and the lattice constant was a=72.7, b=78.17, and c=56.04 Å. This crystal contained 1 molecule in the asymmetric unit, and the Vm value was 2.2 Å$^3$/Dalton.

The structure was analyzed by molecule replacement method using REPLACE (Tong, 1993) included in crystallographic packaging program Xsight (MSI Inc.). 1hcg of protein data bank was used for the initial structure model.

(A-2) Construction of Crystal Structure and Refinement

By using the three dimensional electron density map obtained by the procedure as described above, detailed fitting of A chain (Ile16 to The244)(in chymotrypsin No.) and B chain (Lys87 to Leu137) of the FXa was conducted.

These operations were accomplished by manually operating the model building program Xfit included in the packaging program XtalView (McRee, 1993).

Crystallographic structure of these atom coordinates was refined by using X-PLOR (Brunger, 1987). The refinement was conducted by repeating the calculation by X-PLOR and adjustment of the atom position by manual adjustment to thereby minimize R factor, and this refinement was continued until the value of approximately 20% was obtained.

Coordinate data (PDB format) of the crystal structure of the FXa—Compound A complex after the refinement are shown in Table A.

The columns are as described below. Column 1: record ID of the PDB file; column 2: serial number of coordinate in the PDB file; column 3: atom name; column 4: name of the amino acid residue; column 5: amino acid residue No. (chymotrypsin No.); column 6: X coordinate of the atom; column 7: Y coordinate of the atom; column 8: Z coordinate of the atom; column 9: filling factor (fixed to 1.0); and column 10: temperature factor.

The name of the amino acid residue of Compound A is indicated as M32 for convenience. Hydrogen atoms in the coordinate data are those generated in the course of calculation on program X-PLOR, and the data do not indicate accurate position of the hydrogen atoms.

Figure 43:
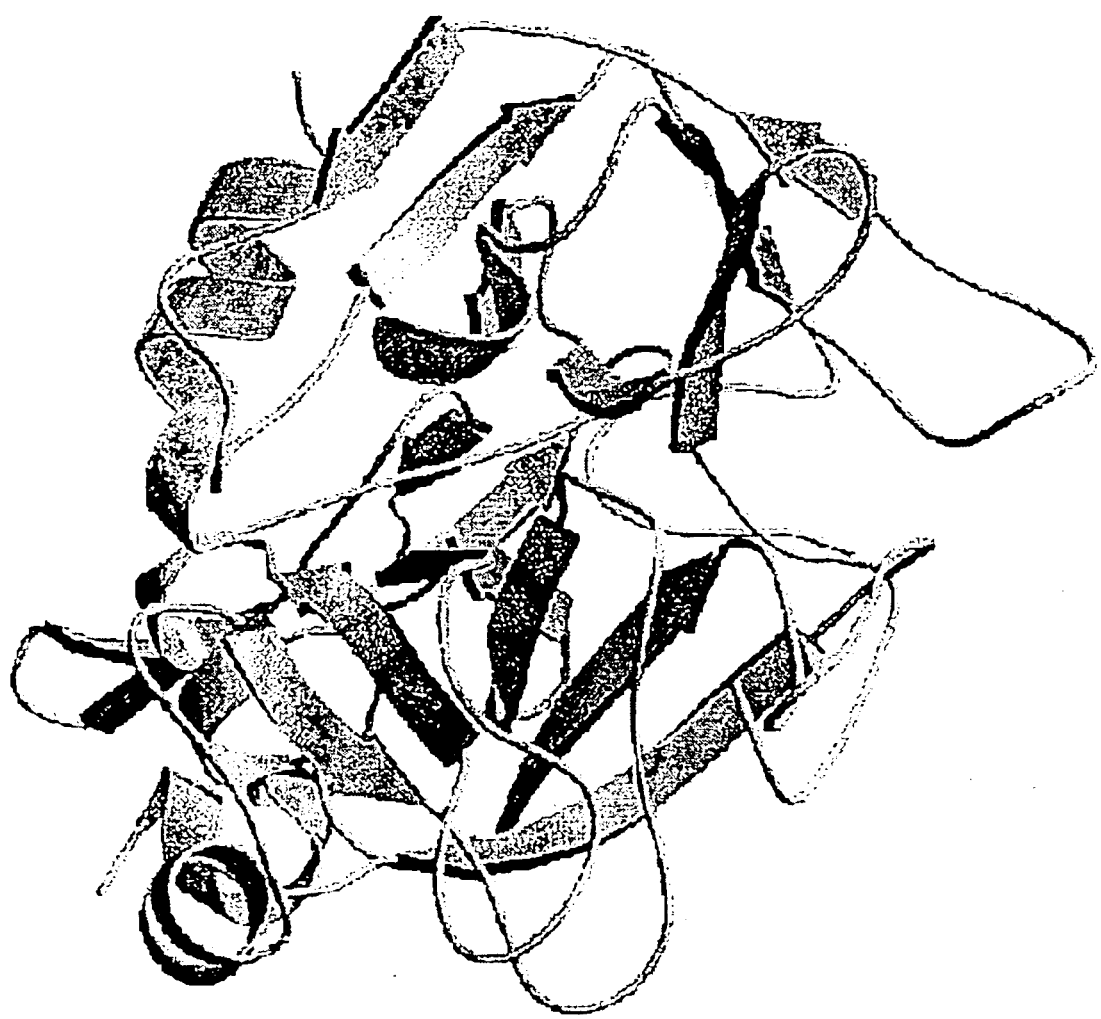
FIG. 43 is a ribbon diagram of human FXa (Des-Gla Domain).
Figure 44:
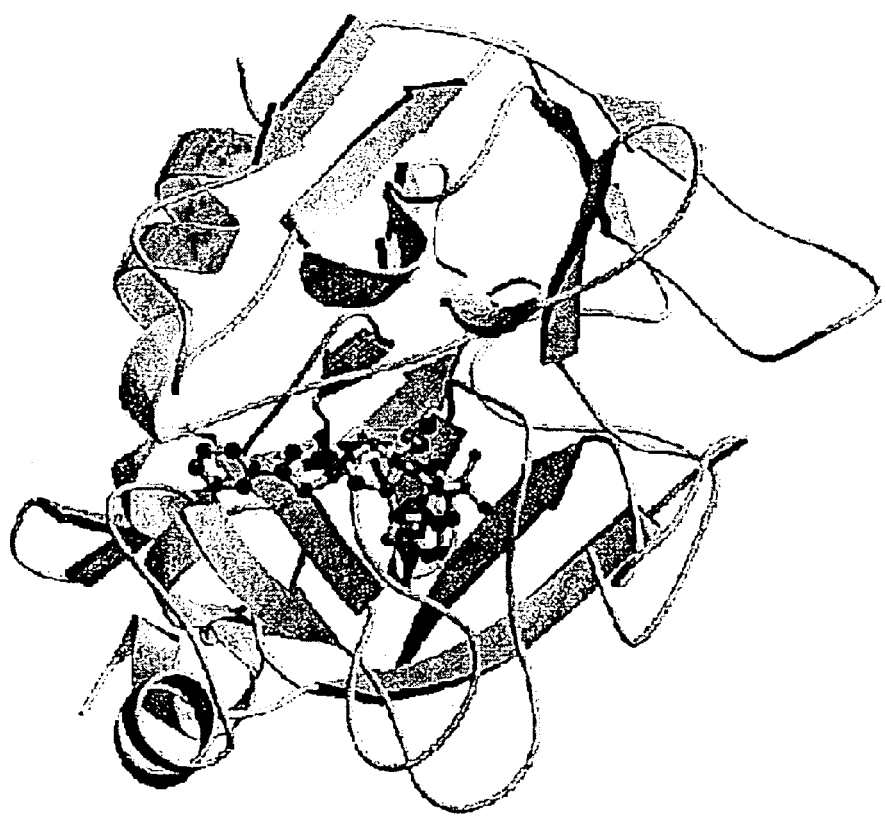
FIG. 44 is a ribbon diagram of human FXa (Des-Gla Domain)-Compound A complex.

On the bases of such data, FIG. 43 shows the structure of the FXa (ribbon diagram), and FIG. 44 shows the crystal structure of the FXa—Compound A complex (ribbon diagram).

FIGS. 43 and 44 were prepared by using the program MOLSCRIPT (Kraulis, P., J. Appl. Crystallogr., 24, 946–950 (1991)).

Figure 45:
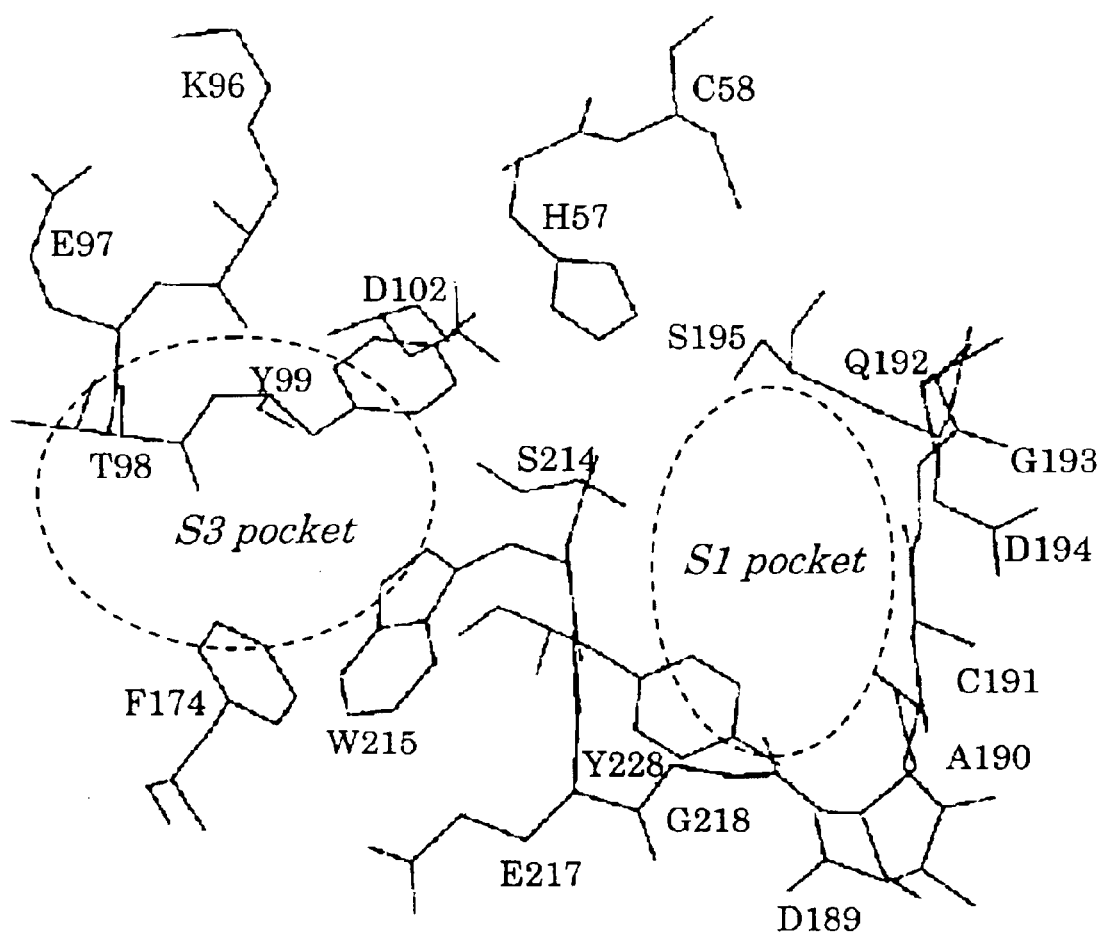
FIG. 45 is a view showing active site of human FXa.

FIG. 45 shows active sites of the human FXa.

Figure 46:
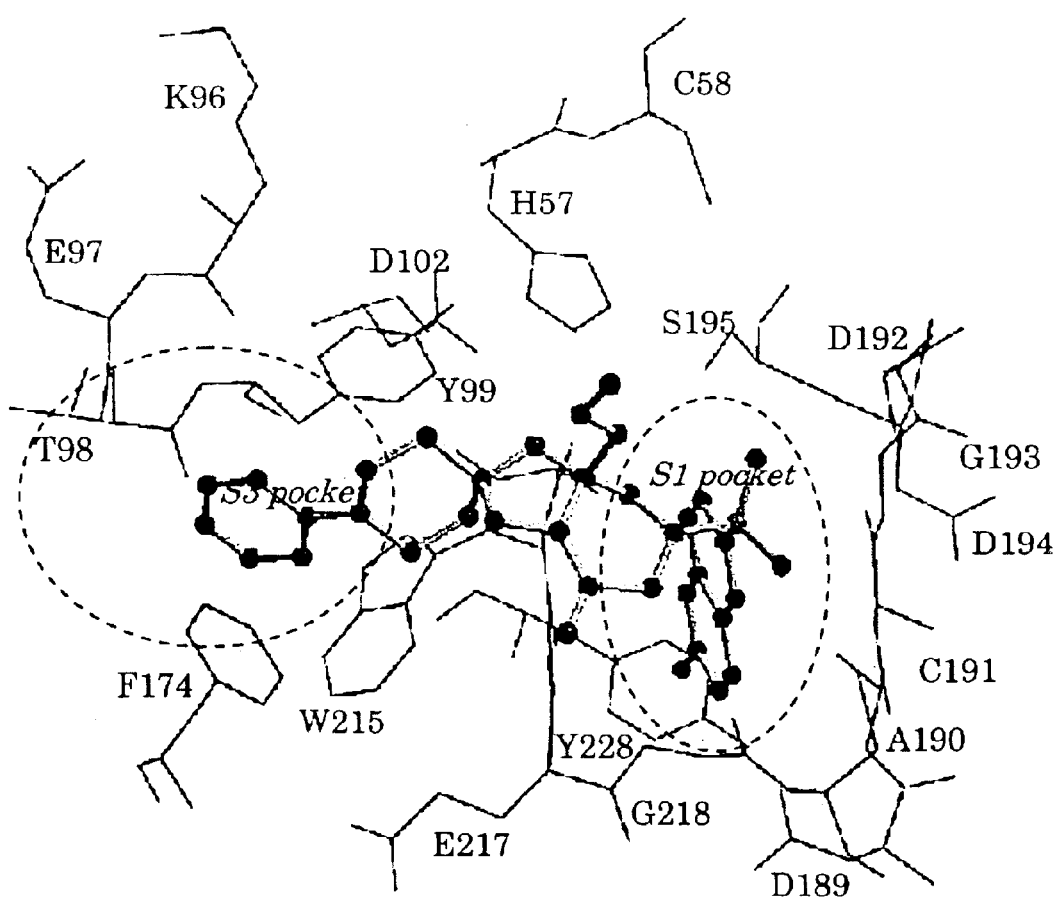
FIG. 46 is a view showing the active site of human FXa-Compound A complex.

FIG. 46 shows active sites of the human FXa—Compound A complex.

The regions corresponding to the S1 pocket and the S3 pocket are surrounded with a broken line for ease of understanding pharmacophore of the present invention.

Figure 47:
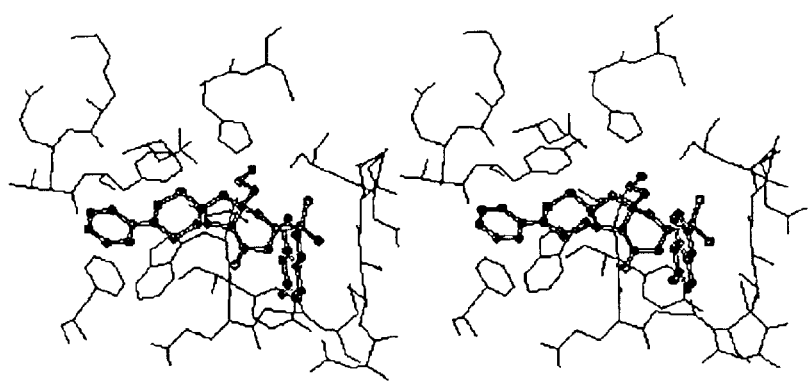
FIG. 47 is a stereo view of the active site of human FXa-Compound A complex.

FIG. 47 shows the stereo view of the active sites of the human FXa—Compound A complex FIG. 47 was prepared by using the program MOLSCRIPT.

As a result of X-ray crystallographic analysis, it was found out that the naphthalene ring moiety of the Compound A is bonded to S1 pocket of the FXa by hydrophobic interaction; the chlorine atom added to the naphthalene has undergone interaction with the benzene ring moiety of the Tyr228 side chain in the S1 pocket; the Compound A has not undergone electrostatic interaction with the Asp189 of the FXa in the S1 pocket; and the binding mode of the Compound A to the S1 pocket is totally different from the binding mode of DX-9065a and FX-2212a which are known FXa inhibitors whose structure of the complex has been found out.

With regard to the remarkably high selectivity of the Compound A for trypsin, it is believed that steric hindrance is induced between the Compound A and Ser 190 of the trypsin and such steric hindrance is a factor for the high selectivity for the trypsin.

4-aminopyridine moiety of the Compound A binds to the S3 pocket by the interaction between the basic moiety of the 4-aminopyridine moiety and the electrically negative condition of the S3 pocket, and such situation is believed to contribute for the selectivity of the Compound A for trypsin, thrombin, protein C and tissue plasminogen activator.

Furthermore, hydrogen bond is formed between the carbonyl oxygen atom of the Compound A and the NH group of the Gly218 backbone. Although the present invention is preferably not confined by any hypothesis, the structural activity correlation of the compound of the present invention is believed to indicate that this bond is not necessary for the inhibition of the FXa, but has secondary effects such as increase of the FXa inhibitory activity.

Construction of the Model Structure of the Compound—FXa Complex

Insight II, Discover, and Search Compare as mentioned below are names of computer programs which are commercially available from Molecular Simulations Inc., San Diego, Calif., USA.

Two Reference Compounds

Compound B: 4-[3-(6-chloronaphthalen-2-ylsulfoneamide)-2-[1-(4-pyridyl)piperidin-4-ylmethyl]aminopropionyl]-1,1-dioxothiomorpholine (The compound of Japanese Patent Application No. 11-180909, Example 8); and Compound C: (R)-4-(6-chloronaphthalen-2-ylsulfonyl)-6-ethoxycarbonyl-1-[1-(4-pyridyl)piperidin-4-ylmethyl]piperazin-2-one (The compound of WO99/33805, Example 60) (Note that the production process of these compounds are found in the specifications of these patent applications. The structural formulae are shown in FIG. 10.) Three-dimensional model structure of these Compounds B and C were prepared on Insight II, and the model structure was optimized by molecular mechanics calculation by using Discover. Subsequently, by manual operation on Insight II, the halogenonaphthalene moiety of the Compound B and that of the Compound C were overlaid with the halogenonaphthalene moiety of the Compound A in the crystal structure of the complex obtained in the crystal structure analysis in the Examples of the present invention to thereby construct the model initial structure of the complex of the FXa and the Compound B or C.

Conformational Search of the Compound

Conformation of the Compounds B and C other than the halogenonaphthalene moiety was searched by using Search Compare with the halogenonaphthalene moiety of the Compounds B and C fixed in the S1 pocket.

The conformation was generated by systematically rotating the bonds in the Compound B or C which were estimated to be rotatable. The rotation angle of the bond was 60 degrees to 300 degrees at an increment of 120 degrees in dihedral angle in the case of the bond between Sp3 atoms; and 0 degree to 330 degrees at an increment of 30 degrees in dihedral angle in the case of the bond between Sp3 atom and Sp2 atom. These rotation angles are the angles that had been recommended by MSI Inc. as the search conditions for generating stable conformation of the compound.

Results of the Analysis

As a result of the conformation search, it was assessed for Compound B that the 4-aminopyridine moiety which is the basic moiety of the Compound B is capable of bonding to the S3 pocket, and the binding conditions of the Compound B to the FXa satisfied all items of the aspect "17-b". It was assessed for Compound C that the 4-aminopyridine moiety which is the basic moiety of the Compound C was also capable of bonding to the S3 pocket, and the binding conditions of the Compound C to the FXa also satisfied all items of the aspect "17-b".

Measurement of the Activity

When the activity was evaluated by the bioassay procedure described in Experimental Example 1, a) of the present invention, Compound B exhibited $IC_{50}$ of 0.031 mM, and Compound C exhibited $IC_{50}$ of 0.028 mM.

The pharmacophore of the present invention has been derived on the basis of the novel tricyclic compound having Spiro union. This compound has played an important role in finding the novel pharmacophore which has never been reported for FXa since the three-dimensional arrangement of the three rings is fixed in this compound. Unexpectedly, it has also been confirmed that the thus derived pharmacophore is quite important and fully applicable by molecular designing means to a compound which does not have such skeleton, and in particular, to a compound having a flexible three-dimensional arrangement.

Industrial Applicability

The compound of the present invention specifically inhibits FXa, and exhibits strong anticoagulation action. The compound of the present invention is also easy to use since it exhibits high oral absorbability as well as long-lasting action and high safety. Accordingly, the compound of the present invention is very useful as an anticoagulant.

Furthermore, the pharmacophore of the present invention derived from the compound of the present invention is capable of providing information useful in identifying or designing the inhibitors which competitively bind to the active site of the FXa or its fragment.

What is claimed is:

1. A compound represented by formula (I) or its pharmaceutically acceptable salt

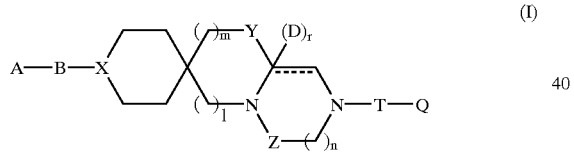

(I)

wherein A is a hydrogen atom, or
  a group selected from (1) a saturated or unsaturated five- or six-membered cyclic hydrocarbon group, or a saturated or unsaturated five- or six-membered heterocyclic group, (2) an amino group, and (3) an imidoyl group (wherein the groups of (1) to (3) are optionally substituted);

B is a single bond, a carbonyl group, —S(O)$_x$—, or an optionally substituted C$_{1-2}$ alkylene group;

D is a hydrogen atom, —CO—R$_5$ (wherein R$_5$ is a hydrogen atom or a substituent), or an optionally substituted C$_{1-6}$ alkyl group;

X is a nitrogen atom or a methine group optionally substituted with a group A'-B'- (wherein A' represents a group selected from those defined for A, and B' represents a group selected from those defined for B);

Y is an oxygen atom, —S(O)$_y$—, or an optionally substituted imino group (—NH—);

Z is a methylene group, a carbonyl group, or a thiocarbonyl group;

T is —S(O)$_z$—, a carbonyl group, or an optionally substituted C$_{1-2}$ alkylene group;

Q is a hydrocarbon group or a heterocyclic group, which are optionally substituted;

l, m, n, x, y, and z are independently an integer selected from 0, 1 and 2 with the proviso that 1 and m are not simultaneously 0; and r is an integer of 0 or 1; and the three rings (the ring containing X, the ring containing Y, and the ring containing Z) are independently optionally substituted; and the bond indicated by the broken line and the solid line in the ring containing Z is a single bond or a double bond (when r is 0).

2. A compound selected from the compounds as described below, or its (+) or (−) optical isomer, or its pharmaceutically acceptable salt:

1,4-diaza-4-(6-chloronaphthalen-2-ylsulfonyl)-6-(methoxymethyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(methoxyethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(hydroxymethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(ethoxycarbonylmethoxymethyl)-7-oxa-1'-(4-pyridyl)spiro[bicyclo[4.3.0]nonane-8,4'-piperidin]-2-one;

6-(acetoxymethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-7-oxa-1'-(4-pyrimidinyl)spiro[bicyclo[4.3.0]nonane-8,4'-piperidin]-2-one;

1,4-diaza-4-((E)-4-chlorostyrylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(2-methoxyethoxymethyl)-7-oxa-1'-(4-pyridyl)spiro[bicyclo[4.3.0]nonane-8,4-piperidin]-2-one;

1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one methanesulfone;

(−)-1,4-diaza-4-(6-chloronaphthalen-2-ylsulfonyl)-6-(ethoxycarbonyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(methoxycarbonyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(isopropoxycarbonyl)-7-oxa-1'-(4-pyridyl) spiro[bicyclo[4.3.0]nonane-8,4'-piperidin]-2-one;

(−)-1,4-diaza-4-(6-chloronaphthalen-2-ylsulfonyl)-7-oxa-6-(propoxycarbonyl)-1'-(4-pyridyl)spiro[bicyclo[4.3.0]nonane-8,4'-piperidin]-2-one;

(−)-6-(allyloxycarbonyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one;

(−)-1,4-diaza-4-(6-chloronaphthalen-2-ylsulfonyl)-6-(2-methoxyethoxycarbonyl)-7-oxa-1'-(4-pyridyl)spiro[bicyclo[4.3.0]nonane-8,4'-piperidin]-2-one;

(−)-1,4-diaza-6-(t-butoxycarbonyl)-4-(6-chloronaphthalen-2-ylsulfonyl)-7-oxa-1'-(4-pyridyl)spiro[bicyclo[4.3.0]nonane-8,4-piperidin]-2-one;

ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine-]-6-carboxylate;

(+)-ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine-]-6-carboxylate;

(−)-ammonium 1,4-diaza-4-(6-chloronaphthalen-2-ylsulfonyl)-7-oxa-2-oxo-1'-(4-pyridyl)spiro[bicyclo[4.3.0]nonane-8,4'-piperidine]-6-carboxylate;

4-[1,4-diaza-4-(6-chloronaphthalen-2-ylsulfonyl)-6-(methoxymethyl)-7-oxa-2-oxospiro[bicyclo[4.3.0]nonane-8,4'-piperidin]-1'-yl]pyridine 1-oxide;

1'-acetimidoyl-1,4-diaza-4-(6-chloronaphthalen-2-ylsulfonyl)-7-oxaspiro[bicyclo[4.3.0]nonane-8,4'-piperidin]-2-one;

6-(aminomethyl)-1,4-diaza-4-(6-chloronaphthalen-2-ylsulfonyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(ethoxycarbonylaminomethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-(morpholinomethyl)-7-oxa-1'-(4-pyridyl)spiro[bicyclo[4.3.0]nonane-8,4'-piperidin]-2-one;

1,4-diaza-4-(6-chloronaphthalen-2-ylsulfonyl)-6-methyl-7-oxa-1'-(4-pyridyl)spiro[bicyclo[4.3.0]nonane-8,4'-piperidin]-2-one;

ammonium 4-(1,4-diaza-4-(6-chloronaphthalen-2-ylsulfonyl)-7-oxa-2-oxo-1'-(4-pyridyl)spiro[bicyclo[4.3.0]nonane-8,4'-piperidin]-6-yl]butylate;

1,4,7-triaza-4-(6-chloronaphthalen-2-ylsulfonyl)-6-(methoxymethyl)-7-methyl-1'-(4-pyridyl)spiro[bicyclo[4.3.0]nonane-8,4'-piperidin]-2-one;

1,4,7-triaza-4-(6-chloronaphthalen-2-ylsulfonyl)-6-(methoxymethyl)-1'-(4-pyridyl)spiro[bicyclo[4.3.0]nonane-8,4'-piperidin]-2-one;

(−)-1,4,7-triaza-4-(6-chloronaphthalen-2-ylsulfonyl)-6-(methoxymethyl)-1'-(4-pyridyl)spiro[bicyclo[4.3.0]nonane-8,4'-piperidin]-2-one;

1,4-diaza-4-(7-chloro-2H-benzopyran-3-ylsulfonyl)-(6-methoxymethyl)-7-oxa-1'-(4-pyridyl)spiro[bicyclo[4.3.0]nonane-8,4'-piperidin]-2-one;

1,4-diaza-4-(7-chloro-2H-benzopyran-3-ylmethyl)-(6-methoxymethyl)-7-oxa-1'-(4-pyridyl)spiro[bicyclo[4.3.0]nonane-8,4'-piperidin]-2-one;

1,4-diaza-4-(6-chlorobenzothiophen-2-ylsulfonyl)-(6-methoxymethyl)-7-oxa-1'-(4-pyridyl)spiro[bicyclo[4.3.0]nonane-8,4'-piperidin]-2-one;

1,4-diaza-4-(6-chlorobenzothiophen-2-ylmethyl)-(6-methoxymethyl)-7-oxa-1'-(4-pyridyl)spiro[bicyclo[4.3.0]nonane-8,4'-piperidin]-2-one;

1,4-diaza-4-(5-chlorobenzofuran-2-ylsulfonyl)-(6-methoxymethyl)-7-oxa-1'-(4-pyridyl)spiro[bicyclo[4.3.0]nonane-8,4'-piperidin]-2-one;

1,4-diaza-4-(5-chlorobenzofuran-2-ylmethyl)-(6-methoxymethyl)-7-oxa-1'-(4-pyridyl)spiro[bicyclo[4.3.0]nonane-8,4'-piperidin]-2-one;

1,4-diaza-4-(6-chlorobenzofuran-2-ylsulfonyl)-(6-methoxymethyl)-7-oxa-1'-(4-pyridyl)spiro[bicyclo[4.3.0]nonane-8,4'-piperidin]-2-one;

1,4-diaza-4-(2H-benzopyran-3-sulfonyl)-7-oxa-1'-(4-pyridyl)spiro[bicyclo[4.3.0]nonane-8,4'-piperidin]-2-one;

1,4-diaza-4-(7-chloro-2H-benzopyran-3-sulfonyl)-7-oxa-1'-(4-pyridyl)spiro[bicyclo[4.3.0]nonane-8,4'-piperidin]-2-one;

1,4-diaza-4-(benzo[b]thiophen-2-ylsulfonyl)-7-oxa-1'-(4-pyridyl)spiro[bicyclo[4.3.0]nonane-8,4'-piperidin]-2-one;

1,4-diaza-4-(5-fluorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(5-chlorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(6-chlorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(6-chloro-5-fluorobenzo[b]thiophen-2-ylsulfonyl)-7-oxa-1'-(4-pyridyl)spiro[bicyclo[4.3.0]nonane-8,4'-piperidin]-2-one;

1,4-diaza-4-(5-chloro-3-methylbenzo[b]thiophen-2-ylsulfonyl)-7-oxa-1'-(4-pyridyl)spiro[bicyclo[4.3.0]nonane-8,4'-piperidin]-2-one;

1,4-diaza-4-(5-chlorobenzo[b]furan-2-ylsulfonyl)-7-oxa-1'-(4-pyridyl)spiro[bicyclo[4.3.0]nonane-8,4'-piperidin]-2-one;

1,4-diaza-4-(5-bromobenzo[b]furan-2-ylsulfonyl)-7-oxa-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-1'-(4-pyridyl)spiro[bicyclo[4.3.0]nonane-8,4'-piperidin]-2-one;

1,4,7-triaza-4-(5-chlorobenzo[b]furan-2-ylsulfonyl)-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-7-methyl-1'-(4-pyridyl)spiro[bicyclo[4.3.0]nonane-8,4'-piperidin]-2-one;

1,4,7-triaza-4-(5-chlorobenzo[b]furan-2-ylsulfonyl)-7-methyl-1'-(4-pyridyl)spiro[bicyclo[4.3.0]nonane-8,4'-piperidin]-2-one;

1,4-diaza-4-(7-chloro-2H-benzopyran-3-sulfonyl)-6-(methoxymethyl)-7-oxa-1'-(4-pyridyl)spiro[bicyclo[4.3.0]nonane-8,4'-piperidin]-2-one;

1,4-diaza-4-(6-chlorobenzo[b]thiophen-2-ylsulfonyl)-6-(methoxymethyl)-7-oxa-1'-(4-pyridyl)spiro[bicyclo[4.3.0]nonane-8,4'-piperidin]-2-one;

1,4-diaza-4-(5-chlorobenzo[b]furan-2-ylsulfonyl)-6-(methoxymethyl)-7-oxa-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-6(methoxymethyl)-1'-(4-pyridyl)spiro[bicyclo[4.3.0]nonane-8,4'-piperidin]-2-one;

1,4,7-triaza-4-(5-chlorobenzo[b]furan-2-ylsulfonyl)-6-(methoxymethyl)-1'-(4-pyridyl)spiro[bicyclo[4.3.0]nonane-8,4'-piperidin]-2-one;

1,4,7-triaza-4-(6-chlorobenzo[b]thiophen-2-ylsulfonyl)-6-(methoxymethyl)-7-methyl-1'-(4-pyridyl)spiro[bicyclo[4.3.0]nonane-8,4'-piperidin]-2-one;

1,4,7-triaza-4-(5-chlorobenzo[b]furan-2-ylsulfonyl)-6-(methoxymethyl)-7-methyl-1'-(4-pyridyl)spiro[bicyclo[4.3.0]nonane-8,4'-piperidin]-2-one;

1,4-diaza-4-(6-chlorobenzo[b]furan-2-ylsulfonyl)-7-oxa-1'-(4-pyridyl)spiro[bicyclo[4.3.0]nonane-8,4'-piperidin]-2-one;

1,4-diaza-4-(indol-2-ylsulfonyl)-7-oxa-1'-(4-pyridyl)spiro[bicyclo[4.3.0]nonane-8,4'-piperidin)-2-one;

1,4-diaza-4-[2-(5-chlorothiophen-2-yl) ethenesulfonyl]-7-oxa-1'-(4-pyridyl)spiro[bicyclo[4.3.0]nonane-8,4'-piperidin]-2-one;

1,4,7-triaza-4-(2-(5-chlorothiophen-2-yl)ethenesulfonyl]-1'-(4-pyridyl)spiro[bicyclo[4.3.0]nonane-8,4'-piperidin]-2-one;

1,4,7-triaza-4-(2-(5-chlorothiophen-2-yl)ethenesulfonyl]-7-methyl-1'-(4-pyridyl)spiro[bicyclo[4.3.0]nonane-8,4'-piperidin]-2-one;

1,4-diaza-4-[2-(5-chlorothiophen-2-yl)ethenesulfonyl]-6-(methoxymethyl)-7-oxa-1'-(4-pyridyl)spiro[bicyclo[4.3.0]nonane-8,4'-piperidin]-2-one;

1,4,7-triaza-4-(2-(5-chlorothiophen-2-yl)ethenesulfonyl]-6-(methoxymethyl)-1'-(4-pyridyl)spiro[bicyclo[4.3.0]nonane-8,4'-piperidin]-2-one;

1,4,7-triaza-4-[2-(5-chlorothiophen-2-yl)ethenesulfonyl]-6-(methoxymethyl)-7-methyl-1'-(4-pyridyl)spiro[bicyclo[4.3.0]nonane-8,4'-piperidin]-2-one;

1,4-diaza-4-(naphthalen-2-ylsulfonyl)-7-oxa-1'-(4-pyridyl)spiro[bicyclo[4.3.0]nonane-8,4'-piperidin]-2-one;

1,4-diaza-4-(2-chloroquinolin-6-ylsulfonyl)-7-oxa-1'-(4-pyridyl)spiro[bicyclo[4.3.0]nonane-8,4'-piperidin]-2-one;

1,4-diaza-4-(5-ethynylbenzo[b]furan-2-ylsulfonyl)-7-oxa-1'-(4-pyridyl)spiro[bicyclo[4.3.0]nonane-8,4'-piperidin]-2-one;

1,4,7-triaza-4-(6-chloronaphthalen-2-ylsulfonyl)-1'-(4-pyridyl)spiro[bicyclo[4.3.0]nonane-8,4'-piperidin]-2-one;

1,4,7-triaza-4-(6-chloronaphthalen-2-ylsulfonyl)-7-methyl-1'-(4-pyridyl)spiro[bicyclo[4.3.0]nonane-8,4'-piperidin]-2-one; and 1,4-diaza-4-(2-chloroquinolin-6-ylsulfonyl)-6-(methoxymethyl)-7-oxa-1'-(4-pyridyl)spiro[bicyclo[4.3.0]nonane-8,4'-piperidin]-2-one.

3. A compound according to claim 1, or its pharmaceutically acceptable salt thereof, wherein Q is said optionally substituted hydrocarbon group and said optionally substituted hydrocarbon group is;

1) a $C_{1-6}$ alkyl group (most preferably a $C_{1-2}$ alkyl group) or a $C_{2-6}$ alkenyl group (most preferably a $C_2$ alkenyl group) substituted with a substituent selected from substituent (a-1) a $C_{6-14}$ aryl group and substituent (b-1) an aromatic group selected from (i) five- or six-membered monocyclic aromatic heterocyclic groups and (ii) eight- to twelve-membered fused aromatic heterocyclic groups, which contain 1 to 4 heteroatoms selected from nitrogen atom, oxygen atom and sulfur atom in addition to the carbon atoms; or 2) a $C_{6-14}$ aryl group which is optionally substituted with 1 to 2 halogen atoms; or a heterocyclic group which is (i) a five- or six-membered, monocyclic, aromatic heterocyclic group, (ii) an eight- to twelve-membered, fused aromatic heterocyclic group, or (iii) a three- to eight-membered, saturated or unsaturated, non-aromatic heterocyclic group, which contains 1 to 4 heteroatoms selected from nitrogen atom, oxygen atom and sulfur atom in addition to the carbon atoms, and wherein the carbon atoms are optionally mono- or di-substituted with a halogen atom, wherein the aromatic ring in the above substituent 1) is optionally substituted with 1 to 3 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di $C_{1-6}$ alkylcarbamoyl, $C_{1-6}$ alkoxycarbonyl, N—$C_{1-6}$ alkylcarbamoyl, N,N-di 1–6 alkylcarbamoyl and $C_{2-6}$ alkenoylamino, and the aromatic ring in the substituents 2) is also optionally mono- or di-substituted at arbitrary position with the substituent selected from $C_{1-6}$ alkyl, $C_{2-6}$ alkenyl, $C_{2-6}$ alkynyl, halogen atom, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N—($C_{1-6}$)alkylcarbamoyl-$C_{1-6}$ alkyl, N,N-di $C_{1-6}$ alkylcarbamoyl-$C_{1-6}$ alkyl, phenyl, phenoxy, phenylthio, phenylsulfinyl, phenylsulfonyl, benzyl, and benzoyl, and the aromatic ring in these substituents may be substituted with 1 to 3 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

4. A pharmaceutical composition comprising a compound represented by formula (I) as described in claim 1 or its pharmaceutically acceptable salt as a therapeutically effective component and a pharmaceutically acceptable carrier.

5. A FXa inhibitor comprising a compound represented by formula (I) as described in claim 1 or its pharmaceutically acceptable salt as a therapeutically effective component.

6. A compound exhibiting inhibitory activity for FXa which has $IC_{50}$ of up to 1 μM and a partial structure represented by formula (I") in its molecule, or its pharmaceutically acceptable salt

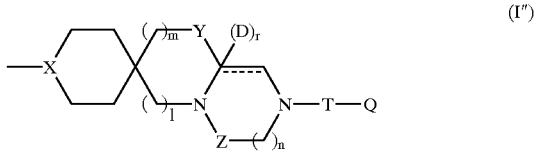

(I″)

wherein X is CH or N; the three rings (the ring containing X, the ring containing y, and the ring containing Z) are independently optionally substituted; Y, Z, D, T, Q, l, m, n, and r are as defined for the formula (I) as described in claim 1.

7. A compound exhibiting inhibitory activity for FXa which has $IC_{50}$ of up to 1 $\mu$M and a partial structure represented by formula (I‴) in its molecule, or its pharmaceutically acceptable salt

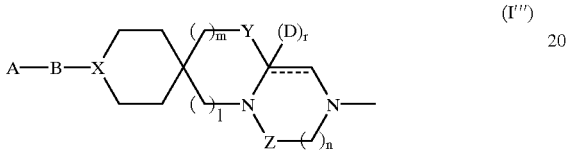

(I‴)

wherein X is methine group or nitrogen atom; the three rings (the ring containing X, the ring containing Y, and the ring containing Z) are independently optionally substituted; A, B, Y, Z, D, l, m, n, and r are as defined for formula (I) as described in claim 1.

8. A compound exhibiting inhibitory activity for FXa represented by the following formula (I′m), or its pharmaceutically acceptable salt

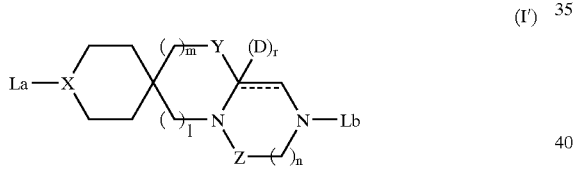

(I′)

wherein D is hydrogen atom, —CO—$R_5$ (wherein $R_5$ is hydrogen atom or a substituent), or an optionally substituted $C_{1-6}$ alkyl group;

X is methine group or a nitrogen atom;

Y is oxygen atom, —S(O)$_y$—, or a optionally substituted imino group (—NH—);

the three rings (the ring containing X, the ring containing Y, and the ring containing Z) are independently optionally substituted;

Z is methylene group, a carbonyl group, or a thiocarbonyl group;

l, m, n, and y are independently an integer selected from 0, 1 and 2 with the proviso that l and m are not simultaneously 0; and r is an integer of 0 or 1;

the bond indicated by the broken line and the solid line is a single bond or a double bond (when r is 0); and La and Lb are groups involved in the binding of the compound of formula (I′) with FXa, and La represents a group which has a basic moiety which associates with S3 pocket of FXa [a space formed at least by amino acid residues Trp215, phe174, Tyr99, Thr98, Glu97, and Lys96], and Lb represents a group which has a hydrophobic moiety which binds to S1 pocket of FXa [a space formed at least by amino acid residues Val213, ser214, Trp215, Gly216, Glu217, Gly218, Cys220, Asp189, Ala190, cys191, Gln192, Gly193, Asp194, ser195, Gly226, Ile227, and Tyr228], and which interacts with Tyr228 side chain in the S1 pocket but which does not covalently bind to ser195 in active center (wherein amino acid No. of the FXa is indicated by chymotrypsin No. used in protein Data Bank (PDB), Registration ID: 1FAX (J. Biol. chem. Nov. 22, 1996; 271 (47): 29988–92)),provided that the compound of formula (I′) is the one wherein, when the hydrophobic moiety of the Lb interacts with the Tyr228 in the binding of the compound of formula (I′) to the FXa, the distance between the centroid (the coordinate obtained by calculating the average for each of X, Y, and Z coordinates of all heavy atoms included in the partial structure; hereinafter simply referred to as centroid) of the hydrophobic moiety of the Lb and the centroid of the Tyr228 side chain is within the range of 6.9 to 7.9 Å, and the compound is also a FXa inhibitory compound which further satisfied at least one of the following conditions 1) to 3):

1) when the compound binds to the FXa, the hydrophobic moiety of the Lb does not either partly or entirely undergo an electrostatic interaction with the Asp189 of the S1 pocket;

2) when the compound binds to the FXa, position of the centroid of the hydrophobic moiety of the Lb satisfies in the s1 pocket at least two of the following conditions that such position is:
   i) at a distance of 3.6 to 4.6 Å from the Cys191 backbone $C_\alpha$ atom;
   ii) at a distance of 6.2 to 7.2 Å from the ser195 backbone $C_\alpha$ atom;
   iii) at a distance of 5.5 to 6.5 Å from the ser214 backbone $C_\alpha$ atom;
   iv) at a distance of 3.6 to 4.6 Å from the Trp215 backbone $C_\alpha$ atom;
   v) at a distance of 6.7 to 7.7 Å from the Glu217 backbone $C_\alpha$ atom; and
   vi) at a distance of 5.8 to 6.8 Å from the cys220 backbone $C_\alpha$ atom;

3) when the compound binds to the FXa, position of the centroid of the partial structure including the basic moiety of the La satisfies in the S3 pocket at least two of the following conditions that such position is:
   i) at a distance of 4.1 to 5.5 Å from the Tyr99 side chain centroid;
   ii) at a distance of 3.1 to 4.5 Å from the Phe174 side chain centroid;
   iii) at a distance of 4.1 to 5.5 Å from the Trp215 side chain centroid;
   iv) at a distance of 4.1 to 6.3 Å from the Lys96 backbone carbonyl oxygen atom; and
   v) at a distance of 3.5 to 5.1 Å from the Glu97 backbone carbonyl oxygen atom).

9. A pharmaceutical composition comprising one or more compound or its pharmaceutically acceptable salt as described in any one of claims 6 to 8 as a therapeutically effective component.

10. A method for inhibiting FXa comprising administering a therapeutically effective amount of the pharmaceutical composition of claim 9 to a mammal which requires inhibition of the FXa.

11. Crystal of a complex between FXa and one or more compound of Formula (I″), Formula (I‴) or Formula (I′) or its salt as described in any one of claims 6 to 8, respectively.

12. A compound according to claim 1, or its pharmaceutically acceptable salt thereof, wherein Q is said optionally substituted heterocyclic group and wherein the heterocyclic group, which is optionally substituted, is at least one selected from the group consisting of:

pyrolyl, furyl, thienyl, oxazolyl, imidazolyl, oxazolyl, isooxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,2,5-triazinyl, 1,3,5-triazinyl, thiadiazinyl, indolyl, isoindolyl, 1H-indazolyl, benzofuranyl (-2-yl), isobenzofuranyl, benzothienyl (-2-yl), isobenzothienyl, benzindazolyl, benzoxazolyl (-2-yl), 1,2-benzoisoxazolyl, benzothiazolyl (-2-yl), 1,2-benzoisothiazolyl, 2H-benzopyranyl (-3-yl), (1H-) benzimidazolyl (-2-yl), 1H-benzotriazolyl, 4H-1,4-benzoxazinyl, 4H-1,4-benzothiazinyl, quinolyl, isoquinolyl, cinnolinyl, quinazolinyl, quinoxalinyl, phthalazinyl, naphthylizinyl, purinyl, pteridinyl, carbazolyl, carbolinyl, acridinyl, phenoxazinyl, phenothiazinyl, phenazinyl, phenoxazinyl, thianthrenyl, phenanthridinyl, phenanthrolinyl, indolizinyl, (4,5,6,7-) tetrahydrothiazolo[5,4-c]pyridyl (-2-yl), (4,5,6,7-) tetrahydrothieno[3,2-c]pyridyl, (1,2,3,4-) tetrahydroisoquinolyl (-6-yl), thiazolo[5,4-c]pyridyl (-2-yl), pyrolo[1,2-b]pyridazinyl, pyrazo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, azetidinyl, oxilanyl, oxetanyl, thietanyl, pyrolidinyl, tetrahydrofuryl, thiolanyl, pyrazolinyl, pyrazolidinyl, pyperidyl, tetrahydropyranyl, pyperadinyl, morpholinyl, thiomorpholinyl, and quinuclidinyl.

\* \* \* \* \*

SEQUENCE LISTING

<160> NUMBER OF SEQ ID NOS: 1

<210> SEQ ID NO 1
<211> LENGTH: 234
<212> TYPE: PRT
<213> ORGANISM: Homo sapiens

<400> SEQUENCE: 1

Ile Val Gly Gly Gln Glu Cys Lys Asp Gly Glu Cys Pro Trp Gln Ala
1               5                   10                  15

Leu Leu Ile Asn Glu Glu Asn Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Ala Ala Glu Glu Gly

-continued

```
       50                  55                  60
Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
                100                 105                 110

Asp Trp Ala Glu Ser Thr Leu Met Thr Gln Lys Thr Gly Ile Val Ser
            115                 120                 125

Gly Phe Gly Arg Thr His Glu Lys Gly Arg Gln Ser Thr Arg Leu Lys
130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
            195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr
225                 230
```